(12) United States Patent
Sabatini et al.

(10) Patent No.: US 10,426,757 B2
(45) Date of Patent: Oct. 1, 2019

(54) COMPOSITIONS AND METHODS FOR PROMOTING INTESTINAL STEM CELL AND/OR NON-STEM PROGENITOR CELL FUNCTION

(71) Applicants: Whitehead Institute for Biomedical Research, Cambridge, MA (US); Massachusetts Institute of Technology, Cambridge, MA (US)

(72) Inventors: David M. Sabatini, Cambridge, MA (US); Omer Yilmaz, Ann Arbor, MI (US); Maria Mihaylova, Somerville, MA (US)

(73) Assignees: Whitehead Institute for Biomedical Research, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/314,852

(22) PCT Filed: May 29, 2015

(86) PCT No.: PCT/US2015/033359
§ 371 (c)(1),
(2) Date: Nov. 29, 2016

(87) PCT Pub. No.: WO2015/184375
PCT Pub. Date: Dec. 3, 2015

(65) Prior Publication Data
US 2017/0258772 A1 Sep. 14, 2017

Related U.S. Application Data

(60) Provisional application No. 62/004,747, filed on May 29, 2014.

(51) Int. Cl.
*A61K 31/426* (2006.01)
*A61K 45/06* (2006.01)

(52) U.S. Cl.
CPC .......... *A61K 31/426* (2013.01); *A61K 45/06* (2013.01)

(58) Field of Classification Search
None
See application file for complete search history.

(56) References Cited

U.S. PATENT DOCUMENTS

2007/0218519 A1   9/2007   Urdea et al.
2008/0039514 A1   2/2008   Dropinski et al.
2011/0158983 A1   6/2011   Bascomb et al.
2012/0027757 A1   2/2012   Sathyanarayanan et al.

FOREIGN PATENT DOCUMENTS

WO   WO 2013/152120 A2      10/2013
WO   WO-2013152120 A2 *     10/2013
WO   WO 2015/184375         12/2015

OTHER PUBLICATIONS

Varnat, F. et al., Gastroenterology 2006 vol. 131, pp. 538-553.*
Varnat, Frédéric, et al. "PPARβ/δ regulates paneth cell differentiation via controlling the hedgehog signaling pathway." *Gastroenterology* 131.2 (2006): 538-553.
Ramanan, Sriram, et al. "Role of PPARs in radiation-induced brain injury." *PPAR research* 2010 (2009): 1-12.
Ham, Sun Ah, et al. "Ligand-activated PPARδ inhibits UVB-induced senescence of human keratinocytes via PTEN-mediated inhibition of superoxide production." *Biochemical Journal* 444.1 (2012):27-38.
Wild, Gary E., et al "Nutritional modulation of the inflammatory response in inflammatory bowel disease from the molecular to the integrative to the clinical." *World journal of gastroenterology* 13.1 (2007): 1-7.
Marin, Holly E., et al. "Ligand activation of peroxisome proliferator—activated receptor β inhibits colon carcinogenesis." *Cancer Research* 66.8 (2006): 4394-4401.
Khandekar, Melin J., Paul Cohen, and Bruce M. Spiegelman. "Molecular mechanisms of cancer development in obesity," *Nature Reviews Cancer* 11.12 (2011): 886-895.
Gupta, Rajnish A., et al. "Activation of nuclear hormone receptor peroxisome proliferator—activated receptor-δ accelerates intestinal adenoma growth." *Nature medicine* 10.3 (2004): 245-247.
Sato, Toshiro, et al. "Single Lgr5 stem cells build crypt villus structures in vitro without a mesenchymal niche." *Nature* 459.7244 (2009): 262-266.
Sato, Toshiro, et al, "Paneth cells constitute the niche for Lgr5 stem cells in intestinal crypts." *Nature* 469.7330 (2011): 415-418.
Mihaylova, M. M., Sabatini, D. M. & Yilmaz, O. H. "Dietary and metabolic control of stem cell function in physiology and cancer." *Cell stem cell* 14 (2014): 292-305.
Barker, N. et al. "Identification of stem cells in small intestine and colon by marker gene Lgr5." *Nature* 449 (2007): 1003-1007.
Munoz, J. et al. "The Lgr5 intestinal stem cell signature: robust expression of proposed quiescent '+4' cell markers." *The EMBO journal* 31 (2012): 3079-3091.
Sato, T. et al. "Paneth cells constitute the niche for Lgr5 stem cells in intestinal crypts." *Nature* 469 (2011): 415-418.
Yilmaz, O. H. et al. "mTORC1 in the Paneth cell niche couples intestinal stem-cell function to calorie intake." *Nature* 486 (2012): 490-495.
Schwitalla, S. et al. "Intestinal tumorigenesis initiated by dedifferentiation and acquisition of stem-cell-like properties." *Cell* 152 (2013): 25-38.
Pellegrinet, L. et al. "DII1-and dII4-mediated notch signaling are required for homeostasis of intestinal stem cells." *Gastroenterology* 140 (2011): 1230-1240.

(Continued)

*Primary Examiner* — Heidi Reese
(74) *Attorney, Agent, or Firm* — Lisa M. Warren, Esq.; Morse, Barnes-Brown & Pendleton, P.C.

(57) ABSTRACT

Disclosed herein are novel methods and compositions useful for promoting intestinal stem cell function. The methods and compositions are particularly useful for stimulating the proliferation of and/or self-renewal of intestinal stem cells, as well as for minimizing, preventing, or ameliorating cellular damage resulting from incidental or accidental exposure to radiation (e.g., cancer radiation therapy).

22 Claims, 50 Drawing Sheets
Specification includes a Sequence Listing.

(56) References Cited

OTHER PUBLICATIONS

Farin, H. F., van Es, J. H. & Clevers, H. "Redundant Sources of Wnt Regulate Intestinal Stem Cells and Promote Formation of Paneth Cells." *Gastroenterology*, (2012).
Mah, A. T., Van Landeghem, L., Gavin, H. E., Magness, S. T. & Lund, P. K. "Impact of diet-induced obesity on intestinal stem cells: hyperproliferation but impaired intrinsic function that requires insulin/IGF1." *Endocrinology* 155 (2014): 3302-3314.
Scholtysek, C. et al. "PPARbeta/delta governs Wnt signaling and bone turnover." *Nature medicine* 19 (2013): 608-613.
Rodilla, V. et al. "Jagged1 is the pathological link between Wnt and Notch pathways in colorectal cancer." *PNAS* 106 (2009): 6315-6320.
Kumar, S. R. et al. "Preferential induction of EphB4 over EphB2 and its implication in colorectal cancer progression." *Cancer research* 69 (2009): 3736-3745.
Wang, K. et al. "SGK1-dependent intestinal tumor growth in APC-deficient mice." *Cell Physiol Biochem* 25 (2010): 271-278.
Wang, K. et al. "Peroxisome proliferator-activated receptor delta promotes colonic inflammation and tumor growth." *PNAS* 111 (2014): 7084-7089.
Wang, D. et al. "Crosstalk between peroxisome proliferator-activated receptor delta and VEGF stimulates cancer progression." *PNAS* 103 (2006): 19069-19074.
Park, B. H., Vogelstein, B. & Kinzler, K. W. "Genetic disruption of PPARdelta decreases the tumorigenicity of human colon cancer cells." *PNAS* 98 (2001) 2598-2603.
Zuo, X. et al. "Targeted genetic disruption of peroxisome proliferator-activated receptor-delta and colonic tumorigenesis." *Journal of the National Cancer Institute* 101 (2009): 762-767.
Barak, Y. et al. "Effects of peroxisome proliferator-activated receptor delta on placentation, adiposity, and colorectal cancer." *PNAS* 99 (2002): 303-308.
Yilmaz, Omer, Abstract "Regulation of the Intestinal Stem Cell Niche in Aging," National Institutes of Health Grant No. K99AG045144-01, funded on Aug. 26, 2013 through R00AG045144-05, funded on May 20, 2016.
Sabatini, David, M., Abstract "Regulation of the mTOR Growth Pathway by Nutrients," National Institutes of Health Grant No. R01CA103866-01, funded on Mar. 24, 2004, through R01CA103866-05, funded on Feb. 28, 2008.
Sabatini, David, M., Abstract "Regulation of the mTOR Pathway by Nutrients," National Institutes of Health Grant No. R01CA103866-06A1, funded on Jul. 7, 2009, through R01CA103866-10, funded on Jun. 10, 2013.
Sabatini, David, M., Abstract "Regulation of the mTOR Pathway by Nutrients," National Institutes of Health Grant No. R01CA103866-11, funded on Apr. 23, 2014, through R01CA103866-13, funded on May 20, 2016.
Sabatini, David, M., Abstract "Cell Growth Signaling in Cancer Development," National Institutes of Health Grant No. R01CA129105-01A1, funded on Apr. 8, 2008, through R01CA129105-05, funded on Mar. 14, 2012.
Sabatini, David, M., Abstract "Cell Growth Signaling in Cancer Development," National Institutes of Health Grant No. R01CA129105-06, funded on Feb. 11, 2013, through R01CA129105-10, funded on Jan. 25, 2017.
Sabatini, David, M., Abstract "Translational Control by Rapamycin-Sensitive Signaling," National Institutes of Health Grant No. R01AI047389-01, funded on Mar. 10, 2000, through R01AI047389-05, funded on Mar. 4, 2004.
Sabatini, David, M., Abstract "Rapamycin-Insensitive Signaling by Rictor-mTOR," National Institutes of Health Grant No. R01AI047389-06, funded on Feb. 14, 2005, through R01AI047389-10, funded on May 4, 2009.
Sabatini, David, M., Abstract "Novel Components of the mTORC1 and mTORC2 Pathways," National Institutes of Health Grant No. R37AI047389-11, funded on Apr. 28, 2010, through R37AI047389-17, funded on Apr. 21, 2016.
International Search Report issued in International Application No.: PCT/US2015/033359, dated Oct. 26, 2015.

\* cited by examiner

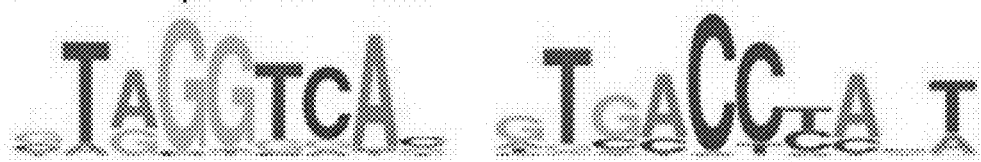
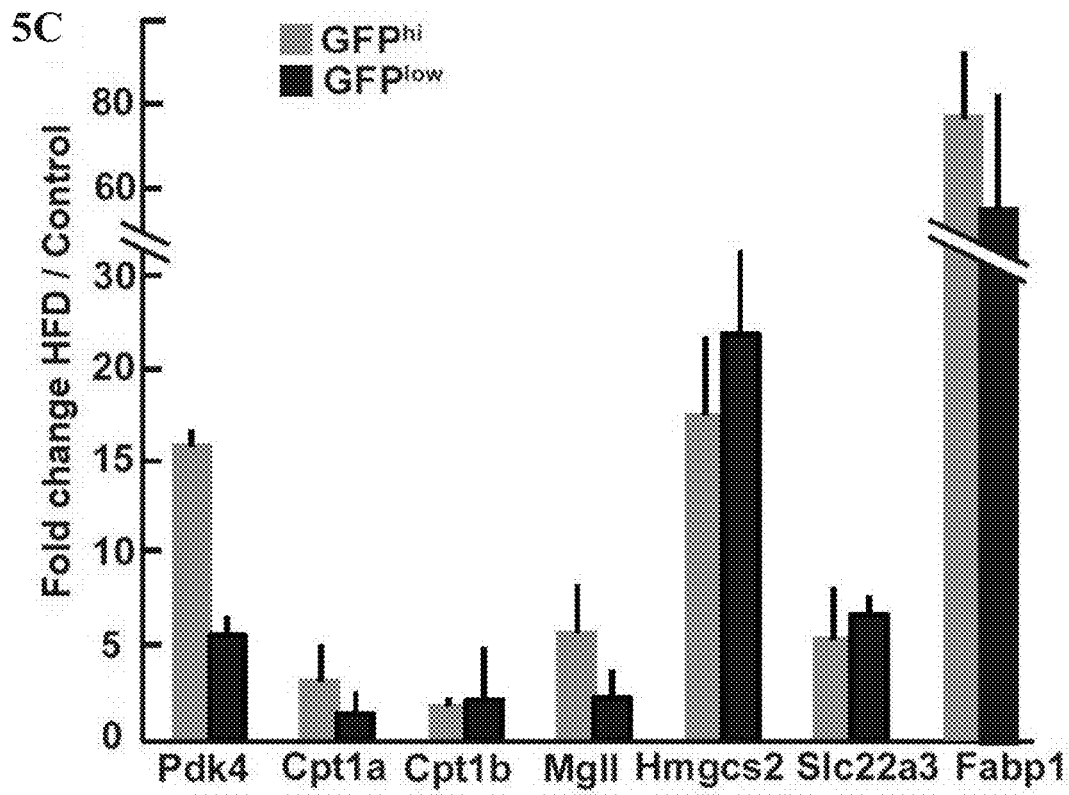
FIGS. 5B-5C

12B

| Stem-cell signature | | |
|---|---|---|
| Gene | FDR | Log₂FC |
| Lgr5 | 9.1E-6 | 2.6 |
| Rnf43 | 4.2E-4 | 1 |
| Jun | 4.8E-4 | 1.6 |
| Cd44 | 1.4E-3 | 1.5 |
| Fgfr4 | 3.9E-3 | 3.2 |

12C

| HFD signature | | |
|---|---|---|
| Gene | FDR | Log₂FC |
| Bmp4 | 2.3E-11 | 21.3 |
| Jag2 | 1.3E-9 | 17 |
| Jag1 | 7.4E-9 | 19.6 |
| Ecad | 8.6E-8 | -3.4 |
| Edn3 | 1.2E-6 | 12.9 |

COMPOSITIONS AND METHODS FOR PROMOTING INTESTINAL STEM CELL AND/OR NON-STEM PROGENITOR CELL FUNCTION

RELATED APPLICATIONS

This application is a national stage filing under 35 U.S.C. 371 of International Application No. PCT/US2015/033359, filed May 29, 2015, which claims the benefit of U.S. Provisional Application Ser. No. 62/004,747, filed May 29, 2014, the entire teachings of which are incorporated herein by reference. International Application No. PCT/US2015/033359 was published under PCT Article 21(2) in English.

GOVERNMENT SUPPORT

This invention was made with government support under NIH AG045144 and NIH AI047389, NIH CA129105, and NIH CA103866 awarded by the National Institutes of Health. The government has certain rights in the invention.

BACKGROUND OF THE INVENTION

Adult stem cells maintain tissues for the life of an organism by achieving equilibrium between self-renewal and differentiation. These stem cells often require cues from their microenvironment or "niche" for their maintenance and function. In the mammalian intestine, for example, most intestinal stem cells (ISCs) reside at the bottom of the crypts and are adjacent to Paneth cells, which constitute a key component of the stem cell niche.

Intestinal atrophy or damage affects a significant portion of hospitalized patients in the US, including those suffering from inflammatory bowel disease, vascular disease, cancer, infection or malnourishment, as well as those exposed to ionizing radiation. Accordingly, there remains a need for therapies capable of modulating the processes of intestinal cell proliferation and remodeling.

SUMMARY OF THE INVENTION

The present disclosure relates in some aspects to novel methods, agents, and compositions useful for promoting intestinal stem cell function and/or intestinal non-stem progenitor cell function. Certain of the methods, agents, and compositions are particularly useful for stimulating the proliferation and/or self-renewal of intestinal stem cells and/or non-stem progenitor cells in mammalian intestinal tissue, for example, by contacting a population of cells in the mammalian intestinal tissue with an effective amount of a high fat diet mimetic, which may be useful for ameliorating afflictions characterized by intestinal atrophy, as well as for preventing or ameliorating harmful effects of ionizing radiation, particularly during radiation cancer therapy or upon accidental or incidental exposure to ionizing radiation.

In some aspects the disclosure provides methods for stimulating the proliferation and/or self-renewal of intestinal stem cells in mammalian intestinal tissue.

In an aspect the disclosure provides a method of stimulating the proliferation and/or self-renewal of one or more intestinal stem cells in mammalian intestinal tissue, the method comprising contacting a population of cells in the mammalian intestinal tissue with an effective amount of an agent that increases the level and/or activity of peroxisome proliferator activated receptor delta (PPAR-δ) or a PPAR-δ target protein, thereby stimulating the proliferation and/or self-renewal of one or more intestinal stem cells.

In an aspect the disclosure provides, a method of promoting regeneration of mammalian intestinal tissue, the method comprising contacting a population of cells in the mammalian intestinal tissue with an effective amount of an agent that increases the level and/or activity of peroxisome proliferator activated receptor delta (PPAR-δ) or a PPAR-δ target protein, thereby promoting regeneration of the mammalian intestinal tissue.

In some embodiments the intestinal stem cells comprise leucine-rich repeat-containing G-protein coupled receptor 5-positive (LGR5$^+$) stem cells. In some embodiments the population of cells is selected from the group consisting of LGR5$^+$ stem cells, non-stem cell progenitor cells, and optionally Paneth cells, and/or goblet cells. In some embodiments the population of cells is contacted with both an agent that increases the level and/or activity of PPAR-δ and an agent that increases the level and/or activity of a PPAR-δ target protein. In some embodiments the PPAR-δ target protein is selected from the group consisting of carnitine palmitoyltransferase 1A (CPT1A), 3-hydroxy-3-methylglutaryl-CoA synthase 2 (HMGCS2), and fatty acid binding protein 1 (FABP1). In some embodiments the agent increases the level and/or activity of both PPAR-δ and the PPAR-δ target protein. In some embodiments the agent increases the level and/or activity of the PPAR-δ target protein in intestinal stem and/or non-stem cell progenitor cells. In some embodiments the agent comprises a high fat diet mimetic. In some embodiments the agent comprises a PPAR-δ agonist. In some embodiments the agent comprises 2-[2-methyl-4-[[4-methyl-2-[4-(trifluoromethyl)phenyl]-1,3-thiazol-5-yl]methylsulfanyl]phenoxy]acetic acid (GW501516) or an analog or derivative thereof. In some embodiments the agent comprises a PPAR-δ target protein agonist selected from the group consisting of a CPT1A agonist, a HMGCS2 agonist, and a FABP1 agonist. In some embodiments the contacting occurs in vitro.

In some embodiments the contacting occurs in vivo in a subject. In some embodiments the subject is selected for treatment of a gastrointestinal disorder selected from the group consisting of inflammatory bowel disease, infectious colitis, ischemic colitis, and inflammatory colitis. In some embodiments the method includes determining that the subject is in need of treatment for a gastrointestinal disorder selected from the group consisting of inflammatory bowel disease, infectious colitis, ischemic colitis, and inflammatory colitis. In some embodiments inflammatory bowel disease is selected from the group consisting of Crohn's disease and ulcerative colitis. In some embodiments the subject is selected for treatment of an affliction characterized by intestinal atrophy selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation. In some embodiments, the affliction characterized by intestinal atrophy is an advanced age.

In some embodiments the method includes determining that the subject is in need of treatment for an affliction characterized by intestinal atrophy selected from the group consisting of an inflammatory disease, an autoimmune disease, vascular disease, cancer, infection, short bowel syndrome, drug-induced or toxin-induced intestinal injury, total parenteral nutrition, exposure to ionizing radiation and advanced age. In some embodiments exposure to ionizing radiation is from an ionizing radiation source selected from the group consisting of a nuclear power plant, a nuclear weapon, radiotherapy, and space or cosmic radiation.

In some embodiments the method includes determining that the subject is in need of enhanced intestinal function. For example, in certain embodiments an aged or aging subject may be in need of enhanced intestinal function. In some embodiments the method includes placing the subject on a high fat diet. In some embodiments the high fat diet comprises a macronutritional composition of at least 60% of total daily calories comprising fat. In some embodiments the high fat diet comprises a diet restricted in terms of total calories. In some embodiments the high fat diet comprises a diet restricted in terms of total daily calories consumed.

In an aspect, the disclosure provides a method of treating an affliction characterized by intestinal atrophy in a subject in need thereof, the method comprising administering to the subject an effective amount of a composition that increases the level and/or activity of PPAR-δ or a PPAR-δ target protein, thereby treating the affliction characterized by intestinal atrophy. In some embodiments the method includes determining that the subject is in need of treatment for an affliction characterized by intestinal atrophy. In some embodiments the affliction is selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation. In some embodiments, the affliction characterized by intestinal atrophy is an advanced aged.

In certain aspects, the affliction is selected from the group consisting of Crohn's disease, infectious colitis, ischemic colitis, inflammatory colitis, and ulcerative colitis. In some embodiments the composition comprises a high fat diet mimetic. In some embodiments the composition comprises a PPAR-δ agonist and a pharmaceutically acceptable carrier, diluent, or excipient. In some embodiments the PPAR-δ agonist comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient.

In certain aspects the disclosure provides a composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the method includes placing the subject on a high fat diet. In some embodiments the high fat diet comprises a calorie restricted diet.

In some aspects the disclosure provides a method of minimizing the risk of exposure to an ionizing radiation source, the method comprising administering to an individual an effective amount of a composition that increases the level and/or activity of PPAR-δ or a PPAR-δ target protein, thereby minimizing the risk of exposure to the ionizing radiation source. In some embodiments the composition comprises a high fat diet mimetic. In some embodiments the composition comprises a PPAR-δ agonist and a pharmaceutically acceptable carrier, diluent, or excipient. In some embodiments the PPAR-δ agonist comprises GW501516 or an analog or derivative thereof. In some embodiments the PPAR-δ target protein is selected from the group consisting of CPT1A, HMGCS2, and FABP1. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the ionizing radiation source is a source of accidental or incidental ionizing radiation selected from the group consisting of a nuclear power plant, a nuclear weapon, and space or cosmic radiation. In some embodiments individual is an individual that is being administered, or about to be administered, radiotherapy.

In an aspect the disclosure provides a method of increasing tolerance to ionizing radiation in an individual, the method comprising administering to the individual an effective amount of a composition that increases the level and/or activity of PPAR-δ or a PPAR-δ target protein, wherein the composition increases the threshold dose of lethal ionizing radiation to above 8 Gy. In some embodiments the composition comprises a high fat diet mimetic. In some embodiments the composition comprises a PPAR-δ agonist and a pharmaceutically acceptable carrier, diluent, or excipient. In some embodiments the PPAR-δ agonist comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the threshold dose of lethal ionizing radiation is increased to about 15 Gy.

In some aspects the disclosure provides a method of treating an individual exposed to harmful ionizing radiation, the method comprising administering to the individual an effective amount of a composition that increases the level and/or activity of PPAR-δ or a PPAR-δ target protein, thereby treating the individual exposed to harmful ionizing radiation. In some embodiments the composition comprises a high fat diet mimetic. In some embodiments the composition comprises a PPAR-δ agonist and a pharmaceutically acceptable carrier, diluent, or excipient. In some embodiments the PPAR-δ agonist comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the harmful ionizing radiation is a source of accidental or incidental ionizing radiation selected from the group consisting of a nuclear power plant, a nuclear weapon, and space or cosmic radiation. In some embodiments the individual is an individual that is being administered, or about to be administered, radiotherapy. In some embodiments the method includes placing the individual on a high fat diet. In some embodiments the high fat diet comprises a calorie restricted diet.

In some aspects the disclosure provides a method of treating cancer in a subject in need thereof, the method comprising: (a) administering to the subject an effective amount of a composition that increases the level and/or activity of PPAR-δ or a PPAR-δ target protein; and (b) administering an effective amount of ionizing radiation to the subject. In some embodiments the composition: (i) increases the subject's tolerance for ionizing radiation; (ii) minimizes undesirable side-effects due to the ionizing radiation; (iii) protects against gastrointestinal drug toxicity. In some embodiments the composition comprises a PPAR-δ agonist and a pharmaceutically acceptable carrier, diluent, or excipient. In some embodiments the PPAR-δ agonist comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the composition is: (i) administered to the patient prior to administering the ionizing radiation to the subject; (ii) co-administered to the subject with the ionizing radiation; (iii) administered to the subject after administering the ionizing radiation to the subject; and combinations thereof. In some embodiments the method includes administering a chemotherapeutic agent to the subject. In some embodiments the method includes placing the individual on a high fat diet. In some embodiments the high fat diet comprises a calorie restricted diet.

In some aspects the disclosure provides a method of administering radiotherapy to a subject in need thereof, the method comprising: (a) administering to the subject an effective amount of a composition that increases the level and/or activity of PPAR-δ; and (b) administering radiotherapy to the subject. In some embodiments, the composition is administered prior to administering the radiotherapy to the subject (e.g., about 1 day, 2 days, 3 days, 4 days, 5 days, 6 days, 7 days, 10 days, 12 days, 14 days, 21 days, 24 days, 28 days, 30 days, 42 days, 60 days, 90 days or more prior to administering the radiotherapy). In some embodiments, the composition is administered to the subject concomitantly with the radiotherapy.

In some aspects the disclosure provides a method administering proton therapy to a subject in need thereof, the method comprising: (a) administering to the subject an effective amount of a composition that increases the level and/or activity of PPAR-δ; and (b) administering proton therapy to the subject. In some embodiments, the composition is administered prior to administering the proton therapy to the subject (e.g., about 1 day, 2 days, 3 days, 4 days, 5 days, 6 days, 7 days, 10 days, 12 days, 14 days, 21 days, 24 days, 28 days, 30 days, 42 days, 60 days, 90 days or more prior to administering the proton therapy). In some embodiments, the composition is administered to the subject concomitantly with the proton therapy.

In some aspects the disclosure provides a method of administering chemotherapy to a subject in need thereof, the method comprising: (a) administering to the subject an effective amount of a composition that increases the level and/or activity of PPAR-δ; and (b) administering chemotherapy to the subject. In some embodiments, the composition is administered prior to administering the chemotherapy to the subject (e.g., about 1 day, 2 days, 3 days, 4 days, 5 days, 6 days, 7 days, 10 days, 12 days, 14 days, 21 days, 24 days, 28 days, 30 days, 42 days, 60 days, 90 days or more prior to administering the chemotherapy). In some embodiments, the composition is administered to the subject concomitantly with the chemotherapy.

In some embodiments the composition comprises a high fat diet mimetic. In some aspects the disclosure provides the composition comprises a PPAR-δ agonist and a pharmaceutically acceptable carrier, diluent, or excipient. In some embodiments the PPAR-δ agonist comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient.

In certain aspects, the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the method includes placing the individual on a high fat diet. In some embodiments the high fat diet comprises a calorie restricted diet.

In some aspects the disclosure provides a radioprotective composition comprising an agent that increases the level and/or activity of PPAR-δ or a PPAR-δ target protein, and a pharmaceutically acceptable carrier, diluent, or excipient.

In some aspects the disclosure provides a chemoprotective composition comprising an agent that increases the level and/or activity of PPAR-δ or a PPAR-δ target protein, and a pharmaceutically acceptable carrier, diluent, or excipient. In some aspects, the agents or the chemoprotective compositions may be administered prior to initiation of chemotherapy (e.g., as a chemotherapy pre-treatment). In some aspects, the agents or the chemoprotective compositions may be concurrently administered with chemotherapy. In some embodiments the agent comprises a high fat diet mimetic. In some embodiments the agent comprises a PPAR-δ agonist. In some embodiments the agent comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the composition includes a chemotherapeutic agent. In some embodiments the composition includes a radiotherapeutic agent. In some embodiments the composition is formulated for administration as an enema. In some embodiments the composition is formulated for oral administration.

Aspects of the disclosure involve the use of an agent that increases the level and/or activity of PPAR-δ and/or a PPAR-δ target protein to promote intestinal regeneration, protect against intestinal tissue damage, and/or stimulate the proliferation and/or self-renewal of one or more intestinal stem cells.

Aspects of the disclosure involve the use of an agent that increases the level and/or activity of PPAR-δ and/or a PPAR-δ target protein to treat an affliction characterized by intestinal atrohny. In some embodiments the affliction is selected from the group consisting of an inflammatory disease, an autoimmune disease, vascular disease, cancer, infection, short bowel syndrome. In some embodiments the affliction is selected from the group consisting of Crohn's disease, infectious colitis, ischemic colitis, inflammatory colitis, and ulcerative colitis. In some embodiments, the affliction characterized by intestinal atrophy is an advanced age.

Aspects of the disclosure involve the use of an agent that increases the level and/or activity of PPAR-δ and/or a PPAR-δ target protein to protect against, mitigate, or alleviate, the harmful effects of exposure to ionizing radiation. In some embodiments exposure to ionizing radiation is from an ionizing radiation source selected from the group consisting of a nuclear power plant, a nuclear weapon, cosmic or space radiation.

Aspects of the disclosure involve the use of an agent that increases the level and/or activity of PPAR-δ and/or a PPAR-δ target protein, in combination with radiotherapy to protect against the harmful effects of ionizing radiation. Certain aspects of the disclosure involve the administration of the agent prior to exposure to ionizing radiation. Certain aspects of the disclosure involve the concomitant administration of the agent during the exposure to ionizing radiation.

Aspects of the disclosure involve the use of an agent that increases the level and/or activity of PPAR-δ and/or a PPAR-δ target protein, in combination with chemotherapy to protect against gastrointestinal drug toxicity. Certain aspects of the disclosure involve the administration of the agent prior to administration of the chemotherapy. Certain aspects of the disclosure involve the concomitant administration of the agent during the administration of the chemotherapy.

Aspects of the disclosure involve the use of an agent that increases the level and/or activity of PPAR-δ and/or a PPAR-δ target protein, in combination with total parenteral nutrition to protect against intestinal atrophy. Certain aspects of the disclosure involve the administration of the agent prior to administration of total parenteral nutrition. Certain aspects of the disclosure involve the concomitant administration of the agent during the administration of total parenteral nutrition.

In some embodiments the agent comprises a high fat diet mimetic. In some embodiments the agent comprises a PPAR-δ agonist. In some embodiments the PPAR-δ agonist comprises GW501516 or an analog or derivative thereof. In some embodiments the agent comprises a PPAR-δ target protein agonist selected from the group consisting of a CPT1A agonist, a HMGCS2 agonist, and a FABP1 agonist.

In some aspects the disclosure provides a method for expanding a population of intestinal stem cells and/or non-stem intestinal progenitor cells comprising contacting a population of intestinal stem cells and/or non-stem intestinal progenitor cells with an effective amount of an agent that increases the level and/or activity of PPAR-δ or a PPAR-δ target protein. In some embodiments the intestinal stem cells comprise LGR5+ stem cells. In some embodiments the agent comprises a high fat diet mimetic. In some embodiments the agent comprises a PPAR-δ agonist. In some embodiments the PPAR-δ agonist comprises GW501516 or an analog or derivative thereof. In some embodiments the agent comprises or a PPAR-δ target protein agonist selected from the group consisting of a CPT1A agonist, a HMGCS2 agonist, and a FABP1 agonist. In some embodiments Paneth cells are not present in the population of intestinal stem cells and/or non-stem intestinal progenitor cells. In some embodiments the method is performed ex vivo. In some embodiments the method is performed in vivo in a subject. In some embodiments the method includes placing the subject on a high fat diet. In some embodiments the diet comprises a calorie restricted diet.

In some aspects the disclosure provides a method of endowing at least one non-stem intestinal progenitor cell with at least one attribute of intestinal stem cells, the method comprising contacting a population of mammalian intestinal cells comprising at least one non-stem progenitor cell with an effective amount of an agent that increases the level and/or activity of PPAR-δ or a PPAR-δ target protein, thereby endowing at least one non-stem intestinal progenitor cell with the at least one attribute of intestinal stem cells. In some embodiments the at least one attribute comprises the ability to form organoid mini-intestines in culture in the absence of the Paneth cell niche. In some embodiments the intestinal stem cells comprise LGR5+ stem cells. In some embodiments the agent comprises a high fat diet mimetic. In some embodiments the agent comprises a PPAR-δ agonist. In some embodiments the PPAR-δ agonist comprises GW501516 or an analog or derivative thereof. In some embodiments the agent comprises or a PPAR-δ target protein agonist selected from the group consisting of a CPT1A agonist, a HMGCS2 agonist, and a FABP1 agonist.

In some aspects the disclosure provides a method of obtaining mammalian intestinal stem cells and/or non-stem intestinal progenitor cells with an enhanced ability to form organoid bodies in culture in the absence of the Paneth cells, the method comprising: (a) administering a high fat diet or a high fat diet mimetic to a mammal, wherein the high fat diet or high fat diet mimetic enhances the ability of intestinal stem cells and/or non-stem intestinal progenitor cells in the mammal to form organoid bodies in culture; and (b) isolating intestinal stem cells and/or non-stem intestinal progenitor cells from the mammal, thereby obtaining mammalian intestinal stem cells and/or non-stem intestinal progenitor cells with the enhanced ability to form organoid bodies in culture. In some embodiments the method includes assessing the ability of the intestinal stem cells and/or non-stem intestinal progenitor cells to form organoid bodies in culture in the absence of Paneth cells. In some embodiments assessing is performed by comparing the ability of the intestinal stem cells and/or non-stem intestinal progenitor cells obtained from the mammal in step (b) to form organoid bodies in culture in the absence of Paneth cells to the ability of intestinal stem cells and/or non-stem intestinal progenitor cells obtained from control mammals which were not administered a high fat diet of high fat diet mimetic to form organoid bodies in culture in the absence of Paneth cells. In some embodiments the method includes a step (c) forming organoid bodies in culture in the absence of Paneth cells. In some embodiments the high fat diet or the high fat diet mimetic increases the level and/or activity of PPAR-δ or a PPAR-δ target protein in the mammal's intestinal stem cells and/or non-stem intestinal progenitor cells. In some embodiments the high fat diet mimetic comprises a PPAR-δ agonist. In some embodiments the high fat diet mimetic comprises a PPAR-δ target protein agonist selected from the group consisting of a CPT1A agonist, a HMGCS2 agonist, and a FABP1 agonist. In some embodiments the mammal comprises a mouse.

Aspects of the disclosure involve the use of PPAR-δ and/or a PPAR-δ target gene as a prognostic biomarker to detect obese individuals at risk for colorectal cancer.

In some aspects the disclosure provides a method of identifying an obese individual at risk of developing colorectal carcinoma, the method comprising: (a) determining the level of expression of PPAR-δ or a PPAR-δ target gene in a biological sample obtained from an obese individual; and (b) identifying an obese individual as being at risk of developing colorectal carcinoma if the level of expression of PPAR-δ or the PPAR-δ target gene in the biological sample is elevated as compared to the level of expression of PPAR-δ or the PPAR-δ target gene in control individuals without colorectal carcinoma. In some embodiments the biological sample comprises a colon biopsy specimen. In some embodiments the biological sample comprises an epithelial cell. In some embodiments the biological sample comprises an intestinal stem cell. In some embodiments the biological sample comprises a non-stem intestinal progenitor cell. In some embodiments the biological sample comprises a Paneth cell. In some embodiments the biological sample comprises a goblet cell. In some embodiments the biological sample is obtained by performing a colonoscopic biopsy. In some embodiments (a) determining the level of expression of PPAR-δ or the PPAR-δ target gene comprises determining the mRNA level of expression of PPAR-δ or the PPAR-δ target gene. In some embodiments (a) determining the level of expression of PPAR-δ or the PPAR-δ target gene is accomplished by performing a hybridization-based assay, a polymerase chain reaction-based assay, or sequencing. In some embodiments (a) determining the level of expression of PPAR-δ or the PPAR-δ target gene comprises determining the protein level of expression of PPAR-δ or the PPAR-δ target gene. In some embodiments (a) determining the level of expression of PPAR-δ or the PPAR-δ target gene is accomplished by ELISA, Western blot, mass spectrometry, or immunohistochemistry.

In certain aspects, disclosed here are methods of reducing loss of intestinal stem cells and/or non-stem intestinal progenitor cells in a subject at risk thereof, the method comprising administering to the subject an effective amount of a composition that increases the level and/or activity of PPAR-δ or a PPAR-δ target protein, thereby intestinal stem cells and/or non-stem intestinal progenitor cells loss. In certain aspects, aged subjects (e.g., human subjects that are at least about 40 years old, 45 years old, 50 years old, 55 years old, 60 years old, 65 years old, 70 years old, 75 years old, 80 years old, 85 years old, 90 years old or older) are at risk of losing or, in certain aspects, at risk of suffering from declining quantities, production and/or function of intestinal stem cells and/or non-stem intestinal progenitor cells. In some embodiments the method includes determining that the subject is in need of treatment for an affliction characterized by intestinal atrophy. In some embodiments, the affliction characterized by intestinal atrophy is an advanced age. In some embodiments the composition comprises a high fat diet mimetic. In some embodiments the composition comprises a PPAR-δ agonist and a pharmaceutically acceptable carrier, diluent, or excipient. In some embodiments the PPAR-δ agonist comprises GW501516 or an analog or derivative thereof. In some embodiments the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In certain aspects the disclosure provides a composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments the method includes placing the subject on a high fat diet. In some embodiments the high fat diet comprises a calorie restricted diet.

In certain aspects the methods and uses disclosed herein further comprise a step of determining, for example, that a subject (e.g., an aged subject) has or is at risk of developing compromised gut regeneration (e.g., as evidenced by a loss of intestinal stem cells and/or non-stem intestinal progenitor cells). Accordingly, in certain embodiments, the methods and uses disclosed herein further comprise a step of determining that the subject is in need of enhanced intestinal function. In some aspects, such a determination may be made by assessing expression of PPAR-δ in one or more tissues or biological samples obtained from the subject. In certain aspects, such a determination may be made by assessing expression of one or more of CPT1A, HMGCS2 and FABP1 in one or more tissues or biological samples obtained from the subject.

In some embodiments, the methods and uses disclosed herein further comprise a step of determining that a subject (e.g., an aged or elderly subject) has or is at risk of developing loss of intestinal stem cells and/or non-stem intestinal progenitor cells. In some aspects, such a determination may comprise assessing expression of PPAR-δ in one or more tissues or biological samples obtained from the subject. In some aspects, such a determination may comprise determining that the subject has loss of intestinal stem cells and/or non-stem intestinal progenitor cells by assessing expression of one or more of CPT1A, HMGCS2 and FABP1 in one or more tissues or biological samples obtained from the subject.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998

(12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at hlttp://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

FIG. 1A demonstrates that High fat diet (HFD) fed Lgr5-GFP-IRES-CreERT2 mice show a selective increase in the number of GFP$^{hi}$ intestinal stem cells (ISCs) as enumerated by flow cytometry. In contrast, high fat does not modulate the numbers of GFP$^{low}$ intestinal progenitor cells. FIG. 1B demonstrates that HFD-derived GFP$^{hi}$ ISCs, in contrast to those isolated from control fed mice, posses the capacity to initiate organoid bodies without co-culture of niche Paneth cells. The co-culture of ISCs with Paneth cells enables control ISCs to form organoid bodies and further enhances the capacity of HFD-derived stem cells to give rise to organoid bodies. (values are mean; error bars indicate standard deviation; **P<0.01.)

FIG. 2A demonstrates that Lgr5-GFP-IRES-CreERT2 mice administered GW501516 at 4 mg/kg for 2-4 weeks show a selective increase in the number of GFP$^{hi}$ intestinal stem cells (ISCs) but not in progenitor cells as enumerated by flow cytometry. FIG. 2B demonstrates that GW501516-derived GFP$^{hi}$ ISCs, in contrast to those isolated from vehicle-treated mice, demonstrate the capacity to initiate organoid bodies without co-culture of niche Paneth cells. FIG. 2C demonstrates that HFD and GW501516-derived GFP$^{low}$ progenitor cells possess the potential to autonomously form organoid bodies in vitro. (values are mean; error bars indicate standard deviation; *P<0.05; **P<0.01.)

FIG. 3A shows that Olfm4+ ISCs were increased in HFD fed mice, whereas FIG. 3B illustrates that the number of cryptdin 4+ Paneth cells were decreased (in situ hybridization, proximal jejunum, n=3 and 4, respectively). Control was ad libitum fed on normal chow. FIG. 3C illustrates that ISCs (or crypt base columnar cells adjacent to Paneth cells) and progenitor cells (or transit-amplifying cells) showed increased BrdU incorporation after a 4 h pulse in HFD treated mice (n=6). FIG. 3D illustrates that HFD-derived crypts were twofold more capable of forming organoids. Representative control and HFD-derived organoids are shown at day 7 (white arrow marks organoids and white asterisk indicates aborted crypts, n=4). FIG. 3E shows that Day 14 HFD-derived organoids possessed less crypt domains than compared to control counterparts (n=7). FIG. 3F shows that dissociated HFD-derived organoids gave rise to two-fold more secondary organoids (n=7). FIG. 3G illustrates that HFD increased the number of surviving crypts after ionizing irradiation-induced (XRT) damage. Yellow arrows mark regenerated crypts and yellow asterisks illustrate aborted crypts (n=3). FIG. 3H shows that HFD increased the frequency of Lgr5-GFP$^{high}$ ISCs (dark green) by nearly twofold but had no effect on Lgr5-GFP$^{low}$ progenitors (light green) (n=10). FIG. 3I shows that HFD-derived Lgr5-GFP$^{hi}$ ISCs were able to initiate organoids efficiently without Paneth cells. Co-culture with Paneth cells boosted organoid-forming capacity for both control and HFD-derived ISCs. A representative image of primary organoids from Lgr5-GFP$^{hi}$ ISCs at day 10 is shown (n=4). (Unless otherwise indicated, in all panels: values are mean; error bars indicate s.d.; *P<0.05, **P<0.01, scale bars in FIGS. 3B and 3C=20 µm, in FIG. 3D=100 µm, in FIG. 3G=50 µm, and in FIG. 3I=200 µm).

FIG. 4A shows that exposure of naïve crypts to 30 µM palmitic acid (PA) had no effect on primary organoid formation (n=5). FIG. 4B shows that organoids exposed to 30 µM PA developed less crypt domains as enumerated after seven days in culture (n=4). FIGS. 4C and 4D demonstrate that individually dissociated primary organoids (FIG. 4C) or 1,000 sorted live cells from primary organoids (n=4) (FIG. 4D) possessed more secondary organoid-forming activity after four weeks of treatment with 30 µM PA (n=3). FIGS. 4E and 4F show that four-week PA treatment increased the frequency (FIG. 4E, n=3) and organoid forming capacity (FIG. 4F, n=3) of Lgr5-GFP$^{hi}$ ISCs. (Unless otherwise indicated, in all panels: values are mean; error bars indicate s.d.; *P<0.05, P<0.01, *P<0.001)

FIGS. 5A-5K illustrate that activated PPAR-δ in ISCs mediates the effects of HFD. FIG. 5A illustrates a heat map of differentially expressed genes in Lgr5-GFP$^{hi}$ ISCs and Lgr5-GFP$^{low}$ progenitors revealed induction of a PPAR-δ program in HFD-fed mice. FIG. 5B shows that PPAR and LXR/RXR motifs were enriched in genes that are upregulated in ISCs from HFD-fed mice. FIGS. 5C, 5D and 5E demonstrate confirmation of upregulated PPAR-δ target gene expression in flow sorted Lgr5-GFP$^{hi}$ ISCs and Lgr5-GFP$^{low}$ progenitors by qRT-PCR (FIG. 5C, all fold changes are significant, n=5, p<0.05) and at the protein level from HFD (FIG. 5D) and GW501516-treated (FIG. 5E) mice. FIGS. 5F and 5G show Olfin4+ISCs numbers per jejunal crypt were increased in GW501516-treated mice (FIG. 5F), whereas, Cryptdin 4+ Paneth cell numbers (FIG. 5G) remained unchanged (in situ hybridization, proximal jejunum, n=3 and 4, respectively). FIG. 5H show that PPAR-δ agonist GW501516 administration enhanced the proliferation of crypt base columnar cells (CBC cells) and transient-amplifying cells as assessed 4 hours after a pulse of BrdU (n=4). FIG. 5I shows that PPAR-δ agonist treatment boosted the organoid-forming capacity of intestinal crypts (n=3). FIG. 5J shows that PPAR-δ agonist administration doubled the number of Lgr5-GFP$^{hi}$ ISCs but had no effect on the Lgr5-GFP$^{low}$ progenitors (n=3). FIG. 5K shows that Lgr5-GFP$^{hi}$ ISCs derived from PPAR-δ agonist-treated mice were capable of forming organoids in the absence of Paneth cells. Representative images of primary organoids at day 12 are illustrated (n=3). (Unless otherwise indicated, in all panels:

Figures 3A, 3B, 3C:
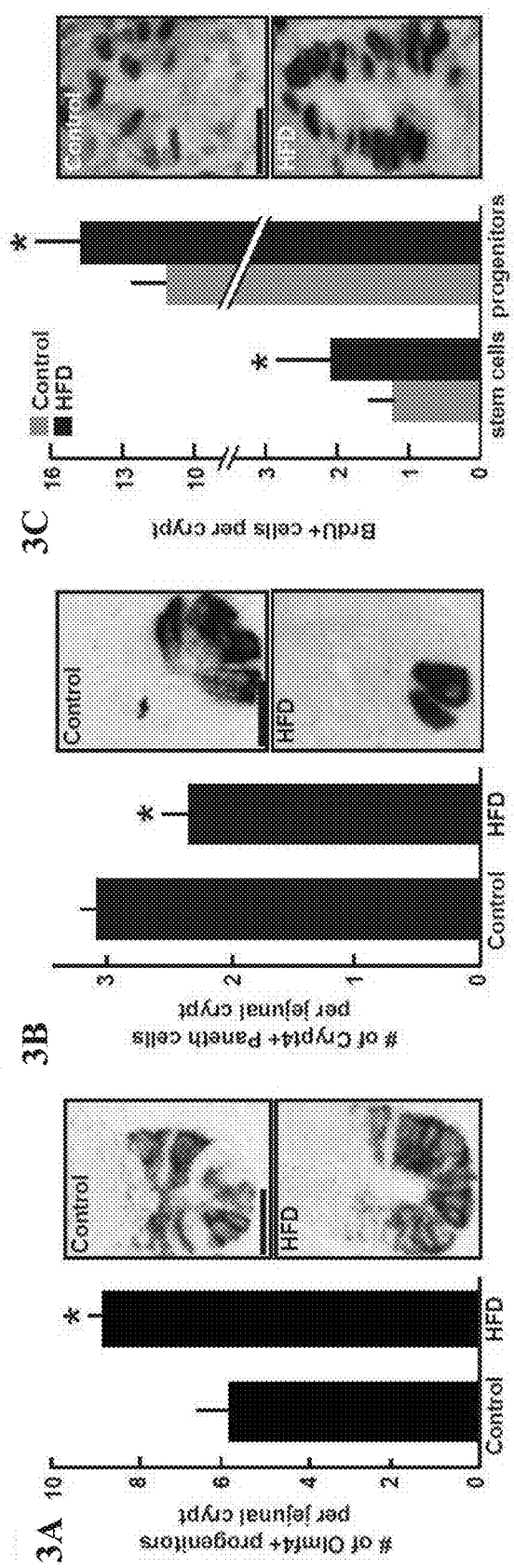
FIGS. 3A-3I demonstrate that high fat diet (HFD) augments ISC numbers and function.
Figures 3D, 3E, 3F:
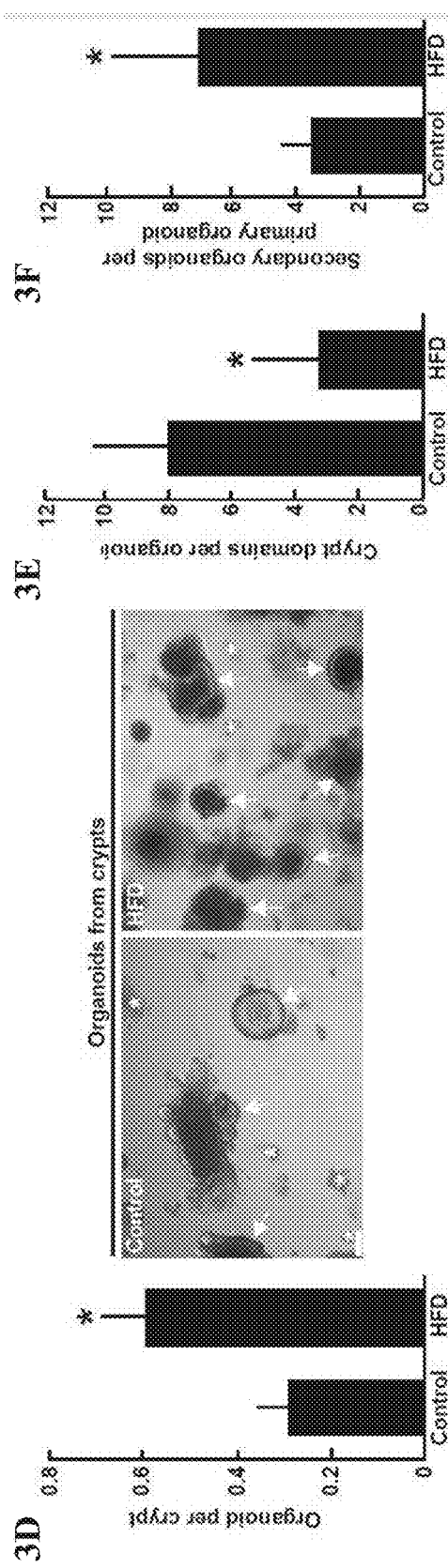
Figures 3G, 3H:
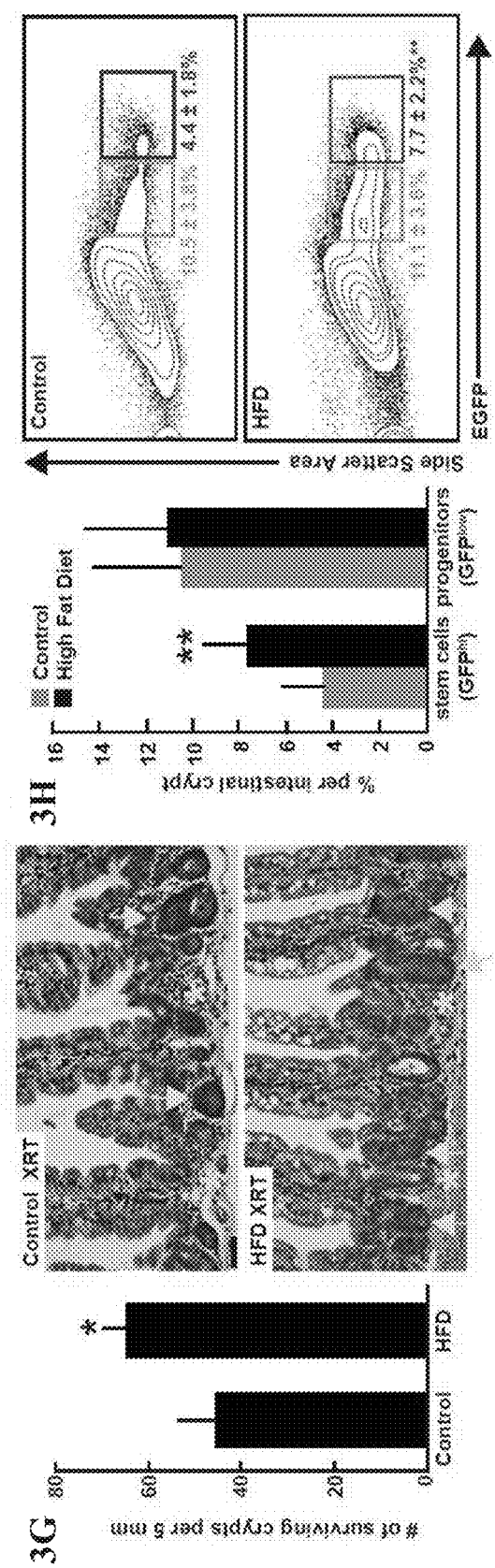

values are mean; error bars indicate s.d.; *P<0.05, **P<0.01; scale bars in FIGS. 3f-3h=20 μm, and FIG. 3k=200 μm.)

Figures 6A, 6B, 6C:
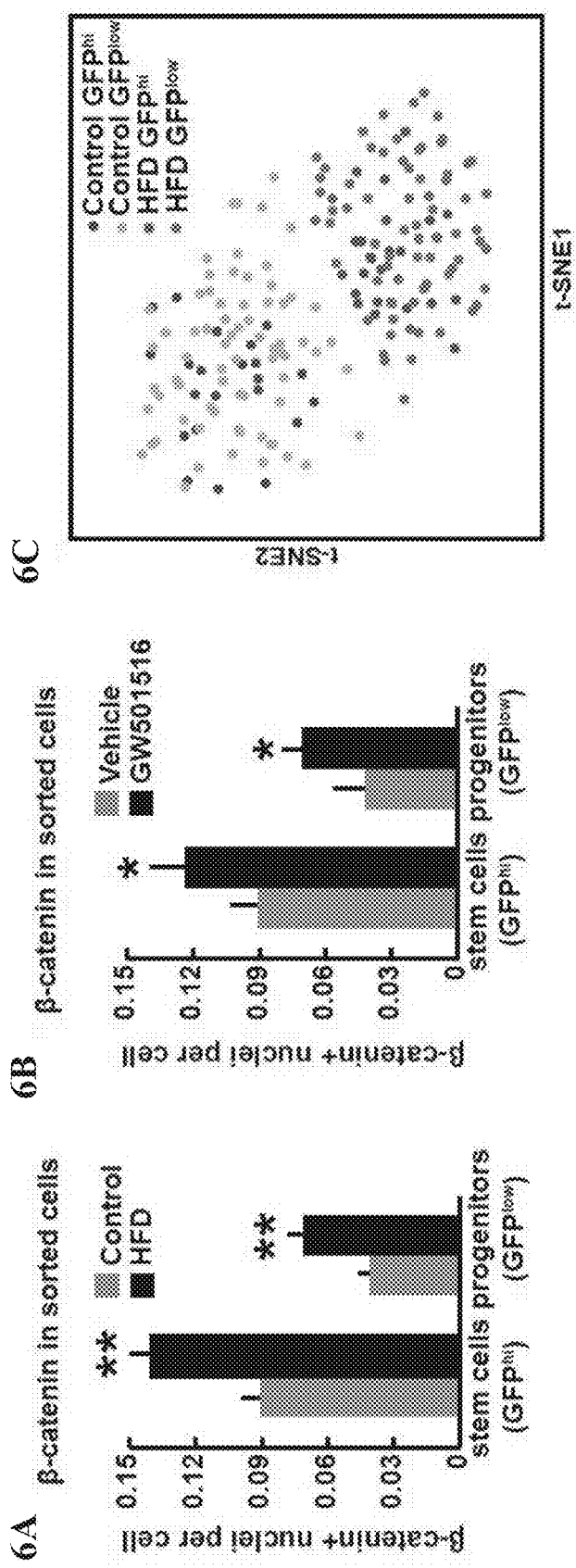
Figures 6D, 6E, 6F, 6G:
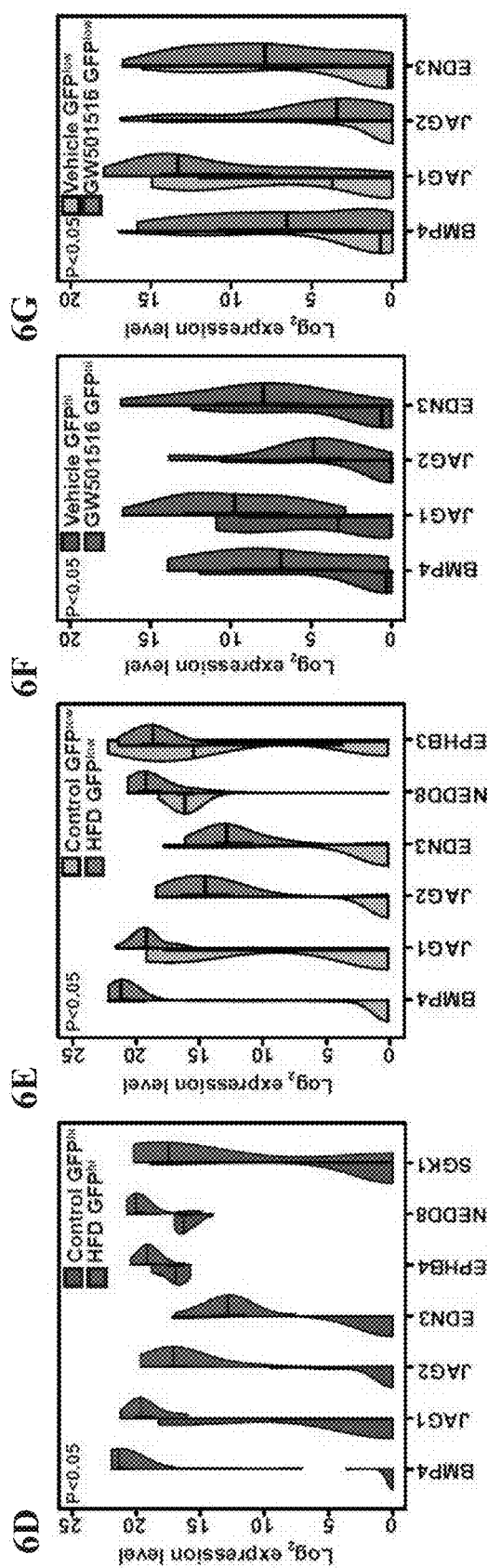

FIGS. 6A-6G illustrate that HFD and PPAR-δ signaling leads to increased β-catenin nuclear localization and target gene expression. FIGS. 6A and 6B show that increased nuclear β-catenin localization was observed by immunostaining in flow sorted Lgr5-GFP$^{hi}$ ISCs and GFP$^{low}$ progenitors isolated from HFD (FIG. 6A) and GW501516-treated (FIG. 6B) mice compared to their respective controls. FIG. 6C shows t-distributed stochastic neighbor embedding (t-SNE) plot of the single-cell gene expression data for all β-catenin target genes. Each mark represents a single cell. FIGS. 6D and 6E show violin plots demonstrated the expression levels of the most upregulated β-catenin target genes in Lgr5-GFP$^{hi}$ ISCs (FIG. 6D) and GFP$^{low}$ progenitors (FIG. 6E) after HFD treatment. FIGS. 6F and 6G confirm PPAR-δ mediated induction of the most upregulated β-catenin transcriptional targets by single cell qRT-PCR in Lgr5-GFP$^{hi}$ ISCs (FIG. 6F) and (FIG. 6G) GFP$^{low}$ progenitors from GW501516-treated mice. (Unless otherwise indicated, in all panels: values are mean; error bars indicate s.d.; *P<0.05, **P<0.01.)

Figure 7A:
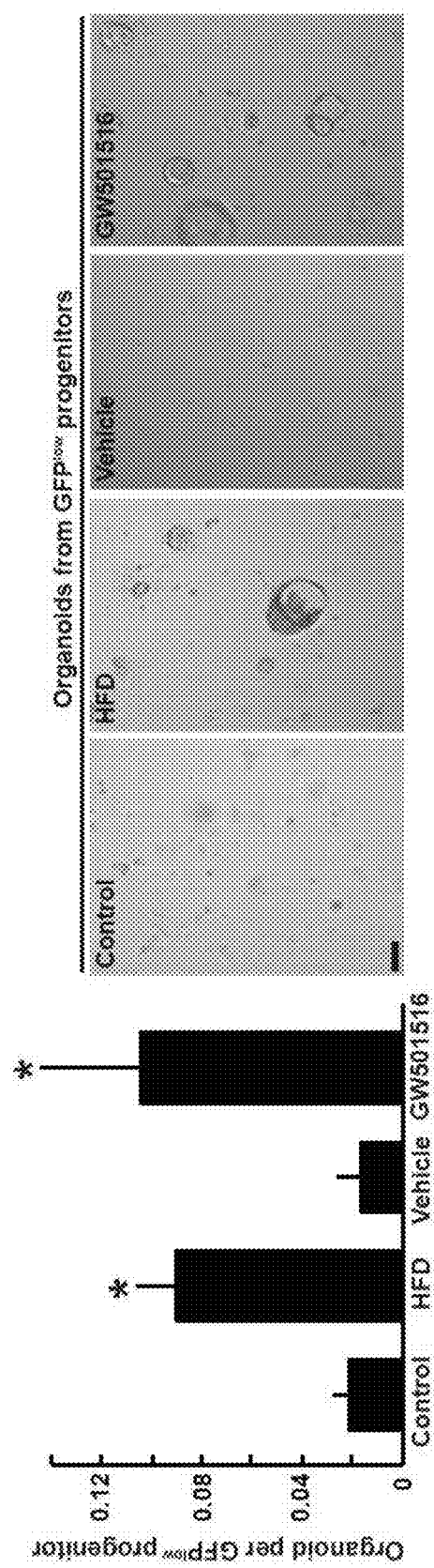
Figures 7B, 7C:
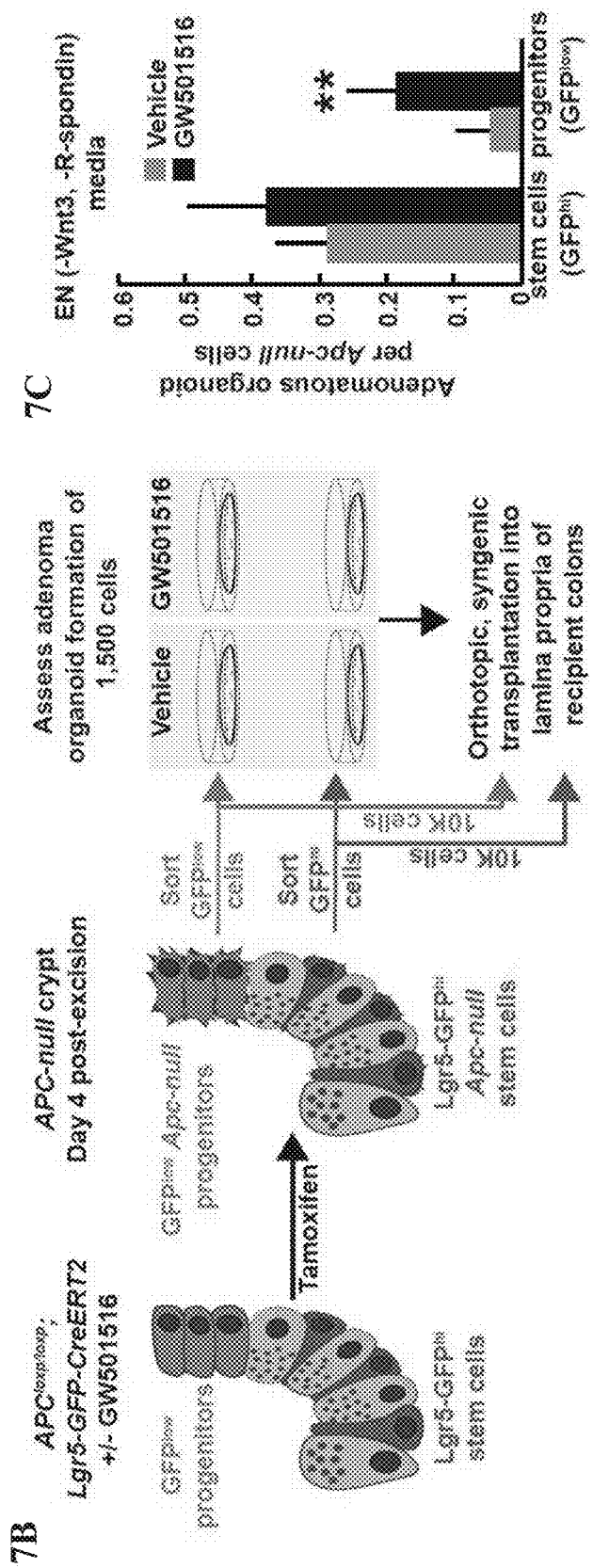
Figure 7D:
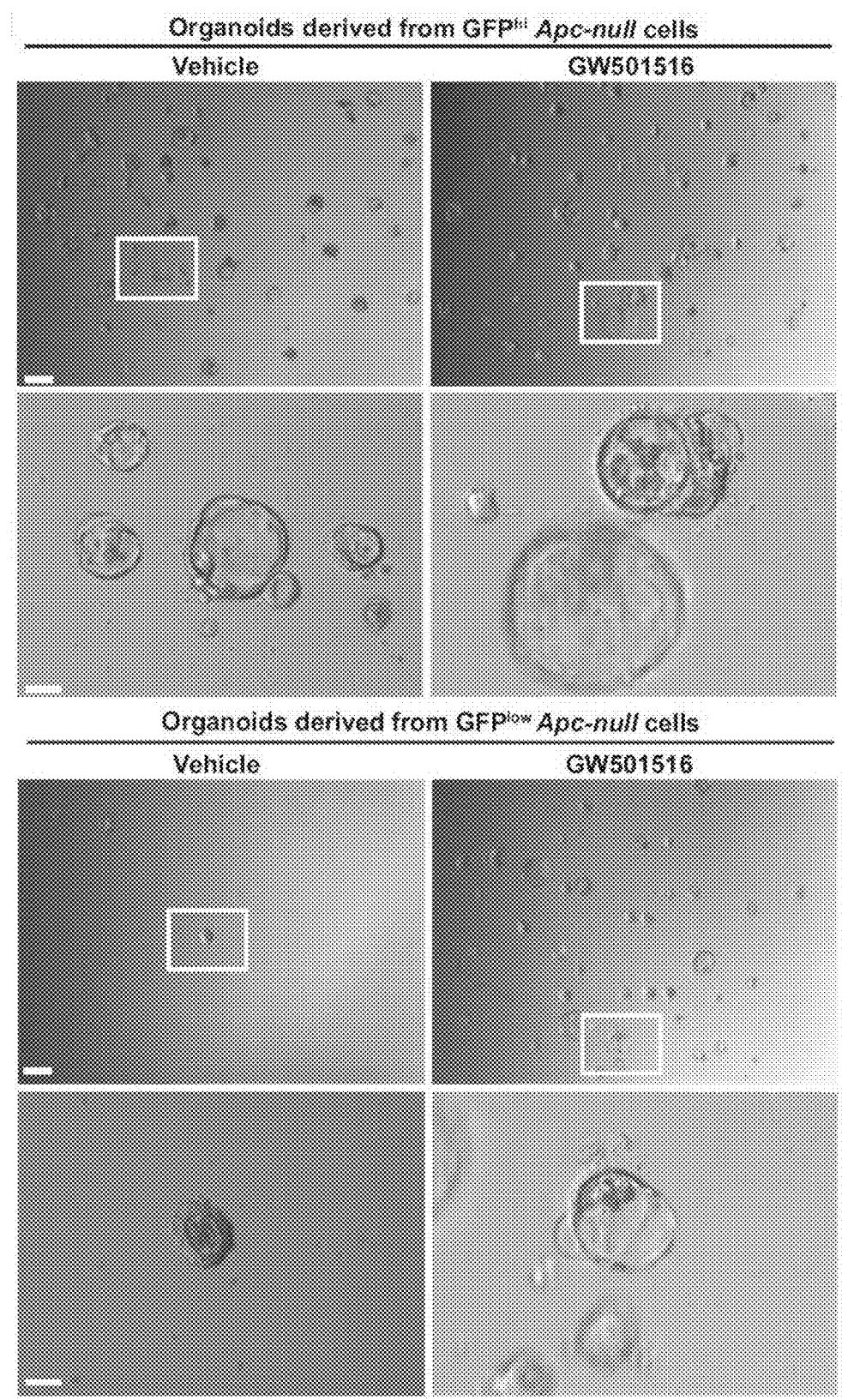
Figure 7E:
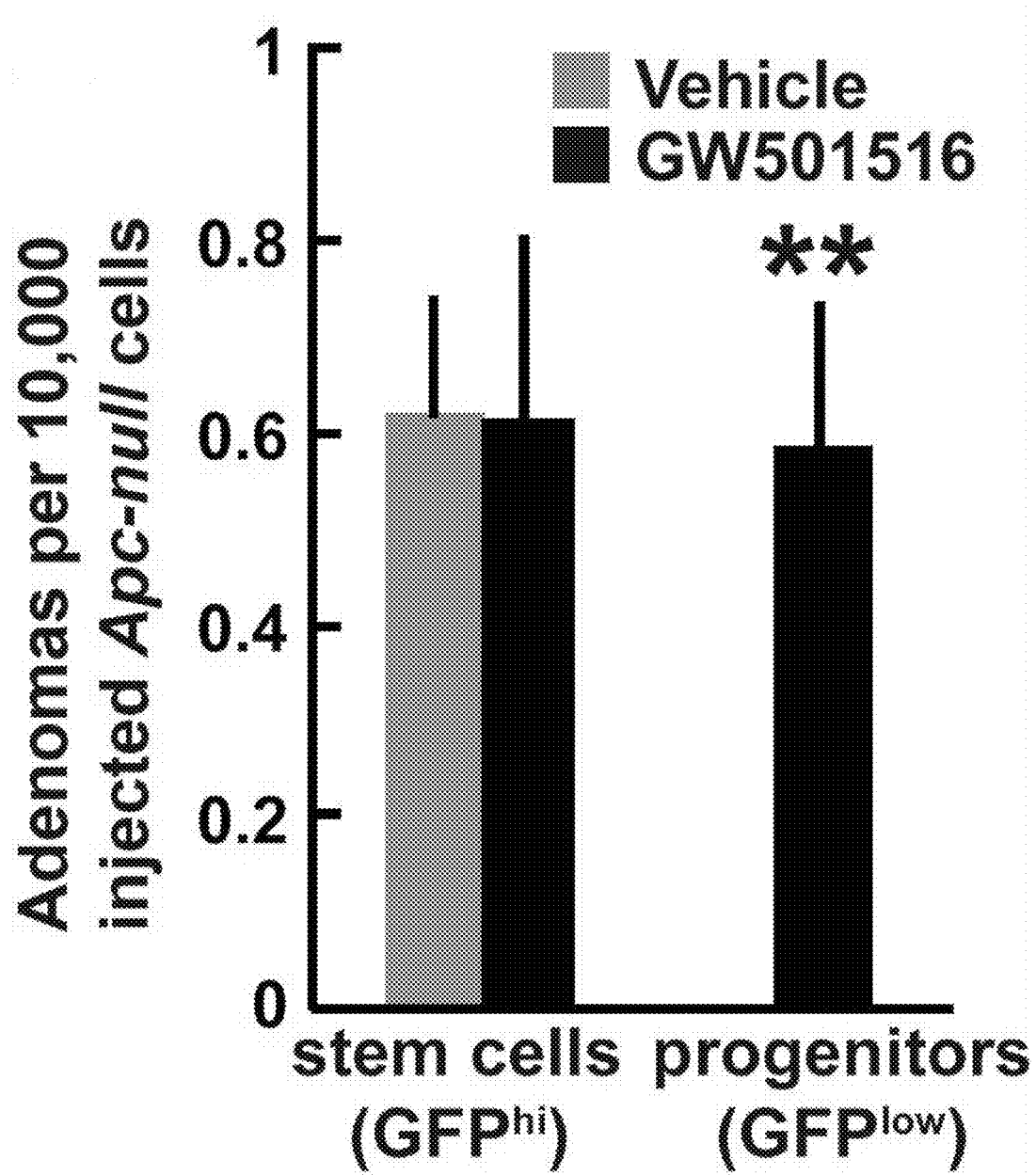
Figure 7F:
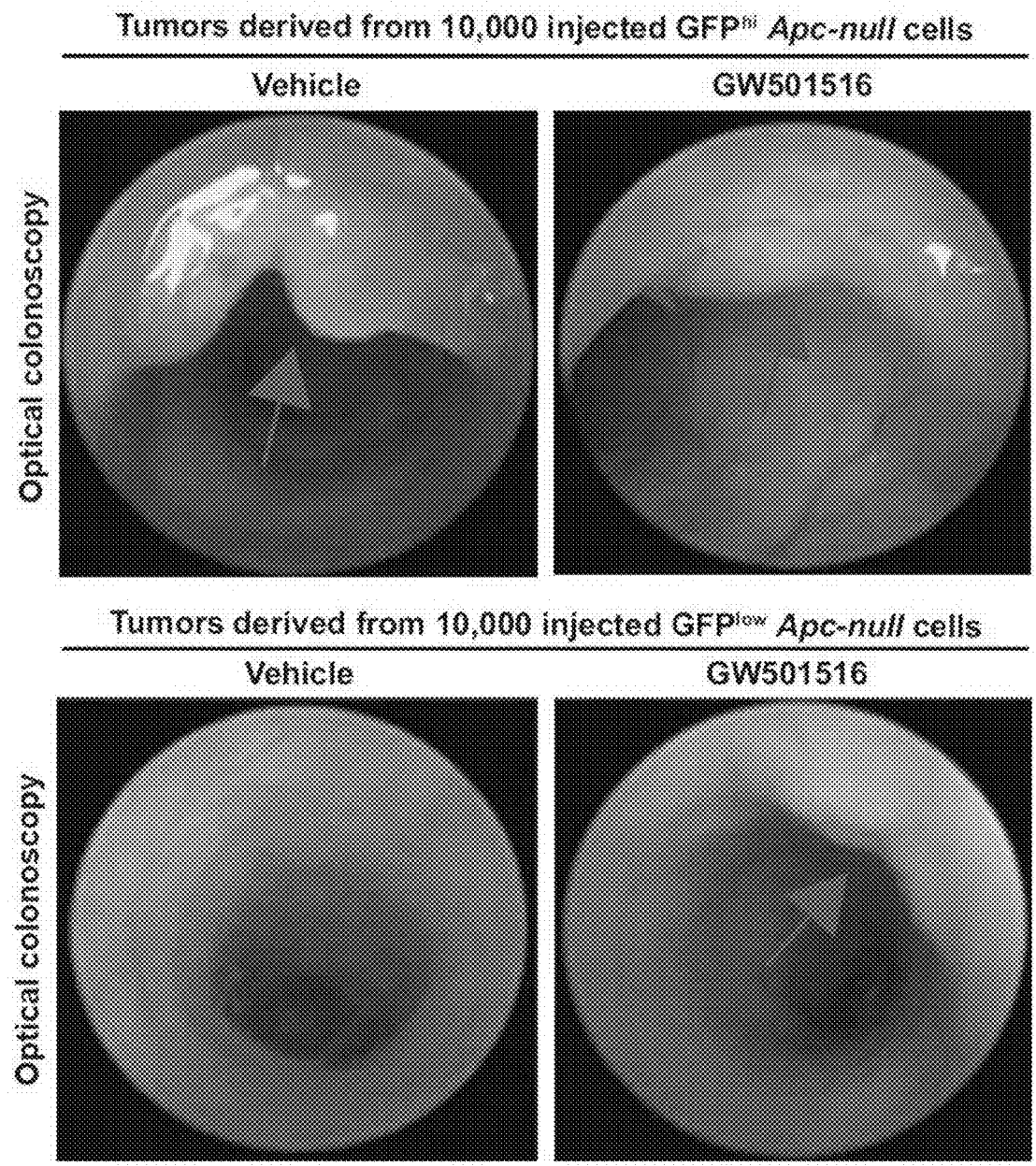
Figure 7G:
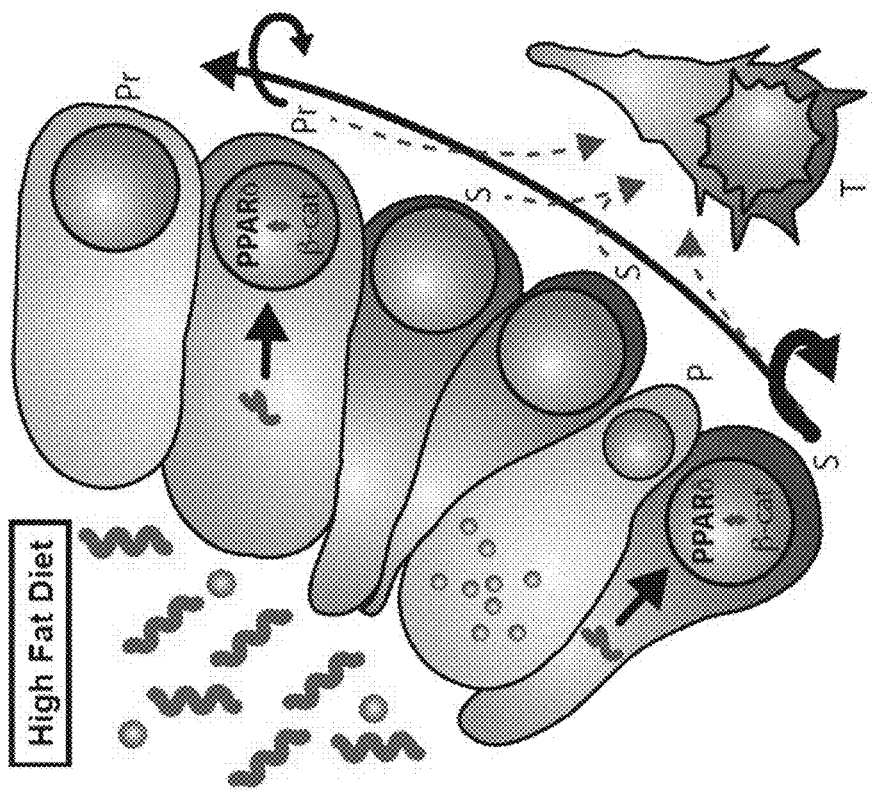
Figure 7G:
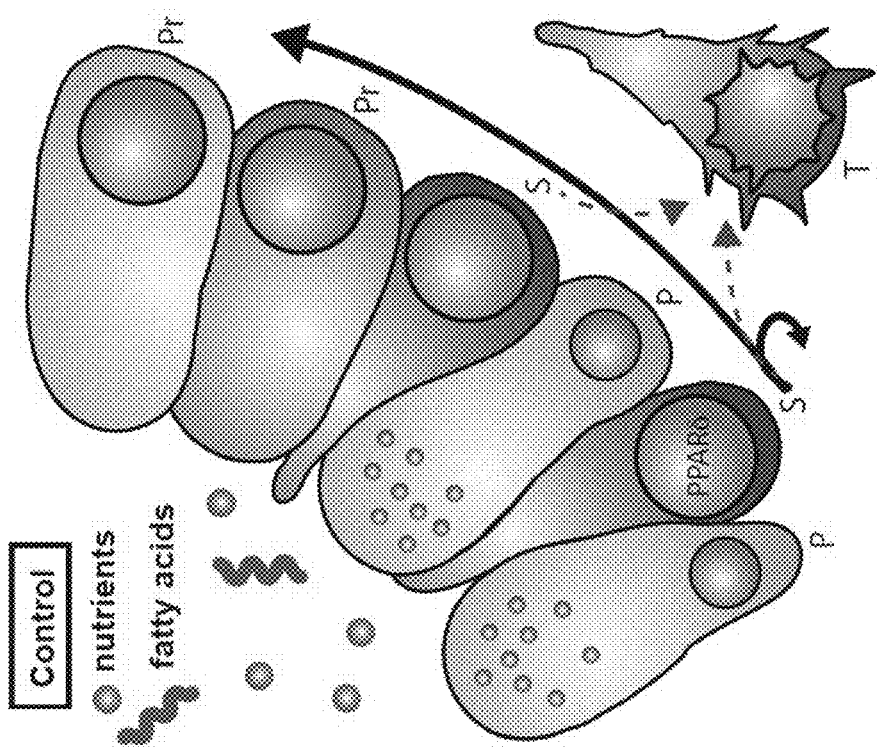
Figure 13:
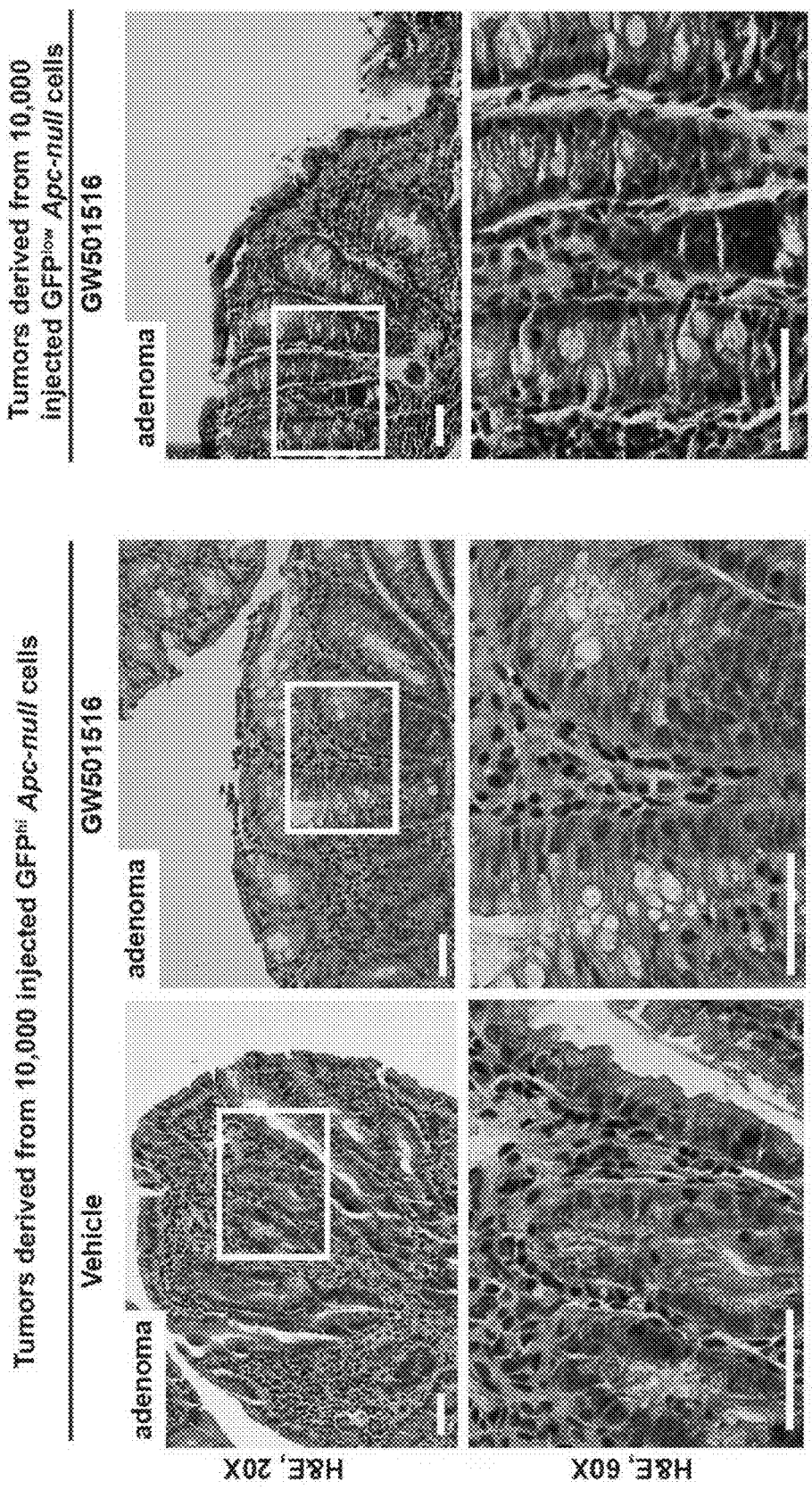

FIGS. 7A-7G show that PPAR-δ activation confers organoid and tumor-initiating capacity to non-stem-cells. FIG. 7A shows that HFD or PPAR-δ agonist treatment conferred organoid-initiating capacity to Lgr5-GFP$^{low}$ progenitors. Representative images of primary organoids at day 7 are shown (n=3). FIG. 7B depicts a schematic for assessing the in vitro and in vivo adenoma-initiating capacity of Apc-null Lgr5-GFP$^{hi}$ ISCs and Lgr5-GFP$^{low}$ progenitors from vehicle or PPAR-δ agonist GW501516-treated mice. FIG. 7C shows that PPAR-δ agonist treatment increased the in vitro adenomatous organoid forming potential of Apc-null Lgr5-GFP$^{low}$ progenitors by four-fold in EN media, which includes Noggin and EGF but lacks Wnt3 and R-spondin. Apc-null Lgr5-GFP$^{hi}$ ISC organoid-forming potential was not altered by PPAR-δ agonist treatment (n=6). FIG. 7D presents representative images of adenomatous organoids derived from Apc-null Lgr5-GFP$^{hi}$ ISCs (top) and Lgr5-GFP$^{low}$ progenitors (bottom). FIGS. 7E and 7F show orthotopic transplantation of Apc-null GFP$^{low}$ progenitors from PPAR-δ agonist-treated mice (bottom), but not from vehicle controls, initiated tumors that were visible with optical colonoscopy and verified by histology (FIG. 13). Transplanted Apc-null Lgr5-GFP$^{hi}$ ISCs from vehicle or PPAR-δ agonist-treated mice formed tumors at similar rates (FIG. 7F, n=4 separate experiments). FIG. 7G illustrates a model of intestinal adaptation to HFD. HFD has opposing effects on the numbers of stem-cells (increases) and their Paneth cell niche (decreases) per intestinal crypt. Mechanistically, HFD activates a PPAR-δ-mediated program that augments the organoid and tumor-initiating potential of ISCs and TA-cells. A feature of the PPAR-δ program includes induction of a subset of β-catenin target genes. S=stem cell, P=Paneth cell, Pr=progenitor cell, T=tumor cell, red dotted line=Apc-null cells with tumor-forming capability. (Unless otherwise indicated, in all panels: values are mean; error bars indicate s.d.; *P<0.05, **P<0.01; scale bars in FIG. 7A=50 μm, FIG. 7D(upper)=200 μm, FIG. 7D(lower)=50 μm, FIG. 7E(lower)=50 μm.)

Figures 8A, 8B, 8C:
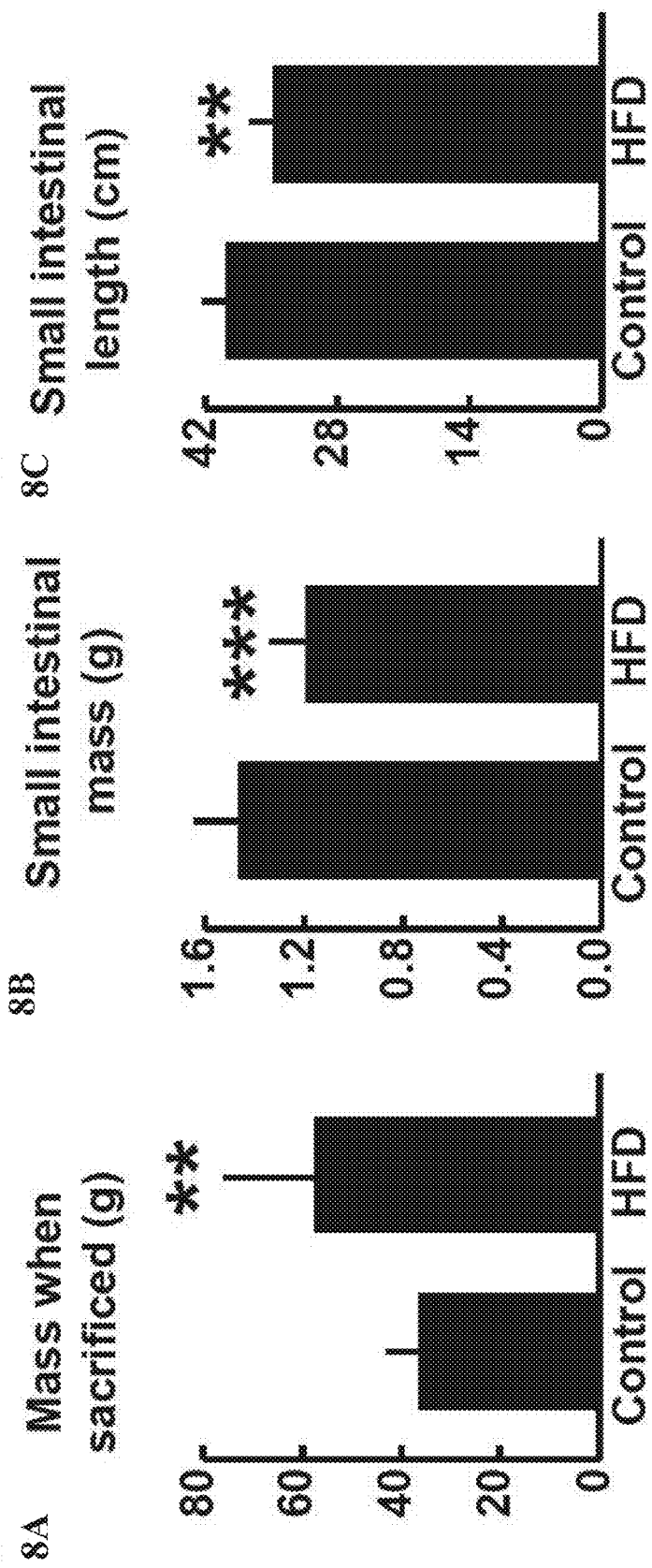
Figures 8D, 8E, 8F:
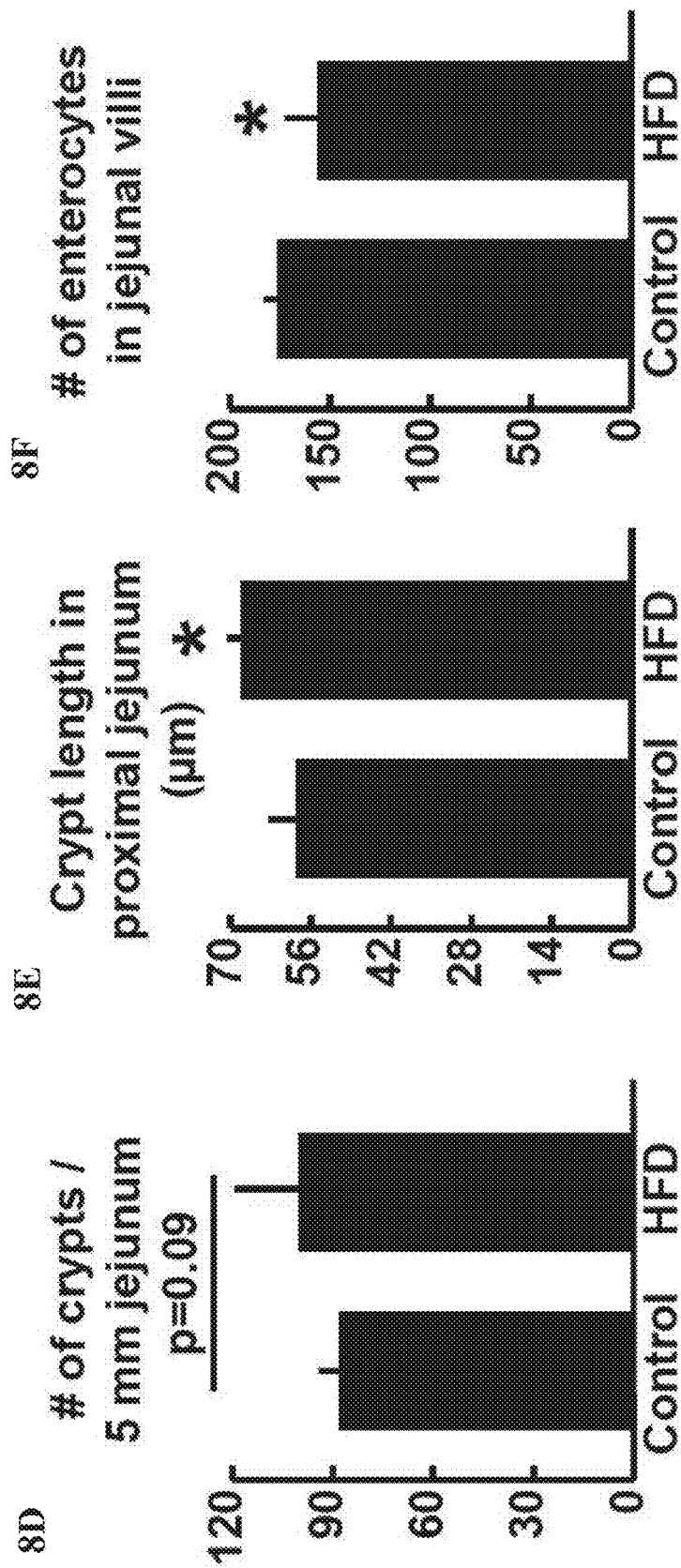
Figure 8G:
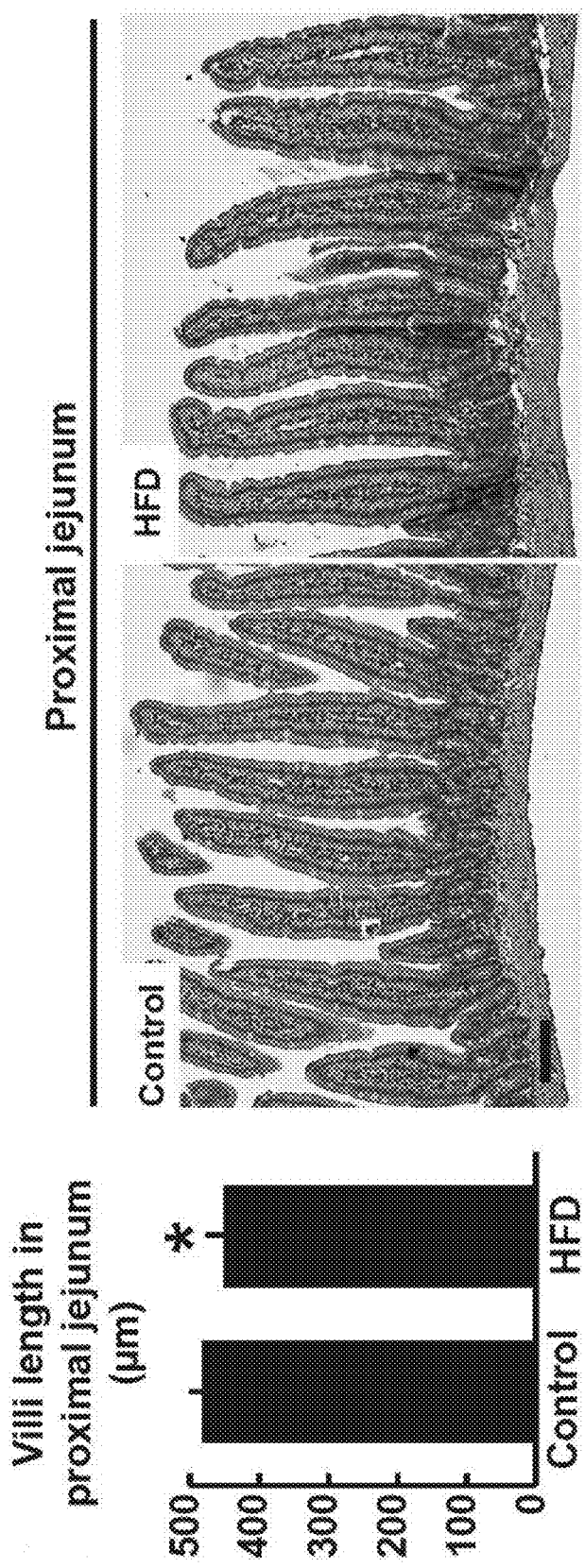
Figure 8H:
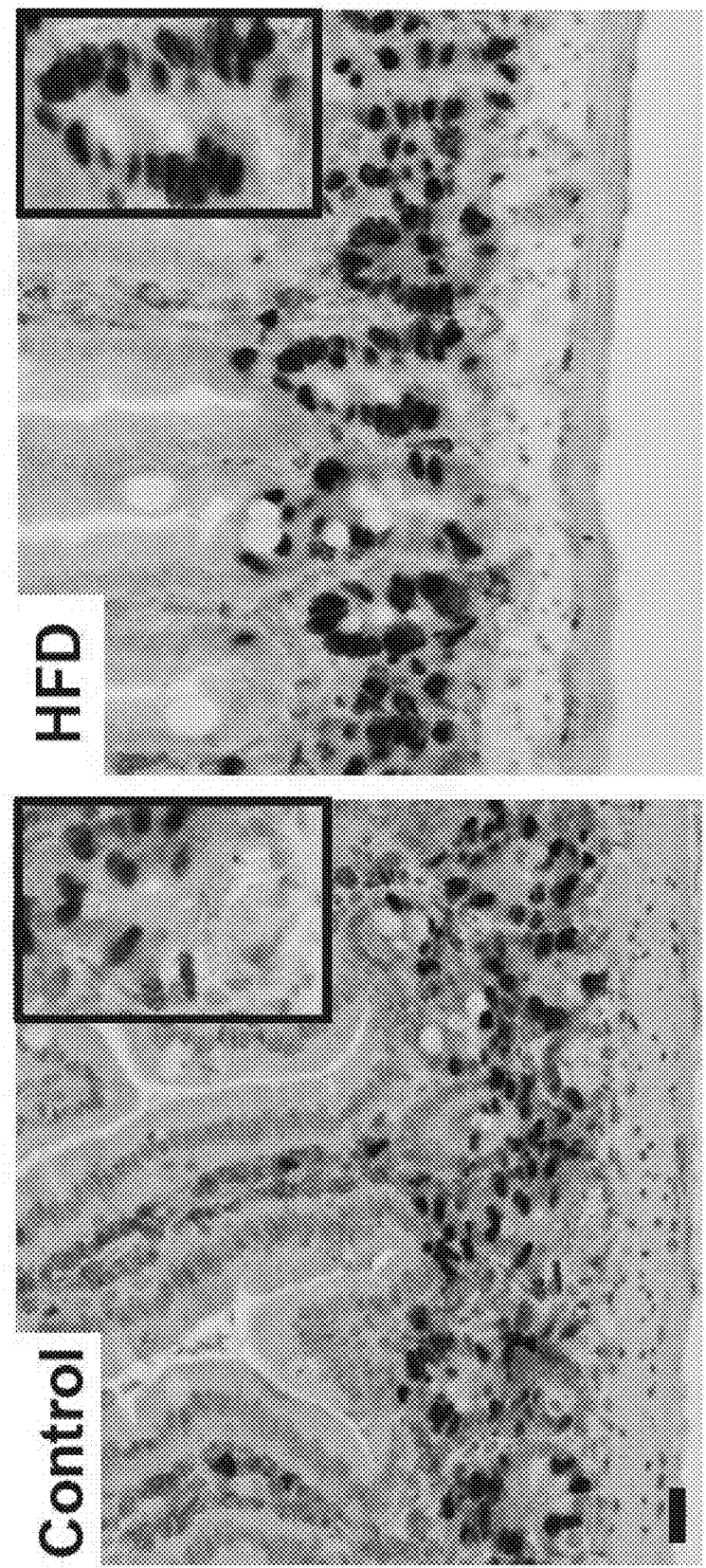
Figure 8I:
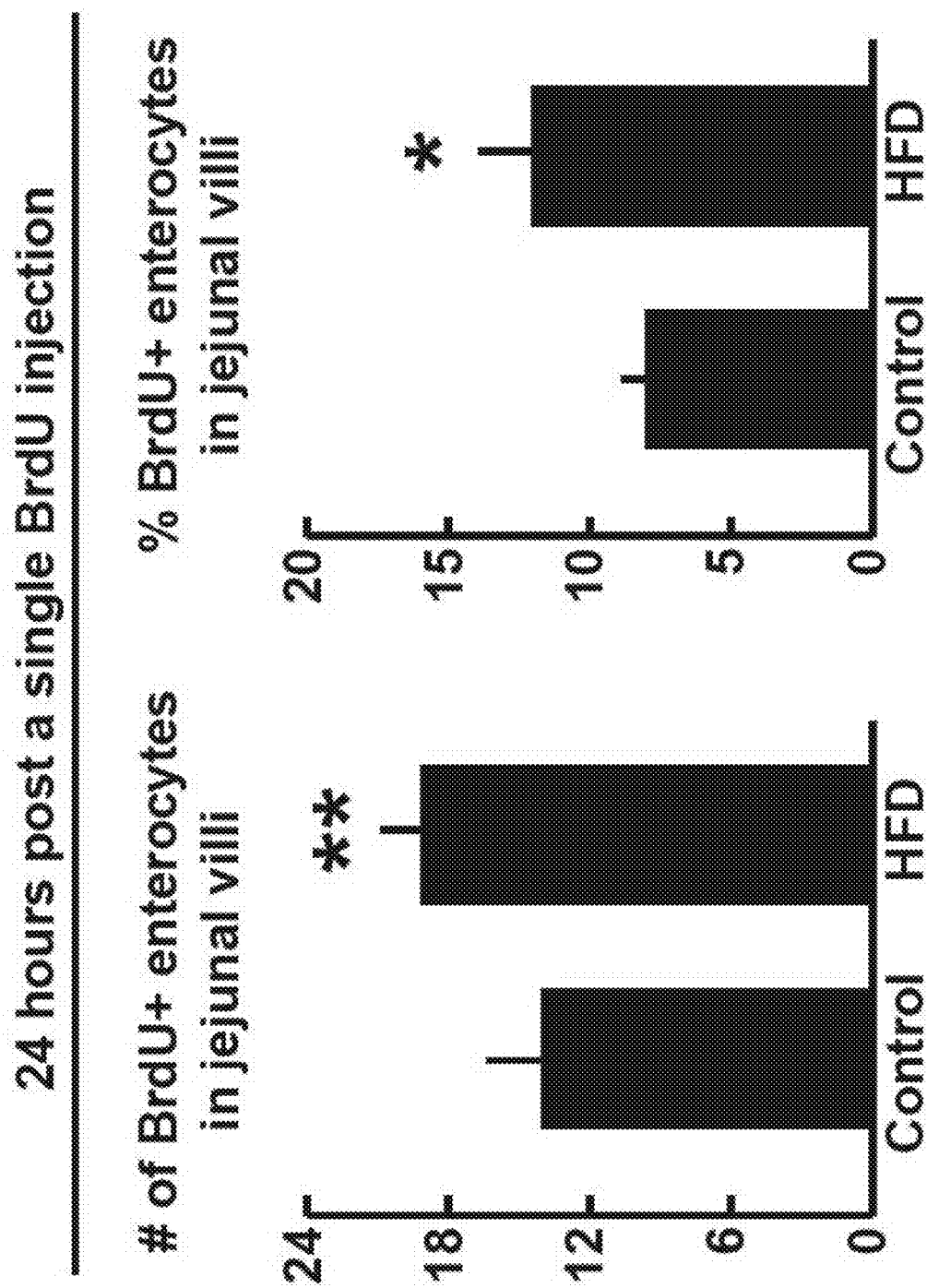
Figure 8J:
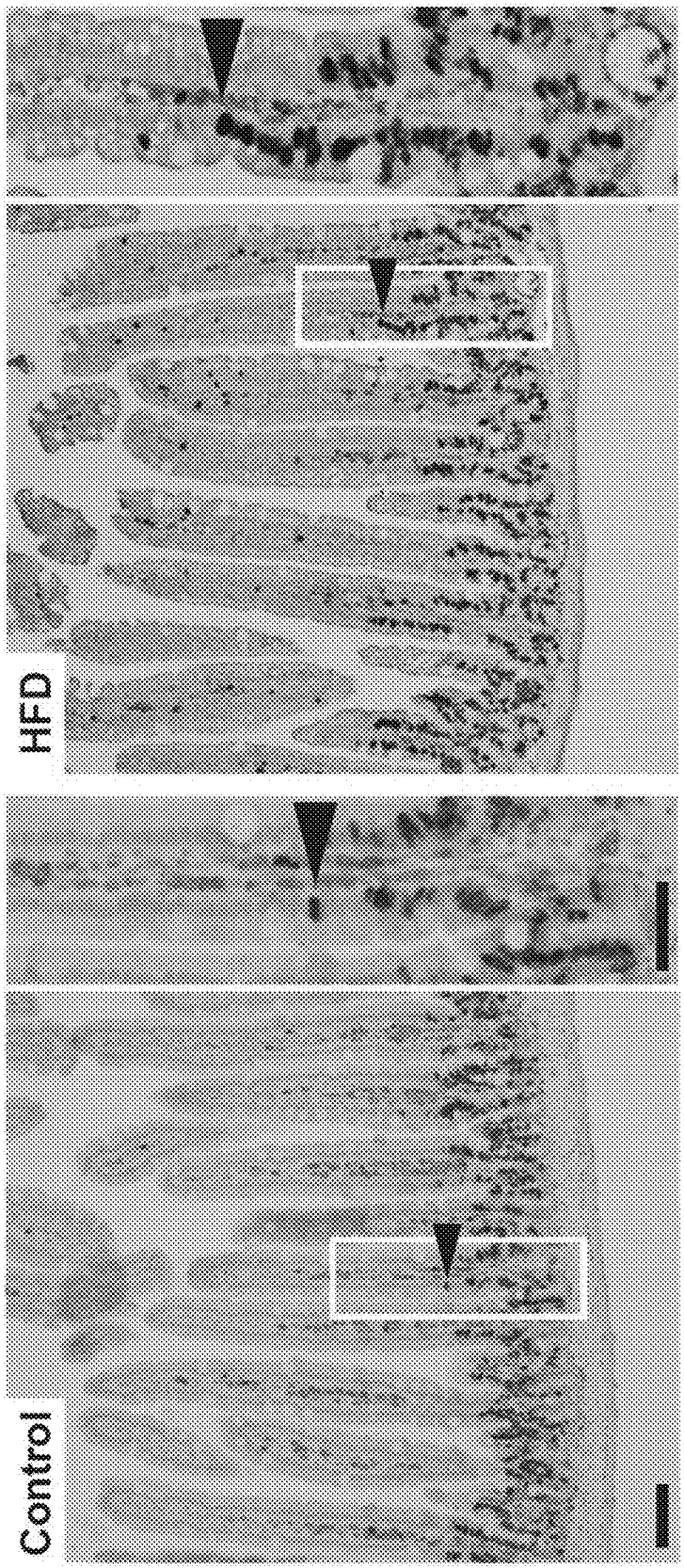
Figure 8K:
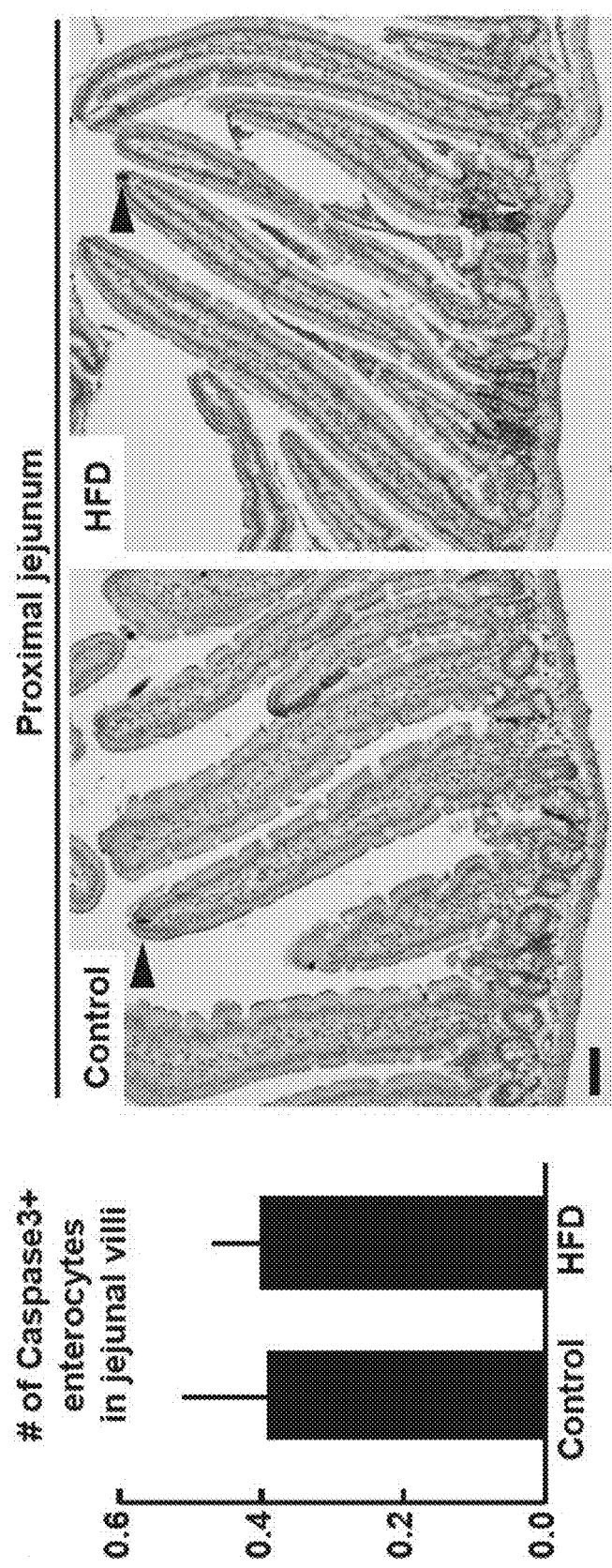

FIGS. 8A-K demonstrate that HFD enhances the proliferation of progenitors in the intestinal crypt. FIGS. 8A-G show that in comparison to mice fed normal chow, mice on a HFD gained on average 50% mass (FIG. 8A, n=11 and 15), had reduced small intestinal mass and length (FIGS. 8B and 8C, n=11 and 15), shorter crypts and villi (FIGS. 8E and 8G, n=3 each), and fewer villus enterocytes (FIG. 8F, n=3 each). HFD did not change the density of crypts (FIG. 8D, n=3 each) in the proximal jejunum. FIGS. 8H and 8I show that HFD enhanced the proliferation of ISCs (or crypt base columnar cells) and progenitor cells (or transient-amplifying cells) as assessed 4 hours (FIG. 8H, n=6) and 24 hours (FIG. 8I, n=6) after a pulse of BrdU. FIG. 8K illustrates that no significant difference in the number of jejunal caspase3$^+$ cells was detected by immunohistochemistry. Images are representative of three separate experiments (n=3); arrows highlight caspase3$^+$ enterocytes. (Unless otherwise indicated, in all panels: values are mean; error bars indicate s.d.; *P<0.05, P<0.01, *P<0.001, scale bars in FIG. 8G=100 μm, FIG. 8H=50 μm, FIG. 8J=100 μm and 50 μm (inset), FIG. 8K=100 μm.)

Figure 9A:
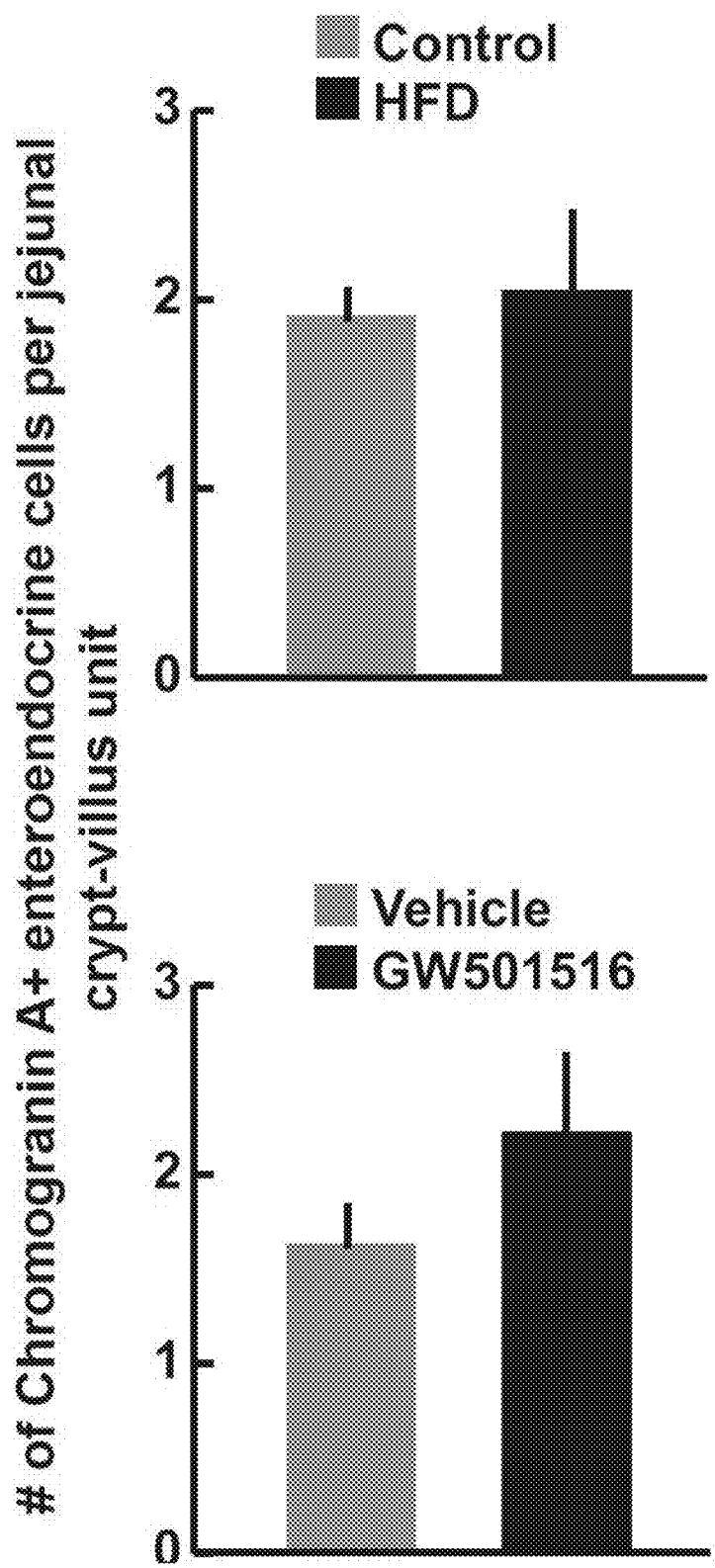
Figure 9B:
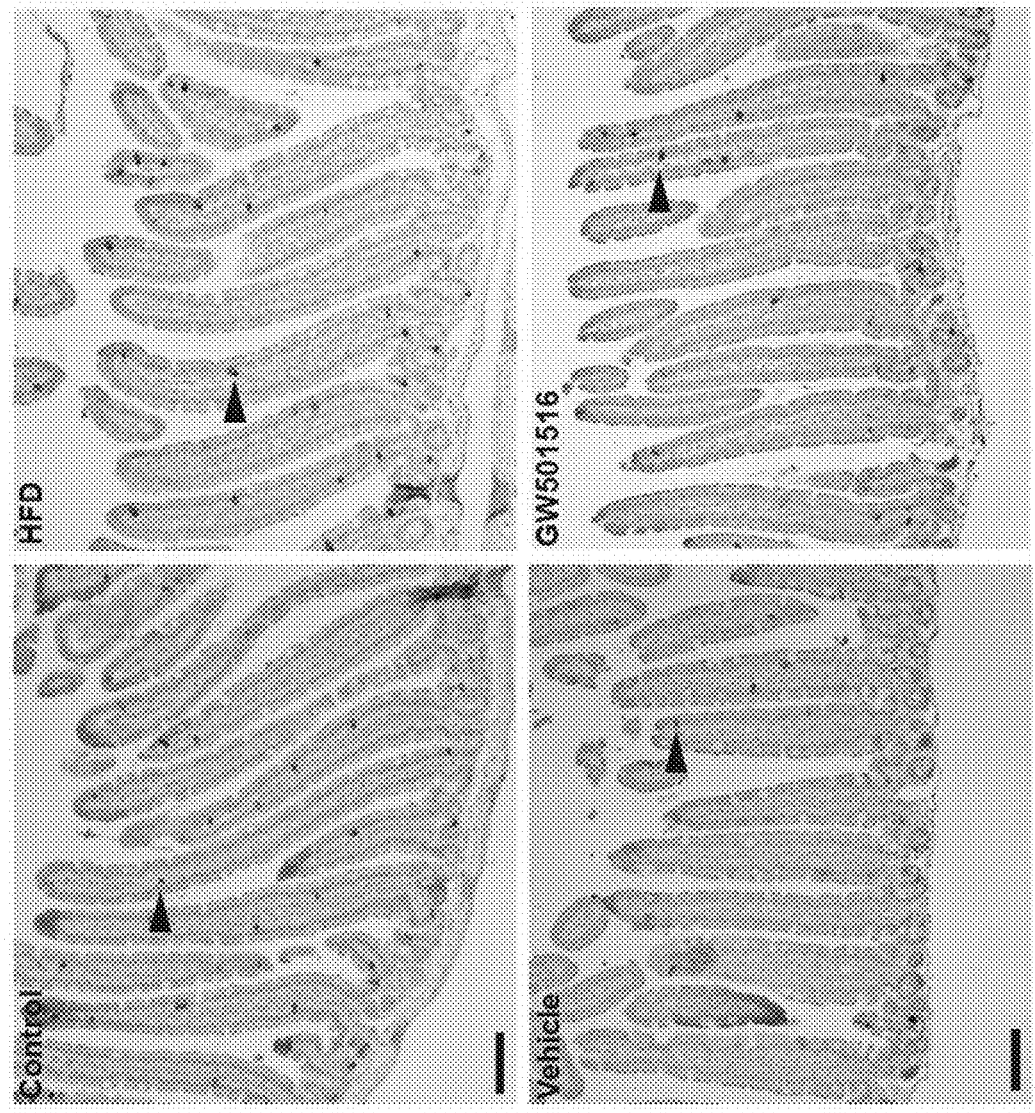
Figure 9C:
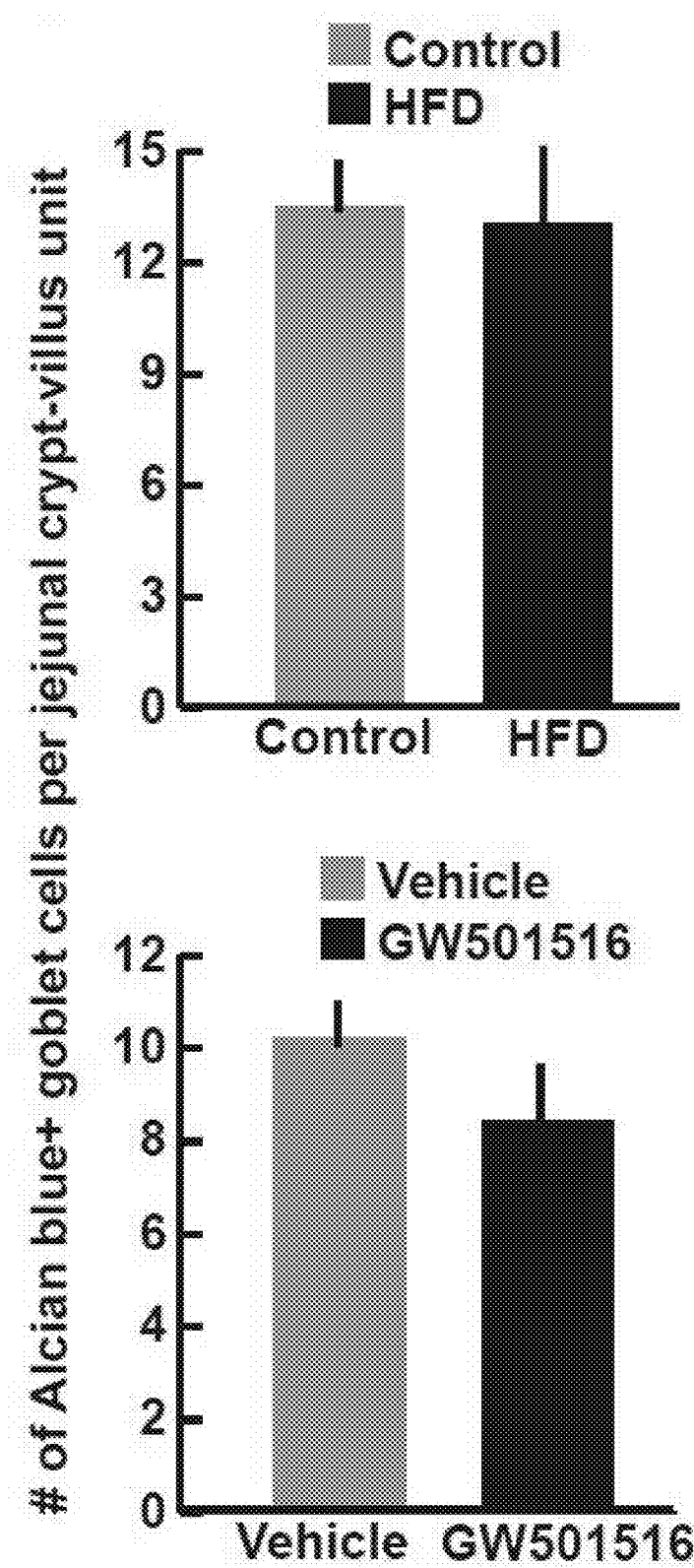
Figure 9D:
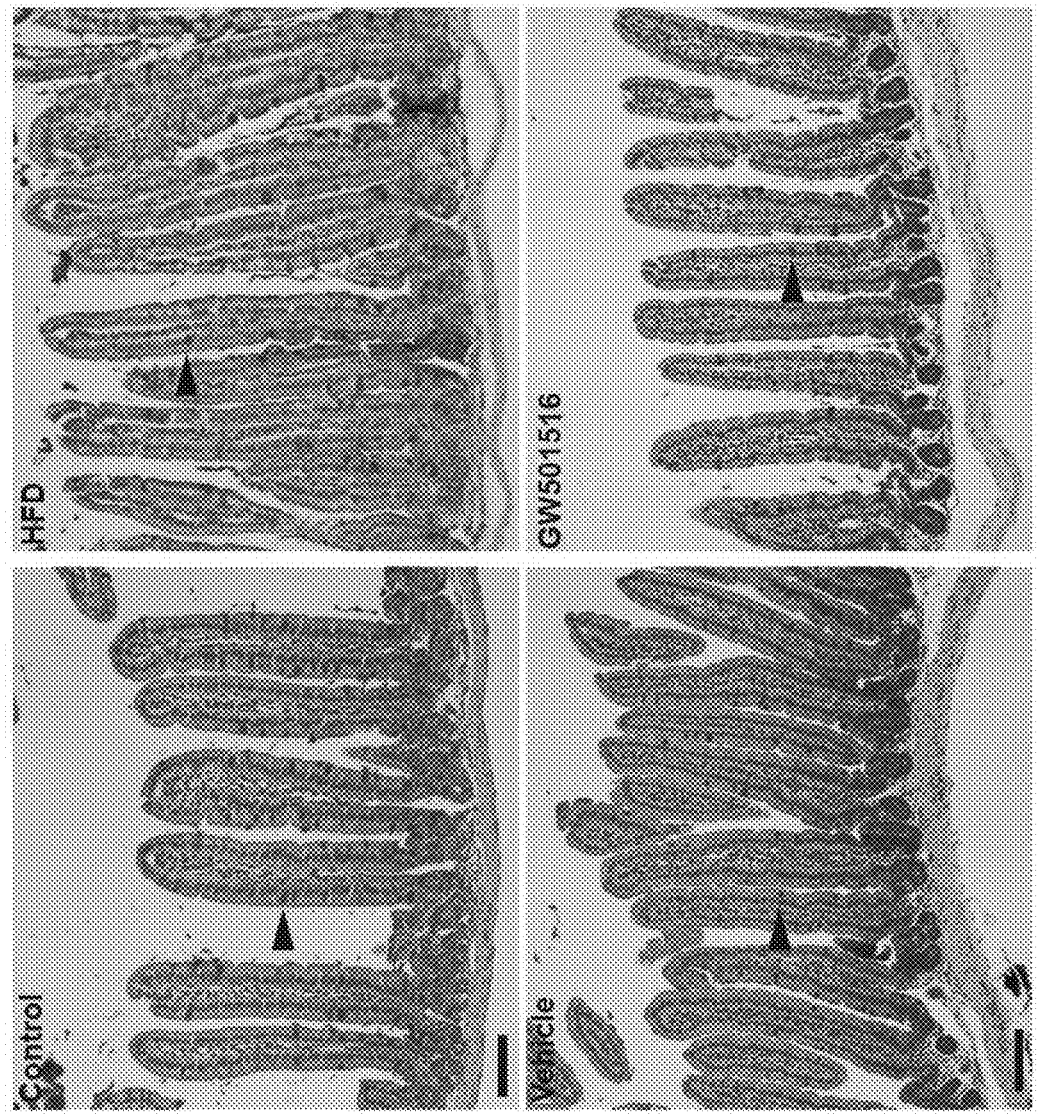

FIGS. 9A-9D illustrate that HFD and PPAR-δ signaling has minimal effects on enteroendocrine and goblet cell differentiation. FIGS. 9A-9B depict that quantification (FIG. 9A) and immunostain (FIG. 9B) for chromogranin A revealed no difference in the numbers of jejunal enteroendocrine cells (FIG. 9B, black arrowhead) per crypt-villous unit in mice from high fat diet compared to control (n=3), or vehicle-treated mice compared to PPAR-δ agonist GW501516-treated mice (n=3). FIGS. 9C-9D depict that quantification (FIG. 9C) and Alcian blue/PAS stain (FIG. 9D) showed no difference in mucinous goblet cells (black arrowhead) in HFD compared to controls (n=4), or vehicle-treated mice compared to PPAR-δ agonist-treated mice (n=4).

Figures 10A, 10B:
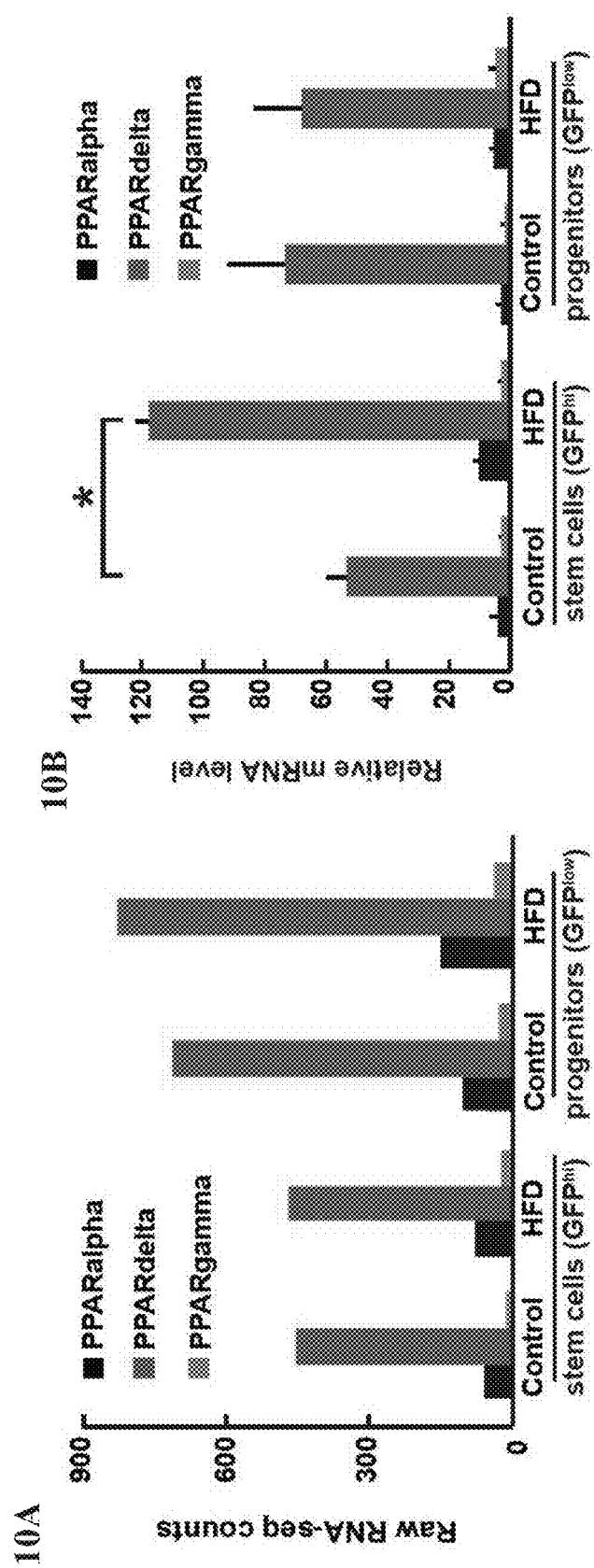
Figure 10C:
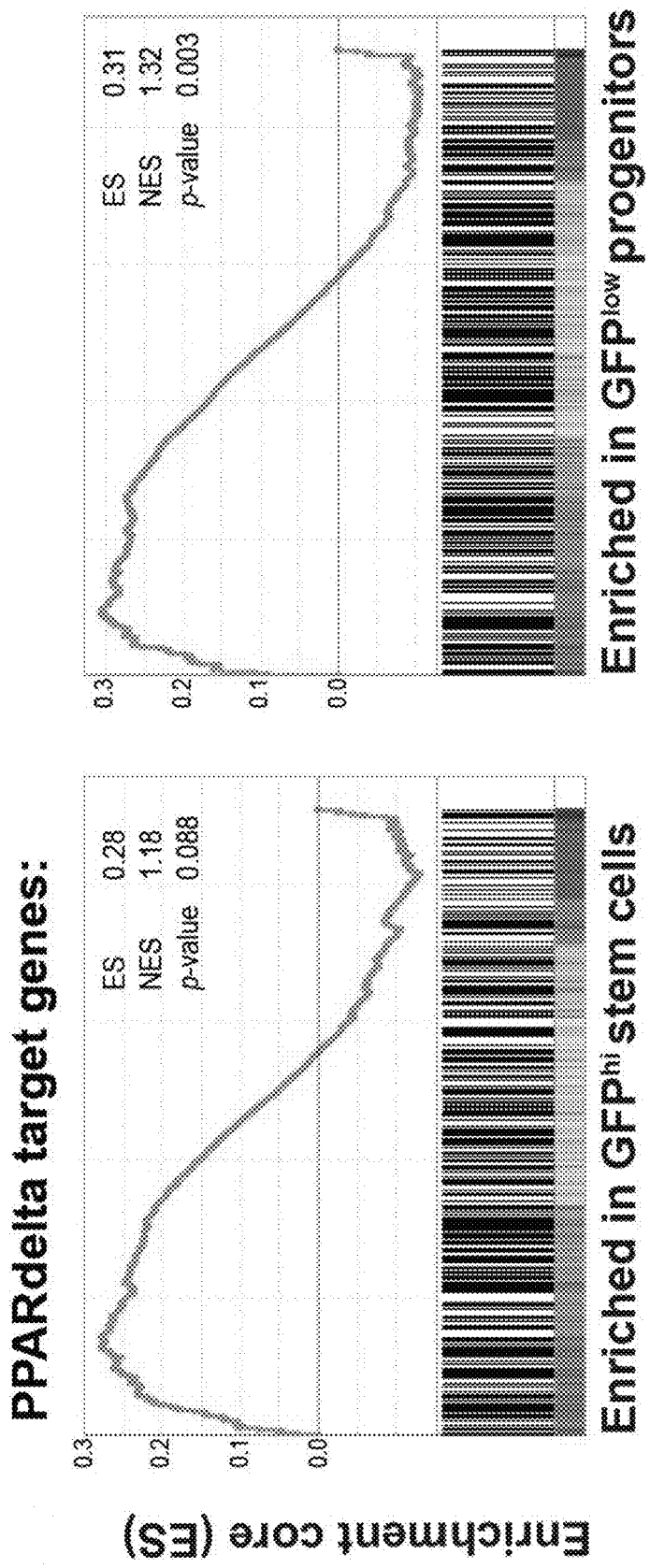

FIGS. 10A-10C show that PPAR-δ is the predominant PPAR family member expressed in intestinal progenitors. FIG. 10A illustrates that PPAR-δ is the most abundant PPAR family member in intestinal progenitors based on RNA-seq data. FIG. 10B shows confirmation of PPAR family member mRNA expression levels in Lgr5-GFP$^{hi}$ ISCs and Lgr5-GFP$^{low}$ progenitors by qPCR. FIG. 10C shows the results of a gene set enrichment analysis (GSEA) of RNA-seq revealed enrichment of PPAR-δ targets in Lgr5-GFP$^{hi}$ ISCs and Lgr5-GFP$^{low}$ progenitors after HFD treatment.

Figure 11A:
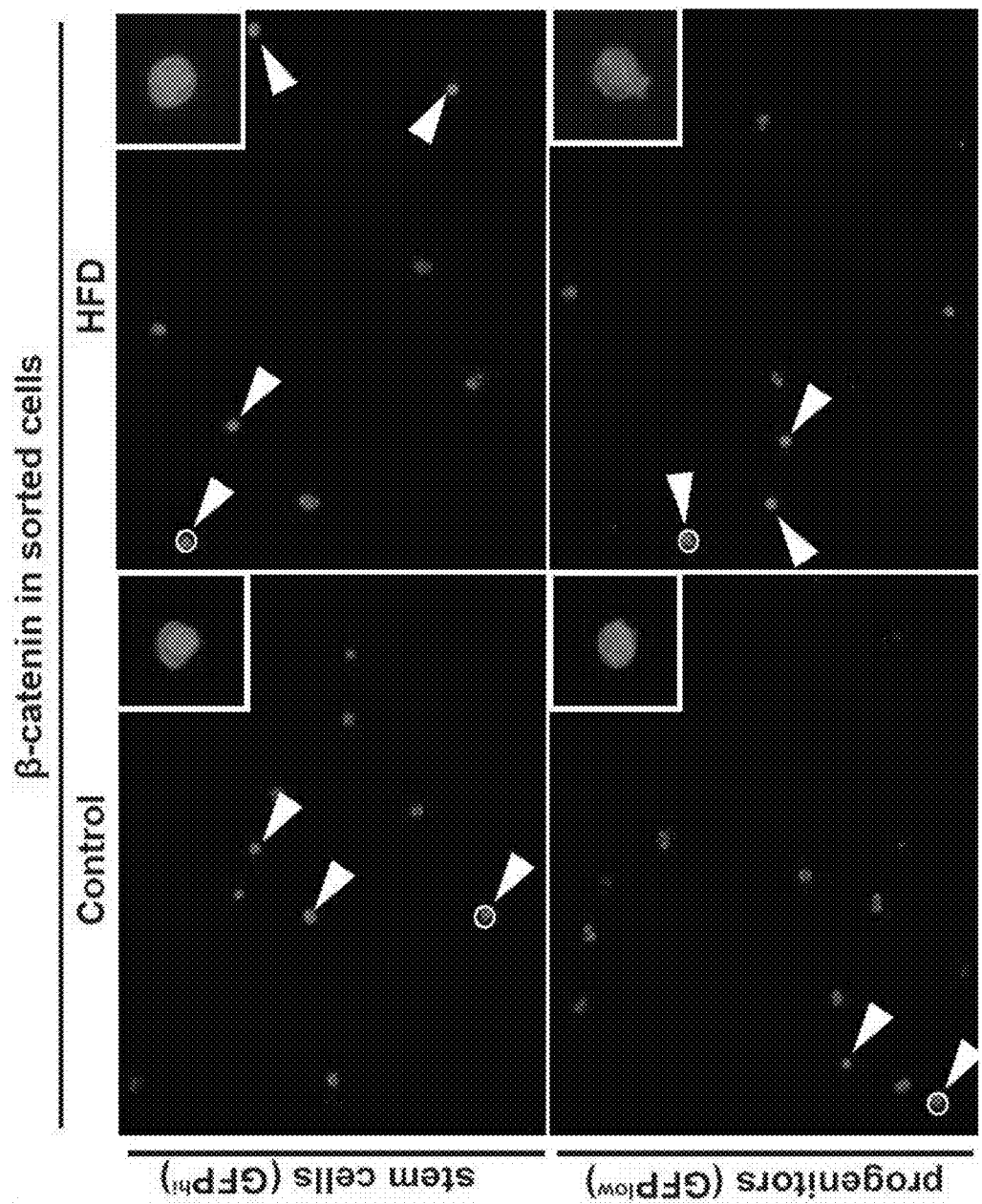
Figure 11B:
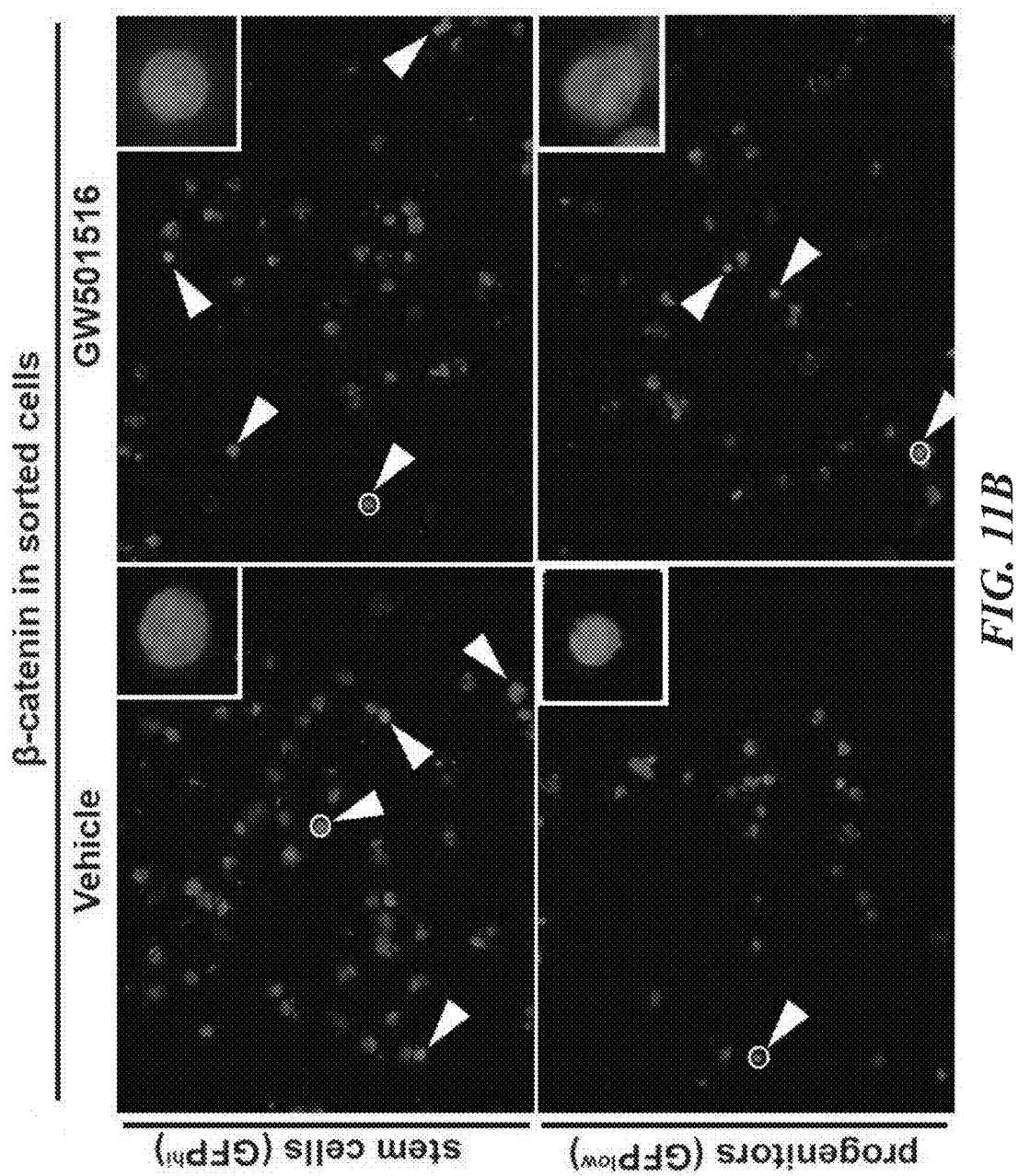
Figures 11C, 11D:
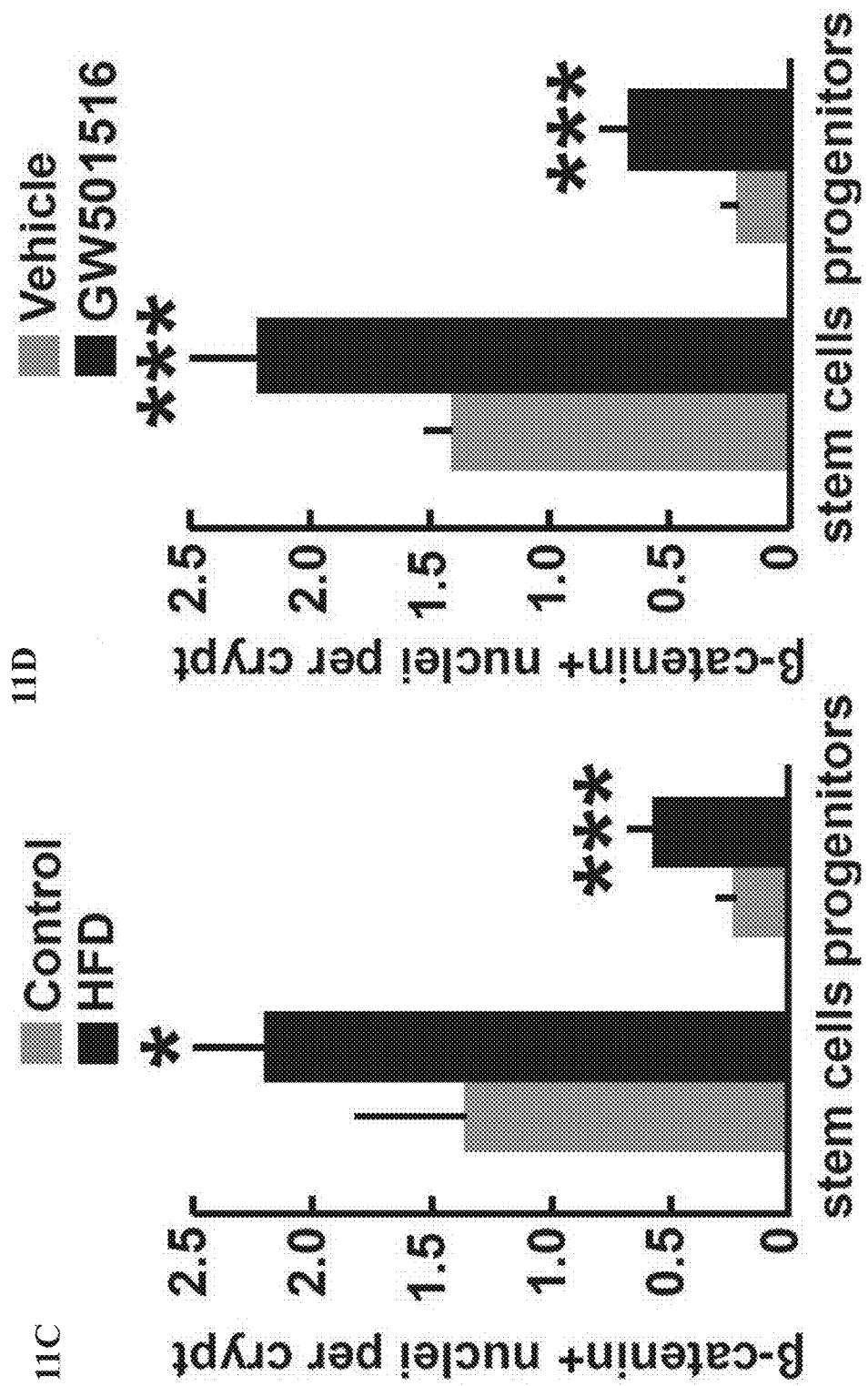
Figure 11E:
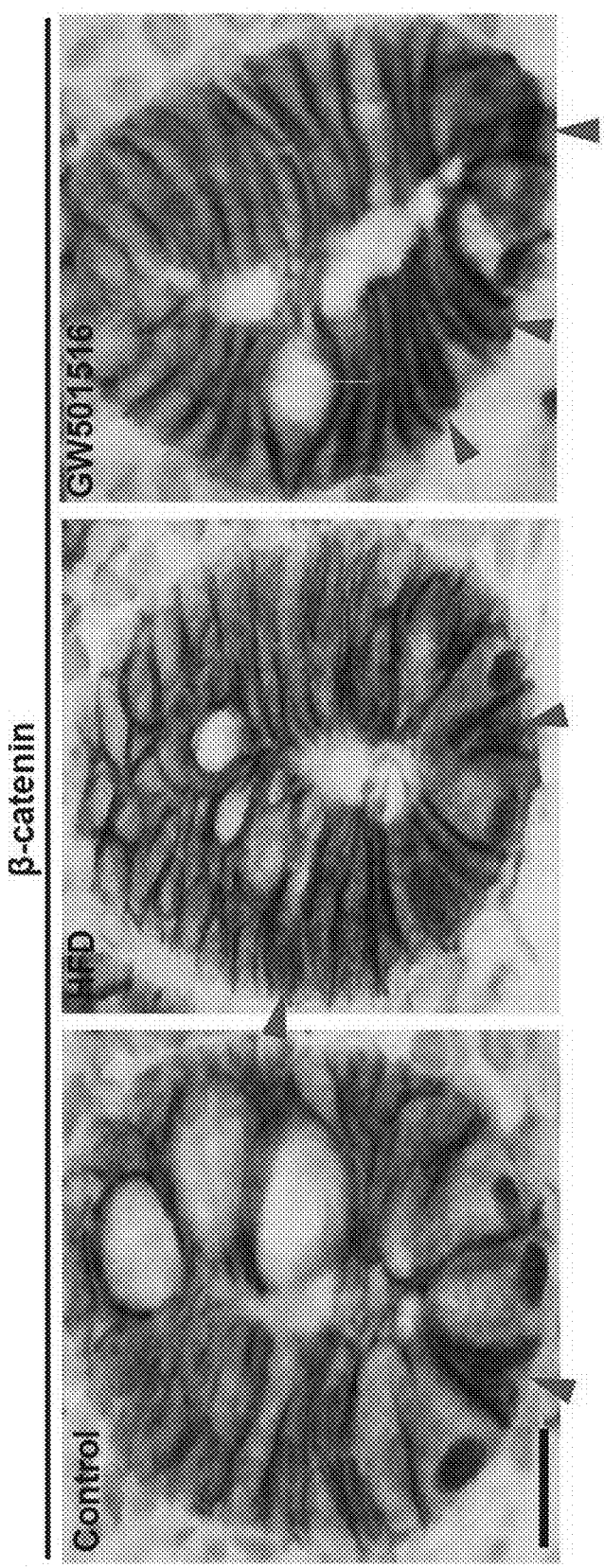

FIGS. 11A-11E illustrate that HFD and PPAR-δ signaling boost nuclear β-catenin localization and target gene expression in intestinal progenitors. FIGS. 11A and 11B show that increased nuclear β-catenin localization was observed in Lgr5-GFP$^{hi}$ ISCs and Lgr5-GFP$^{low}$ progenitors from HFD (FIG. 11A) or PPAR-δ agonist GW501516-treated (FIG. 11B) mice by immunostaining (n=4 each). FIGS. 11C and 11D illustrate that increased nuclear β-catenin localization was observed in the stem and progenitor cells of crypts from HFD (FIG. 11C) or PPAR-δ agonist-treated (FIG. 11D) mice by immunostaining (n=4 each). Representative images are shown in FIG. 11E; arrowheads highlight β-catenin positive nuclei. (Unless otherwise indicated, in all panels: values are mean; error bars indicate s.d.; *P<0.05, P<0.01, *P<0.001, scale bars in FIG. 11E=20 μm).

Figure 12A:
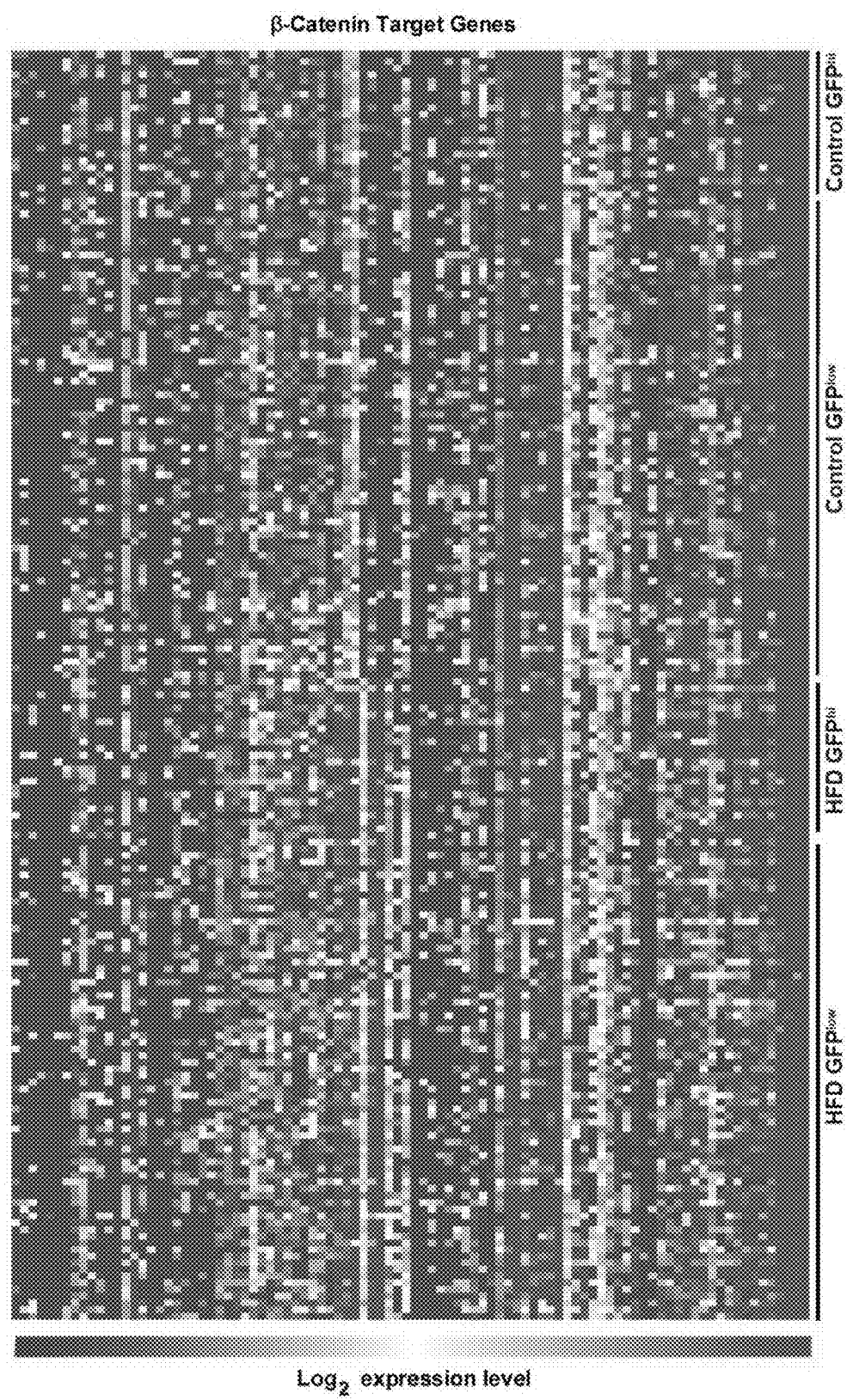
Figure 12D:
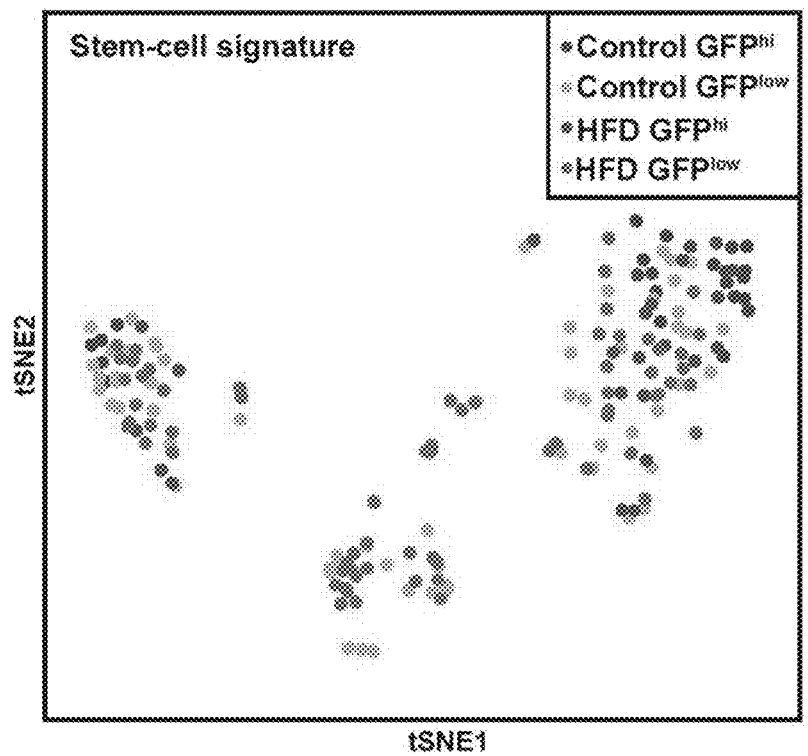
Figure 12E:
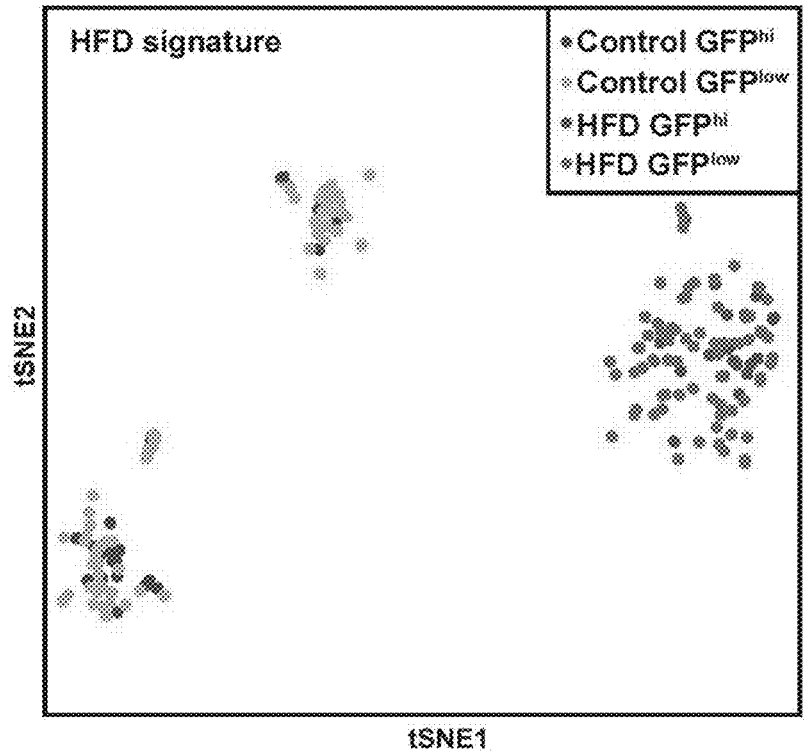

FIGS. 12A-12E illustrate HFD mediated changes in β-catenin target gene expression in single stem and progenitor cells. FIG. 12A shows a heat map representation of β-catenin target gene expression in single Lgr5-GFP$^{hi}$ ISCs and Lgr5-GFP$^{low}$ progenitor cells. FIG. 12B shows stem cell signature genes identified by comparing control Lgr5-GFP$^{hi}$ ISCs to control Lgr5-GFP$^{low}$ progenitor cells. FIG. 12C shows HFD signature genes identified by comparing HFD Lgr5-GFP$^{hi}$ ISCs to control GFP$^{hi}$ ISCs. FIG. 12D shows tSNE analysis of single cells using stem cell signature genes. FIG. 12E shows tSNE analysis of single cells using HFD signature genes.

FIG. 13 illustrates that PPAR-δ activation bestows adenoma-initiating capacity to organoids derived from Apc-null non-LGR5+ cells. Representative adenomas, verified by histology (H&E), derived from orthotopic transplantation of Apc-null Lgr5-GFP$^{hi}$ ISCs from vehicle and PPAR-δ agonist GW501516-treated mice and Lgr5-GFP$^{low}$ progenitors from PPAR-δ agonist-treated mice exhibit lack of maturation and nuclear crowding. The results were interpreted blinding by 2 independent pathologists. Unless otherwise indicated, in all panels: scale bars in (20X)=50 μm, (60X)=20 μm, (H&E, 20X)=50 μm, (60X)=20 μm.)

Figure 14A:
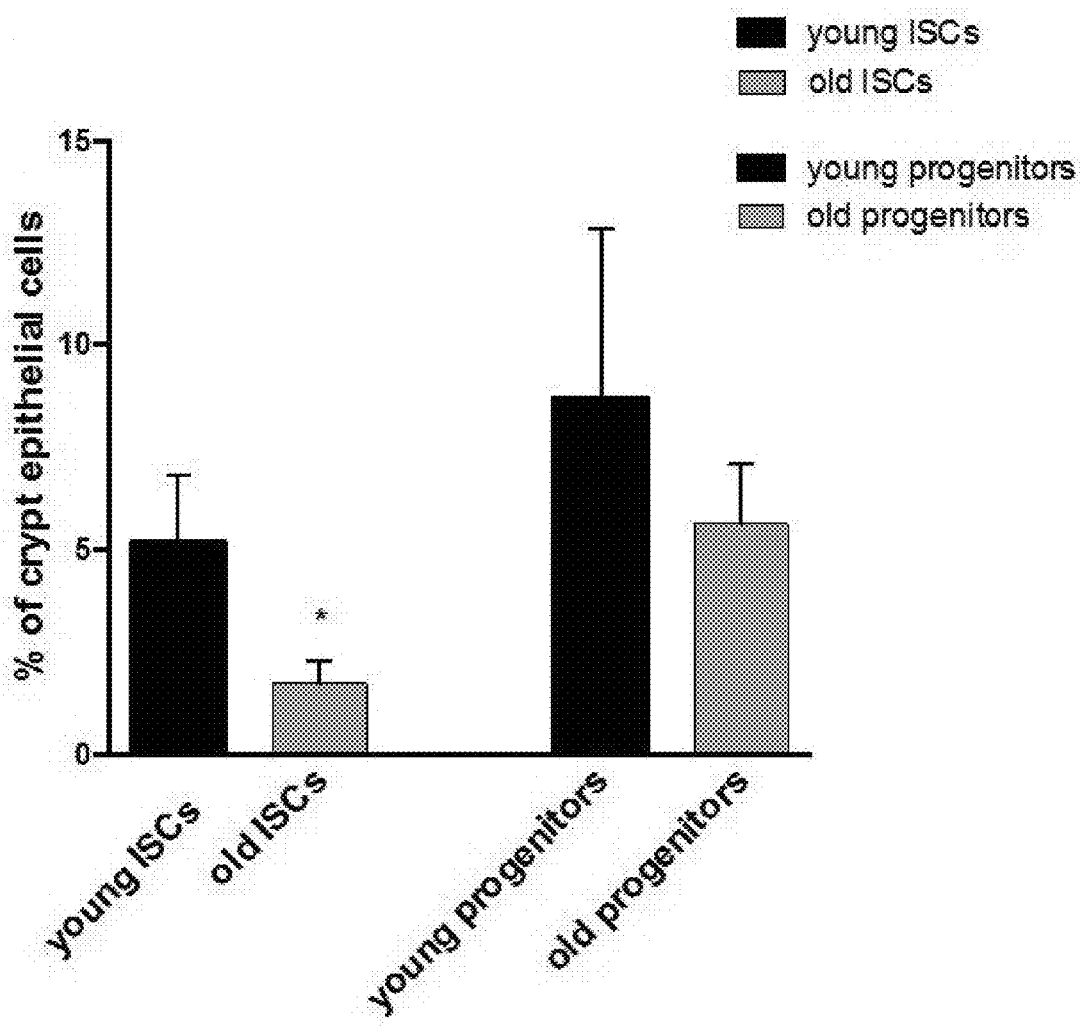
Figure 14B:
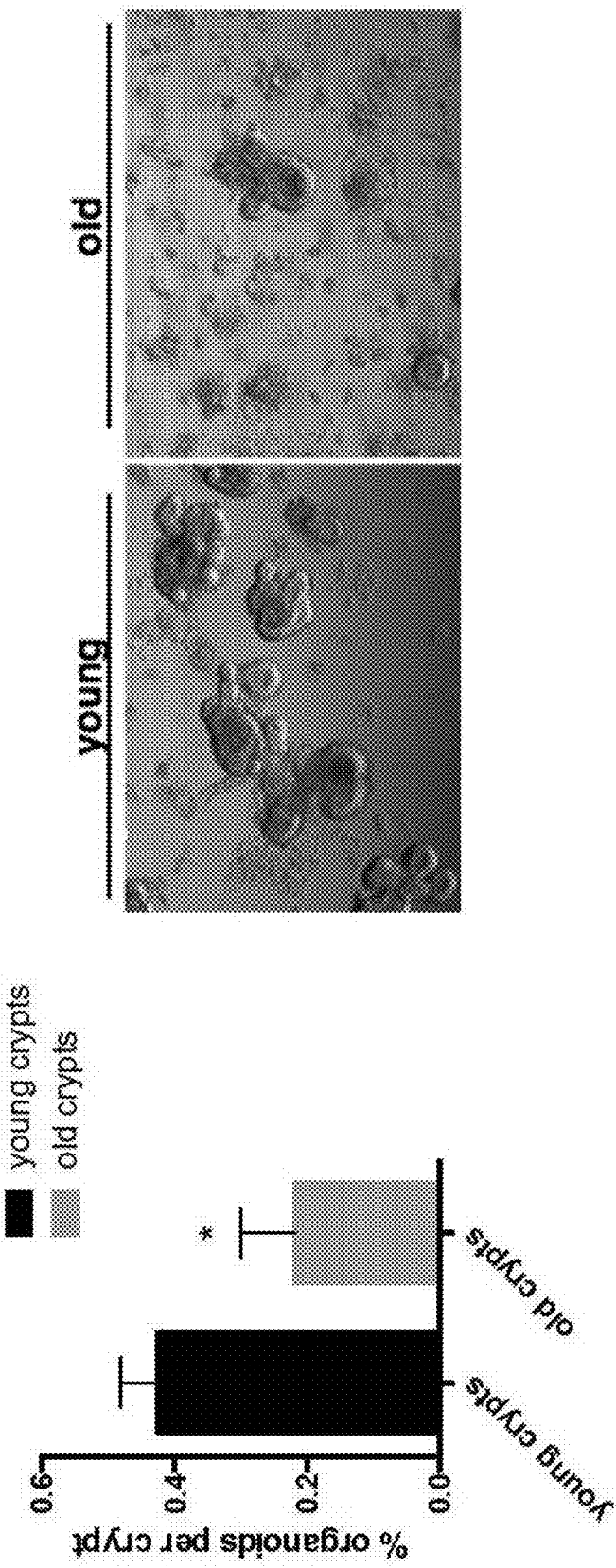

FIGS. 14A-14B demonstrate age associated changes in the intestine. FIG. 14A shows decreased frequencies of ISCs and progenitor cells (TAs) in aged relative to young. FIG. 14B shows decreased frequency of organoid formation in aged crypts compared to young ones.

Figure 15A:
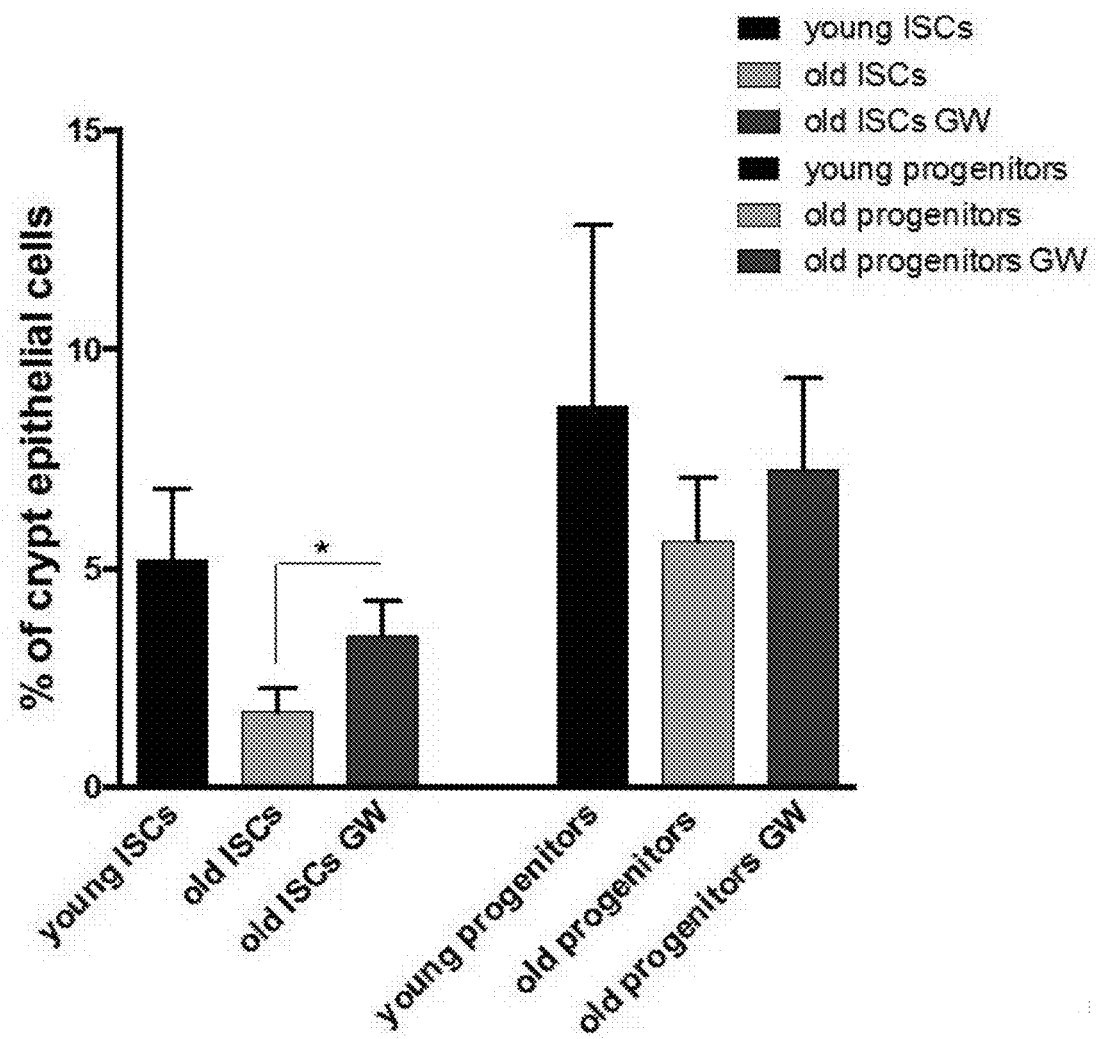
Figure 15B:
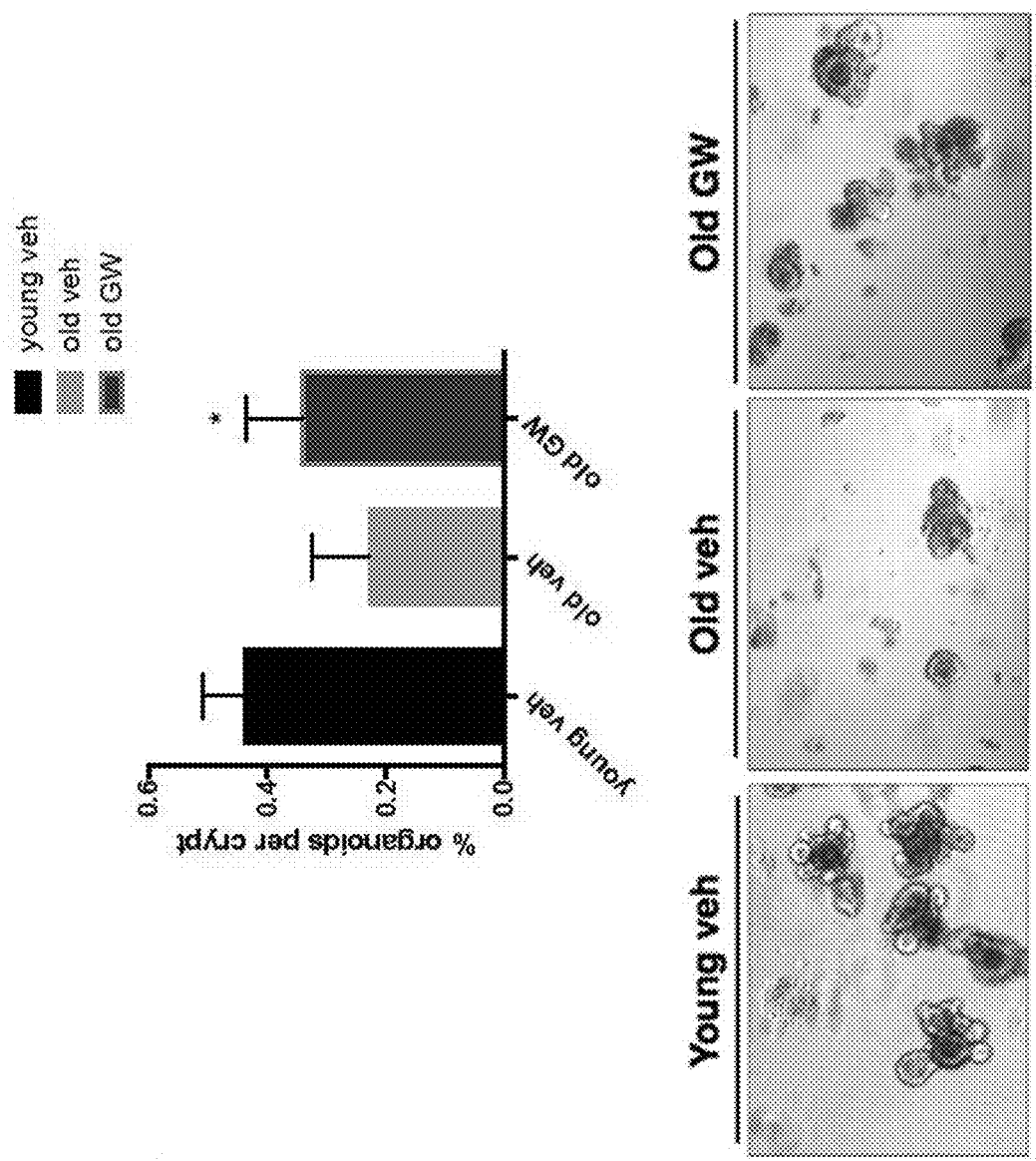

FIGS. 15A-15B illustrate that PPARδ pathway activation improves intestinal crypt function. FIG. 15A shows that GW501516 treatment increases the frequency of stem cells. FIG. 15B shows that GW501516 treatment increases the frequency of organoid formation in aged crypts.

Figure 16A:
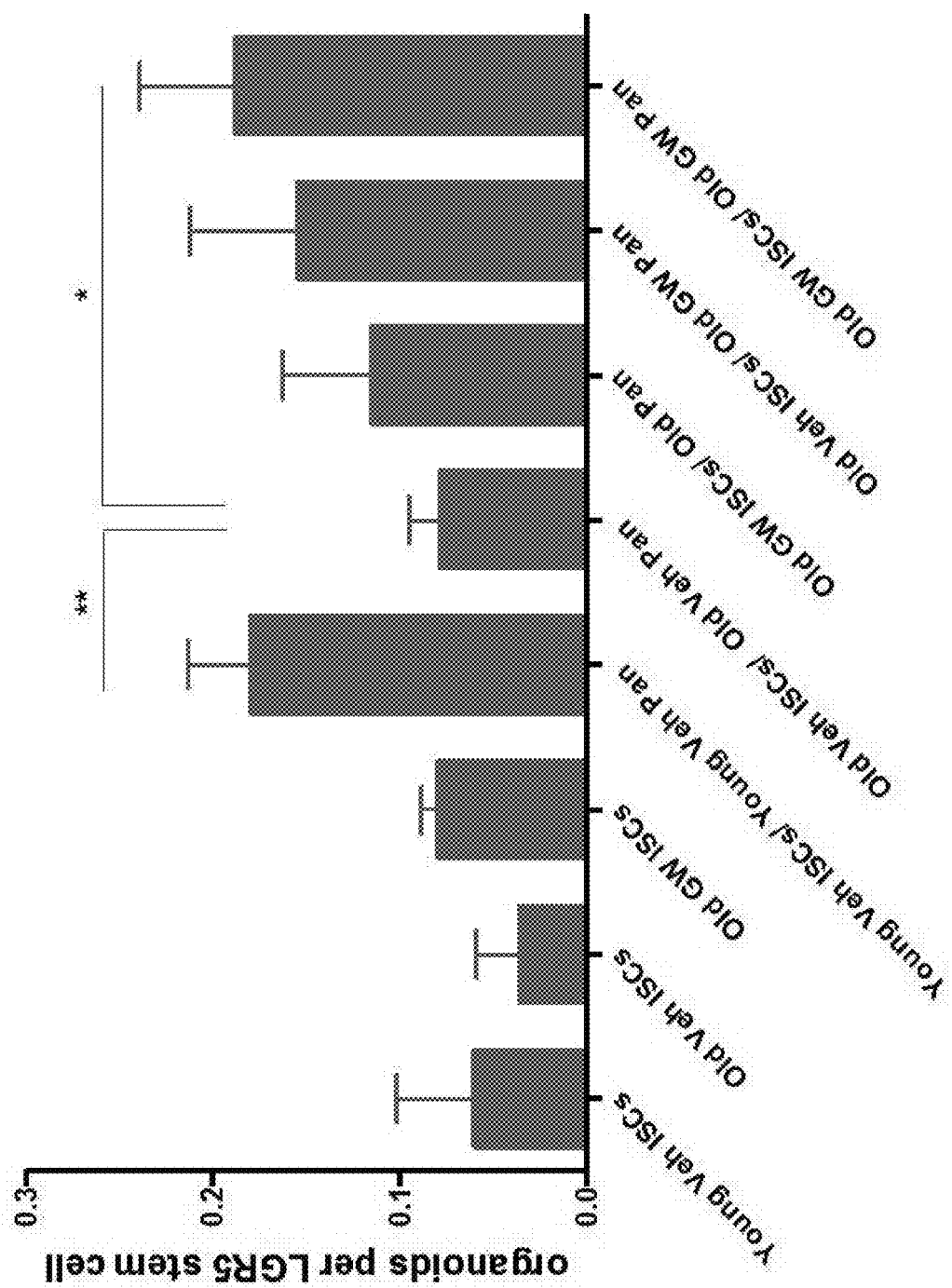
Figure 16B:
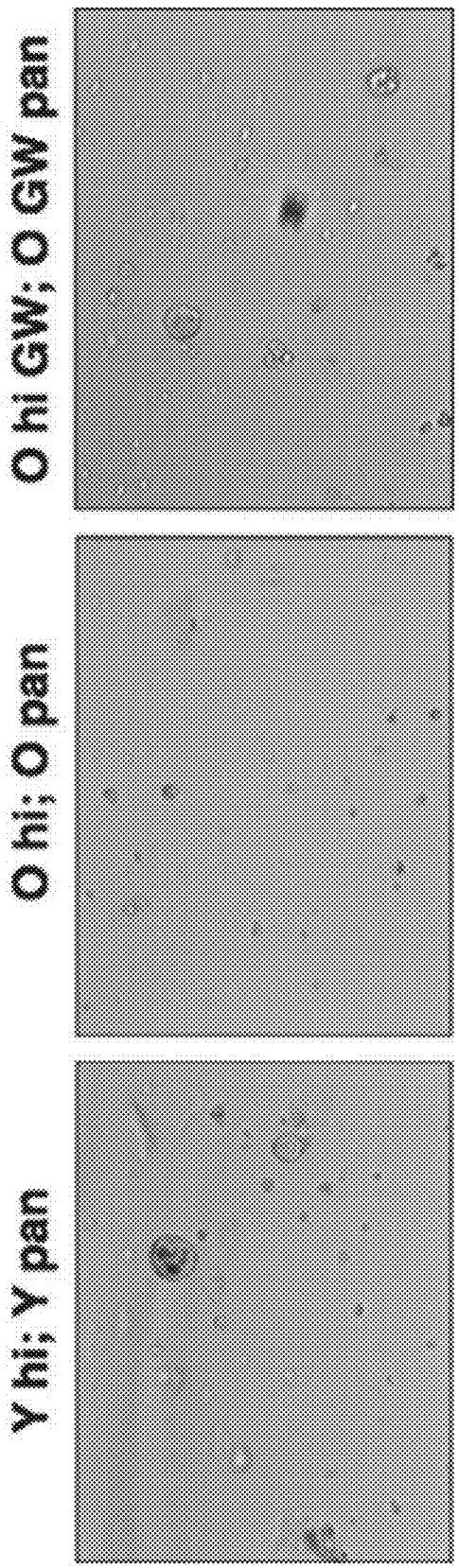

FIGS. 16A-16B illustrate that activation of the PPARδ signaling pathway in vivo increases intestinal organoid formation in aged animals. FIG. 16A shows that co-culturing intestinal stem cells (ISCs) and Paneth cells from aged mice yields a significantly lower frequency of organoid formation compared to co-cultured ISCs and Paneth cells derived from young animals. Co-culturing ISCs and Paneth cells from aged animals treated with the PPARδ agonist GW501516 significantly boosts organoid formation compared to co-cultured old vehicle treated ISCs and Paneth cells. Counts and frequencies were done on day 3 post culturing. FIG. 16B shows representative images from co-culturing experiments. Abbreviations used in the figure: Y=young, O=old; "hi"=intestinal stem cells, "pan"=Paneth cells.

DETAILED DESCRIPTION OF THE INVENTION

Aspects of the disclosure relate to compositions, methods, and agents for stimulating the proliferation and/or self-renewal of one or more intestinal stem cells in, enhancing the number and/or function of non-stem progenitor cells in, and/or promoting regeneration of, mammalian intestinal tissue.

In an aspect, a method of stimulating proliferation and/or self-renewal of one or more intestinal stem cells in mammalian intestinal tissue comprises contacting a population of cells in mammalian intestinal tissue with an effective amount of an agent that increases the level and/or activity of peroxisome proliferator activated receptor delta (PPAR-δ) or a PPAR-δ target protein, thereby stimulating the proliferation and/or self-renewal of one or more intestinal stem cells.

In an aspect, a method of stimulating proliferation and/or self-renewal of one or more intestinal stem cells in mammalian intestinal tissue comprises contacting a population of cells in mammalian intestinal tissue with an effective amount of a high fat diet mimetic, thereby stimulating the proliferation and/or self-renewal of one or more intestinal stem cells.

In an aspect, a method of enhancing non-stem intestinal progenitor cell number and/or function comprises contacting a population of cells in mammalian intestinal tissue with an effective amount of an agent that increases the level and/or activity of (PPAR-δ) or a PPAR-δ target protein, thereby enhancing non-stem intestinal progenitor cell number and/or function In an aspect, a method of enhancing non-stem intestinal progenitor cell number and/or function comprises contacting a population of cells in mammalian intestinal tissue with an effective amount of a high fat diet mimetic, thereby enhancing non-stem intestinal progenitor cell number and/or function.

In an aspect, a method of promoting regeneration of mammalian intestinal tissue comprises contacting a population of cells in the mammalian intestinal tissue with an effective amount of an agent that increases the level and/or activity of PPAR-δ or a PPAR-δ target protein, thereby promoting regeneration of the mammalian intestinal tissue.

In an aspect, a method of promoting regeneration of mammalian intestinal tissue comprises contacting a population of cells in the mammalian intestinal tissue with an effective amount of a high fat diet mimetic, thereby promoting regeneration of the mammalian intestinal tissue.

In some embodiments, any of the methods described herein further includes contacting the population of cells in the mammalian intestinal tissue with an effective amount of a calorie restriction mimetic. In some embodiments, any of the methods described herein further includes contacting the population of cells in the mammalian intestinal tissue with an effective amount of an agent that inhibits the level and/or activity of mTORC1. In some embodiments, any of the methods described herein further include contacting the population f cells in the mammalian intestinal tissue with an effective amount of an agent that increases the level and/or activity of Bst1 or a product of Bst1.

As used herein, "stimulating" and derivations thereof, may be used interchangeably with terms such as "activate", "enhance", "promote", "increase" and like terms, as appropriate in the context. It will be understood that the magnitude or extent of stimulation, activation, enhancement, or an increase described herein may vary.

For example, stimulating proliferation and/or self-renewal of one or more intestinal stem cells and/or non-stem intestinal progenitor cells may refer to an increase in proliferation and/or self-renewal of one or more intestinal stem cells and/or non-stem intestinal progenitor cells by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% relative to level of proliferation and/or self-renewal in the absence of an agent or composition described herein. In some embodiments, stimulating the proliferation and/or self-renewal of one or more intestinal stem cells and/or non-stem intestinal progenitor cells increases the proliferation and/or self-renewal of such cells by at least 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 60 fold, 70 fold, 80 fold, 90 fold, or 100 fold or more.

As another example, promoting regeneration of mammalian intestinal tissue may refer to regeneration of mammalian intestinal tissue (e.g., atrophied, damaged, aged, dysfunctional, etc.) to at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, of its normal condition as compared to the condition of mammalian intestinal tissue in the absence of contact with an agent or composition described herein.

As used herein, "intestinal stem cells" refer to stem cells residing at the base of the small intestinal crypts. Methods for identifying, isolating, and/or purifying intestinal stem cells are available to the skilled artisan art, for example, intestinal stem cells can be identified by determining the presence of expression of one or more markers of intestinal stem cells, such as leucine-rich repeat-containing G-protein coupled receptor 5 (LGR5), oflactomedin 4 (OLFM4), achaete scute-like 2 (ASCL2). In some embodiments, the intestinal stem cells comprise LGR5$^+$ stem cells. In some embodiments, the intestinal stem cells comprise OLFM4$^+$ stem cells. In some embodiments, the intestinal stem cells comprise ASCL2$^+$ stem cells.

As used herein, "non-stem intestinal progenitor cells" refer to non-stem progenitor cells residing above Paneth cells in the intestinal crypts. Methods for identifying, isolating, and/or purifying non-stem progenitor cells are available to the skilled artisan, for example, non-stem intestinal progenitor cells can be identified by the absence of expression or diminished expression of LGR5, OLFM4, and ASCL2, or expression of WDR3 (KIAA0007) in the cells.

As used herein, "mammalian intestinal tissue" refers to the portion of the mammalian alimentary canal that extends from the stomach to the rectum, including the small intestine, the large intestine, and the colon. In some embodiments, mammalian intestinal tissue comprises mouse intestinal tissue. In some embodiments, mammalian intestinal tissue comprises human intestinal tissue.

Aspects of the disclosure involve manipulating (e.g., contacting, isolating, purifying, expanding, etc.) populations of cells. As used herein, a "population of cells" can be a single cell or can comprise multiple cells in various embodiments. In some embodiments a population of cells comprises at least 10, $10^2$, $10^3$, $10^4$, $10^5$, $10^6$, $10^7$, $10^9$, $10^{10}$, $10^{11}$ cells, or more, or any range therebetween. In some embodiments of any relevant aspect herein a population of cells refers to multiple cells in a culture vessel such as a culture plate or dish. In some embodiments a population of cells refers to multiple cells exposed in parallel to the same agents or conditions. In some embodiments a population of cells refers to cells in mammalian intestinal tissue in vivo. One of ordinary skill in the art will appreciate that a "population of cells" of a given type, such as population of intestinal stem cells at the base of the small intestinal crypts, or having particular characteristic(s) comprises at least one cell of such type or having such characteristic(s) and may or may not further comprise one or more cells of different type(s) and/or lacking such characteristic(s). In various embodiments a population of cells is selected or purified to a desired level of uniformity or homogeneity with respect to type and/or characteristic(s). For example, in various embodiments a population of cells contains at least 10%, 20%, 30%, 40%, 50%, 60%, 70%, 80%, 90%, 95%, or more cells of such type and/or having such characteristic(s). It will be understood that many of the methods described herein are often practiced using populations of cells comprising multiple cells, e.g., in vitro or in vivo. In some instances, ex vivo methods described herein are performed using populations of cells. Thus references to "a cell" should be understood as including embodiments in which the cell is a member of a population of cells. References to "cells" should be understood as including embodiments applicable to individual cells within a population comprising multiple cells and embodiments applicable to individual isolated cells. As will be understood by those of ordinary skill in the art, the number of members and/or one or more characteristic(s) of a population of cells may change over time, e.g., during a culture period. For example, at least some cells in the population may divide once or more and/or some cells may die. Hence, if a population of cells is maintained and/or subjected to one or more manipulations or steps, it should be understood that the population may have changed over time, and the term "population of cells" may thus refer to the population as it exists at the relevant time, e.g., the population resulting from the previous manipulation or step. It will also be appreciated that, in general, any manipulation or step performed on a population of cells may be performed on a subpopulation. For example, cells may be passaged, and only a portion of the cells retained for subsequent manipulation or steps, or a population may be divided into multiple aliquots, which may be used for different purposes.

The disclosure contemplates contacting any population of cells in mammalian intestinal tissue that stimulates the proliferation and/or self-renewal of one or more intestinal stem cells and/or non-stem intestinal progenitor cells in the population. In some embodiments, the population of cells comprises LGR5$^+$ stem cells. In some embodiments, the population of cells comprises non-stem cell progenitor cells (e.g. WDR3$^+$ intestinal cells). In some embodiments, the population of cells optionally comprises Paneth cells. In some embodiments, the population of cells optionally comprises goblet cells. In some embodiments, the population of cells is selected from the group consisting of LGR5$^+$ stem cells, non-stem cell progenitor cells, and optionally Paneth cells, and/or goblet cells. It should be appreciated that in embodiments in which calorie restriction mimetics are employed it is preferable that the population of cells comprise Paneth cells, in addition to other intestinal cells in the population (e.g., intestinal stem cells and/or non-stem intestinal progenitor cells).

Aspects of the disclosure involve employing effect amounts of agents and/or compositions. An "effective amount" or "effective dose" of an agent (or composition containing such agent) generally refers to the amount sufficient to achieve a desired biological and/or pharmacological effect, e.g., when contacted with a cell in vitro or administered to a subject according to a selected administration form, route, and/or schedule. As will be appreciated by those of ordinary skill in the art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. It will be understood that agents, compounds, and compositions herein may be employed in an amount effective to achieve a desired biological and/or therapeutic effect. In some embodiments, an "effective amount" refers to an amount of an agent or composition described herein which is stimulates proliferation and/or self-renewal of intestinal stem cells. In some embodiments, an "effective amount" refers to an amount of an agent or composition described herein which is stimulates proliferation and/or self-renewal of non-stem intestinal progenitor cells. In some embodiments, an "effective amount" refers to an amount of agent or composition described herein which promotes the regeneration of intestinal tissue. The skilled artisan can readily determine the effective amount of an agent or composition described herein for achieving its effective purpose using routine methods, without undue experimentation It should be understood that in certain embodiments, an effective amount of the agents and compositions disclosed herein may be administered to a subject for a limited period of time (e.g., several days, weeks or months). In certain embodiments, the agents and compositions disclosed herein may be administered to a subject in conjunction with, for example, chemotherapy or radiotherapy, and in such embodiments the agents or compositions may be discontinued upon completion of such chemotherapy or radiotherapy. Similarly, in certain embodiments where such agents or compositions are administered as a pre-treatment, such agents or compositions may be administered prior to initiation of chemotherapy and discontinued upon initiation or completion of the chemotherapy.

Aspects of the disclosure involve contacting cells or populations of cells with agents or compositions described herein. As used herein, "contacting", "contacting a cell", "contacting a population of cells", and any derivations thereof, are used interchangeably to refer to any means of introducing an agent or composition into sufficient proximity with a target cell for the agent to exert its intended effect on a cell, including chemical and physical means, whether the agent or composition physically contacts the cell directly or is introduced into an environment in which the cell is present. For example, contacting includes binding of an agent to an extracellular or extranuclear domain of a receptor and exerting its effects in that way. "Contacting" encompass methods of exposing a cell, delivering to a cell, or "loading" a cell with an agent or composition by viral or non-viral vectors, and wherein such agent is bioactive upon delivery. The method of delivery will be chosen for the particular agent and use. Parameters that affect delivery, as is known in the medical art, can include, inter alia, the cell type affected, and cellular location. In some embodiments, contacting includes administering the agent to a subject. In some embodiments, contacting refers to exposing mammalian intestinal tissue (e.g., crypts) or an environment in which the cell line is located (e.g., cell culture) to one or more agents or compositions described herein. In some embodiments, the populations of cells in mammalian intestinal tissue are exposed to an agent or composition in vitro. In some embodiments, populations of cells in mammalian intestinal tissue are exposed to an agent or composition in vivo.

Aspects of the disclosure involve contacting populations of cells (e.g., in mammalian intestinal tissue) with agents (e.g., an agent that increases the level and/or activity of PPAR-δ or a PPAR-δ target protein). "Agent" as used herein encompasses proteins, small molecules, nucleic acids, lipids, supramolecular complexes, entities such as viruses or portions thereof, and other biological or chemical entities that can be contacted with cells ex vivo or administered to a subject. An "agent" may comprise multiple different agents of distinct structure or sequence. The term "agent" may be used interchangeably with the term "compound" herein. In general, an agent disclosed herein can be prepared or obtained using any of a variety of methods. Methods suitable for preparation of particular agents or types of agents are known to those of ordinary skill in the art. For example, in various embodiments an agent is isolated from an organism that naturally contains or produces it (e.g., plants, animals, fungi, bacteria). In some embodiments an agent is at least partly synthesized, e.g., using chemical or biological methods. In some embodiments recombinant nucleic acid technology is used to produce an agent, e.g., a gene expression product such as an RNA or protein. Methods for generating genetically modified cells or organisms, e.g., cells (prokaryotic or eukaryotic) or organisms (e.g., animals, plants) that can serve as sources of the agent are known to those of ordinary skill in the art. Exemplary methods are described in various references cited herein. In some embodiments a protein or nucleic acid has or comprises a naturally occurring sequence. In some embodiments a protein or nucleic acid comprises or has a sequence that is at least in part invented or generated by man and/or not known to be found in nature. In some embodiments an agent or composition herein comprises a naturally occurring polypeptide. For purposes herein, a polypeptide is said to be "naturally occurring" if it has the amino acid sequence of a polypeptide found in nature. For example, a recombinantly produced polypeptide identical in sequence to a polypeptide found in nature is said to be a "naturally occurring" polypeptide. One of skill in the art can readily obtain sequences of naturally occurring polypeptides, e.g., from publicly available databases such as those available at the National Center for Biotechnology Information (NCBI) website (e.g., GenBank, OMIM, Gene) using a Gene ID or GenBank Accession Number disclosed herein. In some embodiments, a variant of a naturally occurring polypeptide is used. In some embodiments an agent disclosed herein or used in a method or composition herein (i.e., any such agent) is an isolated or purified agent.

Surprisingly, the present inventors observed that a high fat diet promotes intestinal stem cell and/or non-stem intestinal progenitor cell function, including, for example, increased proliferation and/or self-renewal of intestinal stem cells and/or enhanced number and/or function of non-stem intestinal progenitor cells. Without wishing to be bound by theory, it is believed that a high fat diet and/or a high fat diet mimetic stimulates proliferation and/or self-renewal of intestinal stem cells and/or promotes regeneration of mammalian intestinal tissue, in part, by increasing the level and/or activity of PPAR-δ or a PPAR-δ target protein. Exemplary PPAR-δ target proteins include, without limitation, carnitine palmitoyltransferase 1A (CPT1A), 3-hydroxy-3-methylglutaryl-CoA synthase 2 (HMGCS2), and fatty acid binding protein 1 (FABP1).

PPAR-δ

The PPAR-δ gene (also known as FAAR, NR1C2, NUC1, NUCI, NUCII, PPARB, PPARD; see Gene ID: 5467 for information pertaining to the human PPAR-δ gene; Gene ID: 19015 for information pertaining to the mouse PPAR-δ gene; Gene ID: 25682 for information pertaining to the rat PPAR-δ gene; Accessions: NP_001165289.1 for information pertaining to human PPAR-δ protein isoform 1, NP_803184.1 for information pertaining to human PPAR-δ protein isoform 2, $N_{13}$ 001165290.1 for information pertaining to human PPAR-δ protein isoform 3, NP_001165291.1 for information pertaining to human PPAR-δ protein isoform 4, P35396.1 for information pertaining to mouse PPAR-δ protein, and AAC52419.1 for information pertaining to rat PPAR-δ protein) encodes a member of the peroxisome proliferator-activated receptor (PPAR) family of nuclear hormone receptors that bind peroxisome proliferators to regulate the number and size of peroxisomes made by cells. PPARs regulate a variety of bioprocesses, and the protein encoded by this gene is a potent inhibitor of ligand-induced transcription activity of PPAR alpha and PPAR gamma. PPAR-δ protein is believed to function as an integrator of transcription repression and nuclear receptor signaling, and expression of the PPAR-δ gene is elevated in colorectal cancer cells.

Carnitine Palmitoyltransferase 1A (CPT1A)

CPT1A (also known as CPT1, GPT1-L, and L-CPT1; see, e.g., Gene ID: 1374 for information relating to the human CPT1A gene; Gene ID: 12894 for information pertaining to the mouse CPT1A gene; Gene ID: 25757 for information pertaining to the rat CPT1A gene; Accession: NP_001867.2 for information relating to human CPT1A isoform 1 protein; NP_001027017.1 for information relating to human CPT1A isoform 2 protein; Accession: P97742.4 for information relating to mouse CPT1A protein; Accession: P32198.2 for information relating to rat CPT1A protein) is responsible for catalyzing the transfer of acyl groups of long-chain fatty acid-CoA conjugates onto carnitine, which is an important step for mitochondrial uptake of long-chain fatty acids and their subsequent beta-oxidation in mitochondria. In some embodiments, the CPT1A comprises a PPAR-δ target gene.

3-Hydroxy-3-Methylglutaryl-COA Synthase 2 (HMGCS2)

HMGCS2 (see, e.g., Gene ID: 3158 for information pertaining to the human HMGCS2 gene; Gene ID: 15360 for information pertaining to the mouse HMGCS2 gene; Gene ID: 24450 for information pertaining to the rat HMGCS2 gene; Accession: NP_005509.1 for information relating to human HMGCS2 isoform 1 protein; NP_001159579.1 for information relating to human HMGCS2 isoform 2 protein; Accession: P54869.2 for information pertaining to mouse HMGCS2 protein; and Accession: NP_775117.2 for information relating to rat HMGCS2 protein) is a member of the HMG-coA synthase family, which is a mitochondrial enzyme that is responsible for catalyzing the first reaction of ketogenesis—the metabolic pathway that generates lipid-derived energy for organs under carbohydrate deprivation, for example fasting. In some embodiments, the HMGCS2 comprises a PPAR-δ target gene.

Fatty Acid Binding Protein 1 (FABP1)

FABP1 (also known as FABPL, L-FABP; see, e.g., Gene ID: 2168 for information pertaining to the human FABP1 gene; Gene ID: 14080 for information pertaining to the mouse FABP1 gene; Gene ID: 24360 for information pertaining to the rat FABP1 gene; Accession: NP_001434.1 for information relating to human FABP1 protein; Accession: P12710.2 for information pertaining to mouse FABP1 protein; and Accession: P02692.1 for information relating to rat FABP1 protein). In some embodiments, the FABP1 comprises a PPAR-δ target gene. FABP1 is a fatty acid binding protein expressed in liver. Fatty acid binding proteins comprise a small, highly conserved, family of proteins that bind to long-chain fatty acids and other ligands that are hydrophobic. FABP1 also binds to bile acids. Fatty acid binding proteins are believed to play roles in fatty acid uptake, transport, and metabolism.

In some embodiments, the population of cells is contacted with both an agent that increases the level and/or activity of PPAR-δ and an agent that increases the level and/or activity of a PPAR-δ target protein. In some embodiments, an agent that increases the level and/or activity of PPAR-δ increases the level and/or activity of a PPAR-δ target protein. In some embodiments, the agent increases the level and/or activity of both PPAR-δ and the PPAR-δ target protein. In some embodiments, the agent increases the level and/or activity of the PPAR-δ target protein in intestinal stem and/or non-stem cell progenitor cells.

The present disclosure contemplates the use of any agent which is capable of increasing the level and/or activity of PPAR-δ or a PPAR-δ target protein. It will be understood that the extent of increased level and/or activity may vary. Generally, agents described herein may, for example, increase the level and/or activity of PPAR-δ and/or a PPAR-d target protein by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to level and/or activity of PPAR-δ and/or the PPAR-δ target protein in the absence of use of such agents. Agents can be assessed for their ability to increase the level and/or activity of PPAR-δ and/or a PPAR-δ target protein using assays which are available to the skilled artisan, for example, using the in vitro PPAR-δ activation assay, cell culture and transfection, in vitro transcription assay, and statistical methods described in U.S. Publication No. 2013/0102610, incorporated herein by reference in its entirety.

In some embodiments, the agent that increases the level and/or activity of PPAR-δ and/or a PPAR-δ target protein comprises a high fat diet mimetic. Aspects of the disclosure involve employing high fat diet mimetics. As used herein, "high fat diet mimetic" refers to an agent that attempts to reproduce one or more of the physiological effects that a high fat diet has on a mammal. As used herein, a "high fat diet" refers to a diet in which a significant percentage of total daily calories comprise calories from fats. In some embodiments, a high fat diet mimetic comprises an agent that increases the level and/or activity of PPAR-δ or a PPAR-δ target protein. In some embodiments, the "high fat diet mimetic" increases the level and/or activity of PPAR-δ and/or a PPAR-δ target protein (e.g., in a population of cells in mammalian intestinal tissue, e.g., intestinal stem cells and/or non-stem intestinal progenitor cells) by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to a reference level and/or activity of a PPAR-δ and/or a PPAR-δ target protein (e.g., the level and/or activity of PPAR-δ and/or a PPAR-δ target protein in a population of cells in mammalian intestinal tissue not contacted with a high fat diet mimetic). In some embodiments, the high fat diet mimetic stimulates proliferation and/or self-renewal of intestinal stem cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation and/or self-renewal of intestinal stem cells in the absence of treatment with the high fat diet mimetic. In some embodiments, the high fat diet mimetic stimulates proliferation of non-stem intestinal progenitor cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation of non-stem intestinal progenitor cells in the absence of treatment with the high fat diet mimetic.

In some embodiments, the high fat diet mimetic comprises a fatty acid or a salt or ester thereof. In some embodiments the high fat diet mimetic comprises a derivative or a structural analog of a fatty acid. In some embodiments, the high fat diet mimetic comprises an essential fatty acid. In some embodiments, the fatty acid comprises a poly unsaturated fatty acid. In some embodiments, the fatty acid comprises an omega-3 fatty acid. In some embodiments, the fatty acid comprises an omega-3 fatty acid. In some embodiments, the fatty acid comprises a short chain polyunsaturated fatty acid, e.g., a SCPUFA in Table 1.

Table 1 below lists exemplary short chain polyunsaturated acids (SCPUFAs) with a carbon chain length of 18 or less for use as high fat diet mimetics.

TABLE 1

Exemplary SCPUFAs and sources

| Class | Designation | Common Name | Derivation |
|---|---|---|---|
| Omega 9 | 18:1 ω-9 | Oleic Acid | Olive oil |
| Omega 6 | 18:2 ω-6 | Linoleic acid | Seed/nut oils |
| Omega 3 | 18:3 ω-3 | α-Linolenic acid (ALA) | Seed/nut oils |
| Omega 3 | 18:4 ω-3 | Stearidonic acid (SDA) | Seed oils |

In some embodiments, the fatty acid comprises a long chain polyunsaturated fatty acid, e.g., a LCPUFA in Table 2.

Table 2 below lists exemplary long chain PUFAs (LCPUFAs) with a carbon chain length of 20 or more for use as high fat diet mimetics.

TABLE 2

Exemplary SCPUFAs and sources

| Class | Designation | Common Name | Derivation |
|---|---|---|---|
| Omega 3 | 20:4 ω-3 | Eicosatetraenoic acid | Marine oils |
| Omega 3 | 20:5 ω-3 | Eicosapentaenoic acid (EPA) | Marine oils |
| Omega 3 | 22:5 ω-3 | Docosapentaenoic acid (DPA) | Marine oils |
| Omega 3 | 22:6 ω-3 | Docosahexaenoic acid (DHA) | Marine oils |
| Omega 3 | 24:6 ω-3 | Tetracosahexaenoic acid | Marine oils |

In some embodiments, the high fat diet mimetic comprise palmitic acid. In some embodiments, palmitic acid comprises an in vitro HFD-mimetic. In some embodiments, the high fat diet mimetic comprises an analog or derivative of palmitic acid. In some embodiments, the high fat diet mimetic comprise DHA. In some embodiments, the high fat diet mimetic comprises EPA. In some embodiments, the high fat diet mimetic comprises ALA. In some embodiments, the high fat diet mimetic comprises an agent that increases the level and/or activity of PPAR-δ and/or a PPAR-δ target protein. In some embodiments, the high fat diet mimetic comprises a PPAR-δ agonist. In some embodiments, the high fat diet mimetic comprise a CPT1A agonist. In some embodiments, the high fat diet mimetic comprise a HMGCS2 agonist. In some embodiments, the high fat diet mimetic comprises a FABP1 agonist. In some embodiments, the high fat diet mimetic comprises GW501516. In some embodiments, the high fat diet mimetic comprises GW 0742 CAS #[317318-84-6]. In some embodiments, the high fat diet mimetic comprises L-165,041 CAS #[79558-09-1]. In some embodiments, the high fat diet mimetic comprises CER-002 (being commercially developed by CERENIS Therapeutics).

PPAR-δ Agonists

In some embodiments, the agent that increases the level and/or activity of PPAR-δ and/or a PPAR-δ target protein comprises a PPAR-δ agonist. In some embodiments, the PPAR-δ agonist increases the level and/or activity of PPAR-δ and/or a PPAR-δ target protein (e.g., in a population of cells in mammalian intestinal tissue, e.g., intestinal stem cells and/or non-stem intestinal progenitor cells) by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to a reference level and/or activity of a PPAR-δ and/or a PPAR-δ target protein (e.g., the level and/or activity of PPAR-δ and/or a PPAR-δ target protein in a population of cells in mammalian intestinal tissue not contacted with a PPAR-δ agonist). In some embodiments, the PPAR-δ agonist stimulates proliferation and/or self-renewal of intestinal stem cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation and/or self-renewal of intestinal stem cells in the absence of treatment with a PPAR-δ agonist. In some embodiments, the PPAR-δ agonist stimulates proliferation of non-stem intestinal progenitor cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation of non-stem intestinal progenitor cells in the absence of treatment with the PPAR-δ agonist. In some embodiments, the PPAR-δ agonists described herein comprise high fat diet mimetics. In some embodiments, the PPAR-δ agonists described herein comprise PPAR-δ target protein agonists. In some embodiments, the PPAR-δ agonists described herein comprise CPT1A agonists. In some embodiments, the PPAR-δ agonists described herein comprise HMGGCS2 agonists. In some embodiments, the PPAR-δ agonists described herein comprise FABP1 agonists.

In some embodiments, the PPAR-δ agonist is a compound of formula (I) and pharmaceutically acceptable salts and solvates thereof;

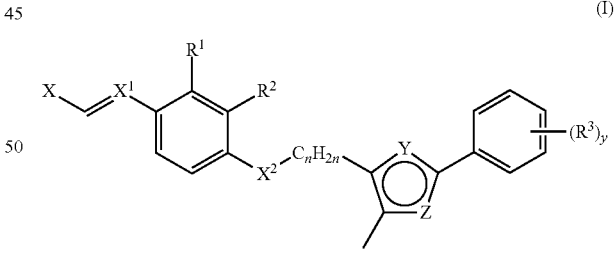

(I)

wherein X represents a COOH (or a hydrolysable ester thereof), $X^1$ is O or S, and the depicted bond with a dashed line is a single bond; $X^2$ represents O, S; $R^1$ and $R^2$ independently represent H, $CH_3$, $OCH_3$ or halogen; n is 1 or 2; one of Y and Z is N and the other is S or O; y represents 1 or 2; each $R^3$ independently represents $CF_3$ or halogen. Methods of synthesizing compounds of formula (I) are described in U.S. Pat. No. 6,710,063, which is incorporated herein by reference in its entirety.

Exemplary compounds of formula (I) include, without limitation, 2-[2-methyl-4-({4-methyl-2-[4-(trifluoromethyl)phenyl]-1,3-oxazol-5-yl}methoxy)phenoxy]acetic acid, 3-[2-methyl-4-({4-methyl-2-[4-(trifluoromethyl)phenyl]-1,3-thiazol-5-yl}methoxy)phenyl]propanoic acid, 3-[2-methyl-4-({4-methyl-2-[4-(trifluoromethyl)phenyl]-1,3-oxazol-5-yl}methoxy)phenyl]propanoic acid, 2-{4-[({4-methyl-2-[4-(trifluoromethyl)phenyl]-1,3-oxazol-5-yl}methyl)sulfanyl]phenyl}acetic acid, 2-[2-methyl-4-({4-methyl-2-[4-(trifluoromethyl)phenyl]-1,3-thiazol-5-yl}methoxy)phenoxy]acetic acid, 3-[4-({4-methyl-2-[4-(trifluoromethyl)phenyl]-1,3-thiazol-5-yl}methoxy)phenyl]propanoic acid, (E)-3-[2-methyl-4-({4-methyl-2-[4-(trifluoromethyl)phenyl]-1,3-oxazol-5-yl}methoxy)phenyl]-2-propenoic acid, methyl 3-[4-({4-methyl-2-[4-(trifluoromethyl)phenyl]-1,3-thiazol-5-yl}methoxy)phenyl]propanoate, 2-{4-[({4-methyl-2-[4-(trifluoromethyl)phenyl]-1,3-thiazol-5-yl}methyl)sulfanyl]phenyl}acetic acid, 2-({4-[({4-methyl-2-[4-(trifluoromethyl)phenyl]-1,3-oxazol-5-yl}methyl)sulfanyl]phenyl}sulfanyl)acetic acid, 2-[methyl-4-({4-methyl-2-[4-(trifluoromethyl)phenyl]-1,3-thiazol-5-yl}methoxy)anilino]acetic acid, 2-{3-chloro-4-[({4-methyl-2-[4-(trifluoromethyl)phenyl]-1,3-oxazol-5-yl}methyl)sulfanyl]phenyl}acetic acid, 2-[2-chloro-4-({4-methyl-2-[4-(trifluoromethyl)phenyl]-1,3-oxazol-5-yl}methoxy)phenoxy]acetic acid, 2-[3-chloro-4-({4-methyl-2-[4-(trifluoromethyl)phenyl]-1,3-thiazol-5-yl}methoxy)phenyl]acetic acid, 2-{4-[({4-methyl-2-[4-(trifluoromethyl)phenyl]-1,3-oxazol-5-yl}methyl)sulfanyl]phenoxy}acetic acid, (E)-3-[4-({4-methyl-2-[4-(trifluoromethyl)phenyl]-1,3-oxazol-5-yl}methoxy)phenyl]-2-propenoic acid, 2-[4-({4-methyl-2-[4-(trifluoromethyl)phenyl]-1,3-oxazol-5-yl}methoxy)phenoxy]acetic acid, 2-[3-fluoro-4-({4-methyl-2-[4-(trifluoromethyl)phenyl]-1,3-thiazol-5-yl}methoxy)phenyl]acetic acid, methyl 2-[3-chloro-4-({4-methyl-2-[4-(trifluoromethyl)phenyl]-1,3-oxazol-5-yl}methoxy)phenyl]acetate, 2-{2-methyl-4-[({4-methyl-2-[4-bromophenyl]-1,3-thiazol-S-yl}methyl)sulfanyl]phenoxy}acetic acid, ethyl 2-{2-methyl-4-[({4-methyl-2-[4-bromophenyl]-1,3-thiazol-5-yl}methyl)sulfanyl]phenoxy}acetate, 2-{2-methyl-4-[({4-methyl-2-[4-chlorophenyl]-1,3-thiazol-5-yl}methyl)sulfanyl]phenoxy}acetic acid, ethyl 2-{2-methyl-4-[({4-methyl-2-[4-chlorophenyl]-1,3-thiazol-5-yl}methyl)sulfanyl]phenoxy}acetate, 2-{2-methyl-4-[({4-methyl-2-[4-fluorophenyl]-1,3-thiazol-5-yl}methyl)sulfanyl]phenoxy}acetic acid, ethyl 2-{2-methyl-4-[({4-methyl-2-[4-fluorophenyl]-1,3-thiazol-5-yl}methyl)sulfanyl]phenoxy}acetate, 2-{2-methyl-4-[({4-methyl-2-[3,4-difluorophenyl]-1,3-thiazol-5-yl}methyl)sulfanyl]phenoxy}acetic acid, ethyl 2-{2-methyl-4-[({4-methyl-2-[3,4-difluorophenyl]-1,3-thiazol-5-yl}methyl)sulfanyl]phenoxy}acetate, 2-{2-methyl-4-[({4-methyl-2-[3,4-dichlorophenyl]-1,3-thiazol-5-yl}methyl)sulfanyl]phenoxy}acetic acid, ethyl-2-{2-methyl-4-[({4-methyl-2-[3,4-dichlorophenyl]-1,3-thiazol-5-yl}methyl)sulfanyl]phenoxy}acetate, 2-{2-methyl-4-[({4-methyl-2-[3,5-bis(trifluoromethyl)phenyl]-1,3-thiazol-5-yl}methyl)sulfanyl]phenoxy}acetic acid, ethyl 2-{2-methyl-4-[({4-methyl-2-[3,5-bis(trifluoromethyl)phenyl]-1,3-thiazol-5-yl}methyl)sulfanyl]phenoxy}acetate, and ethyl 2-{2-methyl-4-[({4-methyl-2-[3-fluoro-4-(trifluoromethyl)phenyl]-1,3-thiazol-5-yl}methyl)sulfanyl]phenoxy}acetate.

In some embodiments, the PPAR-δ agonist is a compound of formula (II) and pharmaceutically acceptable salts

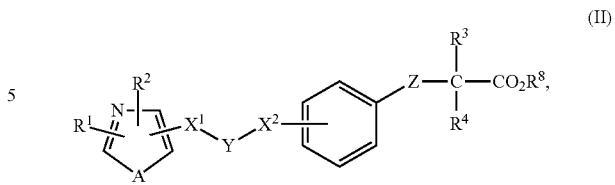

wherein $R^1$ is a hydrogen atom, an alkyl group having 1-8 carbon atoms, an alkyl group having 1-8 carbon atoms and a halogen atom substituent, an alkenyl group having 2-8 carbon atoms, an alkynyl group having 2-8 carbon atoms, a 3-7 membered cycloalkyl group, an alkyl group having 1-8 carbon atom and a 3-7 membered substituent, an arylalkyl group that has a $C_{6-10}$ aryl portion and $C_{1-4}$ alkyl portion and optionally has a substituent, or an aryl or heterocyclic group which optionally has a substituent; $R^2$ is a hydrogen atom, an alkyl group having 1-8 carbon atoms, an alkyl group having 1-8 carbon atoms and a halogen atom substituent, an alkenyl group having 2-8 carbon atoms, an alkynyl group having 2-8 carbon atoms, a 3-7 membered cycloalkyl group, an alkyl group having 1-8 carbon atom and a 3-7 membered substituent, an arylalkyl group that has a $C_{6-10}$ aryl portion and $C_{1-4}$ alkyl portion and optionally has a substituent, or heterocyclic group which optionally has a substituent; A is O, S, or $NR^5$ in which $R^5$ is H or $C_{1-8}$ alkyl; each of $X^1$ and $X^2$ independently is a bond, O, $S(O)_p$ in which p is an integer of 0 to 2, C(=O), C(=N—$OR^6$) in which $R^6$ is H or $C_{1-8}$ alkyl; C(=O)NH, NHC(=O), $SO_2NH$, $NHSO_2$, CH($OR^7$) in which $R^7$ is H or $C_{1-8}$ alkyl, CH=CH, or C≡C; Y is an alkylene chain having 1-8 carbon atoms and optionally a substituent; Z is O or S; each of $R^3$ and $R^4$ independently is an alkyl group having 1-8 carbon atoms and optionally a substituent; and $R^8$ is a hydrogen atom or an alkyl group having 1-8 carbon atoms; provided that $X^2$ is neither O nor $S(O)_p$ when $X^1$ is a bond, while $X^2$ is not a bond when $X^1$ is C(=O)NH. Methods of synthesizing compounds of formula (II) are described in U.S. Pat. No. 6,678,552, which is incorporated herein by reference in its entirety.

In some embodiments, the PPAR-δ agonist is an oxazole derivative compound of formula (II) and pharmaceutically acceptable salts thereof:

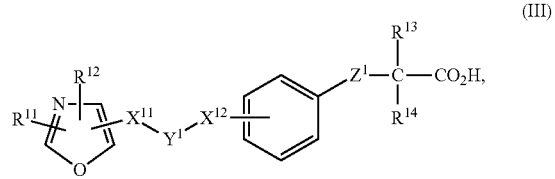

wherein $R^{11}$ is an alkyl group having 1-8 carbon atoms, an alkyl group having 1-8 carbon atoms and 1-3 halogen atom substituents, an alkenyl group having 2-8 carbon atoms, an alkynyl group having 2-8 carbon atoms, a 3-7 membered cycloalkyl group, an alkyl group having 1-8 carbon atom and a 3-7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1-3 halogen substituents, $C_{1-8}$ alkoxy, $C_{1-8}$ alkoxy having 1-3 halogen substituents, phenyl, benzyl, phenyloxy, benzoyl or pyridyl; $R^{12}$ is an alkal group having 1-8 carbon atoms, an alkyl group having 1-8 carbon atoms and 1-3 halogen atom substituents, an alkenyl group having 2-8 carbon atoms, an alkynyl group having 2-8 carbon atoms, a 3-7 membered cycloalkyl group, an alkyl group having 1-8 carbon atom and a 3-7 membered substituent, or a phenylalkyl group having $C_{1-4}$ alkyl portion, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1-3 halogen substituents, $C_{1-8}$ alkoxy, $C_{1-8}$ alkoxy having 1-3 halogen substituents, phenyl, benzyl, phenyloxy, benzoyl or pyridyl; each of $X^{11}$ and $X^{12}$ independently is a bond, $S(O)_q$ in which q is an integer of 0 to 2, $C(=O)$, $C(=N-OR^{16})$ in which $R^{16}$ is H or $C_{1-8}$ alkyl; $C(=O)NH$, $NHC(=O)$, $SO_2NH$, $NHSO_2$, $CH(OR^7)$ in which $R^{17}$ is H or $C_{1-8}$ alkyl, $CH=CH$, or $C\equiv C$; $Y^1$ is an alkylene chain having 1-8 carbon atoms and optionally a $C_{1-8}$ alkyl or $C_{1-8}$ alkoxy substituent; $Z^1$ is O or S; each of $R^{13}$ and $R^{14}$ independently is an alkyl group having 1-8 carbon atoms and optionally a halogen or $C_{1-8}$ alkoxy substituent; provided that $X^{12}$ is neither O nor $S(O)_q$ when $X^{11}$ is a bond, while $X^{12}$ is not a bond when $X^{11}$ is $C(=O)NH$. Methods of synthesizing compounds of formula (III) are described in U.S. Pat. No. 6,678,552, which is incorporated herein by reference in its entirety.

In some embodiments, the PPAR-δ agonist is a thiazole derivative compound of formula (IV) and pharmaceutically acceptable salts thereof:

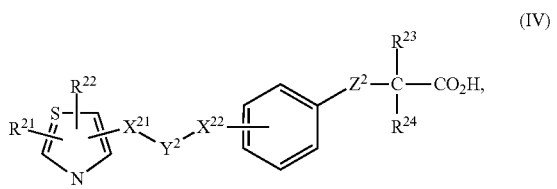

(IV)

wherein each of $R^{21}$ and $R^{22}$ independently is an alkyl group having 1-8 carbon atoms, an alkyl group having 1-8 carbon atoms and 1-3 halogen atom substituents, an alkenyl group having 2-8 carbon atoms, an alkynyl group having 2-8 carbon atoms, a 3-7 membered cycloalkyl group, an alkyl group having 1-8 carbon atom and a 3-7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1-3 halogen substituents, $C_{1-8}$ alkoxy, $C_{1-8}$ alkoxy having 1-3 halogen substituents, phenyl, benzyl, phenyloxy, benzoyl or pyridyl; each of $X^{21}$ and $X^{22}$ independently is a bond, $S(O)_r$ in which r is an integer of 0 to 2, $C(=O)$, $C(=N-OR^{26})$ in which $R^{26}$ is H or $C_{1-8}$ alkyl; $C(=O)NH$, $NHC(=O)$, $SO_2NH$, $NHSO_2$, $CH(OR^{27})$ in which $R^{27}$ is H or $C_{1-8}$ alkyl, $CH=CH$, or $C\equiv C$; $Y^2$ is an alkylene chain having 1-8 carbon atoms and optionally a $C_{1-8}$ alkyl or $C_{1-8}$ alkoxy substituent; $Z^2$ is O or S; each of $R^{23}$ and $R^{24}$ independently is an alkyl group having 1-8 carbon atoms and optionally a halogen or $C_{1-8}$ alkoxy substituent; provided that $X^{22}$ is neither O nor $S(O)_r$ when $X^{21}$ is a bond, while $X^{22}$ is not a bond when $X^{21}$ is $C(=O)NH$. Methods of synthesizing compounds of formula (IV) are described in U.S. Pat. No. 6,678,552, which is incorporated herein by reference in its entirety.

In some embodiments, the PPAR-δ agonist is a compound of formula (V):

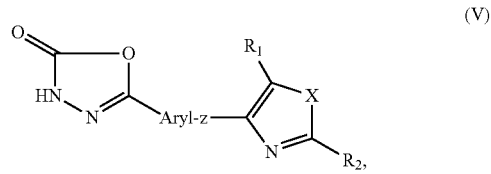

(V)

wherein ARYL is phenyl or pyridinyl, wherein said phenyl or pyridinyl is optionally substituted with one or more substituents selected from the group consisting of halogen, C1-6alkyl, C2-6alkenyl, C1-6alkoxy, C1-6perfluoroalkyl, C1-6alkylthio, hydroxy, hydroxyC1-6alkyl, C1-4acyloxy, nitro, cyano, C1-6alkylsulfonyl, amino, C1-6alkylamino and C1-6alkoxycarbonyl; Z is 0(CH2)n, SO2(CH2)n, (CH2)nY (CH2)n, (CH2)nCO, O(CH2)nCO, or (CH2)nY(C-2)nCO wherein Y is NR3, O or S and R3 is selected from the group consisting of H, C1-6alkyl, C3-8cycloalkyl, C1-6alkyl, C3-8cycloalkyl and benzyl and n is independently an integer from 1 to 5; X is NR3, O or S wherein R3 is as defined above; R1 is H, halogen, C1-6alkyl, C1-6alkoxy, C1-6perfluoroalkyl; hydroxyC16-alkyl, nitro, cyano, and C1-6alkylamino; and R2 is substituted or unsubstituted phenyl, pyridinyl or thienyl wherein the substituents are selected from the group consisting of halogen, C1-6alkyl, C2-6alkenyl, C1-6 eperfluoroalkyl, C1-6alkylthio, hydroxy, hydroxyC1-6alkyl, C1-6acyloxy, nitro, cyano, C1-6alkylsulfonyl, amino, C1-6alkylamino and C1-6alkoxycarbonyl; with the proviso that when Z is O(CH2)n or SO2(CH2)n, and ARYL is phenyl then R2 is other than phenyl; or a stereoisomer, a tautomer or a solvate thereof or a pharmaceutically acceptable salt thereof. Methods of synthesizing compounds of Formula (V) are described in PCT Publication WO/2005/097763, which is incorporated herein by reference in its entirety.

In some embodiments, the PPAR-δ agonist is a compound of formula (VI):

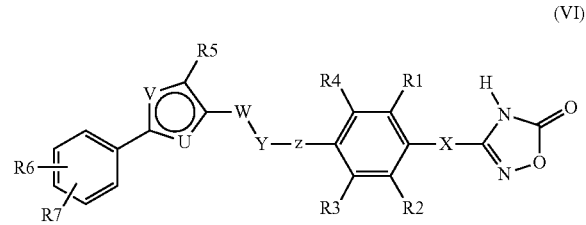

(VI)

wherein,
X is —CH$_2$ or a bond;
R$_1$, R$_2$, R$_3$ and R$_4$ are independently selected from the group comprising H, F, Cl, Br, —CF$_3$, (C$_1$-C$_4$)alkyl, (C0-C$_4$) alkylene-O—(C0-C$_4$)alkylene-H, SCH$_3$, S(O)CH$_3$, S(O)$_2$ CH$_3$, CN, —OCF$_3$, —OCHF$_2$, and —OCH$_2$F;
Z is a bond or —CH$_2$;
Y is O, —S—, —S(O) or —S(O)$_2$;
W is —CH$_2$ or —CH$_2$CH$_2$;
one of U and V is N the other is —S— or —O—;
R$_5$ is selected from the group comprising of (C$_1$-C$_8$) alkyl, (C$_1$-C$_6$)alkylene-O—(C$_0$-C$_4$) alkylene-H, (C$_0$-C$_6$)alkylene-phenyl, (C$_1$-C$_6$)alkylene-O—(C$_0$-C$_4$)alkylene-phenyl, (C$_3$-

$C_6$)cycloalkyl, ($C_2$-$C_8$)alkenyl, and where ($C_1$-$C_8$)alkyl or alkylene can be substituted 1-2 times by —OH or —O—($C_1$-$C_4$)alkyl;

$R_6$, $R_7$ are independently selected from the group comprising H, F, Br, —$CF_3$, —$OCF_3$, ($C_1$-$C_6$)alkyl, ($C_0$-$C_4$)alkylene-O—($C_0$-$C_4$)alkylene-H, —$SCF_3$, —$SF_5$, —$OCF_2$—$CHF_2$, —$OCHF_2$, —$OCH_2F$, O-phenyl, phenyl, $NO_2$;

as well as their physiologically acceptable salts and tautomeric forms. Methods of synthesizing compounds of Formula (VI) are described in PCT Publication WO2005/097786, which is incorporated herein by reference in its entirety.

In some embodiments, the PPAR-δ agonist is selected from the group consisting of 2-{2-methyl-4[({4-methyl-2-[4-(trifluoromethyl)phenyl]-1,3-rhiazol-5 yl}methyl)sulfanyl]phenoxy}acetic acid 2-{2-methyl-4[({4-methyl-2-[4-(trifluoromethyl)phenyl]-1,3-oxazol-5-yl}methyl) sulfanyl]phenoxy}acetic acid methyl 2-{4-[({4-methyl-2-[4-(trifluoromethyl) phenyl]-1, 3-thiazol-5-yl}methyl)sulfanyl]phenoxy}acetate 2-{4-[({4-methyl-2-[4-(trifluoromethyl) phenyl]-1,3-thiazol-5-yl}methyl) sulfanyl]phenoxy}acetic acid (E)-3-[2-methyl-4-(4-methyl-2-[4-(trifluoromethyl) phenyl]-1, 3-thiazol-5-<BR>yl}methoxy) phenyl]-2-propenoic acid 2-{3-chloro-4-[({4-methyl-2-[4-(trifluoromethyl) phenyl]-1,3-thiazol-5-yl}methyl) sulfanyl]phenyl}acetic acid.

In some embodiments, the PPAR-δ agonist is selected from the group consisting of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]2-methylphenoxy] acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof, as described in U.S. Publication No. 2012/0270910, which is incorporated herein by reference in its entirety.

In some embodiments, the PPAR-δ agonist is {2-methyl-4-[4-methyl-2-(4-trifluoromethyl phenyl) thiazol-5-ylmethylthio]phenoxy}-acetic acid and pharmaceutically acceptable salts, solvates, and hydrolyzable esters thereof. Exemplary physiologically acceptable salts include conventional salts formed from pharmaceutical acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like, as described in further detail in PCT Publication WO/2002/028433, which is incorporated herein by reference in its entirety.

In some embodiments, the PPAR-δ agonist is a phenoxy acetic acid compound selected from the group consisting of: (Z)-[2-Methyl-4-[3-(4-methylphenyl)-3-[4-[3-(morpholin-4-yl)propynyl]phenyl]allyloxy]-phenoxy]acetic acid; (E)-[2-Methyl-4-[3-[4-[3-(pyrazol-1-yl)prop-1-ynyl]phenyl]-3-(4-trifluoromethylphenyl)-allyloxy]phenoxy]acetic acid; (E)-[2-Methyl-4-[3-[4-[3-(morpholin-4-yl)propynyl]phenyl]-3-(4-trifluoromethylphenyl) allyloxy]-phenoxy]acetic acid; (E)-[2-Methyl-4-[3-(4-methylphenyl)-3-[4-[3-(morpholin-4-yl)propynyl]phenyl]allyloxy]-phenoxy]acetic acid; and (Z)-[2-Methyl-4-[3-[4-[3-(morpholin-4-yl)propynyl]phenyl]-3-(4-trifluoromethylphenyl) allyloxy]-phenoxy]acetic acid; or a pharmaceutically acceptable salt thereof, as described further in U.S. Pat. No. 8,551,993, which is incorporated herein by reference in its entirety.

In some embodiments, the PPAR-δ agonist is a compound of Formula (VII)

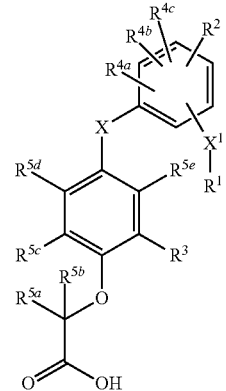

(VII)

or a pharmaceutically acceptable salt thereof, wherein:

X is selected from O, S, $OCH_2$, and $SCH_2$;

$X^1$ is O or S;

$R^1$ is selected from H, $C_{1-8}$alkyl, $C_{2-8}$alkenyl, aryl, heteroaryl, $C_{3-10}$ cycloalkyl, and a heterocyclyl, wherein each $R^1$ group is substituted with 0-4 $R^{1a}$;

$R^{1a}$, at each occurrence, is selected from S substituted with 0-1 $R^{1b}$, O substituted with 0-1 $R^{1b}$, halogen, $NH_2$ substituted with 0-2 $R^{1b}$, —CN, $NO_2$, $C_{1-6}$alkyl substituted with 0-3 $R^{1b}$, $C_{2-6}$alkenyl substituted with 0-2 $R^{1b}$, $C_{2-6}$alkynyl substituted with 0-2 $R^{1b}$, aryl substituted with 0-2 $R^{1b}$, heteroaryl substituted with 0-2 $R^{1b}$, $C_{3-10}$ cycloalkyl substituted with 0-2 $R^{1b}$, and heterocycle substituted with 0-2 $R^{1b}$;

$R^{1b}$, at each occurrence, is selected from S substituted with 0-1 $R^{1c}$, O substituted with 0-1 $R^{1c}$, halogen, methanesulfonyl, $NH_2$ substituted with 0-2 $R^{1c}$, —CN, $NO_2$, $C_{1-6}$alkyl substituted with 0-3 $R^{1c}$, $C_{2-6}$alkenyl substituted with 0-2 $R^{1c}$, aryl substituted with 0-2 $R^{1c}$, heteroaryl substituted with 0-2 $R^{1c}$, $C_{3-10}$ cycloalkyl substituted with 0-2 $R^{1c}$, and a heterocycle substituted with 0-2 $R^{1c}$;

$R^{1c}$, at each occurrence, is selected from S substituted with 0-1 $R^{1d}$, O substituted with 0-1 $R^{1d}$, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, heteroaryl substituted with 0-2 $R^{1d}$, $C_{3-10}$ cycloalkyl substituted with 0-2 $R^{1d}$, and a heterocycle substituted with 0-2 $R^{1d}$;

$R^{1d}$, at each occurrence, is selected from OH, SH, S, O, halogen, $NH_2$, —CN, $NO_2$, $C_{1-6}$ alkyl, $C_{2-6}$alkenyl, aryl, $CF_3$, and $OCF_3$;

$R^2$ is selected from —C≡C—$R^{2a}$, —CH=CH—$R^{2a}$, aryl substituted with 0-3 $R^{2a}$, and heteroaryl substituted with 0-3 $R^{2a}$;

$R^{2a}$, at each occurrence, is selected from S substituted with 0-1 $R^{2b}$, O substituted with 0-1 $R^{2b}$, halogen, $NH_2$ substituted with 0-2 $R^{2b}$, —CN, $NO_2$, $C_{1-6}$alkyl substituted with 0-2 $R^{2b}$, $C_{2-6}$alkenyl substituted with 0-2 $R^{2b}$, aryl substituted with 0-2 $R^{2b}$, heteroaryl substituted with 0-2;

$R^{2b}$, $C_{3-10}$ cycloalkyl substituted with 0-2 $R^{2b}$, and a heterocycle substituted with 0-2;

$R^{2b}$, at each occurrence, is selected from S substituted with 0-1 $R^{2c}$, O substituted with 0-1 $R^{2c}$, halogen, methanesulfonyl, $NH_2$ substituted with 0-2 $R^{2c}$, —CN, $NO_2$, $C_{1-6}$alkyl substituted with 0-2 $R^{2c}$, $C_{2-6}$alkenyl substituted with 0-2 $R^{2c}$, aryl substituted with 0-2 $R^{2c}$, heteroaryl substituted with 0-2 $R^{2c}$, $C_{3-10}$ cycloalkyl substituted with 0-2 $R^{2c}$, and a heterocycle substituted with 0-2 $R^{2c}$;

$R^{2c}$, at each occurrence, is selected from S substituted with 0-1 $R^{2d}$, O substituted with 0-1 $R^{2d}$, halogen, $NH_2$ substituted with 0-2 $R^{2d}$, —CN, $NO_2$, $C_{1-6}$alkyl substituted with 0-2 $R^{2d}$, $C_{2-6}$alkenyl substituted with 0-2 $R^{2d}$, aryl substituted with 0-2 $R^{2d}$, heteroaryl substituted with 0-2 $R^{2d}$, $C_{3-10}$ cycloalkyl substituted with 0-2 $R^{2d}$, and a heterocycle substituted with 0-2 $R^{2d}$ $R^{2d}$, at each occurrence, is selected from OH, SH, S, O, halogen, $NH_2$, —CN, $NO_2$, $C_{1-6}$ alkyl, $C_{2-6}$alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH—C_{1-4}$ alkyl, and $C(O)N(C_{1-4}$ alkyl$)_2$; alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$;

$R^{4d}$, at each occurrence, is selected from OH, O, halogen, $NH_2$, NH—$C_{1-4}$ alkyl, and N($C_{1-4}$ alkyl)$_2$;

$R^{4b}$, at each occurrence, is selected from H, halogen, and $C_{1-6}$ alkyl substituted with 0-2 $R^{4e}$;

$R^{4e}$, at each occurrence, is selected from OH, O, halogen, $NH_2$, NH—$C_{1-4}$alkyl, and N($C_{1-4}$ alkyl)$_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and N($C_{1-4}$ alkyl)$_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$. Methods of synthesizing compounds of Formula (VII) are described in U.S. Pat. No. 8,217,086, which is incorporated herein by reference in its entirety.

In some embodiments, the PPAR-δ agonist is a compound of Formula (VIII) or a salt thereof:

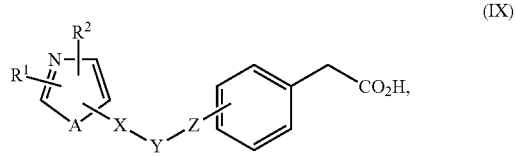

(VIII)

wherein:

$R^1$ is phenyl, naphthyl, pyridyl, thienyl, furyl, quinolyl or benzothienyl, any of which can have substituents selected from the group consisting of $Cj_{-8}$alkyl, $C_{1-8}$alkyl having halogen, $C_{1-8}$alkoxy, $Cl_{-8}$alkoxy having halogen, $C_{2-8}$alkenyl, $C_{2-8}$alkynyl, halogen, $C_{2-7}$acyl, benzoyl, hydroxyl, nitro, amino, phenyl and pyridyl;

$R^2$ is $Ci_{-8}$alkyl, $Ci_{-8}$alkyl having halogen, $C_{2-8}$alkenyl, $C_{2-8}$alkynyl, 3-7 membered cycloalkyl, $Ci_{-8}$alkyl having 3-7 membered cycloalkyl, or $Ci_{-6}$alkyl substituted with phenyl, naphthyl or pyridyl, any of which can have substituents selected from the group consisting of $Ci_{-8}$alkyl, $Ci_{-8}$alkyl having halogen, $Ci_{-8}$alkoxy, $Ci_{-8}$alkoxy having halogen, $C_{2-8}$alkenyl, $C_{2-8}$alkynyl, halogen, $C_{2-7}$acyl, benzoyl, hydroxyl, nitro, amino, phenyl and pyridyl;

A is oxygen, sulfur or $NR^9$ in which $R^9$ is hydrogen or $Cj_{-8}$alkyl; X is a $Ci_{-8}$alkylene chain which can have substituents selected from the group consisting Of $Ci_{-8}$alkyl, $Ci_{-8}$alkoxy and hydroxyl and which can contain a double bond;

Y is C(=O), C(=N—$OR^{10}$), CH($OR^{11}$), CH=CH, C—C, or C(=$CH_2$) in which each of $R^{10}$ and $R^{11}$ is hydrogen or $Ci_{-8}$alkyl; each of $R^3$, $R^4$ and $R^5$ is hydrogen, $Ci_{-8}$alkyl, $Ci_{-8}$alkyl having halogen, $Ci_{-8}$alkoxy, $Ci_{-8}$alkoxy having halogen, $C_{2-8}$alkenyl, $C_{2-8}$alkynyl, halogen, $Qi_{-7}$ acyl, benzoyl, hydroxyl, nitro, amino, phenyl, or pyridyl;

B is CH or nitrogen;

Z is oxygen or sulfur; each of $R^6$ and $R^7$ is hydrogen, $Ci_{-8}$alkyl, $Ci_{-8}$alkyl having halogen; $R^8$ is hydrogen or $Ci_{-8}$alkyl; provided that at least one of $R^3$, $R^4$ and $R^5$ is not hydrogen;

or formula (IX) or a salt thereof:

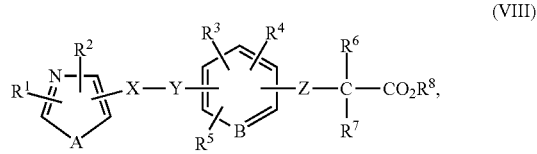

(IX)

wherein: each of $R^1$ and $R^2$ independently is a hydrogen atom, a halogen atom, nitro, an alkyl group having 1-8 carbon atoms, an alkoxy group having 1-8 carbon atoms, an alkyl group having 1-8 carbon atoms which has 1 to 3 halogen substituents, an alkoxy group having 1-8 carbon atoms which has 1 to 3 halogen substituents, an alkenyl group having 2-8 carbon atoms, an alkynyl group having 2-8 carbon atoms, a 3-7 membered cycloalkyl group, an alkyl group having 1-8 carbon atom which has a 3-7 membered cycloalkyl substituent, an aryl group having 6-10 carbon atoms which optionally has a substituent, an arylalkyl group which has a $C_{6-1}$0 aryl portion and $Ci_{-8}$alkyl portion, a heterocyclic group which optionally has a substituent or a heterocyclic-alkyl group having an alkyl group of 1-8 carbon atoms;

A is an oxygen atom, a sulfur atom, or $NR^3$ in which $R^3$ is a hydrogen atom or an alkyl group having 1-8 carbon atoms; each of X and Z independently is —C(=O)—, —C(O)NH—, —C(=N-$0R^4$)—, —CH($OR^5$)—, —NH(C=O)—, —NHSO$_2$—, —SO$_2$NH—, —CH=CH—, —C≡C—, or a bond in which each of $R^4$ and $R^5$ is a hydrogen atom or an alkyl group having 1-8 carbon atoms; Y is an alkylene chain having 1-8 carbon atoms;

or formula (X) or a salt thereof:

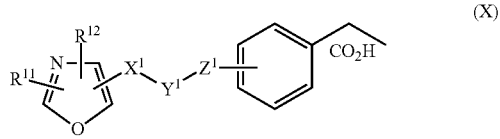

(X)

wherein: each of $R^{11}$ and $R^{12}$ independently is a hydrogen atom, a halogen atom, nitro, hydroxyl, amino, an alkyl group having 1-8 carbon atoms, an alkoxy group having 1-8 carbon atoms, an alkyl group having 1-8 carbon atoms which has 1 to 3 halogen substituents, an alkoxy group having 1-8 carbon atoms which has 1 to 3 halogen substituents, an alkenyl group having 2-8 carbon atoms, an alkynyl group having 2-8 carbon atoms, a 3-7 membered cycloalkyl group, an alkyl group having 1-8 carbon atoms which has a 3-7 membered cycloalkyl substituent, or a phenyl, naphthyl, benzyl, phenethyl, pyridyl, thienyl, furyl, quinolyl, or benzothienyl group which optionally has a substituent selected from the group consisting of a halogen atom, nitro, hydroxyl, amino, an alkyl group having 1-8 carbon atoms, an alkoxy group having 1-8 carbon atoms, an alkyl group having 1-8 carbon atoms which has 1 to 3 halogen substituents, an alkoxy group having 1-8 carbon atoms which has 1 to 3 halogen substituents, an alkenyl group having 2-8 carbon atoms, an alkynyl group having 2-8 carbon atoms, a 3-7 membered cycloalkyl group, an alkyl group having 1-8 carbon atoms which has a 3-7 membered cycloalkyl substituent, phenyl and pyridyl; each of $X^1$ and $Z^1$ independently is —C(=O)-, —C(O)NH—, —C(=N-O$R^{14}$)—, —CH(O$R^{15}$)—, —NH (C=O)—, —NHSO$_2$—, —SO$_2$NH—, —CH=CH—, —C≡C—, or a bond in which each of $R^{14}$ and $R^{15}$ is a hydrogen atom or an alkyl group having 1-8 carbon atoms; $Y^1$ is an alkylene chain having 1-8 carbon atoms; or formula (XI) or a salt thereof:

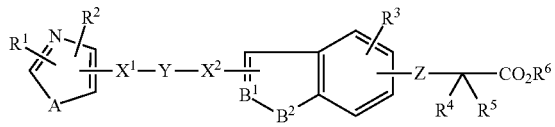

(XI)

wherein:
A is O, S or N$R^7$ in which $R^7$ is hydrogen or C$_{1-8}$alkyl;
$B^1$ is CW or N in which W is hydrogen or a bond; $B^2$ is O, S or N$R^8$ in which $R^8$ is hydrogen or C$_{1-8}$alkyl; each of $X^1$ and $X^2$ is O, S, NH, NHC(=O), C(=O), C(=N-O$R^9$), CH(O$R^{10}$), C=C, C≡C or a bond in which each of $R^9$ and $R^{10}$ is hydrogen or C$_{1-8}$alkyl;
Y is a C$_{1-8}$alkylene chain, which can be substituted with C$_{i-8}$alkyl or C$_{j-8}$alkyl substituted with 1-3 halogens; Z is NH, O or S;
$R^1$ is aryl, which can be substituted with a group or atom selected from the group consisting Of C$_{i-8}$alkyl, C$_{i-8}$alkoxy, C$_{i-8}$alkyl substituted with 1-3 halogens, hydroxyl, nitro, amino, phenyl, pyridyl and halogen, or a heterocyclic group having five to eight membered ring comprising one to three hetero atoms selected from the group consisting of nitrogen, oxygen and sulfur and the other atoms consisting of carbon (benzene ring can be condensed with the heterocyclic ring);

$R^2$ is C$_{2-8}$alkyl, C$_{i-8}$alkyl substituted with 1-3 halogens, C$_{3-7}$cycloalkyl, C$_{2-8}$alkenyl, C$_{2-8}$alkynyl, alkyl (comprising C$_{i-4}$alkyl moiety) substituted with aryl, which can be substituted with a group or atom selected from the group consisting of C$_{i-8}$alkyl, C$_{i-8}$alkoxy, C$_{i-8}$alkyl substituted with 1-3 halogens, hydroxyl, nitro, amino, phenyl, pyridyl and halogen, or alkyl (comprising C$_{i-4}$alkyl moiety) substituted with a heterocyclic group having five to eight membered ring (comprising one to three hetero atoms selected from the group consisting of nitrogen, oxygen and sulfur and the other atoms consisting of carbon);
$R^3$ is halogen, trifluoromethyl, C$_{1-8}$alkyl, C$_{2-8}$alkenyl or C$_{2-8}$alkynyl; each of $R^4$ and $R^5$ is hydrogen, C$_{1-8}$alkyl or C$_{1-8}$alkyl substituted with 1-3 halogens; and $R^6$ is hydrogen, C$_{1-8}$alkyl substituted with amino, C$_{1-8}$alkyl or alkali metal; provided that each of Z and $R^3$ is attached to the benzene ring, and $X^2$ is not attached to the benzene ring. Methods of synthesizing compounds of Formulas VIII-XI are described in further detail in PCT Publication WO/2008/154023, which is incorporated herein by reference in its entirety.

In some embodiments, the PPAR-δ agonist comprises 2-[2-methyl-4-[[4-methyl-2-[4-(trifluoromethyl)phenyl]-1,3-thiazol-5-yl]methylsulfanyl]phenoxy]acetic acid (GW501516) or an analog or derivative thereof.

In some embodiments, the PPAR-δ agonist comprises GW 0742 CAS #[317318-84-6]. In some embodiments, the PPAR-δ agonist comprises L-165,041 CAS #[79558-09-1]. In some embodiments, the PPAR-δ agonist comprises CER-002 (being commercially developed by CERENIS Therapeutics).

In some embodiments, the PPAR-δ agonist comprises a polyunsaturated fatty acid (PUFA). It has been reported that PUFAs activate PPAR-δ with micromolar affinity. As used herein, "PUFA" is used in its generally accepted meaning; it relates to fatty acids with at least 2 carbon-carbon double bonds (preferably 2 to 6, more preferably 4 or 5 or 6 carbon-carbon double bonds), preferably consisting of 16-24 carbon atoms (preferably 18-22 carbon atoms), and comprise n-3, n-6 and n-9 acids. Although the term PUFA defines free acids it is generally understood to also mean their salts and these acids in the form of their naturally occurring esters, i.e. as glycerides (comprising mono-, di- and triglycerides) and in form of esters into which they are converted, e.g. by transesterification, such as ethyl esters. PUFAs of preferred interest in the context of the present invention are n-3 and n-6 PUFAs, especially EPA (eicosapenta-5,8,11,14, 17-enoic acid), DPA (docosapentaenoic acid), DHA (docosahexa-4,7,10,13,16,19-enoic acid), GLA (-linolenic acid) and ARA (arachidonic acid), and stearidonic acid (cis-6,9, 12,15-octadecatetraenoic acid; SDA), preferably of food-grade quality, as single compounds or in mixtures, preferably in the form of their esters, e.g., triglycerides, or ethyl esters, especially as components of oils obtained from marine animals, preferably from fish, from plants or by fermentation. They can be stabilized and/or deodorized by methods known in the art, e.g., by addition of antioxidants, emulsifiers, spices or herbs, such as rosemary or sage extracts. Edible oils and fat compositions comprising PUFAs are generally regarded as safe for human consumption.

In some embodiments, the PPAR-δ agonist is a SCPUFA listed in Table 1.

In some embodiments, the PPAR-δ agonist is a LCPUFA listed in Table 2.

Saturated C16 and C18 fatty acids e.g. Palmitic and Stearic acids occur both in animal and plant derived fats and can be desaturated by mammals. For example Stearic acid is desaturated in mammals to give oleic acid (C18:1 ω9). The marine PUFAs e.g. EPA, DPA and DHA, by way of contrast, contain long chain fatty acids with a carbon chain length of C20-22 respectively. Mammals, and in particular humans, cannot produce the LCPUFAs by further de-saturation of ω-9 fatty acids, nor chain-elongate ω3 and ω6 plant derived fatty acids efficiently. These LCPUFAs can be obtained from diet, and marine lipids are a suitable economic source.

In some embodiments, the PPAR-δ agonist comprises an eicosanoid. It has been reported that eicosanoids activate PPAR-δ with micromolar affinity. Exemplary eicosanoids include, without limitation, PGAI, its semisynthetic analog (cPGI), and PGE2.

In some embodiments, the agent that increases the level and/or activity of PPAR-δ and/or a PPAR-δ target protein comprises an agonist of a transcriptional coactivator to PPAR-δ (e.g., an agonist of PGC1 alpha).

In some embodiments, the agent that increases the level and/or activity of PPAR-δ and/or a PPAR-δ target protein comprises an agonist of a binding partner to PPAR-δ that heterodimerizes with PPAR-δ to form a transcription factor complex that binds to cognate sequences in promoter regions of PPAR-δ target genes (e.g., an agonist or ligand for retinoid X receptor (RXR).

In some embodiment, the agent that increases the level and/or activity of PPAR-δ and/or a PPAR-δ target protein comprises an inhibitor of a transcriptional repressor of PPAR-δ and/or RXR. The term "inhibitor" encompasses agents that inhibit (decrease, reduce) the expression or activity of a target. The term "inhibitor" encompasses agents that inhibit expression and/or inhibit one or more activities of a molecule or complex of interest (the "target"). For example, in various embodiments an agent is an "inhibitor" of a target if one or more activities of the target is reduced in the presence of the compound, or as a consequence of its use, as compared with in the absence of the compound, and/or if the level or amount of the target is reduced in the presence of the compound, or as a consequence of its use, as compared with in the absence of the compound. In certain embodiments, an inhibitor acts directly on a target in that it physically interacts with the target. In some embodiments, an inhibitor acts indirectly, e.g., by inhibiting a second molecule that is needed for synthesis or activity of the target. In some embodiments, an inhibitor is an antagonist. Methods of inhibiting encompass methods that result in a decreased amount of a target and methods that interfere with one or more functions (activities) of a target. In some embodiments, a target is inhibited by inhibiting or interfering with its expression or post-translational processing, so that a decreased amount of functional target is produced, resulting in a decreased overall activity of the target in a cell or system. A variety of methods useful for inhibiting or interfering with expression can be used in various embodiments. In general, such methods result in decreased synthesis of a mRNA and/or polypeptide and as a result, a reduction in the total level of activity present. Other means of inhibition include interfering with proper localization, secretion, or co- or post-translational processing, or promoting increased degradation. Methods of inhibiting activity can include binding to a target or to a receptor or co-receptor for the target and thereby blocking the target from interacting with its receptor(s) or with other molecule(s) needed for activity of the target. In some embodiments an inhibitor binds to an active site or catalytic residue or substrate binding site of an enzyme or blocks dimerization or other protein-protein interactions, etc. For example, in some embodiments a protein that acts as a dimer is inhibited using an agent that blocks dimerization. In some embodiments, an inhibitor comprises an RNAi agent, e.g., an siRNA or shRNA, or an antisense oligonucleotide, that inhibits expression of a target. In some embodiments, an inhibitor comprises an antibody or aptamer or small molecule that binds to and inhibits a target. In some embodiments an inhibitor comprises an agent that acts in a dominant negative fashion to inhibit a target. A dominant negative agent may comprise a fragment of a target molecule that lacks one or more domains necessary for function. For example, in some embodiments a dominant negative form of a TF comprises a DNA binding domain and/or dimerization domain but lacks an activation domain. In some embodiments, the agent that increases the level and/or activity of PPAR-δ and/or a PPAR-δ target protein comprises an inhibitor of degradation of PPAR-δ protein and/or a PPAR-δ target protein.

In some embodiments, the agent comprises GW501516 or an analog or derivative thereof.

Exemplary analogs and/or derivatives of GW50156 may be found in the following U.S. patents and/or published U.S. applications Ser. No.: U.S. Pat. Nos. 7,084,161, 7,091,225, 7,091,237, 7,105,551, 7,176,204, 6,710,063, 6,723,740, 6,518,290, US2009149519, US2011245263, US2010240580, US2012004165, US2012004166, US2012004167, US2012004187, US2012015936, US2012022039, US201112097, US2011118321, US2011178134, US2011183998, US2011207738, US2011224263, U.S. Pat. Nos. 7,683,181, 7,709,481, 7,709, 490, 7,709,494, 7,713,988, 7,718,669, 7,732,440, 7,759,366, 7,772,257, 7,772,268, 7,834,030, 7,851,493, 7,855,289, 7,858,647, 7,229,998, 7,345,178, 7,439,259, 7,449,468, 8,044,198, 8,088,928, 8,093,401, 8,101,583, 8,106,023, 8,148,375, 8,148,395, 8,163,908, 8,173,674, 8,178,536, 8,207,146, 7,897,616, 7,897,625, 7,910,612, 7,923,468, 7,956,085, 7,982,050, 7,612,104, 7,648,999, 7,652,045, 7,655,679, 7,241,901, 7,265,137, US2004242459, US2007149580, US2007179300, US2007190079, US2010249097, US2010261645, US2010286133, US2010331295, US2011046105, US2011053947, US2011059910, US2010105719, US2010152246, US2010190801, US2009163481, US2009203908, US2009240058, US2009264402, US2009264403, US2009298896, US2010029949, US2007249519, US2008274947, US2008287409, US2009012133, US2009076002, US2009082339, US2009082391, US2007037865, US2004029938, US2004072838, US2003077298, US2003171377, U.S. Pat. Nos. 8,236,831, 8,003,636, 8,003,677, each of which are incorporated herein by reference in their entirety.

In some embodiments, the agent that increases the level and/or activity of PPAR-δ and/or a PPAR-δ target protein is a nucleic acid sequence that encodes PPAR-δ. In some embodiments, the agent that increases the level and/or activity of the PPAR-δ target protein is a nucleic acid encoding the PPAR-δ target protein. In some embodiments, the agent comprises a nucleic acid encoding CPT1A. In some embodiments, the agent comprises a nucleic acid encoding HMGCS2. In some embodiments, the agent comprises a nucleic acid encoding FABP1.

"Nucleic acid" is used interchangeably with "polynucleotide" and encompasses polymers of nucleotides. "Oligonucleotide" refers to a relatively short nucleic acid, e.g., typically between about 4 and about 100 nucleotides (nt) long, e.g., between 8-60 nt or between 10-40 nt long. Nucleotides include, e.g., ribonucleotides or deoxyribonucleotides. In some embodiments a nucleic acid comprises or consists of DNA or RNA. In some embodiments a nucleic acid comprises or includes only standard nucleobases (often referred to as "bases"). The standard bases are cytosine, guanine, adenine (which are found in DNA and RNA), thymine (which is found in DNA) and uracil (which is found in RNA), abbreviated as C, G, A, T, and U, respectively. In some embodiments a nucleic acid may comprise one or more non-standard nucleobases, which may be naturally occurring or non-naturally occurring (i.e., artificial; not found in nature) in various embodiments. In some embodiments a nucleic acid may comprise chemically or biologically modified bases (e.g., alkylated (e.g., methylated) bases), modified sugars (e.g., 2'-O-alkyribose (e.g., 2'-O methylribose), 2'-fluororibose, arabinose, or hexose), modified phosphate groups (e.g., phosphorothioates or 5'-N-phosphoramidite linkages). In some embodiments a nucleic acid comprises subunits (residues), e.g., nucleotides, that are linked by phosphodiester bonds. In some embodiments, at least some subunits of a nucleic acid are linked by a non-phosphodiester bond or other backbone structure. In some embodiments, a nucleic acid comprises a locked nucleic acid, morpholino, or peptide nucleic acid. A nucleic acid may be linear or circular in various embodiments. A nucleic acid may be single-stranded, double-stranded, or partially double-stranded in various embodiments. An at least partially double-stranded nucleic acid may be blunt-ended or may have one or more overhangs, e.g., 5' and/or 3' overhang(s). Nucleic acid modifications (e.g., base, sugar, and/or backbone modifications), non-standard nucleotides or nucleosides, etc., such as those known in the art as being useful in the context of RNA interference (RNAi), aptamer, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, ST (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. It will be appreciated that naturally-occurring allelic variants of the reference sequence for a particular nucleic acid or protein may exist in the population, and such variants may be used in certain embodiments. It will also be appreciated that variants arising due to alternative splicing may exist, which are encompassed herein in various embodiments.

In some embodiments, the agent that increases the level and/or activity of PPAR-δ and/or a PPAR-δ target protein is a functional fragment of a nucleic acid sequence that encodes PPAR-δ. In some embodiments, the agent that increases the level and/or activity of the PPAR-δ target protein is a functional fragment of a nucleic acid sequence that encodes the PPAR-δ target protein. In some embodiments, the agent comprises a functional fragment of a nucleic acid sequence that encodes CPT1A. In some embodiments, the agent comprises a functional fragment of a nucleic acid sequence that encodes HMGCS2. In some embodiments, the agent comprises a functional fragment of a nucleic acid sequence that encodes FABP1.

In some embodiments, the agent that increases the level and/or activity of PPAR-δ and/or a PPAR-δ target protein is a variant of a nucleic acid sequence that encodes PPAR-δ. In some embodiments, the agent that increases the level and/or activity of the PPAR-δ target protein is a variant of a nucleic acid sequence that encodes the PPAR-δ target protein. In some embodiments, the agent comprises a variant of a nucleic acid sequence that encodes CPT1A. In some embodiments, the agent comprises a variant of a nucleic acid sequence that encodes HMGCS2. In some embodiments, the agent comprises a variant of a nucleic acid sequence that encodes FABP1.

In some embodiments, the agent that increases the level and/or activity of PPAR-δ and/or a PPAR-δ target protein is a sequence that is homologous to a nucleic acid sequence that encodes PPAR-δ. In some embodiments, the agent that increases the level and/or activity of the PPAR-δ target protein is a sequence that is homologous to a nucleic acid sequence that encodes the PPAR-δ target protein. In some embodiments, the agent comprises a sequence that is homologous to a nucleic acid sequence that encodes CPT1A. In some embodiments, the agent comprises a sequence that is homologous to a nucleic acid sequence that encodes HMGCS2. In some embodiments, the agent comprises a sequence that is homologous to a nucleic acid sequence that encodes FABP1.

In some embodiments, the agent that increases the level and/or activity of PPAR-δ and/or the PPAR-d target protein is a PPAR-δ protein. In some embodiments, the agent that increases the level and/or activity of the PPAR-δ target protein is a PPAR-δ target protein. In some embodiments, the agent comprises a CPT1A protein. In some embodiments, the agent comprises a HMGCS2 protein.

A "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. In some embodiments, a non-standard, naturally occurring amino acid is found in mammals. For example, ornithine, citrulline, and homocysteine are naturally occurring non-standard amino acids that have important roles in mammalian metabolism. Exemplary non-standard amino acids include, e.g., singly or multiply halogenated (e.g., fluorinated) amino acids, D-amino acids, homo-amino acids, N-alkyl amino acids (other than proline), dehydroamino acids, aromatic amino acids (other than histidine, phenylalanine, tyrosine and tryptophan), and α,α disubstituted amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, etc. Modifications may occur anywhere in a polypeptide, e.g., the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like. Modification may occur prior to or after an amino acid is incorporated into a polypeptide in various embodiments. Polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing. One of ordinary skill in the art will understand that a protein may be composed of a single amino acid chain or multiple chains associated covalently or noncovalently.

In some embodiments, the agent that increases the level and/or activity of PPAR-δ and/or the PPAR-δ target protein is a functional domain or fragment of PPAR-δ protein. In some embodiments, the agent that increases the level and/or activity of the PPAR-δ target protein is a functional domain or fragment of the PPAR-δ target protein. In some embodiments, the agent comprises a functional domain or fragment of CPT1A protein. In some embodiments, the agent comprises a functional domain or fragment of HMGCS2 protein. In some embodiments, the agent comprises a functional domain or fragment of FABP1 protein.

In some embodiments, the agent that increases the level and/or activity of PPAR-δ and/or the PPAR-δ target protein is a functional homolog of PPAR-δ protein. In some embodiments, the agent that increases the level and/or activity of the PPAR-δ target protein is a functional homolog of the PPAR-δ target protein. In some embodiments, the agent comprises a functional homolog of CPT1A protein. In some embodiments, the agent comprises is a functional homolog of HMGCS2 protein. In some embodiments, the agent comprises is a functional homolog of FABP1 protein.

In some embodiments, the agent that increases the level and/or activity of PPAR-δ and/or the PPAR-δ target protein is a fusion protein comprising PPAR-δ protein. In some embodiments, the agent that increases the level and/or activity of the PPAR-δ target protein is a fusion protein comprising the PPAR-δ target protein. In some embodiments, the agent is a fusion protein comprising CPT1A protein. In some embodiments, the agent is a fusion protein comprising HMGCS2 protein. In some embodiments, the agent is a fusion protein comprising FABP1 protein.

A "variant" of a particular polypeptide or polynucleotide has one or more alterations (e.g., additions, substitutions, and/or deletions, which may be referred to collectively as "mutations") with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polynucleotide hybridizes to an original polynucleotide under stringent conditions, e.g., high stringency conditions, for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the original polypeptide over at least 20%, 30%, 40%, 50%, 60%, 70%, 80%, 90%, 95%, 96%, 97%, 98%, 99%, or 100% of the original polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the original polypeptide over at least 20%, 30%, 40%, 50%, 60%, 70%, 80%, 90%, 95%, 96%, 97%, 98%, 99%, or 100% of the original polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to an original sequence, wherein N is any integer between 1 and 10 or between 1 and 20 or any integer up to 1%, 2%, 5%, or 10% of the number of amino acids in the original polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
|---|---|---|
| | | I L V |
| | Polar - uncharged | C S T M |
| | | N Q |

TABLE A-continued

| | Polar - charged | D E K R |
| --- | --- | --- |
| Aromatic | | H F W Y |

It should be appreciated that the nucleic acids and proteins of the present invention (e.g., PPAR-δ, CPT1A, HMGCS2, and variants, homologs, and functional fragments thereof) can include stability and expression enhancing modifications. Suitable stability and expression enhancing modifications are apparent to those of ordinary skill in the art.

CPT1A Agonists

In some embodiments, a PPAR-δ target protein agonist comprises a CPT1A agonist. In some embodiments, the CPT1A agonists comprise high fat diet mimetics. Without wishing to be bound by theory, it is also believed that high fat diet stimulates proliferation and/or self-renewal of intestinal stem cells and/or enhances the number and/or function of non-stem progenitor cells, and/or promotes regeneration of mammalian intestinal tissue, in part, by increasing the level and/or activity of CPT1A or a product of CPT1A (e.g., in mammals, e.g., in mammalian intestinal stem cells and/or non-stem intestinal progenitor cells). Accordingly, in some embodiments, the high fat diet mimetic comprises an agent that increases the level and/or activity of CPT1A or a product of CPT1A.

In some embodiments, the CPT1A agonist stimulates proliferation and/or self-renewal of intestinal stem cells, e.g., by at least about 5%, 10%, 15%, 20%, 25%, 30%, 35%, 40%, 45%, 50%, 55%, 60%, 65%, 70%, 75%, 80%, 85%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation and/or self-renewal of intestinal stem cells in the absence of treatment with a CPT1A agonist. In some embodiments, the CPT1A agonist stimulates proliferation of non-stem intestinal progenitor cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation of non-stem intestinal progenitor cells in the absence of treatment with the CPT1A agonist.

Exemplary CPT1A agonists include, without limitation, nucleic acids encoding CPT1A, functional fragments of nucleic acid sequences that encode CPT1A, variants of nucleic acid sequences that encode CPT1A, nucleic acid sequences homologous to nucleic acid sequences that encode CPT1A, CPT1A proteins, functional domains or fragments of CPT1A proteins, functional homologs of CPT1A proteins, and fusion proteins comprising CPT1A protein, or a functional domain, fragment, or homolog of CPT1A protein.

HMGCS2 Agonists

In some embodiments, a PPAR-δ target protein agonist comprises a HMGCS2 agonist. In some embodiments, the HMGCS2 agonists comprise high fat diet mimetics. Without wishing to be bound by theory, it is also believed that high fat diet stimulates proliferation and/or self-renewal of intestinal stem cells and/or enhances the number and/or function of non-stem progenitor cells, and/or promotes regeneration of mammalian intestinal tissue, in part, by increasing the level and/or activity of HMGCS2 or a product of HMGCS2 (e.g., in mammals, e.g., in mammalian intestinal stem cells and/or non-stem intestinal progenitor cells, etc.). Accordingly, in some embodiments, the high fat diet mimetic comprises an agent that increases the level and/or activity of HMGCS2 or a product of HMGCS2 as described herein.

In some embodiments, the HMGCS2 agonist stimulates proliferation and/or self-renewal of intestinal stem cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation and/or self-renewal of intestinal stem cells in the absence of treatment with a HMGCS2 agonist. In some embodiments, the HMGCS2 agonist stimulates proliferation of non-stem intestinal progenitor cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 11 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation of non-stem intestinal progenitor cells in the absence of treatment with the HMGCS2 agonist.

Exemplary HMGCS2 agonists include, without limitation, nucleic acids encoding HMGCS2, functional fragments of nucleic acid sequences that encode HMGCS2, variants of nucleic acid sequences that encode HMGCS2, nucleic acid sequences homologous to nucleic acid sequences that encode HMGCS2, HMGCS2 proteins, functional domains or fragments of HMGCS2 proteins, functional homologs of HMGCS2 proteins, and fusion proteins comprising HMGCS2 protein, or a functional domain, fragment, or homolog of HMGCS2 protein.

FABP1 Agonists

In some embodiments, a PPAR-δ target protein agonist comprises a FABP1 agonist. In some embodiments, the FABP1 agonists comprise high fat diet mimetics. Without wishing to be bound by theory, it is also believed that high fat diet stimulates proliferation and/or self-renewal of intestinal stem cells and/or enhances the number and/or function of non-stem progenitor cells, and/or promotes regeneration of mammalian intestinal tissue, in part, by increasing the level and/or activity of FABP1 (e.g., in mammals, e.g., in mammalian intestinal stem cells and/or non-stem intestinal progenitor cells, etc.). Accordingly, in some embodiments, the high fat diet mimetic comprises an agent that increases the level and/or activity of FABP1 as described herein.

In some embodiments, the FABP1 agonist stimulates proliferation and/or self-renewal of intestinal stem cells, e.g., by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation and/or self-renewal of intestinal stem cells in the absence of treatment with a FABP1 agonist. In some embodiments, the FABP1 agonist stimulates proliferation of non-stem intestinal progenitor cells, e.g., by at least about 5%, 10%, 15%, 20%, 25%, 30%, 35%, 40%, 45%, 50%, 55%, 60%, 65%, 70%, 75%, 80%, 85%, 95%, 96%, 97%, 98%, 99%, 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold, 9 fold, 10 fold, 20 fold, 25 fold, 33 fold, 40 fold, 50 fold, 66 fold, 70 fold, 80 fold, 90 fold, 100, or 1000 fold or more relative to the level of proliferation of non-stem intestinal progenitor cells in the absence of treatment with the FABP1 agonist.

Exemplary FABP1 agonists include, without limitation, nucleic acids encoding FABP1, functional fragments of nucleic acid sequences that encode FABP1, variants of nucleic acid sequences that encode FABP1, nucleic acid sequences homologous to nucleic acid sequences that encode FABP1, FABP1 proteins, functional domains or fragments of FABP1 proteins, functional homologs of FABP1 proteins, and fusion proteins comprising FABP1 protein, or a functional domain, fragment, or homolog of FABP1 protein.

Calorie Restriction Mimetics

Aspects of the methods described herein can be used in combination with one or more methods, compositions, and or agents (e.g., a calorie restriction mimetic, a calorie restriction regimen, an agent that inhibits the level and/or activity of mTORC1, a radioprotective agent, etc.) described in PCT Application Publication WO2013/152120, "COMPOSITIONS AND METHODS FOR PROMOTING INTESTINAL STEM CELL FUNCTION", which is incorporated herein by reference in its entirety.

Accordingly, aspects of the present disclosure involve using calorie and/or a calorie restriction mimetic in combination with a high fat diet, a high fat diet mimetic and/or an agent that increases the level and/or activity of PPAR-δ or a PPAR-δ target protein to stimulate proliferation and/or self-renewal of intestinal stem cells and/or enhance the number and/or function of non-stem intestinal progenitor cells and/or stimulate proliferation and/or preserve the morphology of Paneth cells, and/or promote regeneration of mammalian intestinal tissue, e.g., to treat a gastrointestinal disorder, and/or an affliction characterized by intestinal atrophy, and/or to minimize the risk of exposure to ionizing radiation, and/or treat the harmful effects of exposure to ionizing radiation, and/or to increase an individual's tolerance to ionizing radiation, and/or in combination with radiotherapy, proton therapy, immunotherapy, and/or chemotherapy to protect against drug-induced gastrointestinal injury and or exposure to ionizing radiation.

Without wishing to be bound by theory, it is believed that employing a combination of (a) any combination of one or more of (i) a calorie restriction mimetic, (ii) a calorie restriction regimen, and/or (iii) an agent that inhibits the level and/or activity; and (b) any combination of one or more of (i) a high fat diet, (ii) a high fat diet mimetic, and/or (iii) an agent that increases the level and/or activity of PPAR-δ or a PPAR-δ target protein, provides a synergistic effect in enhancing mammalian intestinal stem cell function, e.g., stimulating the proliferation and/or self-renewal of intestinal stem cells, enhancing the number and/or function of non-stem intestinal progenitor cells, stimulating the proliferation of and/or preserving the morphology of Paneth cells, and promoting intestinal regeneration.

As used herein, "calorie restriction mimetic" refers to an agent that attempts to reproduce one or more of the physiological effects that calorie restriction has on a mammal. As used herein, "calorie restriction" (CR), refers to the protocol of reducing caloric intake while maintaining adequate nutrition of a mammal. Without wishing to be bound by theory, it is believed that CR stimulates proliferation and self-renewal of intestinal stem cells, in part, by inhibiting the level and/or activity of mTORC1 in Paneth cells. In some embodiments, the calorie restriction mimetic comprises an agent that inhibits the level and/or activity of mTORC1. In some embodiments, the calorie restriction mimetic comprises an agent that increases the level and/or activity of Bst1 or a product of Bst1.

Exemplary calorie restriction mimetics include, without limitation, sirolimus (aka rapamycin) and rapalogs thereof. Exemplary rapalogs include, without limitation, temsirolimus, everolimus, and ridaforolimus. In some embodiments, the calorie restriction mimetic comprises a sirolimus analog having a compound of any one of Formula (V), Formula (VI), and Formula (VII), as described in PCT Application Publication WO2013/152120. Additional exemplary agents that inhibit the level and/or activity of mTORC1 include, without limitation, biguanidines, Rag GTPAse inhibitors, agents that phenocopy TSC1, and/or TSC2, AMPK activators.

In some embodiments, the contacting occurs in vitro or ex vivo. For in vitro methods, populations of cells in mammalian intestinal tissue can be obtained from different sources. For example, intestinal stem cells and/or non-stem intestinal progenitor cells can be obtained from a subject, or derived from non intestinal cells from a subject. In some embodiments, an intestinal stem cell and/or non-stem intestinal progenitor cell is a whole cell.

In some embodiments, the contacting occurs in vivo in a subject. For in vivo methods, a therapeutically effective amount of an agent or composition described herein can be administered to a subject. Methods of administering compounds to a subject are known in the art and easily available to one of skill in the art.

In some embodiments, the subject is suffering from or at risk of developing a gastrointestinal disorder. In some embodiments, the subject is suffering from or at risk of developing inflammatory bowel disease. In some embodiments, the subject is suffering from or at risk of developing infectious colitis. In some embodiments, the subject is suffering from or at risk of developing ischemic colitis. In some embodiments, the subject is suffering from or at risk of developing inflammatory colitis. In some embodiments, the subject is suffering from or at risk of developing ulcerative colitis. In some embodiments, the subject is suffering from or at risk of developing Crohn's disease. In some embodiments, the subject is selected for treatment of a gastrointestinal disorder selected from the group consisting of inflammatory bowel disease, infectious colitis, ischemic colitis, and inflammatory colitis. In some embodiments, the method further comprises determining that the subject is in need of treatment for a gastrointestinal disorder, e.g., that the subject is in need of treatment for inflammatory bowel disease (e.g., Crohn's disease and/or ulcerative colitis), infectious colitis, ischemic colitis, and inflammatory colitis.

In some embodiments, the subject is suffering from or at risk of developing an affliction characterized by intestinal atrophy. In some embodiments, the subject is suffering from or at risk of developing an inflammatory disease. In some embodiments, the subject is suffering from or at risk of developing an autoimmune disease. In some embodiments, the subject is suffering from or at risk of developing vascular disease. In some embodiments, the subject is suffering from or at risk of developing cancer. In some embodiments, the subject is suffering from or at risk of developing infection. In some embodiments, the subject is suffering from or at risk of developing short bowel syndrome. In some embodiments, the subject is suffering from or at risk of developing drug-induced or toxin-induced intestinal injury. In some embodiments, the subject is suffering from or at risk of developing a disorder requiring total parenteral nutrition or lifelong parenteral nutrition intervention. In some embodiments, the subject is suffering from or at risk of exposure to ionizing radiation. In some embodiments, the subject is selected for treatment of an affliction characterized by intestinal atrophy selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation. In some embodiments, the subject is aged or has an advanced aged (e.g., mammalian subjects that are at least about 40 years old, 45 years old, 50 years old, 55 years old, 60 years old, 65 years old, 70 years old, 75 years old, 80 years old, 85 years old, 90 years old or older), rendering the subject at an increased risk of loss or decline in the production and/or functionality of intestinal stem cells and/or non-stem intestinal progenitor cells. In some embodiments, the method further comprises determining that the subject is in need of treatment for an affliction characterized by intestinal atrophy selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation. In some embodiments, the subject is human. In some embodiments, the method further comprises determining that the subject is in need of enhanced intestinal function. A subject may be in need of enhanced intestinal function, for example, if the subject exhibits intestinal atrophy, is suffering from or at risk of developing a gastrointestinal disorder or affliction characterized by intestinal atrophy described herein. A subject may be in need of enhanced intestinal function, for example, if the subject exhibits decreased numbers of intestinal stem cells and/or non-stem intestinal progenitor cells relative to a control subject with normal numbers of intestinal stem cells and/or non-stem intestinal progenitor cells, or a reference normal level of intestinal stem cells and/or non stem intestinal progenitor cells.

Aspects of the disclosure involve placing subjects on a high fat diet. In some embodiments, a method described herein further comprises placing a subject on a high fat diet. In some embodiment, the high fat diet comprises consumption of a macronutritional composition comprising at least 25%, at least 30%, at least 35%, at least 40%, at least 45%, or at least 50% of total daily calories comprising fat. In some embodiment, the high fat diet comprises consumption of a macronutritional composition comprising at least 60% of total daily calories comprising fat. In some embodiment, the high fat diet comprises consumption of a macronutritional composition comprising at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of total daily calories comprising fat. In some embodiments, the high fat diet comprises consumption of a macronutritional composition comprising 100% of total daily calories comprising fat.

In some embodiments, the high fat diet comprises a diet restricted in terms of total daily calories consumed. In some embodiments, the high fat diet comprises a diet restricted to 95%, 90%, 85%, 80%, 75%, 70%, 65%, 60%, 55%, 50%, 45%, 40%, 35%, 30%, or 25% of the total daily calories recommended for a healthy subject of a particular age, gender, and body weight. In some embodiments, the high fat diet comprises a diet restricted to 2000, 1900, 1800, 1700, 1600, 1500, 1400, 1300, 1200, 1100, 1000, 900, 800, 750, 700, 650, 600, 550, 500 or less total daily calories. In some embodiments, the high fat diet comprises a diet restricted to 2000, 1900, 1800, 1700, 1600, 1500, 1400, 1300, 1200, 1100, 1000, 900, 800, 750, 700, 650, 600, 550, 500 or less total daily calories, at least 25%, at least 30%, at least 35%, at least 40%, at least 50%, at least 55%, at least 60%, at least 65%, at least 70%, or at least 75% of which consist of fat.

As one of skill in the art is aware, stimulating the proliferation and/or renewal of intestinal stem cells and/or enhancing the number and/or function of non-stem intestinal progenitor cells, and/or promoting regeneration of mammalian intestinal tissue in a subject can lead to treatment, prevention or amelioration of a number of gastrointestinal disorders and/or afflictions characterized by intestinal atrophy.

Aspects of the disclosure relate to treating afflictions characterized by intestinal atrophy, "Treat", "treating" and similar terms refer to providing medical and/or surgical management of a subject. Treatment can include, but is not limited to, administering an agent or composition (e.g., a pharmaceutical composition) to a subject. Treatment is typically undertaken in an effort to alter the course of a disease, disorder, or undesirable condition in a manner beneficial to the subject. The effect of treatment can generally include reversing, alleviating, reducing severity of, delaying the onset of, curing, inhibiting the progression of, and/or reducing the likelihood of occurrence or reoccurrence of the disease, disorder, or condition to which such term applies, or one or more symptoms or manifestations of such disease, disorder or condition. In some embodiments an agent or composition is administered to a subject who has developed a disease or condition or is at increased risk of doing so relative to a member of the general population. In some embodiments an agent or composition is administered prophylactically, i.e., before development of any symptom or manifestation of a condition. Typically in this case the subject will be at risk of developing the condition. It will be understood that "administering" encompasses self-administration. "Preventing" can refer to administering an agent or composition (e.g., a pharmaceutical composition) to a subject who has not developed a disease or condition, so as to reduce the likelihood that the disease or condition will occur or so as to reduce the severity of the disease or condition should it occur.

A subject may be identified as at risk of developing the disease or condition (e.g., at increased risk relative to many most other members of the population who may be matched with respect to various demographic factors such as age, sex, ethnicity, etc.) or as having one or more risk factors that increases likelihood of developing the disease or condition. For example, a subject at or approaching an advanced age may have or may be at an increased risk of developing compromised gut regeneration (e.g., loss of intestinal stem cells and/or non-stem intestinal progenitor cells), or may otherwise be at risk of developing a disease or condition. In those aged subjects, exposure to secondary insults (e.g., chemotherapy, infection, etc.) may render such aged subjects at further risk of developing compromised gut regeneration. Such an aged subject may be identified based on their age (e.g., age greater than sixty years old) or, for example, on the basis of decreased frequency of organoid formation in aged crypts compared to a younger population of subjects, or by exhibiting a failure to thrive. In some embodiments, an aged subject at risk for developing a disease or condition (e.g., compromised gut regeneration or loss of intestinal stem cells and/or non-stem intestinal progenitor cells) may be identified on the basis of their low PPAR-delta activity (e.g., by assessing expression of PPAR-delta and/or one or more PPAR-delta target genes such as CPT1A, HMGCS2, FABP1) in a biological sample obtained from the subject. In certain aspects, aged subjects may present with, or may be suspected of having inflammatory or infectious colitis, further rendering such aged subjects at an increased risk for developing a disease or condition, and making such subjects candidates for receiving the compositions and agents described herein. Similarly, aged subjects undergoing chemotherapy, radiotherapy or proton therapy may be at an increased risk for developing a disease or condition, again making such subjects candidates for receiving the compositions and agents described herein.

In certain aspects the methods and uses disclosed herein further comprise a step of determining, for example, that a subject has or is at risk of developing compromised gut regeneration. Similarly, in some embodiments, the methods and uses disclosed herein further comprise a step of determining that a subject (e.g., an aged or elderly subject) has or is at risk of developing loss of intestinal stem cells and/or non-stem intestinal progenitor cells. Accordingly, in certain embodiments, the methods and uses disclosed here further comprise a step of determining that the subject is in need of enhanced intestinal function. Such a determination may be made, for example, by assessing expression of PPAR-δ in one or more tissues or biological samples obtained from the subject. In certain aspects, such a determination may be made, for example, by assessing expression of one or more of CPT1A, HMGCS2 and FABP1 in one or more tissues or biological samples obtained from the subject.

It is believed that treating an affliction characterized by intestinal atrophy can be achieved by stimulating the proliferation and/or self-renewal of intestinal stem cells in a subject and/or enhancing the number and/or function of non-stem intestinal progenitor cells in a subject and/or promoting intestinal regeneration. In some aspects, stimulating the proliferation and/or self-renewal of intestinal stem cells and/or enhancing the number and/or function of non-stem intestinal progenitor cells and/or promoting intestinal regeneration in the subject can be achieved by administering to the subject an effective amount of a composition comprising a high fat diet mimetic. In some aspects, stimulating the proliferation and/or self-renewal of intestinal stem cells and/or enhancing the number and/or function of non-stem intestinal progenitor cells and/or promoting intestinal regeneration in the subject can be achieved by administering to the subject an effective amount of a composition comprising an agent that increases the level and/or activity of PPAR-δ or a PPAR-δ target protein. It should be appreciated that, in some instances, it may be advantageous to place the patient on a high fat diet concomitantly with administration of the high fat diet mimetic or agent that increases the level and/or activity of PPAR-δ or a PPAR-δ target protein. In certain instances, it may be advantageous to place the patient on a high fat diet intervention alone to stimulate the proliferation and/or self-renewal of intestinal stem cells and/or enhance the number and/or function of non-stem intestinal progenitor cells and/or promote intestinal tissue regeneration in the subject. For example, a high fat diet may be appropriate before administering a high fat diet mimetic or agent that increases the level and/or activity of PPAR-δ or a PPAR-δ target protein to the subject, and the number of intestinal stem cells and/or non-stem intestinal progenitor cells in the subject can be assayed for an increase in the number intestinal stem cells and/or non-stem intestinal progenitor cells. The results of the assay can thus be used as a quantitative measure of the success of the high fat diet alone, and to determine whether it may be advantageous to administer a high fat diet mimetic or agent that increases the level and/or activity of PPAR-δ or a PPAR-δ target protein. It may also be advantageous to place the patient on a high fat diet regiment if, for example, the subject is taking medication which is contraindicated for the high fat diet mimetic or agent that increases the level and/or activity of PPAR-δ or a PPAR-δ target protein. It is believed that stimulating the proliferation and/or self-renewal of intestinal stem cells and/or enhancing the number and/or function of non-stem intestinal progenitor cells may ameliorate intestinal atrophy by regenerating intestinal tissue as the intestinal stem cells in the intestine proliferate and self-renew.

In an aspect, a method of treating an affliction characterized by intestinal atrophy in a subject in need thereof comprises administering to the subject an effective amount of a composition that increases the level and/or activity of PPAR-δ or a PPAR-δ target protein, thereby treating the affliction characterized by intestinal atrophy. In some embodiments, the method further comprises placing the subject on a high fat diet. In some embodiments, the method further comprises administering a calorie restriction intervention to the subject. In some embodiments, the method further comprises administering to the subject an effective amount of a calorie restriction mimetic. In some embodiments, the method further comprises administering to the subject an effective amount of an agent that inhibits the level and/or activity of mTORC1. In some embodiments, the method further comprises administering to the subject an effective amount of an agent that increases the level and/or activity of Bst1 or a product of Bst1.

In some embodiments, the composition comprises a high fat diet mimetic. In some embodiments, the composition comprises a PPAR-δ agonist and a pharmaceutically acceptable carrier, diluent, or excipient. In some embodiments, the composition comprises at least one PPAR-δ target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments, the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments, the composition comprises a combination of (a) any one or combination of (i) a high fat diet mimetic, (ii) a PPAR-δ agonist; (iii) a CPT1A agonist, (iv) a HMGCS2 agonist, and (v) a FABP1 agonist; and (b) any one or a combination of (i) a calorie restriction mimetic, (ii) an agent that inhibits the level and/or activity of mTORC1, (iii) an agent that increases the level and/or activity of Bst1 or a product of Bst1; and a pharmaceutically acceptable carrier, diluent, or excipient.

Non-limiting examples of afflictions that are characterized by intestinal atrophy and for which a high fat diet and/or high fat diet mimetic (e.g., a composition or agent that increases the level and/or activity of PPAR-δ or a PPAR-δ target protein) disclosed herein may provide a useful remedy include inflammatory diseases (e.g, inflammatory bowel disease, e.g., Crohn's disease, ulcerative colitis), autoimmune diseases, vascular disease, cancer, infection, drug-induced or toxin-induced intestinal injury (e.g., cancer chemotherapy induced GI damage), an affliction treatable by parenteral nutrition (PN) or life-long parenteral nutrition, and exposure to ionizing radiation.

In some embodiments, compositions which increase the level and/or activity of PPAR-δ and/or PPAR-δ target proteins can be administered over a limited duration of time in order to treat a gastrointestinal disorder and/or affliction characterized by intestinal atrophy described herein. The composition can be administered once or more daily (e.g., once, twice, thrice, etc.) over the limited duration of time, e.g., up to 1 week, 2 weeks, 4 weeks, 6 weeks, 8 weeks, 12 weeks, etc. until regeneration of intestinal tissue has reached a satisfactory level. For example, the composition can be administered after an insult, such as an infection, exposure to a toxin, drug, or ionizing radiation, injury, and/or ischemic event until intestinal atrophy, damage, or injury resulting from that insult is restored to the condition it was in prior to that insult, or to a condition in which major symptoms or manifestations of such insult subside or reduce to manageable levels. In some instances, the compositions can be administered over one or more courses separated by time periods in which the compositions are not administered. For example, a high fat diet mimetic and/or a PPAR-δ agonist may be administered for 1 week, 2 weeks, 4 weeks, 6 weeks, 8 weeks, 12 weeks, or more, to promote intestinal regeneration in a subject suffering from an affliction characterized by intestinal atrophy, e.g., cancer while the subject is undergoing chemotherapy, radiotherapy, proton therapy, and/or immunotherapy for treatment of the affliction, e.g., cancer, and then placed on a high fat, calorie restricted diet for a subsequent limited time interval, e.g., 1 week, 2 weeks, 4 weeks, 6 weeks, 8 weeks, 12 weeks, or more while the subject continues to receive the chemotherapy, radiotherapy, proton therapy, and/or immunotherapy, and then chemotherapy, radiotherapy, proton therapy, and/or immunotherapy can be halted while the subject is administered the high fat diet mimetic and/or PPAR-δ agonist, optionally while being placed on a high fat, calorie restricted diet, for a period of 1 week, 2 weeks, 4 weeks, 6 weeks, 8 weeks, 12 weeks, to allow the patient to recover from the chemotherapy, radiotherapy, proton therapy, and/or immunotherapy while the patient's intestines regenerate from administration of the high fat diet mimetic and/or PPAR-δ agonist. Multiple cycles can be repeated as often as desired and in various intervals based on the patient's progression toward the treatment of the affliction and the regeneration of atrophied intestines.

In some embodiments, the present disclosure contemplates compositions, agents, and methods for treating colitis, and particularly contemplates any suitable therapy for treating any type of colitis manifesting throughout the entire gastrointestinal tract (including, for example, colon, small intestine, and large intestine). Illustrative examples of the types of colitis that can be treated by the compositions, agents, and methods of the present disclosure include, but are not limited to infectious colitis, inflammatory colitis, vascular colitis (e.g., ischemic colitis), pseudomembranous colitis (e.g., caused by bacteria, such as *Clostridium difficile*, for example), microscopic colitis, drug-induced colitis, allergic colitis, colitis related to diverticular disease, and intestinal lesions (e.g., ulcers) resulting from any of foregoing, or gastrointestinal lesions resulting from any other cause whether causes by any other factors (e.g., genetics, physical injury, stress, to name only a few). In some embodiments, a high fat diet and/or high fat diet mimetic, a composition comprising the high fat diet mimetic, and/or an agent or composition that increases the level and/or activity of PPAR-δ and/or a PPAR-δ target protein can be used to treat pseudomembranous colitis (e.g., microorganism induced colitis, e.g., bacteria, e.g., *C. difficile*). In some embodiments, a method for treating colitis resulting at least in part from infection by a pathogen, e.g., pseudomembranous colitis resulting at least in part from infection by a pathogen comprises: (a) administering an effective amount of an antibiotic to a patient, wherein the antibiotic rids or helps rid the patient of a pathogen; and (b) grafting gastrointestinal tissue generated ex vivo into the patient; and optionally (c) administering to the patient and effective amount of a high fat diet mimetic. In some embodiments, such method further comprises (d) placing the patient on a high fat diet. In some embodiments, the gastrointestinal tissue comprises crypts generated ex vivo. In some embodiments, the gastrointestinal tissue generated ex vivo replaces damaged intestinal lining. In some embodiments, the gastrointestinal tissue generated ex vivo replaces denuded intestinal lining. In some embodiments, the high fat diet mimetic is administered to the patient for a pre-determined period of time prior to administration of the antibiotic and/or grafting the gastrointestinal tissue generated ex vivo into the patient. Administering the high fat diet mimetic to the patient prior to administration of the antibiotic and/or grafting the gastrointestinal tissue can advantageously serve as a way to prime the gastrointestinal cells of the patient (intestinal stem cells and/or non-stem intestinal progenitor cells) to minimize drug induced injury resulting from administration of the antibiotic, as well as, to prime the existing gastrointestinal tissue to facilitate the grafting of the gastrointestinal tissue generated ex vivo, for example, to aid the process of healing of the tissue as the existing tissue and the grafted tissue become whole. The pre-determined period of time can range widely, for example, from up to one month prior to administration of the antibiotic agent and/or grafting of the ex vivo produced gastrointestinal tissue, until as little as a few hours prior thereto (e.g., 1-4 hours). It should be appreciated that any antibiotic agent that is known to treat the bacterial infection can be used to rid the patient of pathogens, for example, *C. difficile* can be treated with the antibiotics metronidazole and vanocin.

In some embodiments, a high fat diet mimetic can be employed in combination with parenteral nutrition (PN) treatment.

In some embodiments, a high fat diet mimetic can be used to treat short bowel syndrome (SBS). SBS in infants and children include necrotizing enterocolitis, midgut volvulus, intestinal atresia, and gastroschisis. In adults, SBS typically occurs as a post-surgical event post resection of substantial portions of the small intestine, such as, for example, surgery due to cancer, gastrointestinal bleeding (e.g., repeated or intractable, inflammatory bowel disease, trauma, etc.). In some embodiments, a method for treating SBS comprises administering to a patient in need thereof an effective amount of a high fat diet mimetic, and administering to the patient parenteral nutrition (PN). In some embodiments, such method for treating SBS further comprises administering to the patient an effective amount of glucagon-like peptide-2 (GLP-2) or an analog of GLP-2, for example, teduglutide (Tee et al. Clin. Exper. Gastroenterology. 4: 189-196, 2011).

Aspects of the disclosure relate to radioprotective compositions and/or chemoprotective compositions for protecting cells against ionizing radiation and/or drug induced intestinal injury. In some embodiments, the radioprotective and/or chemoprotective compositions stimulate the proliferation and/or self-renewal of intestinal stem cells. In some embodiments, the radioprotective and/or chemoprotective compositions enhance the number and/or function of non-stem intestinal progenitor cells. In some embodiments, the radioprotective and/or chemoprotective compositions promote regeneration of intestinal tissue. In embodiments disclosed herein, a radioprotective and/or chemoprotective composition disclosed herein may prevent or ameliorate the harmful effects of ionizing radiation on mammalian cells (e.g., damage to gastrointestinal cells).

In an aspect, a radioprotective composition comprises an agent that increases the level and/or activity of PPAR-δ or a PPAR-δ target protein, and a pharmaceutically acceptable carrier, diluent, or excipient.

In an aspect, a chemoprotective composition comprises an agent that increases the level and/or activity of PPAR-δ or a PPAR-δ target protein, and a pharmaceutically acceptable carrier, diluent, or excipient.

In some embodiments, the composition further comprises a chemotherapeutic agent.

In some embodiments, the composition further comprises a radiotherapeutic agent.

In some embodiments, the composition further comprises an immunotherapeutic agent.

In some embodiments, the composition further comprises a calorie restriction mimetic.

In some embodiments, the composition further comprises an agent that inhibits the level and/or activity of mTORC1.

In some embodiments, the composition further comprises an agent that increases the level and/or activity of Bst1 or a product of Bst1.

In some embodiments, the composition further comprises sirolimus or a derivative or analog thereof, such as temsirolimus, everolimus, and ridaforlimus.

In some embodiments, the composition is formulated for administration as an enema.

In some embodiments, the composition is formulated for oral administration.

In some embodiments, an agent of the present invention is administered in combination with a cancer therapeutic agent. It should be appreciated that the combined administration of an agent of the present invention and a cancer therapeutic agent can be achieved by formulating the cancer therapeutic agent and agent in the same composition or by administering the cancer therapeutic agent and agent separately (e.g., before, after, or interspersed with doses or administration of the cancer therapeutic agent). In some embodiments, the an agent of the present invention (e.g., a radioprotective agent) is administered to a patient undergoing conventional chemotherapy and/or radiotherapy e.g., to prevent, minimize or ameliorate harmful effects to the patient as a result of drug induced GI toxicity or damage, and/or exposure to the cancer therapeutic agent or ionizing radiation of the radiotherapy. In some embodiments, the cancer therapeutic agent is a chemotherapeutic agent. In some embodiments, the cancer therapeutic agent is an immunotherapeutic agent. In some embodiments, the cancer therapeutic agent is a radiotherapeutic agent.

Exemplary chemotherapeutic agents that can be administered in combination with the agents of the present invention (e.g., a radioprotective agent) include alkylating agents (e.g. cisplatin, carboplatin, oxaloplatin, mechlorethamine, cyclophosphamide, chorambucil, nitrosureas); anti-metabolites (e.g. methotrexate, pemetrexed, 6-mercaptopurine, dacarbazine, fludarabine, 5-fluorouracil, arabinosycytosine, capecitabine, gemcitabine, decitabine); plant alkaloids and terpenoids including vinca alkaloids (e.g. vincristine, vinblastine, vinorelbine), podophyllotoxin (e.g. etoposide, teniposide), taxanes (e.g. paclitaxel, docetaxel); topoisomerase inhibitors (e.g. notecan, topotecan, amasacrine, etoposide phosphate); antitumor antibiotics (dactinomycin, doxorubicin, epirubicin, and bleomycin); ribonucleotides reductase inhibitors; antimicrotubule agents; and retinoids. (See, e.g., Cancer: Principles and Practice of Oncology (V. T. DeVita, et al., eds., J.B. Lippincott Company, $9^{th}$ ed., 2011; Brunton, L., et al. (eds.) Goodman and Gilman's The Pharmacological Basis of Therapeutics, $12^{th}$ Ed., McGraw Hill, 2010).

Exemplary immunotherapeutic agents include cytokines, such as, for example interleukin-1 (IL-I), IL-2, IL-4, IL-5, IL-β, IL-7, IL-10, IL-12, IL-5, IL-18, CSF-GM, CSF-G, IFN-γ, IFN-α, TNF, TGF-β but not limited thereto.

In some embodiments, an agent of the present invention can be linked or conjugated to a delivery vehicle, which may also contain cancer therapeutic. Suitable delivery vehicles include liposomes (Hughes et al. Cancer Res 49(22):6214-20, 1989, which is hereby incorporated by reference in its entirety), nanoparticles (Farokhzad et al. Proc Nat'l Acad Sci USA 103(16):6315-20, 2006, which is hereby incorporated by reference in its entirety), biodegradable microspheres, microparticles, and collagen minipellets. The delivery vehicle can contain any of the radioprotective, chemotherapeutic, radiotherapeutic, or immunotherapeutic agents described supra.

In one embodiment, an agent of the present invention can be conjugated to a liposome delivery vehicle (Sofou and Sgouros, Exp Opin Drug Deliv. 5(2):189-204, 2008, which is hereby incorporated by reference in its entirety). Liposomes are vesicles comprised of one or more concentrically ordered lipid bilayers which encapsulate an aqueous phase. Suitable liposomal delivery vehicles are apparent to those skilled in the art. Different types of liposomes can be prepared according to Bangham et al. J. Mol. Biol. 13:238-52, 1965; U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

These liposomes can be produced such that they contain, in addition to the therapeutic agents of the present invention, other therapeutic agents, such as immunotherapeutic cytokines, which would then be released at the target site (e.g., Wolff et al., Biochim. Biophys. Acta. 802:259-73, 1984, which is hereby incorporated by reference in its entirety).

The present disclosure also contemplates a composition comprising an agent of the present invention (e.g., an agent that stimulates the proliferation and/or self-renewal of ISCs, enhances the number and/or function of non-stem intestinal progenitor cells, and/or promotes regeneration of intestinal tissue) and a pharmaceutically acceptable carrier, diluent, or excipient. Therapeutic formulations of the agents of the present invention can be prepared having the desired degree of purity with optional pharmaceutically acceptable carriers, excipients or stabilizers (REMINGTON'S PHARMACEUTICAL SCIENCES (A. Osol ed. 1980), which is hereby incorporated by reference in its entirety), in the form of lyophilized formulations or aqueous solutions. Acceptable carriers, excipients, or stabilizers are nontoxic to recipients at the dosages and concentrations employed, and include buffers such as acetate, Tris-phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG).

The active therapeutic ingredients of the pharmaceutical compositions (e.g., radioprotective agents alone or in combination with or linked to a cancer therapeutic agent or agent that increases the level and/or activity of PPAR-δ or a PPAR-δ target protein can be entrapped in microcapsules prepared using coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in REMINGTON'S PHARMACEUTICAL SCIENCES (A. Osol ed. 1980), which is hereby incorporated by reference in its entirety. In some embodiments, the radioprotective agents of the present invention can be conjugated to the microcapsule delivery vehicle to target the delivery of the therapeutic agent to the site of the cells exposed to toxic effects of ionizing radiation. Sustained-release preparations may be prepared. Suitable examples of sustained-release preparations include semipermeable matrices of solid hydrophobic polymers containing the antibody or polypeptide, which matrices are in the form of shaped articles, e.g., films or microcapsules. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

In some embodiments, an agent of the present disclosure can be provided with an enteric coating or otherwise protected from hydrolysis or low stomach pH. In some embodiments, an agent of the present disclosure can be formulated for release in the small intestine, for example, lectins, can be used to target agents to the gastrointestinal tract, and particularly can recognize and bind to villus and crypt cells in the intestines (see, e.g., Handbook of plant lectins: properties and biomedical applications, Els J. M. Van Damme, et al., eds., John Wiley and Sons, 1998).

The therapeutically effective compositions containing the agents of the disclosure are administered to a subject, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. In some embodiments, a radioprotective agent comprises a radioprotective agent. In some embodiments, an agent or composition of the present invention is administered as an enema. Administration of the agents and compositions as an enema may be advantageous, for example, administration as an enema facilitates local, rather than systemic, delivery to the targeted area (GI system) where the agent exerts its biological effects, as well as avoids factors which result in diminished or insufficient absorption of a drug and its ultimate transport to its biological target resulting from elimination and metabolism of drugs that are administered systemically (e.g., oral administration). Accordingly, administration of the agents and compositions of the present invention as an enema may result in an enhanced therapeutic effect while minimizing side effects. In some embodiments, a method of treating or preventing harm resulting from exposure to ionizing radiation comprises administering an effective amount of agent or composition of the present disclosure to a subject in need thereof, wherein the agent or composition is administered as an enema.

Other therapeutic regimens may be combined with the administration of the agents of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect. In some embodiments, a composition of the present disclosure is administered in combination with a therapy selected from the group consisting of chemotherapy, radiotherapy, proton therapy, surgery, and combinations thereof.

The composition can include any number of additional active ingredients which can act in concert to provide a therapeutic effect, (e.g., a synergistic therapeutic effect), such as a chemotherapeutic agent, a radiotherapeutic agent, an immunotherapeutic agent, and combinations thereof.

Aspects of the disclosure involve methods of minimizing the risk of exposure to an ionizing radiation source, treating individuals exposed to harmful levels of ionizing radiation, and/or increasing an individual's tolerance to ionizing radiation.

In an aspect, a method of minimizing the risk of exposure to an ionizing radiation source comprises administering to an individual an effective amount of a composition that increases the level and/or activity of PPAR-δ or a PPAR-δ target protein, thereby minimizing the risk of exposure to the ionizing radiation source.

In an aspect, a method of treating an individual exposed to ionizing radiation comprises administering to the individual an effective amount of a composition that increases the level and/or activity of PPAR-δ or a PPAR-δ target protein, thereby treating the individual exposed to harmful ionizing radiation. In some embodiments, the ionizing radiation comprise harmful ionizing radiation.

In an aspect, a method of increasing tolerance to ionizing radiation in an individual comprises administering to the individual an effective amount of a composition that increases the level and/or activity of PPAR-δ or a PPAR-δ target protein, wherein the composition increases the threshold dose of lethal ionizing radiation to above 8 Gy. In some embodiments, the composition increases the threshold dose of lethal ionizing radiation to about 9 Gy, about 10 Gy, about 11 Gy, about 12 Gy, about 13 Gy, about 14 Gy, or about 15 Gy. In some embodiments, the high fat diet mimetic increases a threshold dose of lethal ionizing radiation in a human mammal. In some embodiments, the high fat diet mimetic increases a threshold dose of lethal ionizing radiation in a non-human mammal.

In some embodiments, the composition comprises a high fat diet mimetic. In some embodiments, the composition comprises a PPAR-δ agonist and a pharmaceutically acceptable carrier, diluent, or excipient. In some embodiments, the composition comprises at least one PPAR-δ target protein agonist selected from the group consisting of (i) a CPT1A agonist, (ii) a HMGCS2 agonist, (iii) a FABP1 agonist, and (vv) any combination of (i)-(iii); and a pharmaceutically acceptable carrier, diluent, or excipient. In some embodiments, the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments, the composition comprises a combination of (a) any one or combination of (i) a high fat diet mimetic, (ii) a PPAR-δ agonist; (iii) a CPT1A agonist, (iv) a HMGCS2 agonist, and (v) a FABP1 agonist; and (b) any one or a combination of (i) a calorie restriction mimetic, (ii) an agent that inhibits the level and/or activity of mTORC1, (iii) an agent that increases the level and/or activity of Bst1 or a product of Bst1; and a pharmaceutically acceptable carrier, diluent, or excipient.

The high fat diet mimetic and/or agent that increases the level and/or activity of PPAR-δ or a PPAR-δ target protein can be used to minimize the risk of exposure to any ionizing radiation source and/or treat exposure to harmful ionizing radiation from any ionizing radiation source, and/or increase an individual's tolerance to ionizing radiation from any source, including any source of accidental or incidental ionizing radiation, such as radioactive material, a nuclear power plant, a nuclear weapon, or cosmic radiation, to name but a few. In some embodiments, the ionizing radiation source is cosmic radiation in outer space. In some embodiments, the cosmic radiation is cosmic radiation that has not penetrated the Earth's atmosphere. In some embodiments, the cosmic radiation has penetrated at least a portion of the Earth's atmosphere. In some embodiments, the high fat diet mimetic can be used to minimize the risk of exposure to cosmic radiation in the ionosphere. In some embodiments, the high fat diet mimetic can be used to minimize the risk of exposure to cosmic radiation in the thermosphere. In some embodiments, the high fat diet mimetic can be used to minimize the risk of exposure to cosmic radiation in the mesosphere. In some embodiments, the high fat diet mimetic can be used to minimize the risk of exposure to cosmic radiation in the stratosphere. In some embodiments, the high fat diet mimetic can be used to minimize the risk of exposure to cosmic radiation in the troposphere. In some embodiments, the high fat diet mimetic can be used to minimize the risk of exposure to cosmic radiation at sea level.

The high fat diet mimetic and/or agent that increases the level and/or activity of PPAR-δ or a PPAR-δ target protein can also be administered to an individual that is being administered radiotherapy, or an individual that is about to be administered radiotherapy, to minimize the risk of exposure to the ionizing radiation administered during the radiotherapy. In some instances, a method of minimizing the risk of exposure to an ionizing radiation source comprises placing the individual on a high fat diet for a pre-determined period of time prior to exposure to the ionizing radiation source. In some embodiments, the pre-determined period of time for placing an individual on a high fat diet prior to exposure to an ionizing radiation source can range from hours to months (e.g., from about 1 hour, about 2 hours, about 3 hours, about 4 hours, about 5 hours, about 6 hours, about 12 hours, about 1 day, about 2 days, about 3 days, about 4 days, about 5 days, about 6 days, about 1 week, about a week and half, about two weeks, about three weeks, about a month, two months, three months, four months, five months, six months, seven months, eight months, nine months, 10 months, 11 months, or 12 months, and any interval therebetween). In certain instances, the method of minimizing the risk of exposure to an ionizing radiation source comprises placing the individual on a high fat diet prior to exposure to an ionizing radiation source, and administering to the individual an effective amount of composition that increases the level and/or activity of PPAR-δ or a PPAR-δ target protein.

In some embodiments, the method further comprises placing the individual on a high fat diet. In some embodiments, the method further comprises placing the individual on a high fat, calorie restricted diet.

The disclosure contemplates treating individuals exposed to any amount of ionizing radiation from any source described herein. For example, an individual may have been exposed to at least 0.1 Gy, 0.2 Gy, 0.3 Gy, 0.4 Gy, 0.5 Gy, 0.6 Gy, 0.7 Gy, 0.8 Gy, 0.9 Gy, 1 Gy, 1.5 Gy, 2 Gy, 2.5 Gy, 3 Gy, 3.5 Gy, 4 Gy, 4.5 Gy, 5 Gy, 5.5 Gy, 6 Gy, 6.5 Gy, 6.6 Gy, 6.7 Gy, 6.8 Gy, 6.9 Gy, 7.0 Gy, 7.5 Gy, 8 Gy, 9 Gy, 10 Gy, 11 Gy, 12 Gy, 13 Gy, 14 Gy, or up to 15 Gy or more.

In still other embodiments, the disclosure relates to methods of treating cancer. In an aspect, a method of treating cancer in a subject in need thereof comprises: (a) administering to the subject an effective amount of a composition that increases the level and/or activity of PPAR-δ or a PPAR-δ target protein; and (b) administering an effective amount of ionizing radiation to the subject. In some embodiments, the composition: (i) increases the subject's tolerance for ionizing radiation; (ii) minimizes undesirable side-effects due to the ionizing radiation; (iii) protects against gastrointestinal drug toxicity.

In an aspect, a method of administering radiotherapy to a subject in need thereof comprises: (a) administering to the subject an effective amount of a composition that increases the level and/or activity of PPAR-δ and/or a PPAR-δ target protein, and (b) administering radiotherapy to the subject.

In an aspect, a method administering proton therapy to a subject in need thereof comprises: (a) administering to the subject an effective amount of a composition that increases the level and/or activity of PPAR-δ and/or a PPAR-δ target protein; and (b) administering proton therapy to the subject.

In an aspect, a method of administering chemotherapy to a subject in need thereof comprises (a) administering to the subject an effective amount of a composition that increases the level and/or activity of PPAR-δ and/or a PPAR-δ target protein; and (b) administering chemotherapy to the subject.

In some embodiments, the composition comprises a high fat diet mimetic. In some embodiments, the composition comprises a PPAR-δ agonist and a pharmaceutically acceptable carrier, diluent, or excipient. In some embodiments, the composition comprises at least one PPAR-d target protein agonist selected from the group consisting of (i) a CPT1A agonist, (ii) a HMGCS2 agonist, (iii) a FABP1 agonist, and (iv) any combination of (i)-(iii); and a pharmaceutically acceptable carrier, diluent, or excipient. In some embodiments, the composition comprises (a) at least one PPAR-δ agonist; (b) at least one PPAR-δ target protein agonist selected from the group consisting of (i) a CPT1A agonist, (ii) a HMGCS2 agonist, (iii) a FABP1 agonist, and (iv) any combination of (i)-(iii); and (c) a pharmaceutically acceptable carrier, diluent, or excipient. In some embodiments, the composition comprises a combination of (a) any one or combination of (i) a high fat diet mimetic, (ii) a PPAR-δ agonist; (iii) a CPT1A agonist, (iv) a HMGCS2 agonist, and (v) a FABP1 agonist; and (b) any one or a combination of (i) a calorie restriction mimetic, (ii) an agent that inhibits the level and/or activity of mTORC1, (iii) an agent that increases the level and/or activity of Bst1 or a product of Bst1; and a pharmaceutically acceptable carrier, diluent, or excipient.

One of skill in the art should appreciate that the composition that increases the level and/or activity of PPAR-δ and/or the PPAR-δ target protein or high fat diet mimetic can be employed in the course of treating any cancer that involves radiotherapy. In some instances, the method of treatment can include placing the subject on a high fat diet prior to, or during the course of, administering the ionizing radiation. In some instances, the method of treatment can also include administering to the subject a chemotherapeutic agent, a radiotherapeutic agent, surgery, and combinations thereof. The high fat diet mimetic can be administered prior, during, or after administering the ionizing radiation to the patient.

In an aspect, the disclosure relates to the use of an agent that increases the level and/or activity of PPAR-δ and/or a PPAR-δ target protein to promote intestinal regeneration, protect against intestinal tissue damage, and/or stimulate the proliferation and/or self-renewal of one or more intestinal stem cells.

In an aspect, the disclosure relates to the use of an agent that increases the level and/or activity of PPAR-δ and/or a PPAR-δ target protein to treat an affliction characterized by intestinal atrophy. Exemplary afflictions include, without limitation, an inflammatory disease, an autoimmune disease, vascular disease, cancer, infection, short bowel syndrome, Crohn's disease, infectious colitis, ischemic colitis, inflammatory colitis, and ulcerative colitis.

In an aspect, the disclosure relates to the use of an agent that increases the level and/or activity of PPAR-δ and/or a PPAR-δ target protein to protect against, mitigate, or alleviate, the harmful effects of exposure to ionizing radiation. Exposure to ionizing radiation can be from an ionizing radiation source selected from the group consisting of a nuclear power plant, a nuclear weapon, cosmic or space radiation.

In an aspect, the disclosure relates to the use of an agent that increases the level and/or activity of PPAR-δ and/or a PPAR-δ target protein, in combination with radiotherapy to protect against the harmful effects of ionizing radiation.

In an aspect, the disclosure relates to the use of an agent that increases the level and/or activity of PPAR-δ and/or a PPAR-δ target protein, in combination with chemotherapy to protect against gastrointestinal drug toxicity.

In an aspect, the disclosure relates to the use of an agent that increases the level and/or activity of PPAR-δ and/or a PPAR-δ target protein, in combination with total parenteral nutrition to protect against intestinal atrophy.

In another aspect, the present disclosure includes a method for expanding a population of intestinal stem cells and/or non-stem intestinal progenitor cells comprising contacting a population of intestinal stem cells and/or non-stem intestinal progenitor cells with an effective amount of an agent that increases the level and/or activity of PPAR-δ or a PPAR-δ target protein. In some embodiments, Paneth cells are not present in the population of intestinal stem cells and/or non-stem intestinal progenitor cells. In some embodiments, the population of intestinal stem cells and/or non-stem intestinal progenitor cells comprises Paneth cells.

In some embodiments, the method for expanding the ISCs is performed in vitro. In some embodiments, method for expanding the ISCs is performed ex vivo. It should be appreciated that the ex vivo methods and compositions of the present invention for generating ISCs and intestinal tissues, as well as grafting those generated cells and tissues, can be used for any condition that would benefit from restoration and/or augmentation of intestinal function. In some embodiments, the method for expanding ISCs can be used to maintain intestinal stem cells for a patient that may be preserved and eventually engrafted into an atrophic or damaged intestine or used ex vivo in the construction of an artificial organ which may subsequently be implanted into a subject. In some embodiments, the ex vivo methods of the present invention can be used to study intestinal transport, metabolism (of drugs, etc.) and drug design to enhance absorption and bioavailability.

In some aspects, compositions for ex vivo expansion of intestinal stem cells and/or non-stem intestinal progenitor cells are disclosed. In an aspect, a composition for ex vivo expansion of intestinal stem cells and/or non-stem intestinal progenitor cells comprises a population of intestinal stem cells and/or non-stem intestinal progenitor cells and a high fat diet mimetic. In some embodiments, a composition for ex vivo expansion of intestinal stem cells and/or non-stem intestinal progenitor cells includes Paneth cells. In some embodiments, a composition for ex vivo expansion of intestinal stem cells and/or non-stem intestinal progenitor cells includes Paneth-like cells. It should be appreciated that intestinal stem cells and/or Paneth or Paneth-like cells for use in the ex vivo expansion compositions and methods of the present invention can be autologous or non-autologous. Intestinal stem cells and/or non-stem intestinal progenitor cells, and/or Paneth cells are found within the crypts of the mucosa of the intestine, e.g., small intestines or colon. Such cells can be isolated and/or extracted according to routine methods (e.g., non-limiting examples of obtaining intestinal stem cells and/or non-stem intestinal progenitor cells and/or Paneth cells include, surgery and biopsy, for example). In some instances, it may be preferable to utilize intact crypts, organoid bodies, intestinal stem cells, non-stem intestinal progenitor cells and/or Paneth cells that have been removed from a patient during a small-intestine (or small-bowel) biopsy as part of diagnosis of a disease of the intestinal mucosa. In such instances, the cells thus obtained can be banked and maintained for subsequent use in the ex vivo expansion compositions and methods of the present invention. In some instances, the ISCs can be obtained from pluripotent stem cells (PSCs) or embryonic stem cells (ESCs) that have been induced or directed to differentiate into ISCs, for example, by a process to direct the differentiation of human PSCs into intestinal tissue in vitro using growth factors to simulate embryonic intestinal development (Wells et al. Nature. 470 (7332): 105-109, 2011). This process of directed differentiation can be used to produce ISCs, for example, from fibroblasts obtained from a skin biopsy of the patient. In some embodiments, a method for expanding ISCs of a patient comprises: (a) obtaining a pluripotent stem cell non-invasively from a patient (e.g., skin biopsy of fibroblast cells); (b) directing differentiation of the pluripotent stem cells obtained non-invasively in step (a) by manipulating the pluripotent stem cells with one or more appropriate growth factors, wherein the pluripotent stem cells differentiate into intestinal tissue; and (c) contacting a population of intestinal stem cells and/or non-stem intestinal progenitor cells in the intestinal tissue generated in step (b) with an effective amount of an agent that increases the level and/or activity of PPAR-δ and/or a PPAR-δ target protein, thereby activating and expanding the ISCs of the patient. In some embodiments, a composition for ex vivo expansion of intestinal stem cells and/or non-stem intestinal progenitor cells includes a culture medium. Suitable culture mediums are apparent to those skilled in the art (see, for example, materials and methods below). In some embodiments, a pluripotent cell is an induced pluripotent stem (iPS) cell that has been derived in vitro from a non-pluripotent somatic cell such as a skin cell, fibroblast or myoblast (or is descended from a cell that has been so derived). An iPS cell can be derived using a variety of different protocols. In some embodiments an iPS cell is derived by causing a somatic cell to express at least one, two, or three of the pluripotency factors Oct4, Nanog, and Sox2. Optionally the cells are caused to overexpress c-Myc. In some embodiments an iPS cell is derived by causing a somatic cell to express at least one, two, three, or four of the transcription factors Oct4, Nanog, Sox2, and Lin28. In some embodiments viral transduction is used to cause a cell to express a reprogramming factor. In some embodiments an iPS cell is generated without use of retroviruses or other integrating viruses and/or without inserting exogenous DNA into the genome of the cell. A variety of techniques, e.g., involving small molecules and/or protein transduction and/or non-integrating vectors and/or introducing translatable RNA molecules (e.g., encoding one or more pluripotency factor(s)) into cells can employed in the generation of iPS cells in various embodiments. See, e.g., PCT/US2008/004516 (WO 2008/124133) REPROGRAMMING OF SOMATIC CELLS); Lyssiotis, CA., Proc Natl Acad Sci USA. 2009 Jun. 2; 106(22):8912-7. Epub 2009 May 15; Carey B W, Proc Natl Acad Sci USA. 2009 Jan. 6; 106(1):157-62. Epub 2008 Dec. 24, and references cited in any of the foregoing, for additional information regarding iPS cells. Use of any of the compositions and methods described in PCT/US2009/057692, "Compositions and Methods for Enhancing Cell Reprogramming", filed 21 Sep. 2009, is contemplated.

In an aspect, the disclosure provides a method of endowing at least one non-stem intestinal progenitor cell with at least one attribute of intestinal stem cells, the method comprising contacting a population of mammalian intestinal cells comprising at least one non-stem progenitor cell with an effective amount of an agent that increases the level and/or activity of PPAR-δ or a PPAR-δ target protein, thereby endowing at least one non-stem intestinal progenitor cell with the at least one attribute of intestinal stem cells. In some embodiments, the at least one attribute comprises the ability to form organoid mini-intestines in culture in the absence of the Paneth cell niche. In some embodiments, the intestinal stem cells comprise LGR5$^+$ stem cells. In some embodiments, the non-stem intestinal progenitor cells comprise WDR43$^+$ non-stem cells. In some embodiments, the non-stem intestinal progenitor cells express diminished expression of LGR5, OLFM4, and ASCL2, and express WDR43. In some embodiments, the non-stem intestinal progenitor cells do not express LGR5, OLFM4, or ASCL2, and express WDR43.

In an aspect, the disclosure provides a method for obtaining mammalian intestinal stem cells and/or non-stem intestinal progenitor cells with an enhanced ability to form organoid bodies in culture in the absence of the Paneth cells, the method comprising: (a) administering a high fat diet or a high fat diet mimetic to a mammal, wherein the high fat diet or high fat diet mimetic enhances the ability of intestinal stem cells and/or non-stem intestinal progenitor cells in the mammal to form organoid bodies in culture; and (b) isolating intestinal stem cells and/or non-stem intestinal progenitor cells from the mammal, thereby obtaining mammalian intestinal stem cells and/or non-stem intestinal progenitor cells with the enhanced ability to form organoid bodies in culture.

In some embodiments, the method includes assessing the ability of the intestinal stem cells and/or non-stem intestinal progenitor cells to form organoid bodies in culture in the absence of Paneth cells. In some embodiments, assessing is performed by comparing the ability of the intestinal stem cells and/or non-stem intestinal progenitor cells obtained from the mammal in step (b) to form organoid bodies in culture in the absence of Paneth cells to the ability of intestinal stem cells and/or non-stem intestinal progenitor cells obtained from control mammals which were not administered a high fat diet of high fat diet mimetic to form organoid bodies in culture in the absence of Paneth cells.

In some embodiments, the method includes a step (c) forming organoid bodies in culture in the absence of Paneth cells.

In some embodiments, the high fat diet or the high fat diet mimetic increases the level and/or activity of PPAR-δ or a PPAR-δ target protein in the mammal's intestinal stem cells and/or non-stem intestinal progenitor cells.

Aspects of the disclosure relate to the use of PPAR-δ and/or a PPAR-δ target gene as a prognostic biomarker to detect obese individuals at risk for colorectal cancer.

In an aspect, the disclosure provides a method of identifying an obese individual at risk of developing colorectal carcinoma, the method comprising: (a) determining the level of expression of PPAR-δ or a PPAR-δ target gene in a biological sample obtained from an obese individual; and (b) identifying an obese individual as being at risk of developing colorectal carcinoma if the level of expression of PPAR-δ or the PPAR-δ target gene in the biological sample is elevated as compared to the level of expression of PPAR-δ or the PPAR-δ target gene in control individuals without colorectal carcinoma.

Aspects of the disclosed methods include obtaining a biological sample from a subject comprising a cell or tissue of interest e.g., a cell or tissue that is affected by a disease, e.g., a gastrointestinal disorder described herein or an affliction characterized by intestinal atrophy described herein. A biological sample used in the methods described herein will typically comprise or be derived from cells or tissues isolated from a subject. The cells or tissues may comprise cells or tissues affected by a disease described herein. In some embodiments, the cells or tissues are isolated from a tumor cell or tissue described herein.

Samples can be, e.g., surgical samples, tissue biopsy samples, fine needle aspiration biopsy samples, core needle samples. The sample may be obtained using methods known in the art. A sample can be subjected to one or more processing steps. In some embodiments the sample is frozen and/or fixed. In some embodiments the sample is sectioned and/or embedded, e.g., in paraffin. In some embodiments, tumor cells, e.g., epithelial tumor cells, are separated from at least some surrounding stromal tissue (e.g., stromal cells and/or extracellular matrix). Cells or tissue of interest can be isolated using, e.g., tissue microdissection, e.g., laser capture microdissection. It should be appreciated that a sample can be a sample isolated from any of the subjects described herein.

In some embodiments, cells of the sample are lysed. Nucleic acids or polypeptides may be isolated from the samples (e.g., cells or tissues of interest). In some embodiments DNA, optionally isolated from a sample, is amplified. A wide variety of methods are available for detection of DNA, e.g., DNA encoding PPAR-δ or a PPAR-δ target protein. In some embodiments RNA, optionally isolated from a sample, is reverse transcribed and/or amplified. A wide variety of solution phase or solid phase methods are available for detection of RNA, e.g., mRNA encoding PPAR-δ or a PPAR-δ target protein. Suitable methods include e.g., hybridization-based approaches (e.g., nuclease protection assays, Northern blots, microarrays, in situ hybridization), amplification-based approaches (e.g., reverse transcription polymerase chain reaction (which can be a real-time PCR reaction), or sequencing (e.g., RNA-Seq, which uses high throughput sequencing techniques to quantify RNA transcripts (see, e.g., Wang, Z., et al. Nature Reviews Genetics 10, 57-63, 2009)). In some embodiments of interest a quantitative PCR (qPCR) assay is used. Other methods include electrochemical detection, bioluminescence-based methods, fluorescence-correlation spectroscopy, etc.

Aspects of the methods described herein involve detecting the levels or presence of expression products, e.g., an expression product of PPAR-δ or a PPAR-δ target gene. Levels of expression products may be assessed using any suitable method. Either mRNA or protein level may be measured. Exemplary methods for measuring mRNA include hybridization based assays, polymerase chain reaction assay, sequencing, in situ hybridization, etc. Exemplary methods for measuring protein levels include ELISA assays, Western blot, mass spectrometry, or immunohistochemistry. It will be understood that suitable controls and normalization procedures can be used to accurately quantify expression. Values can also be normalized to account for the fact that different samples may contain different proportions of a cell type of interest, e.g., tumor cells or tissues compared to corresponding non-tumor cells or tissues (e.g., health cells or tissues).

In some embodiments, the biological sample comprises a colon biopsy specimen. In some embodiments, the biological sample comprises an epithelial cell. In some embodiments the biological sample comprises an intestinal stem cell. In some embodiments the biological sample comprises a non-stem intestinal progenitor cell. In some embodiments the biological sample comprises a Paneth cell. In some embodiments the biological sample comprises a goblet cell. In some embodiments, the biological sample is obtained by performing a colonoscopic biopsy. In some embodiments, (a) determining the level of expression of PPAR-δ or the PPAR-δ target gene comprises determining the mRNA level of expression of PPAR-δ or the PPAR-δ target gene. In some embodiments, (a) determining the level of expression of PPAR-δ or the PPAR-δ target gene is accomplished by performing a hybridization-based assay, a polymerase chain reaction-based assay, or sequencing. In some embodiments, (a) determining the level of expression of PPAR-δ or the PPAR-δ target gene comprises determining the protein level of expression of PPAR-δ or the PPAR-δ target gene. In some embodiments, (a) determining the level of expression of PPAR-δ or the PPAR-δ target gene is accomplished by ELISA, Western blot, mass spectrometry, or immunohistochemistry.

In another aspect, the present invention includes a method for identifying an agent that is capable of stimulating the proliferation of and/or self-renewal of intestinal stem cells and/or non-stem intestinal progenitor cells. In some embodiments, a method for identifying an agent that is capable of stimulating the proliferation of and/or self-renewal of intestinal stem cells and/or enhancing the number and/or function of non-stem intestinal progenitor cells comprises: (a) contacting a cell culture comprising small intestinal crypt cells with a candidate agent; and (b) assaying for (i) an increase in the amount of an intestinal stem cell marker in the cell culture, wherein an increase in the amount of the intestinal stem cell marker in the cell culture is indicative of the proliferation and/or self-renewal of ISCs in the cell culture, and indicates that the candidate agent is an agent that is capable of stimulating the proliferation of and/or self-renewal of ISCs or (ii) a decrease in the amount of or absence of an intestinal stem cell marker in the cell culture and/or an increase in the amount of a non-stem intestinal progenitor cell marker in the cell culture, wherein a decrease in the amount of or absence of an intestinal stem cell marker in the cell culture and/or an increase in the amount of the non-stem intestinal progenitor cell marker in the culture indicates that the candidate agent is an agent that is capable of enhancing the number and/or function of non-stem intestinal progenitor cells. In some embodiments, an intestinal stem cell marker comprises Olmf4. In such embodiments, step (b) of the method comprises assaying for an increase in Olmf4 in the cell culture, wherein increase in the level of Olmf4 in the cell culture is indicative of the proliferation and self-renewal of ISCs in the cell culture. In some embodiments, an intestinal stem cell marker comprises LGR5. In such embodiments, step (b) of the method comprises assaying for an increase in LGR5 in the cell culture, wherein increase in the level of LGR5 in the cell culture is indicative of the proliferation and self-renewal of ISCs in the cell culture. In some embodiments, an intestinal stem cell marker comprises ASCL2. In such embodiments, step (b) of the method comprises assaying for an increase in ASCL2 in the cell culture, wherein increase in the level of ASCL2 in the cell culture is indicative of the proliferation and self-renewal of ISCs in the cell culture. In some embodiments, the non-stem intestinal progenitor cell marker comprises WDR43.

In some embodiments, a method for identifying an agent that is capable of stimulating the proliferation of and/or self-renewal of intestinal stem cells comprises: (a) contacting a cell culture comprising intestinal crypts, e.g., small intestinal crypts with a candidate agent; and (b) assaying $Lgr5^+$ ISCs in the cell culture for an increase in the amount of organoid bodies formed, wherein an increase in the amount of organoid bodies formed by the $Lgr5^+$ ISCs is indicative of the proliferation of Paneth cells in the culture.

A wide variety of test agents can be used in the methods. For example, a test agent can be a small molecule, polypeptide, peptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multwell plates. They can be dissolved in a solvent (e.g., DMSO) or provided in dry form, e.g., as a powder or solid. Collections of synthetic, semisynthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see https://mli.nih.gov/mli/). The NIH Clinical Collection (NCC) is a plated array of approximately 450 small molecules that have a history of use in human clinical trials. These compounds are highly drug-like with known safety profiles. The NCC collection is arrayed in six 96-well plates. 50 µl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test agent may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or anti-hormonal drug, etc. In some embodiments, a compound is one that has undergone at least some preclinical or clinical development or has been determined or predicted to have "drug-like" properties. For example, the test agent may have completed a Phase I trial or at least a preclinical study in non-human animals and shown evidence of safety and tolerability. In some embodiments, a test agent is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant adverse effect on cell viability and/or proliferation, or the reduction in viability or proliferation can be no more than 1%, 5%, or 10% in various embodiments.

In various embodiments of any aspect herein pertaining to screening methods (e.g., methods of identifying agents), the screen may be performed using a single test agent or multiple test agents in a given reaction vessel. In various embodiments the number of reaction vessels and/or test agents is at least 10; 100; 1000; 10,000; 100,000, or more. In some embodiments of any aspect herein pertaining at least in part to screening methods (e.g., methods of identifying agents) a high throughput screen (HTS) is performed. High throughput screens often involve testing large numbers of test agents with high efficiency, e.g., in parallel. For example, tens or hundreds of thousands of agents may be routinely screened in short periods of time, e.g., hours to days. Such screening is often performed in multiwell plates (sometimes referred to as microwell or microtiter plates or microplates) containing, e.g., 96, 384, 1536, 3456, or more wells or other vessels in which multiple physically separated depressions, wells, cavities, or areas (collectively "wells") are present in or on a substrate. Different test agent(s) may be present in or added to the different wells. It will be understood that some wells may be empty, may comprise replicates, or may contain control agents or vehicle. High throughput screens may involve use of automation, e.g., for liquid handling, imaging, and/or data acquisition or processing, etc. In some embodiments an integrated robot system comprising one or more robots transports assay-microplates from station to station for, e.g., addition, mixing, and/or incubation of assay constituents (e.g., test agent, target, substrate) and, in some embodiments, readout or detection. A HTS system may prepare, incubate, and analyze many plates simultaneously. Certain general principles and techniques that may be applied in embodiments of a HTS are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser. Test agent(s) showing an activity of interest (sometimes termed "hits") may be retested and/or, optionally (e.g., depending at least in part on results of retesting) selected for further testing, development, or use. In some embodiments one or more structural analogs of a hit is synthesized. Such analogs may, for example, comprise substitution of one or more functional groups or heteroatoms present in the hit by a different functional group or heteroatom or substituting a heteroatom or functional group present in place of a hydrogen in the hit, etc. In some embodiments one or more such analog(s) are then tested for a property or activity of interest (e.g., ability to increase the level and/or activity of PPAR-δ and/or a PPAR-δ target protein or to mimic the physiological response to a high fat diet.).

Positive and/or negative controls may be used in any of the screens. An appropriate positive or negative control can be selected based at least in part on the assay. A negative control may be to perform the assay in the absence of a test agent.

In some embodiments, information derived from sequence analysis, mutational analysis, and/or structural analysis is used in the identification of a modulator. For example, in some embodiments a structure (e.g., a two-dimensional or three-dimensional structure) of a target, e.g., a TF, generated at least in part using, e.g., nuclear magnetic resonance, homology modeling, and/or X-ray crystallography is used. In some embodiments a structure obtained with a ligand (e.g., an inhibitor) bound to the target may be used. In some embodiments a computer-aided computational approach sometimes referred to as "virtual screening" is used in the identification of candidate modulators. Structures of compounds, e.g., small molecules may be screened for ability to bind to a region (e.g., a "pocket") accessible to the compound. The region may be any region accessible to the compound, e.g., a concave region on the surface or a cleft or a region involved in dimerization. A variety of docking and pharmacophore-based algorithms are known in the art, and computer programs implementing such algorithms are available. Commonly used programs include Gold, Dock, Glide, FlexX, Fred, and LigandFit (including the most recent releases thereof). See, e.g., Ghosh, S., et al., Current Opinion in Chemical Biology, 10(3): 194-2-2, 2006; McInnes C., Current Opinion in Chemical Biology; 11(5): 494-502, 2007, and references in either of the foregoing articles, which are incorporated herein by reference. In some embodiments a virtual screening algorithm may involve two major phases: searching (also called "docking") and scoring. During the first phase, the program automatically generates a set of candidate complexes of two molecules (test compound and target molecule) and determines the energy of interaction of the candidate complexes. The scoring phase assigns scores to the candidate complexes and selects a structure that displays favorable interactions based at least in part on the energy. To perform virtual screening, this process may be repeated with a large number of test compounds to identify those that, for example, display the most favorable interactions with the target. In some embodiments, low-energy binding modes of a small molecule within an active site or possible active site or other target region are identified. In some embodiments a compound capable of docking at a site where mutations are known to inhibit activity of the target is identified. Variations may include the use of rigid or flexible docking algorithms and/or including the potential binding of water molecules. In some embodiments the three-dimensional structure of an enzyme's active site may be used to identify potential inhibitors. Agent(s) that have the potential to bind in or near an active site may be identified. These predictions may then be tested using the actual compound. A new inhibitor thus identified may then be used to obtain a structure of the enzyme in an inhibitor/enzyme complex to show how the molecule is binding to the active site. Further changes may be made to the inhibitor, e.g., to try to improve binding. This cycle may be repeated until an inhibitor of sufficient predicted or actual potency (e.g., a desired potency for therapeutic purposes) is identified. Numerous small molecule structures are available and can be used for virtual screening. A collection of compound structures may sometimes referred to as a "virtual library". For example, ZINC is a publicly available database containing structures of millions of commercially available compounds that can be used for virtual screening (http://zinc.docking.org/; Shoichet, J. Chem. Inf. Model., 45(1): 177-82, 2005). A database containing about 250,000 small molecule structures is available on the National Cancer Institute (U.S.) website (at http://129.43.27.140/ncidb2/). In some embodiments multiple small molecules may be screened, e.g., up to 50,000; 100,000; 250,000; 500,000, or up to 1 million, 2 million, 5 million, 10 million, or more. Compounds can be scored and, optionally, ranked by their potential to bind to a target. Compounds identified in virtual screens can be tested in cell-free or cell-based assays or in animal models to confirm their ability to inhibit activity of a target molecule, their ability to activate a target molecule, and/or to assess their biological and/or pharmacological activity. Computational approaches may be used to predict one or more physico-chemical, pharmacokinetic and/or pharmacodynamic properties of compounds identified in a physical or virtual screen. Such information may be used, e.g., to select one or more hits for, e.g., further testing, development, or use. For example, small molecules having characteristics typical of "drug-like" molecules may be selected and/or small molecules having one or more undesired characteristics may be avoided.

In some aspects of any screening and/or characterization methods, test agents are contacted with test cells (and optionally control cells) or used in cell-free assays at a predetermined concentration. In some embodiment the concentration is about up to 1 nM. In some embodiments the concentration is between about 1 nM and about 100 nM. In some embodiments the concentration is between about 100 nM and about 10 μM. In some embodiments the concentration is at or above 10 μM, e.g., between 10 μM and 100 μM. Following incubation for an appropriate time, optionally a predetermined time, the effect of compounds or composition on a parameter of interest in the test cells is determined by an appropriate method known to one of ordinary skill in the art, e.g., as described herein. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously. If desired, the compound can be removed prior to assessing the effect on the cells.

One skilled in the art readily appreciates that the present disclosure is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Diet is a modifiable lifestyle factor that has a profound impact on mammalian physiology, health, and disease. Long-lived mammalian tissue-specific stem cells play a key role in how tissues adapt to diverse diet-induced physiological states. Such stem-cells dynamically remodel tissue composition in response to physiological cues by altering the balance between self-renewal and differentiation divisions.[1] However, the mechanisms through which diet perturbs tissue stem and progenitor cell biology and influences pathologies, such as cancer, are poorly understood.

The mammalian intestine is known to respond to dietary cues. In low calories states the mammalian intestinal stem cell niche orchestrates tissue remodeling by sensing organismal physiology and pharmacologic targeting of the stem cell niche can promote tissue regeneration. Lgr5$^+$ cells at the base of intestinal crypts constitute a majority of the intestinal stem cells (ISCs) that drive the rapid renewal of the intestinal epithelium.[2,3] These Lgr5$^+$ ISCs are adjacent to Paneth cells, which are a central component of the ISC niche. In addition to elaborating key growth factors essential for ISC identity, recent data illustrate that Paneth cells regulate ISC function in response to the physiologic state evoked by calorie restriction (CR, a reduction in calorie intake of 20-40%).[4,5] For example, the presence of Paneth cells in co-culture experiments enhance the potential of Lgr5$^+$ ISCs to propagate organoid bodies or "mini-intestines", and Paneth cells derived from mice on a CR regimen further boost the organoid-forming potential of these ISCs.[4,5] These findings raise the question of whether the Paneth cell niche invariably directs ISC function in response to all dietary cues or whether some diets, such as pro-obesity diets, can alter stem cell function by acting directly on them.

While in diverse species CR diets promote lifespan, health, or both; generally enhance tissue progenitor function; and reduce cancer growth[1,5-8], pro-obesity diets are associated with metabolic syndrome and linked to increases in many cancer types.[1] However, little is known about how stem and progenitor cell adaptation to a pro-obesity diet alters their potential to initiate tumors.[1] In the mouse intestine, Lgr5$^+$ stem cells serve as the cell-of-origin for precancerous adenomatous lesions upon loss of the Apc tumor suppressor gene; yet, it is unclear whether this is the case in the context of obesity-linked intestinal tumorigenesis.[9,10] In the following studies, the present inventors interrogate how long-term high fat diet (HFD)-induced obesity influences intestinal stem and progenitor cell function and the implications of this physiologic state on the cellular origins of intestinal dysplasia.

Example 1

The present inventors conducted studies to identify methods and processes that augment the function of endogenous stem cells in order to enhance tissue regeneration. The inventors demonstrated that high fat diet-induced obesity by activating a PPAR-delta transcriptional program boosts the function of not only intestinal stem cells (ISCs) but also that of their immediate differentiated progeny (non-stem cell progenitor cells). The PPARs, including PPAR-delta, are a subgroup of nuclear hormone receptors that transcriptionally regulate nutrient and metabolic pathways, including the sensing of fatty acids.

Figure 1A:
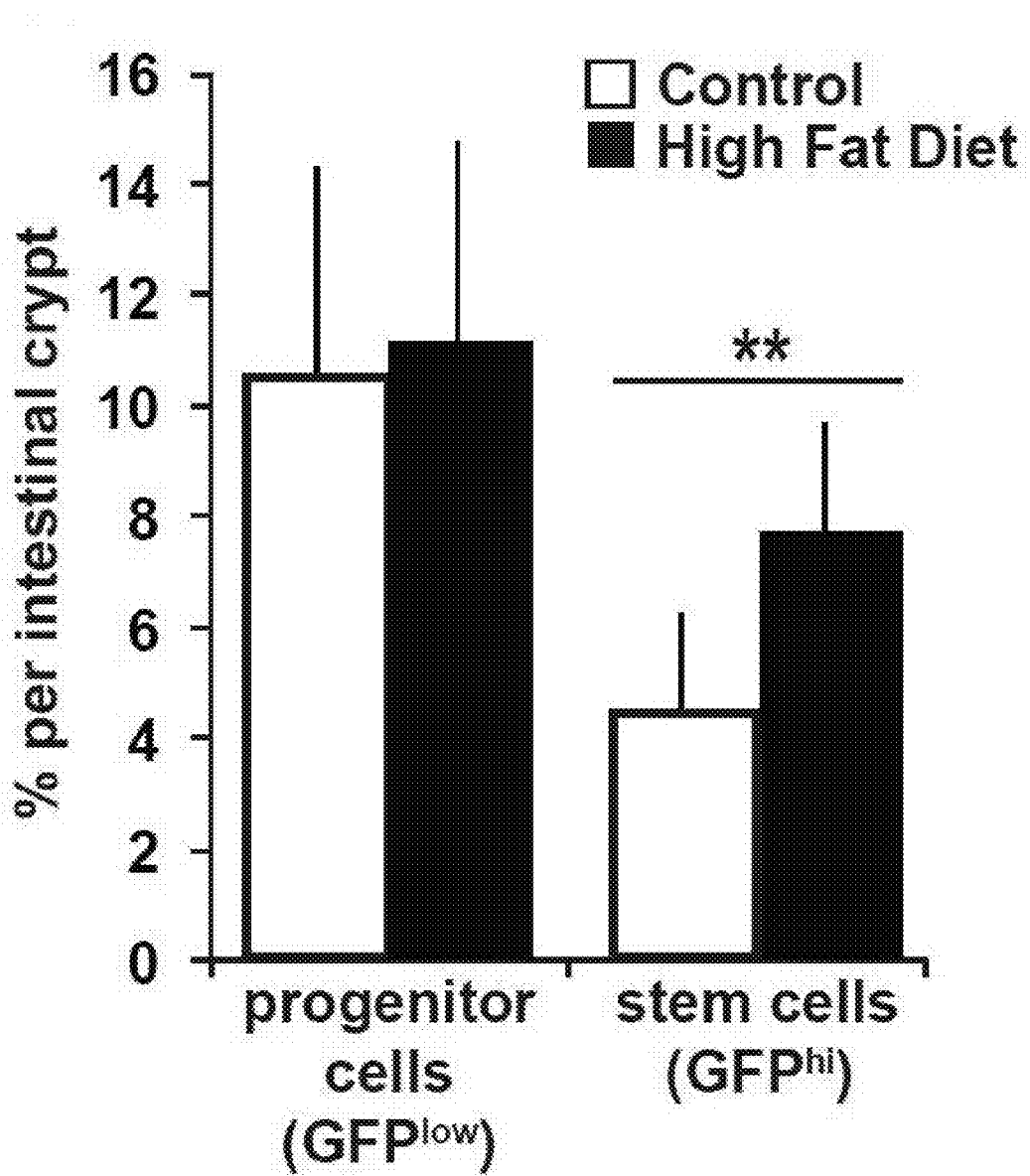
FIGS. 1A-1B demonstrate that high fat diet High Fat Diet increases intestinal stem cell numbers and permits Paneth Cell independent organoid initiation.
Figure 1B:
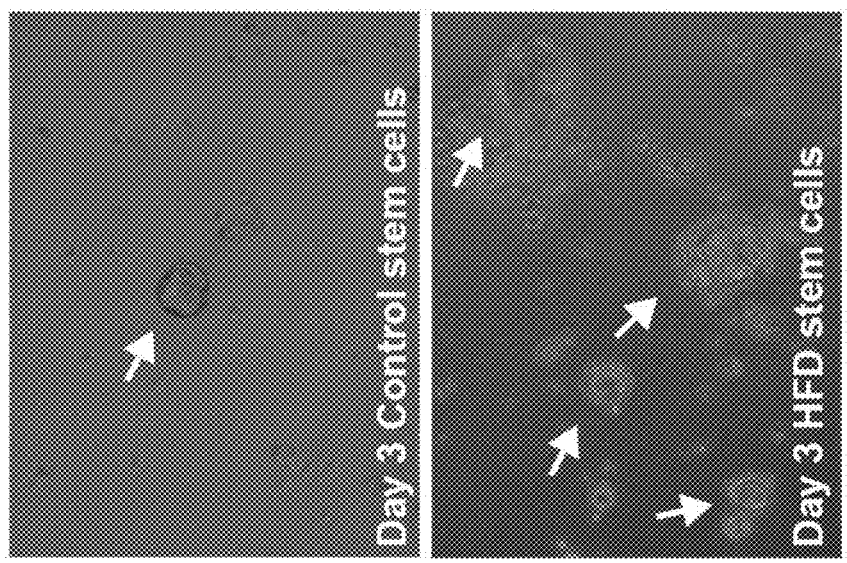
Figure 1B:
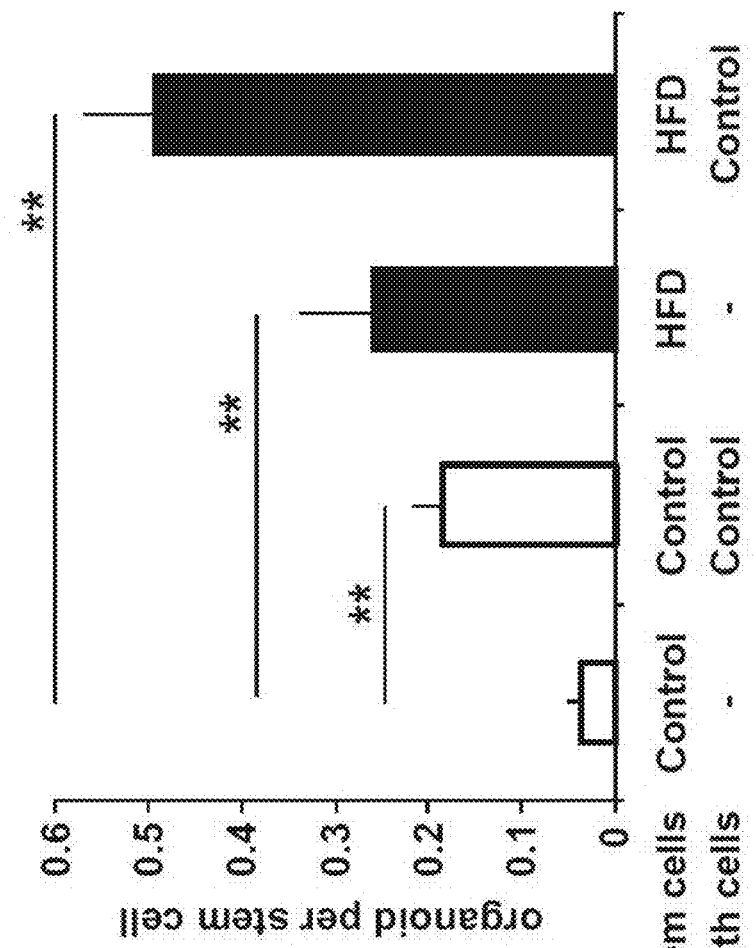
Figures 2A, 2B:
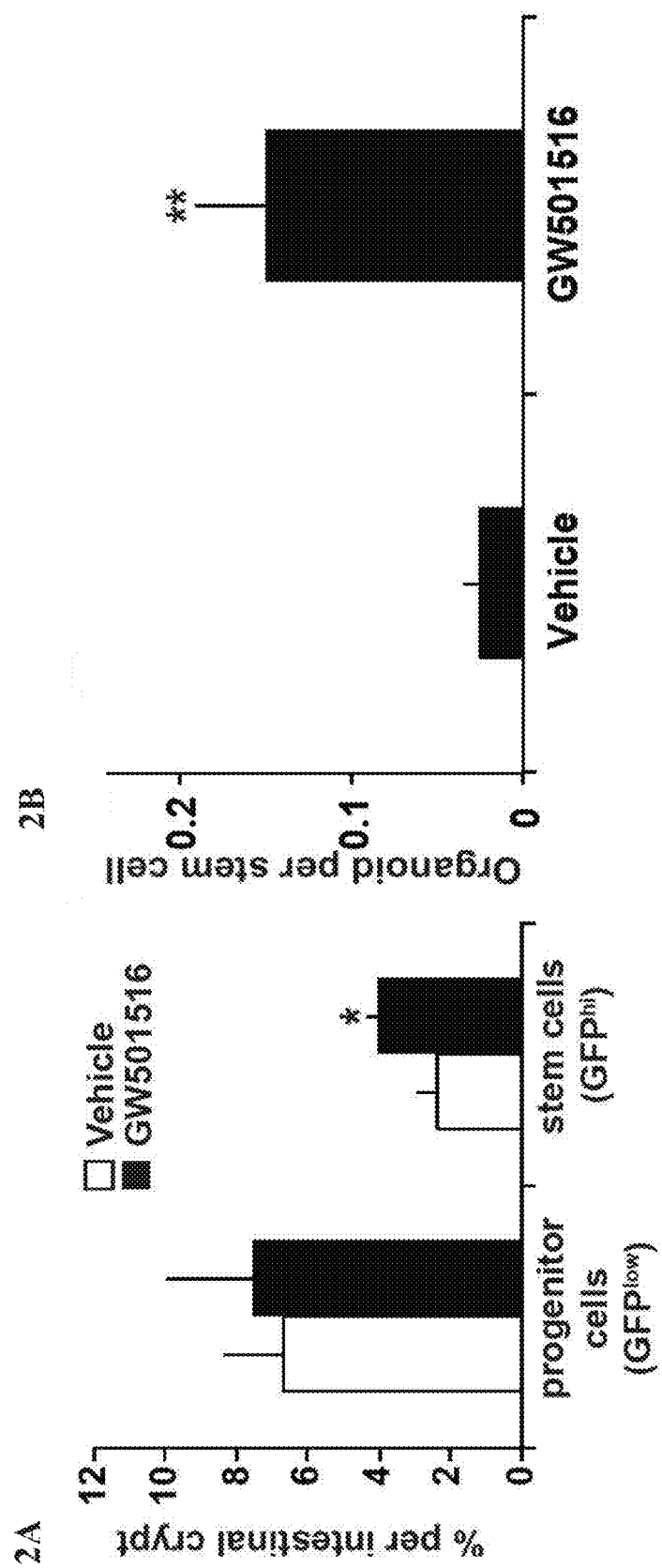
FIGS. 2A-2C demonstrate that peroxisome proliferator activated receptor delta (PPAR-δ) agonist, GW501516, boosts intestinal stem cell numbers and allows for niche independent organoid formation by stem cells and progenitor cells.
Figure 2C:
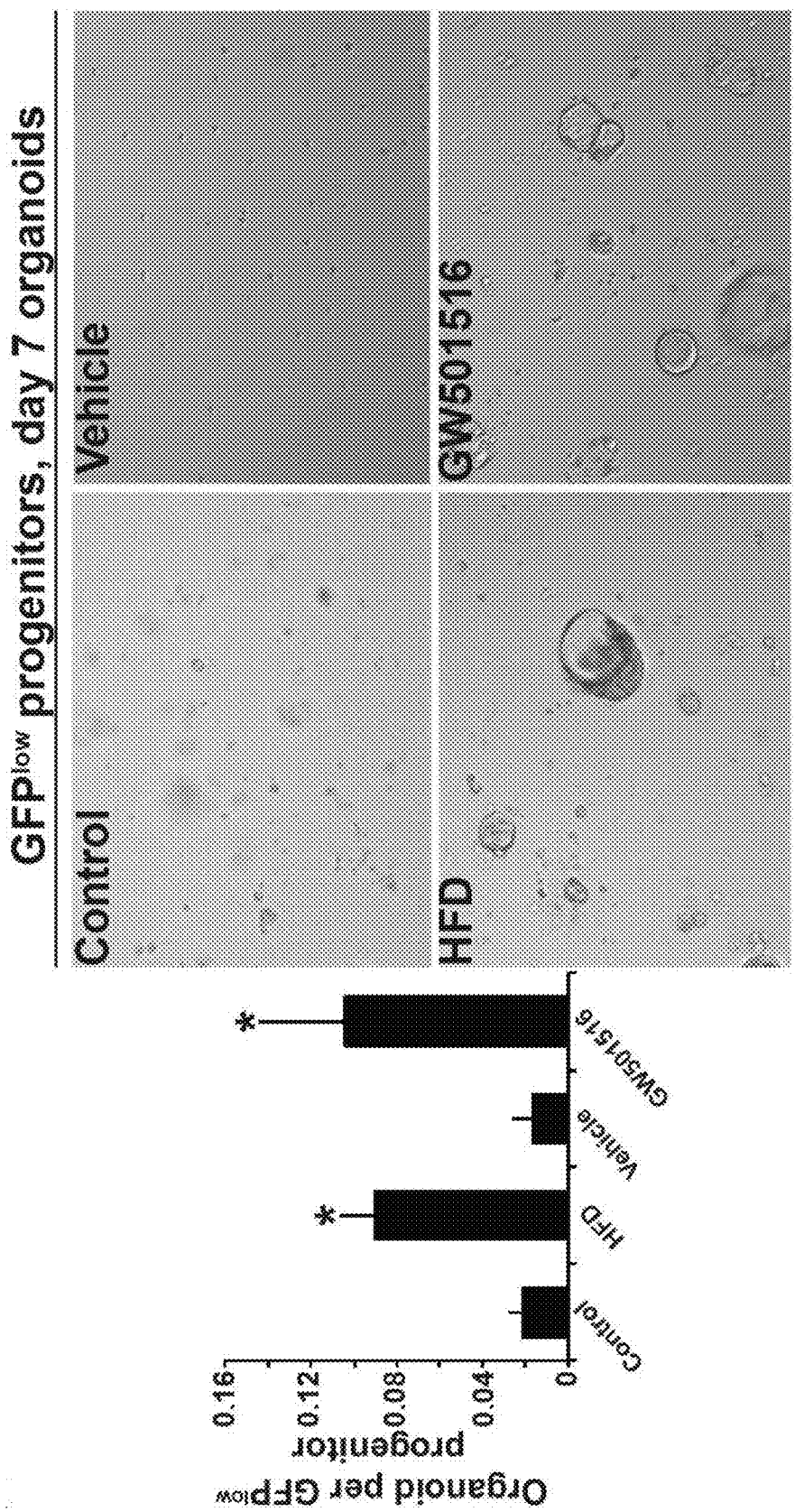

The inventors placed mice on a 60% high fat diet for greater than 8 months and found that this increased the number and function of ISCs (FIG. 1A) and moreover, that a high fat diet increases the incidence of spontaneous intestinal carcinoma. In a functional 3-dimensional organoid assay, high fat diet-derived ISCs where able to form mini-intestines (organoid bodies) in culture without their endogenous Paneth cells niche, which are required in order for ISCs from regular chow fed mice to form organoid bodies (FIG. 1B). Further, we found that non-stem cell progenitors isolated from high fat diet mice had acquired the ability to initiate and maintain these organoid mini-intestines in contrast to those isolated from regular chow fed mice (FIG. 2C). Mechanistically, our data indicate that a high fat diet-induced PPAR-delta program mediates this ISC and progenitor phenotype in high fat diet-induced obesity. Pharmacologically, we are able to mimic many of the effects of HFD on ISCs and intestinal progenitors. Daily IP injections of a PPAR-delta agonist, GW501515, at 4 mg/kg for 2-3 weeks was sufficient to enhance the numbers of iSCs in vivo (FIG. 2A) and the niche independent organoid-initiating capacity of ISCs and progenitor cells (FIGS. 2B and 2C).

Example 2

To assess the effects of obesity on intestinal homeostasis, the present inventors maintained mice on a long-term HFD for 9-14 months, which is sufficient time to observe many of the metabolic phenotypes associated with obesity.[11,12] Consistent with previous reports, HFD-fed mice gained considerably more mass (36.18±4.78 versus 53.3±15.8 g) than their regular chow fed counterparts (FIG. 8A). While the small intestines from HFD-fed mice were shorter in length (39.7±2.3 versus 34.7±2.8 cm; FIG. 8C) and weighed less (1.46±0.19 versus 1.20±0.20; FIG. 8B), there was no change in the density of crypt-villous units (FIG. 8D) or in the number of apoptotic cells (FIG. 8K). Morphologically, HFD led to a mild reduction in villi length (480±8 versus 448±18 um; FIG. 8G), an associated decrease in villous enterocyte numbers (155±5 versus 135±10; FIG. 8F), and an increase in crypt depth (FIG. 8E). HFD did not change the numbers of chromogranin A+enteroendocrine cells or alcian blue+ goblet cells per crypt-villous unit of the small intestine (FIGS. 9A and 9B). The HFD also augmented mitochondria numbers in progenitors relative to control, and a HFD also increased mitochondrial numbers in stem cells relative to control as measured by relative mitochondrial DNA quality per cell. To address how HFD affected the frequency of primitive intestinal progenitor cells, the present inventors performed in situ hybridization for olfactomedin 4 (Olfm4), a marker that is expressed by the Lgr5$^+$ stem cells (also termed crypt base columnar cells or CBCs).[13] Compared to mice fed a regular chow diet, those on a HFD had a 50% increase in the number of Olfm4$^+$ primitive progenitors, as shown in FIG. 3A. Interestingly, HFD had the opposite effect on cryptidin 4+Paneth cell numbers, leading to a 23% reduction in these niche cells (FIG. 3B). These observations lead to two important conclusions: first, HFD enhances ISCs numbers and self-renewal (e.g. deeper crypts with more Olfm4$^+$ ISCs) at the expense of differentiation (e.g. shorter and less cellular villi); second, the increase in ISCs occurs despite a decrease in the numbers of Paneth cells, raising the possibility that under a HFD ISCs adapt to decreased Paneth cell interactions.

The fact that HFD boosted the numbers of ISCs and crypt depth in the small intestine indicated that HFD potentially enhanced the proliferation of ISCs and their more differentiated progeny (i.e. progenitors or also termed transit-amplifying cells). To address this possibility, the inventors assessed incorporation of 5-bromodeoxyuridine (BrdU) into ISCs and TA-cells. After a 4-h pulse of BrdU, crypts of HFD mice had nearly two-fold more BrdU+ISCs compared to crypts from controls (1.2±0.3 versus 2.1±0.7; FIG. 3C and FIG. 8H). Furthermore, HFD augmented the number of BrdU+cells in the larger pool of progenitors (11.6±2.0 versus 14.7±2.04), indicating that output and migration from this compartment into the villi may also increase. Indeed, HFD mice 24-h after a single dose of BrdU had more absolute numbers of BrdU-labelled cells in the villi (14.0±2.6 versus 19.1±1.7; FIG. 8I) and a greater percentage of villus enterocytes that were BrdU+(8.0±1.4 versus 12.0±2.3%; FIG. 8I). These findings demonstrate that in HFD increased stem and progenitor cell proliferation translates into enhanced output and migration of cells from the crypt compartment into the villi.

Example 3

Given that ISC numbers and proliferation increased in HFD, the present inventors sought to determine whether it also boosted the regeneration of the small intestine using in vitro and in vivo assays. To test in vitro function, we isolated small intestinal crypts, which contain all of the stem-cell activity of the epithelium, and assessed, in an unbiased manner (independent of stem-cell markers), their ability to give rise to organoid bodies in 3-D culture. These organoids recapitulate the epithelial architecture and cellular diversity of the mammalian intestine and are a proxy for ISC activity as only stem cells can initiate and maintain these structures long-term.[5,14]

HFD-derived crypts were almost twofold more likely to initiate these mini-intestines in culture than those derived from controls (0.29±0.05 versus 0.58±0.09; FIG. 3D). Furthermore, these organoids were more cystic (i.e. less differentiated[15]) in structure and contained fewer crypt domains (8.3±2.4 versus 3.4±2.2; FIG. 3E), and when sub-cloned the HFD-derived primary organoids generated more secondary organoids (3.4±0.8 versus 6.9±2.8; FIG. 3F). Collectively, these data illustrate that HFD crypts and primary organoids derived from them possess more stem-cell activity.

To determine whether HFD also enhances crypt regeneration in vivo, we performed a clonogenic microcolony assay to test for ISC activity.[5,16] After administration of a lethal dose of irradiation, HFD-fed mice manifested increased numbers of surviving and regenerating crypts (FIG. 3G). The foregoing data therefore support the notion that HFD-treatment boosts the numbers and regenerative capacity of ISCs in vitro and in vivo.

Example 4

To interrogate the effects of the HFD on stem and progenitor cells, the present inventors utilized Lgr5-EGFP-IRES-CreERT2 knock-in mice, which allow for the quantification and isolation of Lgr5-GFP$^{hi}$ stem-cells and Lgr5-GFP$^{low}$ progenitors.[2] Compared to controls, mice on a HFD had a nearly a 2-fold increase in the frequency of Lgr5-GFP$^{hi}$ ISCs (4.4±1.8% versus 7.7±2.2%; FIG. 3H), which corroborates that observed in Olfm4$^+$ ISCs (FIG. 3A).

Figure 3I:
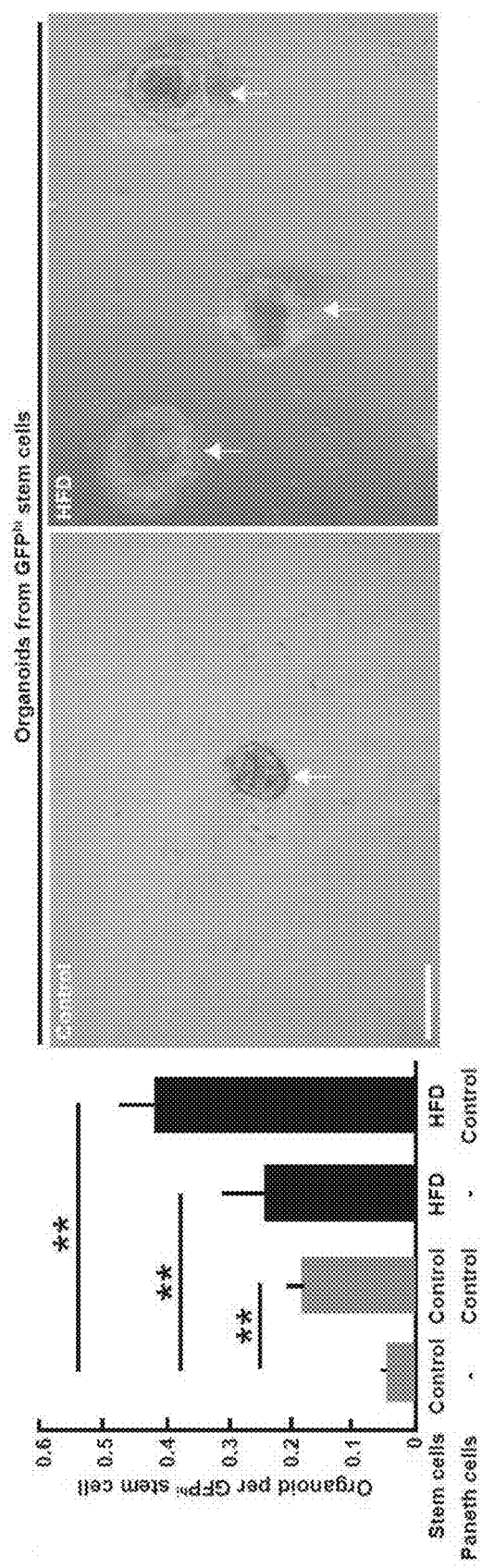

The opposing effects of HFD on ISC and Paneth cell numbers led the present inventors to ask whether HFD altered ISC function and their niche dependence. We assayed the clonogenic potential of ISCs from control and HFD-fed mice either alone or in combination with the niche Paneth cells.[5] Consistent with earlier studies[4,5,14], control ISCs by themselves were inefficient at forming organoids in culture, but, when co-cultured with Paneth cells, 19% of the stem-cells initiated organoid bodies (FIG. 3I). Surprisingly, HFD-derived ISCs by themselves (without Paneth cells) had an augmented capacity (4.0±1.4% versus 24.3±7.4%) to initiate organoids, and co-culture with Paneth cells further increased their organoid-initiating activity (FIG. 3I). The foregoing data, together with the observation that HFD uncouples the in vivo expansion of ISCs from their Paneth cell niche, suggest that ISCs undergo autonomous changes in response to a HFD that poises them for niche-independent growth.

Example 5

Figures 4A, 4B, 4C, 4D:
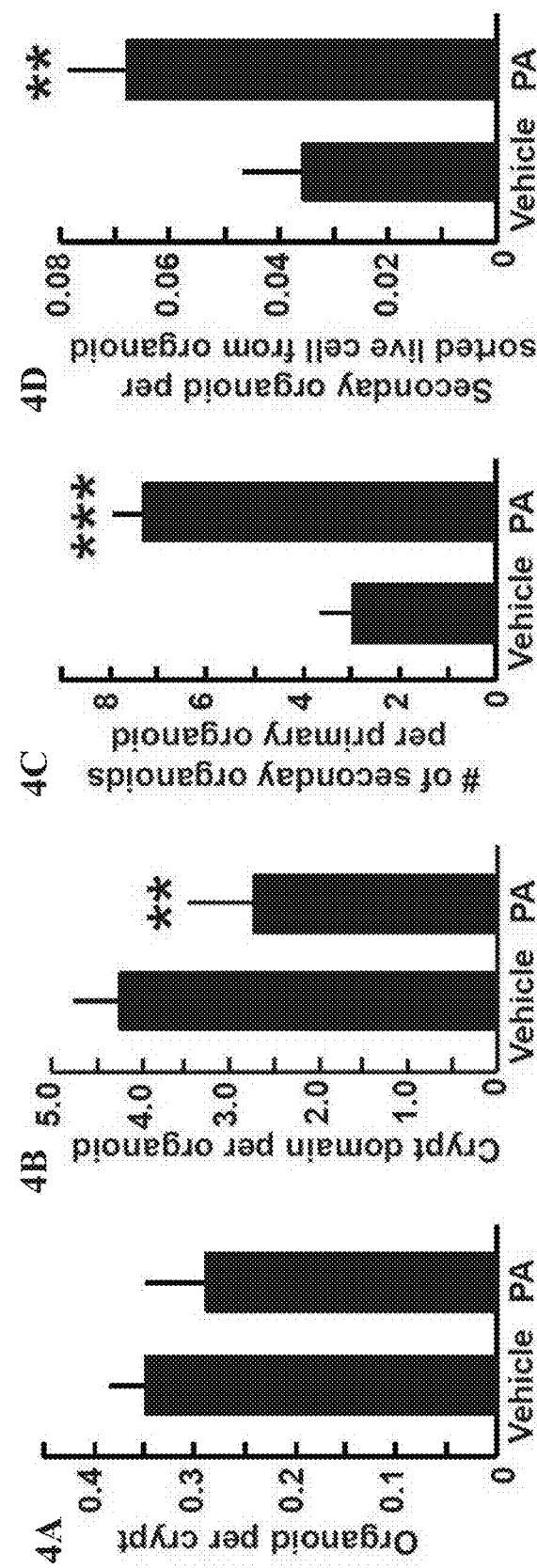
FIGS. 4A-F illustrate that ex vivo exposure of ISCs to palmitic acid recapitulates aspects of a HFD.
Figures 4E, 4F:
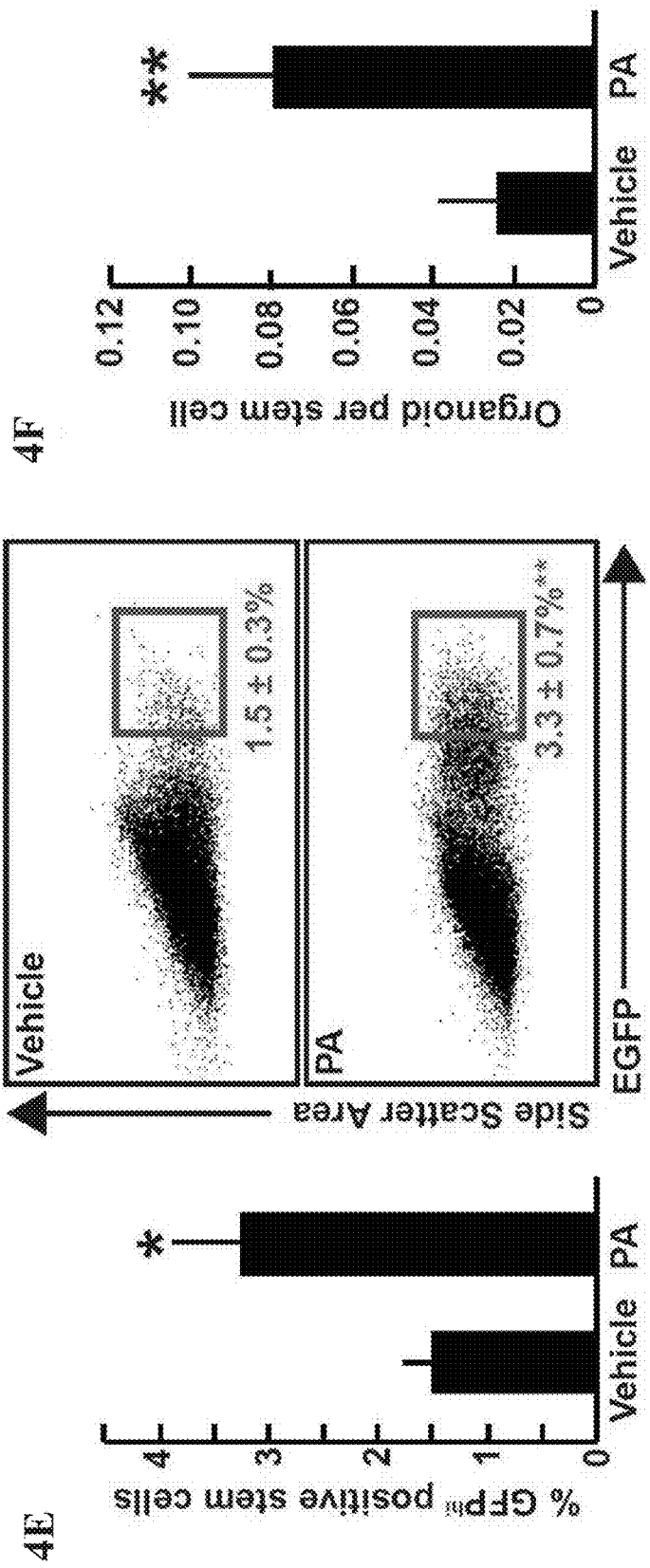

To address whether dietary constituents of the HFD can recapitulate aspects of the stem-cell phenotype induced by the HFD, the present inventors expanded control diet-derived organoids in crypt media supplemented with palmitic acid (PA), which is an abundant fatty acid constituent of the HFD regimen.[17] Low doses of PA did not change the clonogenic potential of control crypts in primary culture (FIG. 4A); however, just as observed with organoids from HFD mice, the PA-treated organoids had fewer crypt domains per organoid (4.2±0.6 versus 2.8±0.7; FIG. 4B). To examine whether PA, like a HFD, augmented the numbers of ISCs per primary organoid, we assayed the self-renewal capacity of the primary organoids in secondary cultures and assessed how PA-treatment influenced the frequency of ISCs. Cells from PA-treated organoids gave rise to a more than twofold increase in secondary organoids (FIGS. 2C and 2D), which correlated with a twofold increase in ISCs (FIG. 4E). Similar to their counterparts derived from HFD mice, these PA-treated ISCs were primed for Paneth cell-independent organoid formation (0.024±0.014 versus 0.079±0.021; FIG. 4F). The foregoing data therefore indicates that key dietary constituents of HFD, like PA, may mediate aspects of the in vivo HFD stem-cell phenotype.

Example 6

Figure 5A:
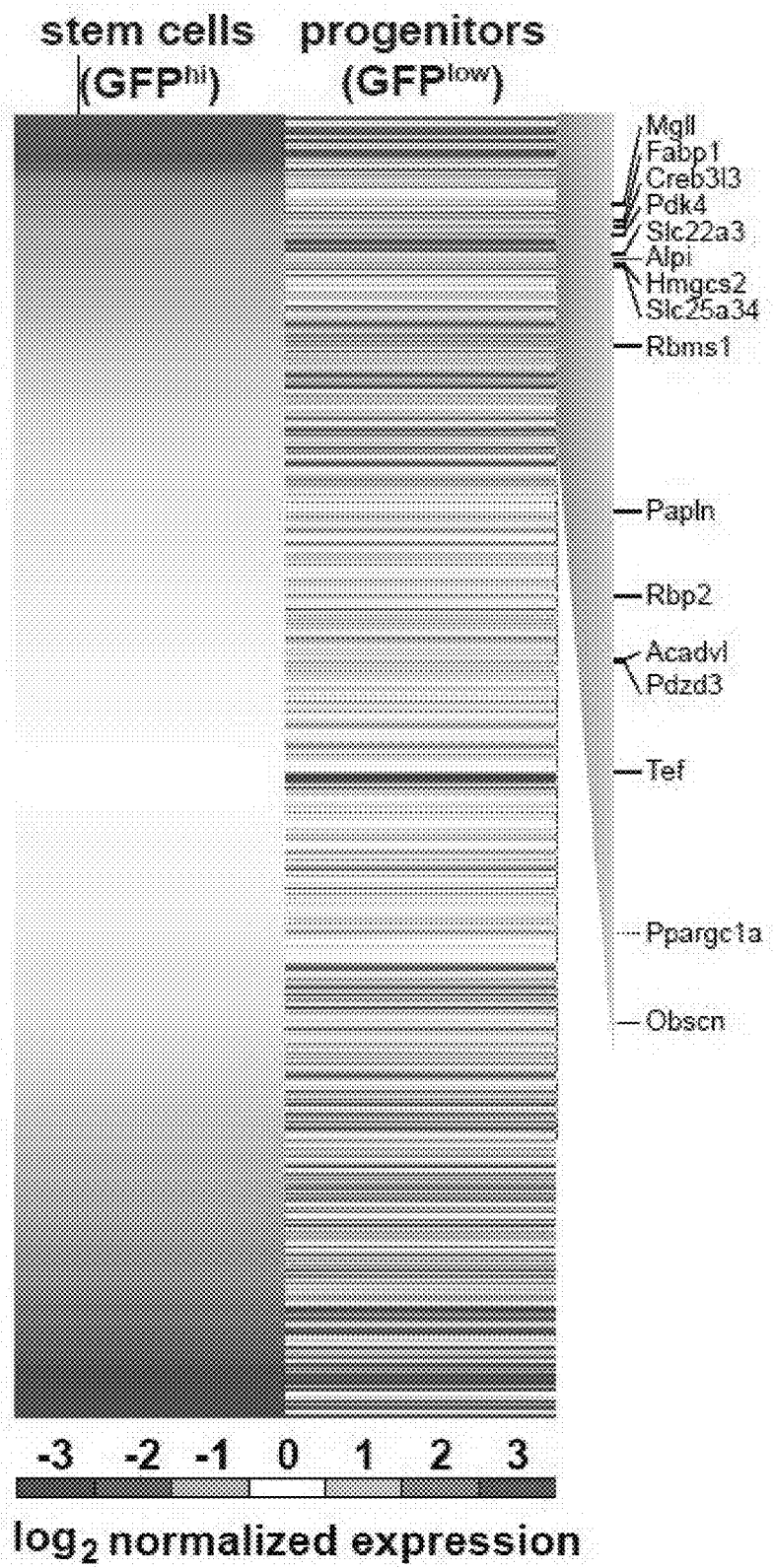

Several lines of evidence suggest that HFD engages a stable cell state in ISCs: first, HFD-derived organoids maintain increased self-renewal capacity in culture conditions that are not supplemented with fatty acids (FIG. 3F); and second, HFD-derived ISCs are poised for niche-independent growth in the organoid assay, indicating that these ISCs have autonomously activated a program that compensates for reduced Paneth cell interactions. To gain mechanistic insight into how HFD mediates its effects, the present inventors performed mRNA-sequencing on flow sorted Lgr5-GFP$^{hi}$ ISCs and Lgr5-GFP$^{low}$ progenitor cells from control and HFD-fed mice, respectively (pooling 2 mice from each treatment group; FIG. 5A). GSEA pathway and transcription factor binding motif analysis revealed enrichment for transcriptional targets and binding motifs of the nuclear receptor PPAR (peroxisome proliferator-activated receptor) family and PPAR heterodimeric binding partners liver/retinoid X receptor (LXR/RXR; FIGS. 5A, 3B and 10C).[18,19] The PPAR family is comprised of three members (alpha, beta/delta, and gamma); amongst these PPAR-delta (PPAR-δ) is the dominant member expressed in intestinal stem and progenitor cells at the mRNA level in control and HFD mice (greater than 6 to 26-fold overexpressed compared to PPAR-alpha and PPAR-gamma, respectively; FIGS. 10A and 10B). Therefore, we focused our attention on PPAR-δ and its potential role in coupling HFD to ISC function.

Figures 5D, 5E:
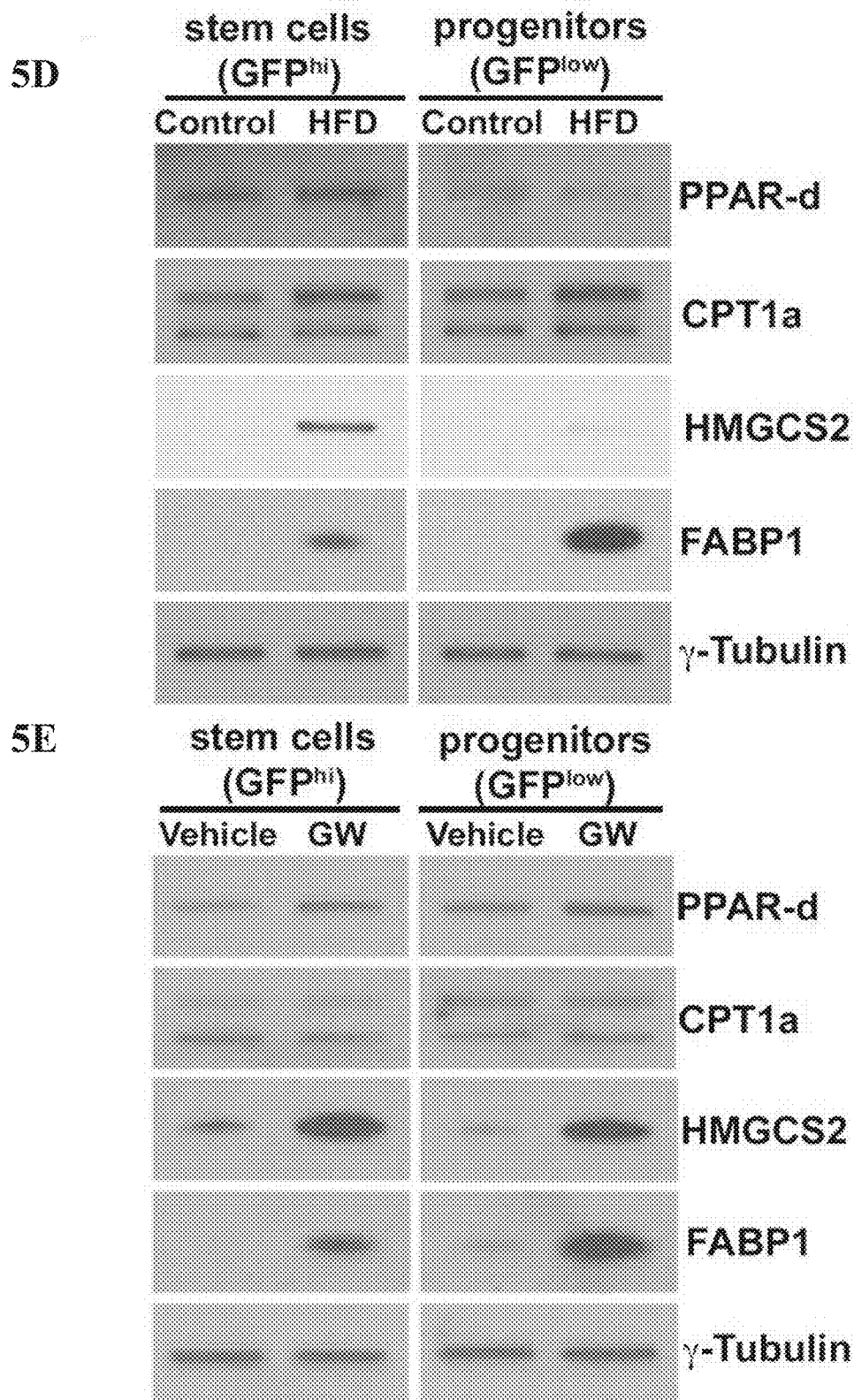
Figures 5F, 5G, 5H:
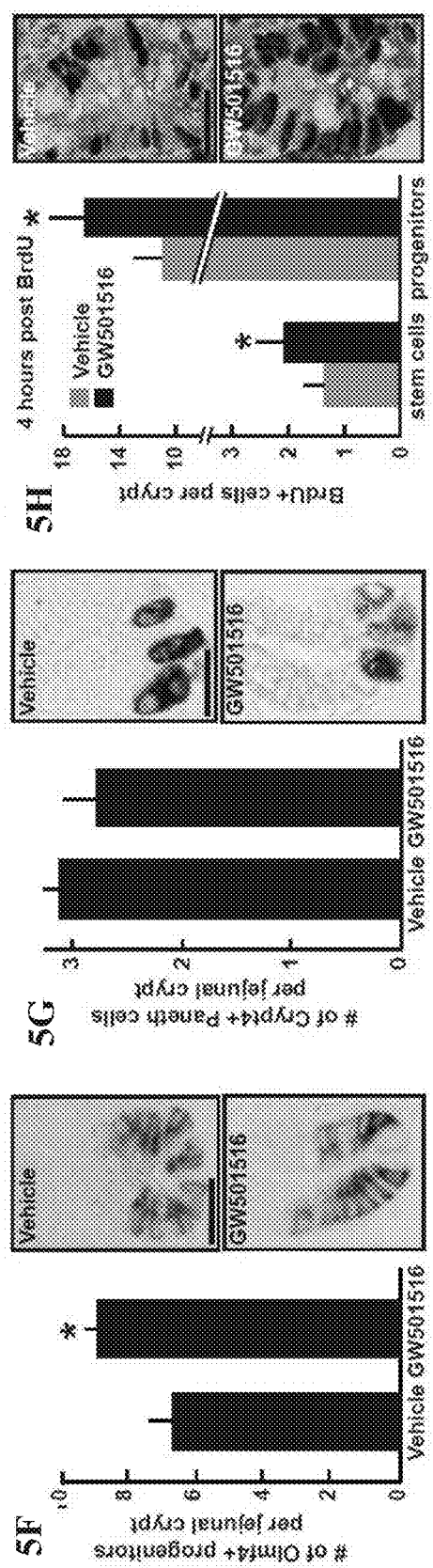
Figures 5I, 5J, 5K:
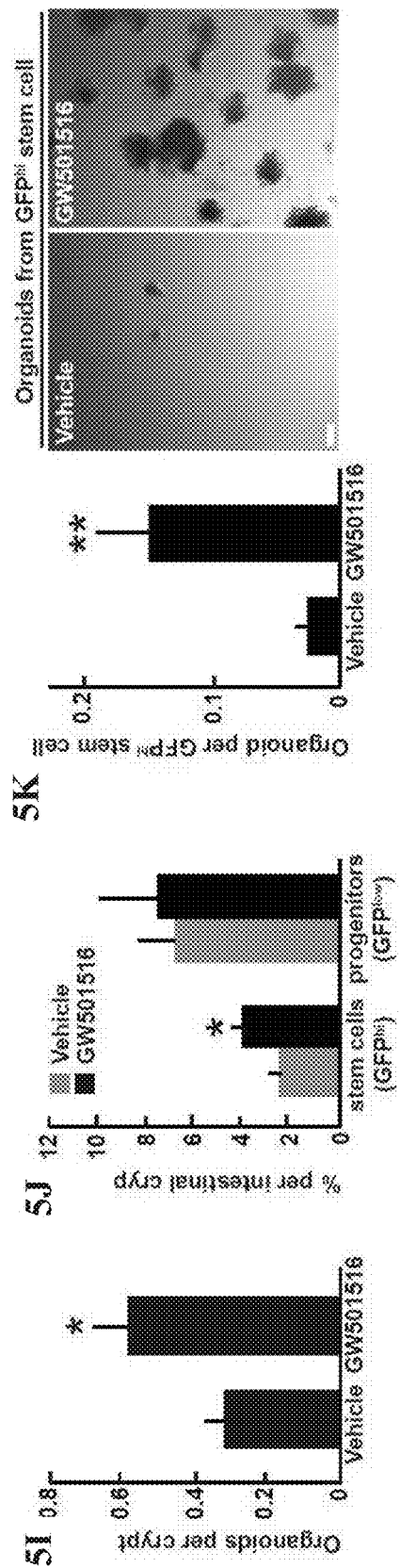

Although PPAR-δ expression itself does not substantially change (FIG. 10B), a HFD robustly increased the expression of many of its target genes at the mRNA and protein level in ISCs and progenitors (FIGS. 5C and 5D). To functionally address whether engagement of a PPAR-δ program mimics the HFD, the present inventors administered the PPAR-δ agonist GW501516 for 4 weeks to Lgr5-EGFP-IRES-Cre-ERT2 mice.[20,21] This led to the strong induction of PPAR-δ target proteins in ISCs and progenitors (FIG. 5E). Furthermore, agonist-activated PPAR-δ signaling augmented the in vivo frequencies of Olfm4$^+$ and Lgr5$^+$ ISCs (FIGS. 5F and 5J) and proliferation of stem and TA-cells (FIG. 5H) but had no impact on Paneth cell numbers (FIG. 5G). Notably, crypts from agonist-treated mice gave rise to more organoids than those from vehicle-treated mice (FIG. 5I), and isolated ISCs were much more effective at Paneth cell-independent organoid-initiation than their control counterparts (0.025±0.009 versus 0.15±0.04; FIG. 5K). The foregoing data indicate that HFD activates PPAR-δ signaling, which in turn can mediate many of the effects of the HFD on ISC function.

Example 7

Because HFD and PPAR-δ activation confer increased stem-cell function, the present inventors sought to determine whether these interventions regulate the Wnt/β-catenin pathway, which is required for ISC identity. [2,22] β-catenin translocation from the cytoplasm to the nucleus is an essential step in pathway activation that enables β-catenin-mediated transcriptional stimulation, and nuclear localization is often a proxy for its activity.[9,23] We examined β-catenin localization in isolated Lgr5-GFP$^{hi}$ ISCs and Lgr5-GFP$^{low}$ progenitors, and found that HFD and agonist-induced PPAR-δ signaling led to more nuclear β-catenin accumulation, as illustrated in FIGS. 6A and 6B and in FIGS. 11A and 11B. This finding was confirmed separately with β-catenin immunohistochemistry on intestinal sections: a greater percentage of CBCs and TA-cells demonstrated nuclear β-catenin with a HFD (FIGS. 11C and 11E) or PPAR-δ agonist administration compared to their respective controls (FIGS. 11D and 11E).

To address how HFD and agonist-activated PPAR-δ influenced β-catenin transcriptional activity, we performed microfluidic-based multiplexed single-cell qPCR using primers for a curated list of known β-catenin target genes and intestinal stem cell markers, shown below in Table 3. Single cell analyses of β-catenin target gene expression revealed heterogeneity in control and HFD-derived ISCs and progenitors (FIG. 12A). t-Distributed stochastic neighbor embedding (t-SNE) analysis of single cell gene expression data of all β-catenin target genes demonstrated clustering of HFD-derived ISCs and progenitors (FIG. 7C) from their control fed counterparts, consistent with the notion that HFD perturbs β-catenin target gene expression in primitive intestinal progenitors.

While HFD did not alter expression of stem cell signature genes (β-catenin target genes that differ between stem and progenitor cells, FIGS. 12B and 12D)[24], it significantly evoked expression of several other β-catenin target genes, including Bmp4, Jag1, Jag2 and Edn3 in ISCs (FIG. 6D) and progenitors (FIG. 6E). Furthermore, we found that that while the HFD-induced β-catenin signature genes (HFD signature; FIG. 12C) are heterogeneously expressed in control ISCs and progenitors, they form a distinct cluster upon HFD as shown in the tSNE analysis (FIG. 12E). We then confirmed using single cell qPCR that agonist-activated PPAR-δ also induced transcription of the HFD-induced β-catenin signature genes: Bmp4, Jag1, Jag2 and Edn3 (FIGS. 6F and 6G). Collectively, these results support a model in which HFD-induced PPAR-δ signaling mediates a distinct β-catenin program in ISCs and progenitor cells.

TABLE 3

Primer Sequences for Single Cell Analysis (SEQ ID NOs: 1-188)

| Sequence Name | SEQ ID NO. | Forward Primer | Sequence Name | Reverse Primer | SEQ ID NO. |
|---|---|---|---|---|---|
| ABCB1F | 1 | CAGCAGTCAGTGTGCTTACAA | ABCB1R | ATGGCTCTTTTATCGGCCTCA | 2 |
| ADAM10F | 3 | ATGGTGTTGCCGACAGTGTTA | ADAM10R | GTTTGGCACGCTGGTGTTTTT | 4 |
| ALEX1F | 5 | CTGGTGCCTGCTACTGTGTAT | ALEX1R | CCCCTACCCCAACATTAGTCT | 6 |
| ASCL2F | 7 | AAGCACACCTTGACTGGTACG | ASCL2R | AAGTGGACGTTTGCACCTTCA | 8 |
| AXIN2F | 9 | TGACTCTCCTTCCAGATCCCA | AXIN2R | TGCCCACACTAGGCTGACA | 10 |
| BAMB1F | 11 | GATCGCCACTCCAGCTACTTC | BAMB1R | GCAGGCACTAAGCTCAGACTT | 12 |
| BCL2L2F | 13 | GCGGAGTTCACAGCTCTATAC | BCL2L2R | AAAAGGCCCCTACAGTTACCA | 14 |
| BCL2L1F | 15 | GACAAGGAGATGCAGGTATTGG | BCL2L1R | TCCCGTAGAGATCCACAAAAGT | 16 |
| BIRC5F | 17 | GAGGCTGGCTTCATCCACTG | BIRC5R | CTTTTTGCTTGTTGTTGGTCTCC | 18 |
| BMI1F | 19 | ATCCCCACTTAATGTGTGTCCT | BMI1R | CTTGCTGGTCTCCAAGTAACG | 20 |
| BMP4F | 21 | TTCCTGGTAACCGAATGCTGA | BMP4R | CCTGAATCTCGGCGACTTTTT | 22 |
| CCND1F | 23 | GCGTACCCTGACACCAATCTC | CCND1R | CTCCTCTTCGCACTTCTGCTC | 24 |
| CD44F | 25 | CACCATTGCCTCAACTGTGC | CD44R | TTGTGGGCTCCTGAGTCTGA | 26 |
| CDKN2AF | 27 | CGCAGGTTCTTGGTCACTGT | CDKN2AR | TGTTCACGAAAGCCAGAGCG | 28 |
| CDX1F | 29 | GGACGCCCTACGAATGGATG | CDX1R | GTACCGGCTGTAGTGAAACTC | 30 |
| CLDN1F | 31 | GGGGACAACATCGTGACCG | CLDN1R | AGGAGTCGAAGACTTTGCACT | 32 |
| COX2F | 33 | TGAGCAACTATTCCAAACCAGC | COX2R | GCACGTAGTCTTCGATCACTATC | 34 |
| DKK1F | 35 | CTCATCAATTCCAACGCGATCA | DKK1R | GCCCTCATAGAGAACTCCCG | 36 |
| DKK4F | 37 | GTACTGGTGACCTTGCTTGGA | DKK4R | CCGTTCATCGTGAAACGCTAAG | 38 |
| DNMT1F | 39 | AAGAATGGTGTTGTCTACCGAC | DNMT1R | CATCCAGGTTGCTCCCCTTG | 40 |
| EDN1F | 41 | GCACCGGAGCTGAGAATGG | EDN1R | GTGGCAGAAGTAGACACACTC | 42 |
| EFNB1F | 43 | TGTGGCTATGGTCGTGCTG | EFNB1R | CCAAGCCCTTCCCACTTAGG | 44 |
| ENC1F | 45 | CTGTTTCATAAGTCCTCCTACGC | ENC1R | CACCACTGAACATGGCTTCG | 46 |
| EPHB2F | 47 | GCGGCTACGACGAGAACAT | EPHB2R | GGCTAAGTCAAAATCAGCCTCA | 48 |
| EPHB3F | 49 | CATGGACACGAAATGGGTGAC | EPHB3R | GCGGATAGGATTCATGGCTTCA | 50 |
| FGF18F | 51 | CCTGCACTTGCCTGTGTTTAC | FGF18R | TGCTTCCGACTCACATCATCT | 52 |
| FGFBP1F | 53 | CTAAATCTCTGACGCATGGCA | FGFBP1R | AACTCCTGATCGGCTTGTGTG | 54 |
| FGFBP3F | 55 | GGTCGCTTCGTGAGTCCAG | FGFBP3R | AGCAGCCGTCTCCAGTAGT | 56 |
| FRA1F | 57 | ATGTACCGAGACTACGGGAA | FRA1R | CTGCTGCTGTCGATGCTTG | 58 |
| FSCN1F | 59 | GACTGCGAAGGTCGCTACC | FSCN1R | CTGATCGGTCTCTTCATCCTGA | 60 |
| GASTF | 61 | CGCTCCCAGCTACAGGATG | GASTR | GGTCTGCTATGAAGTGTTGAGG | 62 |
| HATH1F | 63 | GAGTGGGCTGAGGTAAAAGAGT | HATH1R | GGTCGGTGCTATCCAGGAG | 64 |
| NEDD9F | 65 | ATGTGGGCGAGGAATCTTATGG | NEDD9R | TTCCCTGGGACAATGCCTTG | 66 |
| HES1F | 67 | CCAGCCAGTGTCAACACGA | HES1R | AATGCCGGGAGCTATCTTTCT | 68 |

TABLE 3-continued

Primer Sequences for Single Cell Analysis (SEQ ID NOs: 1-188)

| Sequence Name | SEQ ID NO. | Forward Primer | Sequence Name | Reverse Primer | SEQ ID NO. |
|---|---|---|---|---|---|
| ID2F | 69 | ATGAAAGCCTTCAGTCCGGTG | ID2R | AGCAGACTCATCGGGTCGT | 70 |
| TCF4F | 71 | CGAAAAGTTCCTCCGGGTTTG | TCF4R | CGTAGCCGGGCTGATTCAT | 72 |
| JAG1F | 73 | CCTCGGGTCAGTTTGAGCTG | JAG1R | CCTTGAGGCACACTTTGAAGTA | 74 |
| JUNF | 75 | CCTTCTACGACGATGCCCTC | JUNR | GGTTCAAGGTCATGCTCTGTTT | 76 |
| L1CAMF | 77 | AAAGGTGCAAGGGTGACATTC | L1CAMR | TCCCCACGTTCCTGTAGGT | 78 |
| LAMC2F | 79 | CAGACACGGGAGATTGCTACT | LAMC2R | CCACGTTCCCCAAAGGGAT | 80 |
| LEF1F | 81 | TGTTTATCCCATCACGGGTGG | LEF1R | CATGGAAGTGTCGCCTGACAG | 82 |
| LGR5F | 83 | CCTACTCGAAGACTTACCCAGT | LGR5R | GCATTGGGGTGAATGATAGCA | 84 |
| MENAF | 85 | GCCCAGAGCAAGGTTACTG | MENAR | GCCCACAGAAAATACATCGCAA | 86 |
| METF | 87 | GTGAACATGAAGTATCAGCTCCC | METR | TGTAGTTTGTGGCTCCGAGAT | 88 |
| MMP14F | 89 | CAGTATGGCTACCTACCTCCAG | MMP14R | GCCTTGCCTGTCACTTGTAAA | 90 |
| MMP7F | 91 | CTGCCACTGTCCCAGGAAG | MMP7R | GGGAGAGTTTTCCAGTCATGG | 92 |
| MYBF | 93 | AGACCCCGACACAGCATCTA | MYBR | CAGCAGCCCATCGTAGTCAT | 94 |
| MYCF | 95 | ATGCCCCTCAACGTGAACTTC | MYCR | CGCAACATAGGATGGAGAGCA | 96 |
| MYCBPF | 97 | GCTGGACACGCTGACGAAA | MYCBPR | TCTAGGCGAAGCAGCTCTATTT | 98 |
| NOS2F | 99 | GTTCTCAGCCCAACAATACAAGA | NOS2R | GTGGACGGGTCGATGTCAC | 100 |
| NOTCH2F | 101 | ATGTGGACGAGTGTCTGTTGC | NOTCH2R | GGAAGCATAGGCACAGTCATC | 102 |
| NRCAMF | 103 | AAAGGGAAACCTCCCCCAAG | NRCAMR | TGTTGATGACAAGGGTTCCTGA | 104 |
| PLAUF | 105 | GCGCCTTGGTGGTGAAAAAC | PLAUR | TTGTAGGACACGCATACACCT | 106 |
| PLAURF | 107 | CAGAGCTTTCCACCGAATGG | PLAURR | GTCCCCGGCAGTTGATGAG | 108 |
| PPARDF | 109 | TCCATCGTCAACAAAGACGGG | PPARDR | ACTTGGGCTCAATGATGTCAC | 110 |
| S100A4F | 111 | TCCACAAATACTCAGGCAAAGAG | S100A4R | GCAGCTCCCTGGTCAGTAG | 112 |
| SGK1F | 113 | CTGCTCGAAGCACCCTTACC | SGK1R | TCCTGAGGATGGGACATTTTCA | 114 |
| SMC3F | 115 | CGAAGTTACCGAGACCAAACA | SMC3R | TCACTGAGAACAAACTGGATTGC | 116 |
| SOX9F | 117 | AGTACCCGCATCTGCACAAC | SOX9R | ACGAAGGGTCTCTTCTCGCT | 118 |
| SP5F | 119 | TGGGTTCACCCTCCAGACTTT | SP5R | CCGGCGAGAACTCGTAAGG | 120 |
| SRSF3F | 121 | GCGCAGATCCCCAAGAAGG | SRSF3R | ATCGGCTACGAGACCTAGAGA | 122 |
| SUZ12F | 123 | AACTCGAAATCTTATCGCACCAA | SUZ12R | TGCAAATGTGCAGACAAGCTAT | 124 |
| TCF1F | 125 | AGGAGTGTAATAGGGCGGAGT | TCF1R | GAGGTCCGTTATAGGTGTCCA | 126 |
| TIAM1F | 127 | GAAGCACACTTCACGCTCC | TIAM1R | CTCCAGGCCATTTTCAGCCA | 128 |
| TNCF | 129 | ACGGCTACCACAGAAGCTG | TNCR | ATGGCTGTTGTTGCTATGGCA | 130 |
| VEGFF | 131 | GCCAGACAGGGTTGCCATAC | VEGFR | GGAGTGGGATGGATGATGTCAG | 132 |
| YAP1F | 133 | TACTGATGCAGGTACTGCGG | YAP1R | TCAGGGATCTCAAAGGAGGAC | 134 |
| CCND3F | 135 | CGAGCCTCCTACTTCCAGTG | CCND3R | GGACAGGTAGCGATCCAGGT | 136 |
| FZD1F | 137 | CAGCAGTACAACGGCGAAC | FZD1R | GTCCTCCTGATTCGTGTGGC | 138 |
| FZ7F | 139 | GCCACACGAACCAAGAGGAC | FZ7R | CGGGTGCGTACATAGAGCATAA | 140 |
| BTRCPF | 141 | AAGACTGTAATAATGGCGAACCC | BTRCPR | TCTCTTGGTTTATGCAAAGCCTG | 142 |

TABLE 3-continued

Primer Sequences for Single Cell Analysis (SEQ ID NOs: 1-188)

| Sequence Name | SEQ ID NO. | Forward Primer | Sequence Name | Reverse Primer | SEQ ID NO. |
|---|---|---|---|---|---|
| BCATENINF | 143 | ATGGAGCCGGACAGAAAAGC | BCATENINR | CTTGCCACTCAGGGAAGGA | 144 |
| NEMOF | 145 | AAGCACCCCTGGAAGAACC | NEMOR | CCTGCTCTGAAGGCAGATGTA | 146 |
| NAKED1F | 147 | AGGAAAGGCATCGAGGAGTG | NAKED1R | TCGCTCAGTCTCTCCATTCTC | 148 |
| RNF43F | 149 | TCCGAAAGATCAGCAGAACAGA | RNF43R | GGACTGCATTAGCTTCCCTTC | 150 |
| LRP6F | 151 | TTGTTGCTTTATGCAAACAGACG | LRP6R | GTTCGTTTAATGGCTTCTTCGC | 152 |
| LRP5F | 153 | AAGGGTGCTGTGTACTGGAC | LRP5R | AGAAGAGAACCTTACGGGACG | 154 |
| OLFM4F | 155 | CAGCCACTTTCCAATTTCACTG | OLFM4R | GCTGGACATACTCCTTCACCTTA | 156 |
| PREX1F | 157 | TTTAACCAGGTCGATTCCATCCA | PREX1R | CGGACCGTGCATTCCTCTTT | 158 |
| RAC1F | 159 | GAGACGGAGCTGTTGGTAAAA | RAC1R | ATAGGCCCAGATTCACTGGTT | 160 |
| Cldn15F | 161 | ATGTCGGTAGCTGTGGAGAC | Cldn15R | GGACGGAAAGTCCCAGCAG | 162 |
| Edn3F | 163 | CCCTGGTGAGAGGATTGTGTC | Edn3R | CCTTGTCCTTGTAAGTGAAGCAC | 164 |
| EFNB2F | 165 | ATTATTTGCCCCAAAGTGGACTC | EFNB2R | GCAGCGGGGTATTCTCCTTC | 166 |
| EPHB4F | 167 | TATGCCACGATACGCTTCACC | EPHB4R | AGCTTCGCTCTCGTAATAGAAGA | 168 |
| FGFR4F | 169 | GCTCGGAGGTAGAGGTCTTGT | FGFR4R | CCACGCTGACTGGTAGGAA | 170 |
| NEDD8F | 171 | GGAGCGAATCAAGGAGCGT | NEDD8R | ACGGAACCACCTAGAATCTTGT | 172 |
| TCF7F | 173 | AGCTTTCTCCACTCTACGAACA | TCF7R | AATCCAGAGAGATCGGGGGTC | 174 |
| JAG2F | 175 | CAATGACACCACTCCAGATGAG | JAG2R | GGCCAAAGAAGTCGTTGCG | 176 |
| SMC2F | 177 | GGCTGGGATTACCAAAGCCTC | SMC2R | CACCAATAACCACCTGTCTTGT | 178 |
| Sox9F | 179 | GAGCCGGATCTGAAGAGGGA | Sox9R | GCTTGACGTGTGGCTTGTTC | 180 |
| NcadherinF | 181 | ATGTGCCGGATAGCGGGAGC | NcadherinR | TACACCGTGCCGTCCTCGTC | 182 |
| EcadherinF | 183 | CACCTGGAGAGAGGCCATGT | EcadherinR | TGGGAAACATGAGCAGCTCT | 184 |
| ACTINBF | 185 | GGCTGTATTCCCCTCCATCG | ACTINBR | CCAGTTGGTAACAATGCCATGT | 186 |
| GAPDHF | 187 | AGGTCGGTGTGAACGGATTTG | GAPDHR | TGTAGACCATGTAGTTGAGGTCA | 188 |

Example 8

It is understood that somatic stem cells often accumulate the initial mutations that lead to oncogenic transformation. Because HFD-induced PPAR-δ activates a β-catenin signature in progenitor cells, the present inventors hypothesized that in diet-induced obesity non-stem cell populations can acquire stem-cell features and potentially serve as an additional cells-of-origin for tumor initiation.[1,25] To explore this possibility, the present inventors sought to determine whether HFD and agonist-activated PPAR-δ influenced the organoid-initiating capacity of progenitors (non-ISCs). Interestingly, Lgr5-GFP$^{low}$ progenitors from HFD and PPAR-δ agonist treated mice were capable of forming organoids, as illustrated in FIG. 7A, albeit at a lower frequency than their respective Lgr5-GFP$^{hi}$ stem-cell counterparts (FIGS. 3I and 5K), raising the possibility that enforced PPAR-δ signaling in intestinal progenitors not only bestows organoid-initiating capacity but also tumor-initiating potential.

To test this possibility, the present inventors generated Apc$^{loxp/loxp}$; Lgr5-EGFP-IRES-CreERT2 mice to assess whether pharmacological PPAR-δ activation modifies the tumorigenic capacity of the Lgr5-GFP$^{low}$ progenitors. Injection with tamoxifen leads to Apc-loss in the Lgr5-GFP$^{hi}$ ISCs, which in turn generate Apc-null Lgr5-GFP$^{low}$ progenitors. Four days after tamoxifen administration, we flow sorted Apc-null Lgr5-GFP$^{hi}$ ISCs and Lgr5-GFP$^{low}$ progenitors from vehicle and PPAR-δ agonist treated mice to assess the tumor-forming potential of these populations using separate assays (FIG. 7B): first, we examined their ability to give rise to adenomatous organoids in culture; and second, we interrogated the ability of 10,000 freshly sorted stem and progenitor cells to initiate adenomatous lesions in syngeneic recipient colons.

We found that Apc-null ISCs from PPAR-δ agonist-treated mice were as clonogenic as those from vehicle controls, as illustrated in FIG. 7C, but that enforced PPAR-δ signaling in Apc-null progenitors dramatically boosted their in vitro adenoma-initiating potential (0.04±0.05 versus 0.18±0.07; FIG. 7C). Next, we assessed the potential of freshly isolated intestinal stem and progenitor cells to form in vivo adenomatous lesions (FIG. 7B). As in the organoid assay, the PPAR-δ agonist had no additive effect on the ability of Apc-null stem-cells to form intestinal adenomas (0.67±0.13 versus 0.61±0.19; FIGS. 5E and 5F) compared to the vehicle controls. However, enforced PPAR-δ signaling permitted Apc-null progenitors, but not their vehicle-treated counterparts, to robustly initiate adenomas upon transplantation into recipient colons (0±0 versus 0.58±0.16; FIG. 7F and FIG. 13). The foregoing data indicate that PPAR-δ activation enables a subset of non-stem cells to initiate adenomatous growth in vitro and in vivo after Apc-loss.

It is interesting to note that enforced PPAR-δ signaling differentially affects the adenoma-initiating capacity of stem and progenitor cells upon Apc loss. One possible explanation for this divergence may be that ISCs, in contrast to progenitors, are in a cellular state that is facilitative for β-catenin signaling. Progenitors, however, are in a more differentiated cellular state that is less responsive to β-catenin signaling, and perhaps enforced PPAR-δ signaling in a subset of progenitors augments this responsiveness-thus enabling them to initiate tumors upon Apc-loss.

Discussion

The foregoing data favor a model in which a HFD augments ISC self-renewal and bestows features of stemness (i.e. organoid-initiating capacity) to non-stem cell progenitors through a PPAR-δ regulated program, as illustrated in FIG. 7G. Previous studies on calorie restriction demonstrated that this dietary regimen concordantly enhanced stem and Paneth cell numbers and regulated ISC function non-cell autonomously through the Paneth cell niche with no noticeable effect on progenitor cell function.[5] In contrast, here we find that long-term HFD uncouples stem and Paneth cell numbers and, functionally, these stem-cells have less dependence on Paneth cells in functional assays. Under normal physiological conditions the Paneth cell niche tightly controls ISC growth and function[4]; however, decreased contact between stem-cells and their niche in HFD (i.e. more stem-cells than Paneth cells) may result in uncoordinated stem-cell proliferation and render them more susceptible to acquiring mutations.

The fact that we find up-regulation of β-catenin targets Jag1 and Jag2 in stem and progenitor cells, both of which are Notch ligands, implicates a possible role for Notch signaling. Paneth cells normally elaborate Notch ligands[26] and prevent Lgr5$^+$ stem-cells from adopting a differentiated cellular state.[27] Because ISC numbers increase in relation to Paneth cells under a HFD or upon PPAR-δ activation, lateral Notch inhibition between proximate stem-cells or progenitor cells may serve as a surrogate source of Notch ligands for Lgr5$^+$ stem-cells that are not in direct contact with Paneth cells, allowing them to persist in vivo and in the organoid assay.

Significant epidemiologic and rodent studies link obesity to colon cancer incidence.[1,28-30] A recent study suggests that the number of somatic stem-cell self-renewal divisions accounts for the majority of variation in human cancer.[31] An implication of this model is that dietary interventions that boost stem cell self-renewal should increase the potential pool of cells that can undergo mutagenesis. Our data and a previous study[32] demonstrate that pro-obesity diets augment the numbers and proliferation of primitive intestinal progenitors, which may partially account for the increase of intestinal tumors with obesity. Another possibility raised by our results is that a diet-induced PPAR-δ program also enhances the susceptibility of non-stem cells to undergo transformation, leading to the generation of a larger and more diverse pool of cells capable of initiating tumors in the obese state. Consistent with this possibility, it has been proposed that differentiated cells in the background of Apc-deficiency and genetic activation of KRAS and NF-kB possess the capacity to initiate tumors.[10] However, the role that PPAR-δ signaling in ISCs and progenitors plays in connecting obesity-related inflammation to tumor initiation remains to be elucidated. Possessing more stem cells or non-stem cells that can undergo oncogenic transformation may be potential contributors as to why diet-induced obesity increase cancer incidence.

We found that fatty acid constituents of the HFD, and HFD-activated pathways, have the potential to increase stem and progenitor cell function and intestinal regeneration but with the potential untoward risk of increasing cancer incidence. A recent report[33] that PPAR-δ in the bone amplifies β-catenin signaling is consistent with our finding that diet-activated PPAR-δ engages a restricted β-catenin program. Notably, genes within this PPAR-δ-activated β-catenin program includes genes such as Jag1, Jag2, and BMP4 that are often deregulated in early intestinal tumorigenesis (FIGS. 6D and 6F).[34-36] Furthermore, sustained treatment with a PPAR-δ agonist has been linked to colorectal cancer initiation and progression.[37-42] Although a goal will be to exploit potential downstream mediators of PPAR-δ signaling that safely enhance intestinal regeneration and minimize carcinogenesis, it is possible that PPAR-δ effectors regulate both of these processes. Strategies that harness the pro-regenerative effects of dietary interventions that mimic HFD or agonist-activated PPAR-δ signaling may have an application in patients afflicted with intestinal atrophy and disease.

Materials and Methods

Mice, High Fat Diet, and Drug Treatment

Mice were housed in the Unit for Laboratory Animal Medicine at the Whitehead Institute for Biomedical Research and Koch Institute for Integrative Cancer Research. Lgr5-EGFP-IRES-CreERT2 mice (strain name: B6.129P2-Lgr5$^{tm1(cre/ERT2)Cle}$/J, stock number 008875), and Rosa26-lacZ mice (strain name: B6.129S4-Gt(ROSA) 26Sor$^{tm1Sor}$/J, stock number 003474) were obtained from the Jackson Laboratory. Apc$^{loxp}$ exon14 has been previously described.[43] Long-term high fat diet was achieved by feeding mice a dietary chow consisting of 60 kcal % fat (Research Diets D12492) beginning at the age of 8-12 weeks and extending for 9 to 14 months. Control mice were age-matched and fed normal chow ad libitum. GW501516 (Enzo) was reconstituted in DMSO at 4.5 mg ml$^{-1}$ and diluted 1:10 in a solution of 5% PEG400 (Hampton Research), 5% Tween80 (Sigma), 90% H$_2$O for a daily intraperitoneal injection of 4 mg/kg. Apc exon 14 was excised by tamoxifen suspended in sunflower seed oil (Spectrum S1929) at a concentration of 10 mg ml$^{-1}$, and 250 µl per 25 g of body weight was administered by intraperitoneal injection to mice twice over 4 days before harvesting tissue. BrdU was prepared at 10 mg ml$^{-1}$ in PBS, passed through 0.22 µm filter and injected at 100 mg kg$^{-1}$.

Immunohistochemistry (IHC) and Immunofluorescence (IF)

As previously described[5], tissues were fixed in 10% formalin, paraffin embedded and sectioned. Antigen retrieval was performed with Borg Decloaker RTU solution (Biocare Medical) in a pressurized Decloaking Chamber (Biocare Medical) for 3 minutes. Antibodies used: rat anti-BrdU (1:2000, Abcam 6326), rabbit chromogranin A (1:3000, Abcam 15160), rabbit monoclonal non-phospho β-catenin (1:800(IHC), 1:400(IF), CST 8814S), mouse monoclonal β-catenin (1:200, BD Biosciences 610154), rabbit monoclonal anti-cyclinD1 (1:50, CST 2978S), Biotin-conjugated secondary donkey anti-rabbit or anti-rat antibodies were used from Jackson ImmunoResearch. The Vectastain Elite ABC immunoperoxidase detection kit (Vector Labs PK-6101) followed by Dako Liquid DAB+Substrate (Dako) was used for visualization. For immunofluorescence, Alexa Fluor 568 secondary antibody (Invitrogen) was used with Prolong Gold (Life Technologies) mounting media. All antibody incubations were performed with Common Antibody Diluent (Biogenex).

In Situ Hybridization

The in situ hybridization probes used in this study correspond to expressed sequence tags or fully sequenced cDNAs obtained from Open Biosystems. The accession numbers (IMAGE mouse cDNA clone in parenthesis) for these probes are as follows: mouse Olfm4 BC141127 (9055739), mouse Cryptdin 4 BC134360 (40134597). Both sense and antisense probes were generated to ensure specificity by in vitro transcription using DIG RNA labelling mix (Roche) according to the manufacturer's instructions and to previously published detailed methods.[24,44]

Radiation and Clonogenic Microcolony Assay

Adult mice were exposed to 15 Gy of ionizing irradiation from a 137-cesium source (GammaCell) and killed after 72 hours. The number of surviving crypts per length of the intestine was enumerated from haematoxyiin and eosin stained sections.[16]

Immunoblotting

Antibodies: rabbit polyclonal anti-PPAR-δ (1:100, Thermo PA1-823A), rabbit polyclonal anti-Cpt1a (1:250, ProteinTech 15184-1-AP), rabbit polyclonal anti-HMGCS2 (1:500, Sigma AV41562), rabbit monoclonal anti-FABP1 (1:1000, Abcam ab129203), rabbit polyclonal anti-γ-tubulin (1:1000, Sigma T5192). Lgr5-GFP$^{hi}$ ISCs or GFP$^{low}$ progenitors were sorted directly into sample buffer and boiled for five minutes. Samples were resolved by SDS-PAGE and analyzed by immunoblotting with goat anti-rabbit IgG-HRP secondary antibodies (1:10,000, Santa Cruz Biotechnology sc-2054) and Western Lightning Plus-ECL detection kit (Perkin Elmer, NEL 104001EA).

qRT-PCR

Cells were sorted into Tri Reagent (Life Technologies) and total RNA was isolated according to the manufacturer's instructions with following modification: the aqueous phase containing total RNA was purified using RNeasy plus kit (Qiagen). RNA was converted to eDNA with cDNA synthesis kit (Bio-Rad). qRT-PCR was performed with SYBR green master mix (Bio-Rad) on Bio-Rad iCycler RT-PCR detection system. Primers used are listed on Table 4 below.

Flow Cytometry and Isolation of ISCs and Paneth Cells

As previously reported and briefly summarized here, small intestines were removed, washed with cold PBS−/−, opened laterally and cut into 3-5 mm fragments. Pieces were washed multiple times with cold PBS−/− until clean, washed 2-3 with PBS−/−/EDTA (10 mM), and incubated on ice for 90-120 minutes while mixing at 30-minute intervals. Crypts were then mechanically separated from the connective tissue by shaking, and filtered through a 70-μm mesh into a 50-ml conical tube to remove villous material and tissue fragments. At this point the suspension was mainly composed of crypts. Crypts were removed from this step for crypt culture experiments and embedded in Matrigel™ with crypt culture media. For ISC isolation, the crypt suspensions were dissociated to individual cells with TrypLE Express (Invitrogen). Cell labeling consisted of an antibody cocktail comprising CD45-PE (eBioscience, 30-F1 1), CD31-PE (Biolegend, Mecl3.3), Ter119-PE (Biolegend, Ter119), CD24-Pacific Blue (Biolegend, M1/69), CD117-APC/Cy7 (Biolegend, 2BS), and EPCAM-APC (eBioscience, G8.8). ISCs were isolated as Lgr5-EGFP$^{hi}$Epcam$^+$CD24$^{low/−}$CD31$^−$Ter119$^−$CD45$^−$7-AAD$^−$. EGFP$^{low}$ progenitors were isolated as EGFP$^{low}$Epcam$^+$CD24$^{low/−}$CD31$^−$Ter119$^−$CD45$^−$7-AAD$^−$, and Paneth cells were isolated as CD24$^{hi}$Sidescatter$^{hi}$Lgr5-EGFP$^−$Epcam$^+$CD31$^−$Ter119$^−$CD45$^−$7-AAD$^−$ with a BD FACS Aria II SORP cell sorter into supplemented crypt culture medium for culture. Dead cells were excluded from the analysis with the viability dye 7-AAD (Life Technologies). When indicated, populations were cytospun (Thermo Cytospin 4) at 800 r.p.m. for 2 minutes, or allowed to settle at 37° C. in fully humidified chambers containing 5% $CO_2$ onto poly-L-lysine-coated slides (Polysciences). The cells were subsequently fixed in 4% paraformaldehyde (pH 7.4, Electron Microscopy Sciences) before staining.

Culture Media for Crypts and Isolated Cells

Isolated crypts were counted and embedded in Matrigel™ (Corning 356231 growth factor reduced) at 5-10 crypts per μl and cultured in a modified form of medium as described previously.[14] Briefly, Advanced DMEM (Gibco) was

TABLE 4

Primer Sequences for qRT-PCR
(SEQ ID NOs: 189-212)

| Gene | SEQ ID NO:Forward Primer | | Gene | SEQ ID NO:Reverse Primer | |
|---|---|---|---|---|---|
| Pparg_F | 189 | CCACCAACTTCGGAATCAGCT | Pparg_R | 190 | TTTGTGGATCCGGCAGTTAAGA |
| Ppara_F | 191 | AGAGCCCCATCTGTCCTCTC | Ppara_R | 192 | ACTGGTAGTCTGCAAAACCAAA |
| Ppard_F | 193 | TCCATCGTCAACAAAGACGGG | Ppard_R | 194 | ACTTGGGCTCAATGATGTCAC |
| MglI_F | 195 | CGGACTTCCAAGTTTTTGTCAGA | MglI_R | 196 | GCAGCCACTAGGATGGAGATG |
| Slc22a3_F | 197 | CGTTTCTGCTCTTTCGGCTG | Slc22a3_R | 198 | TGCAACTGTGAACTGCCAAG |
| Fabp1_F | 199 | GGGAAGAAAATCAAACTCAC-CATC | Fabp1_R | 200 | AGTTGTCACCATTTTATTGT-CACC |
| Pdk4_F | 201 | AGGGAGGTCGAGCTGTTCTC | Pdk4_R | 202 | GGAGTGTTCACTAAGCGGTCA |
| Hmgcs2_F | 203 | ATACCACCAACGCCTGTTATGG | Hmgcs2_R | 204 | CAATGTCACCACAGACCACCAG |
| Cpt1a_F | 205 | CCATGAAGCCCTCAAACAGATC | Cpt1a_R | 206 | ATCACACCCACCACCACGATA |
| Actb_F | 207 | GGCTGTATTCCCCTCCATCG | Actb_R | 208 | CCAGTTGGTAACGCCATGT |
| mtCytB_F | 209 | CATTTATTATCGCGGCCCTA | mtCytB_R | 210 | TGTTGGGTTGTTTGATCCTG |
| bglobin_F | 211 | GAAGCGATTCTAGGGAGCAG | bglobin_R | 212 | GGAGCAGCGATTCTGAGTAGA | supplemented by EGF 40 ng ml$^{-1}$ (R&D), Noggin 200 ng ml$^{-1}$ (Peprotech), R-spondin 500 ng ml$^F$(R&D or Sino Biological), N-acetyl-L-cysteine 1 µM (Sigma-Aldrich), N2 1X (Life Technologies), B27 1X (Life Technologies), Chiron 10 µM (Stemgent), Y-27632 dihydrochloride monohydrate 20 ng ml$^{-1}$ (Sigma-Aldrich). 25 µL drops of Matrigel™ with crypts were plated onto a flat bottom 48-well plate (Corning 3548) and allowed to solidify for 20-30 minutes in a 37° C. incubator. Three hundred microliters of crypt culture medium was then overlaid onto the Matrigel™, changed every three days, and maintained at 37° C. in fully humidified chambers containing 5% $CO_2$. Clonogenicity (colony-forming efficiency) was calculated by plating 50-300 crypts and assessing organoid formation 3-7 days or as specified after initiation of cultures.

Isolated ISCs or progenitor cells were centrifuged for 5 minutes at 250 g, re-suspended in the appropriate volume of crypt culture medium (500-1,000 cells µl$^{-1}$), then seeded onto 25-30 µl Matrigel™ (Corning 356231 growth factor reduced) containing 1 µM jagged (Ana-Spec) in a flat bottom 48-well plate (Corning 3548). Alternatively, ISCs and Paneth cells were mixed after sorting in a 1:1 ratio, centrifuged, and then seeded onto Matrigel™. The Matrigel™ and cells were allowed to solidify before adding 300 µl of crypt culture medium. The crypt media was changed every second or third day. Organoid bodies were quantified on days 3, 7 and 10 of culture, unless otherwise specified. With respect to the study results presented in FIGS. 14-16, organoid bodies were quantified on day 3-4. In secondary experiments, individual primary organoids were mechanically dissociated and re-plated, or organoids were dissociated for 10 minutes in TrypLE Express at 32° C., re-suspended with SMEM (Life Technologies), centrifuged and re-suspended in cold SMEM with viability dye 7-AAD. Live cells were sorted and seeded onto Matrigel™ as previously described.

RNASeq

RNA Isolation. For RNA-seq, total RNA was extracted from 200K sorted Lgr5-GFP$^{hi}$ ISCs or Lgr5-GFP$^{low}$ progenitors by pooling two to five 71-week old male mice per HFD and HFD-control using Tri Reagent (Life Technologies) according to the manufacturer's instructions, except for a overnight isopropanol precipitation at −20° C. From the total RNA, poly(A)$^+$ RNA was selected using Oligo(dT)$_{25}$-Dynabeads (Life technologies) according to the manufacturer's protocol.

RNA-Seq Library Preparation. Strand-specific RNA-seq libraries were prepared using the dUTP-based, Illumina-compatible NEXTflex Directional RNA-Seq Kit (Bioo Scientific) according to the manufacturer's directions. All libraries were sequenced with an Illumina HiSeq 2000 sequencing machine.

Processing of RNA-seq reads and measuring expression level. For RNA-seq data analysis, raw stranded reads (40 nt) were trimmed to remove adapter and bases with quality scores below 20, and reads shorter than 35 nt were excluded. High-quality reads were mapped to the mouse genome (mm 10) with TopHat version 1.4.1[45], using known splice junctions from Ensembl Release 70 and allowing at most 2 mismatches. Genes were quantified with htseq-count (with the "intersect strict" mode) using Ensembl Release 70 gene models. Gene counts were normalized across all samples using estimateSizeFactors( ) from the DESeq R/Bioconductor package[46]. Differential expression analysis was also performed between two samples of interest with DESeq. Gene Set Enrichment analysis (www.broadinsitute.org/gsea) was performed by using the pre-ranked (according to their ratios) 8,240 differentially expressed genes as the expression data set.

Motif Analysis was performed using Haystack motif enrichment tool.

Single Cell Gene Expression Analysis 24 single Lgr5-GFP$^{hi}$ ISCs and 72 single Lgr5-GFP$^{low}$ progenitor cells were sorted from control or HFD mice for single cell gene expression analysis. For one-tube single-cell sequence-specific pre-amplification, individual primer sets of β-catenin target genes (total of 96) were pooled to 0.1 mM final concentration for each primer. Single cells were directly sorted into 96 well plates containing 5 ul RT-PCR master mix (2.5 ul CellsDirect reaction mix, Invitrogen; 0.5 ul primer pool; 0.1 ul RT/Taq enzyme, Invitrogen; 1.9 ul nuclease free water) in each well. Immediately after, plates were placed on PCR machine for pre-amplification. Sequence specific pre-amplification PCR protocol was as following: 1) 60 minutes at 50° C. for cell lyses and sequence specific reverse transcription, 2) 3 minutes at 95° C. for reverse transcriptase inactivation and Taq polymerase activation. Then, cDNA was amplified by 20 cycles of 15 seconds at 95° C. for initial denaturation, 15 minutes at 60° C. for annealing and elongation. After pre-amplification, samples were diluted 1:5 prior to high throughput microfluidic real time PCR analysis using Fluidgm platform. Amplified single cell cDNA samples were assayed for gene expression using individual qPCR primers and 96.96 dynamic arrays on a BioMark System by following manufacturers protocol (Fluidgm). For confirming PPAR-δ mediated induction of the most upregulated genes, regular single cell qRT-PCR was performed using preamplified cDNA with corresponding primers. Threshold crossing (Ct) values were calculated using the BioMark Real-Time PCR Analysis software (Fluidgm). Gene expression levels were estimated by subtracting the Ct values from the background level of 32, which approximately represent the $\log_2$ gene expression levels. The t-SNE analysis[47] was performed using the MATLAB toolbox for dimensionality reduction. Differential expression analysis was done using the two-sided Wilcoxon-Mann-Whitney rank sum test implemented in the R coin package (www.r-project.org). P-values were adjusted for multiple testing[48] using the p.adjust function in R with method="fdr" option. Fold-changes were calculated as the difference of median of $\log_2$ expression levels for the two cell populations. Violin plots were generated using the vioplot package in R. The master heatmap was generated with the MultiExperiment Viewer (MeV) program (http://www.tm4.org/mev.html) using the correlation-based distance and average linkage method as parameters of the unsupervised hierarchical clustering of genes.

Orthotopic Transplantation

Apc$^{loxp/loxp}$; Lgr5-EGFP-IRES-CreERT2 mice were treated with vehicle or GW501516 for one month, and then injected with two doses of tamoxifen I.P. Four days later, Apc-null Lgr5-GFP$^{hi}$ ISCs and Lgr5-GFP$^{low}$ progenitors were sorted by flow cytometry, as described above. For primary cell transplantations, 10,000 Apc-null Lgr5-GFP$^{hi}$ ISCs and Lgr5-GFP$^{low}$ progenitors were resuspended into 90% crypt culture media (as described) and 10% Matrigel™, then transplanted into the colonic lamina propria of C57BL/6 recipient mice by optical colonoscopy using an injection needle (Hamilton Inc., part number 7750-21, 30 gauge, Kel-F Hub NDL, 14 inches length, 45 degree bevel) and specialized syringe (Hamilton Inc, part number 81242, 500 µL, Model 1750 LT Threaded Plunger). Optical colonoscopy was performed using a Karl Storz Image 1 HD Camera System, Image 1 HUB CCU, 175 Watt Xenon Light Source, and Richard Wolf 1.9 mm/9.5 Fr Integrated Telescope (part number 8626.431). Four injections were performed per mouse. Mice then underwent colonoscopy four weeks later to assess tumor formation. Colonoscopy videos and images were saved for offline analysis. Following sacrifice, the distal colons were excised and fixed in 10% formalin, then examined by hematoxylin and eosin section to identify adenomas. All histology images were reviewed by a gastrointestinal pathologist who was blinded to treatment groups (S.S. and V.D.).

Drug Treatment and Mice

Lgr5-EGFP-IRES-CreERT2 mice (strain name: B6.129P2-Lgr5$^{tm1(cre/ERT2)Cle}$/J, stock number 008875), and Rosa26-lacZ mice (strain name: B6.129S4-Gt(ROSA) 26Sor$^{tm1Sor}$/J stock number 003474) were obtained from the Jackson Laboratory. GW501516 (Enzo) was reconstituted in DMSO at 4.5 mg ml$^{-1}$ and diluted 1:10 in a solution of 5% PEG400 (Hampton Research), 5% Tween80 (Sigma), 90% $H_2O$ for a daily intraperitoneal injection of 4 mg/kg. Control mice were injected with vehicle.

With respect to the study results presented in FIGS. 14-16, young mice were 2-4 months old. Old mice range from 18-25 months of age. The mice were on a standard chow diet. Mice received a single daily injection with the indicated amount of GW501516 or vehicle in the afternoon. Intestines were harvested the following morning.

Flow Cytometry and Isolation of ISCs and Paneth Cells

As described elsewhere herein and briefly summarized here, small intestines were removed, washed with cold PBS−/−, opened laterally and cut into 3-5 mm fragments. Pieces were washed multiple times with cold PBS−/− until clean, washed 2-3 with PBS−/−/EDTA (10 mM), and incubated on ice for 90-120 minutes while mixing at 30-minute intervals. Crypts were then mechanically separated from the connective tissue by shaking, and filtered through a 70-µm mesh into a 50-ml conical tube to remove villous material and tissue fragments. At this point the suspension was mainly composed of crypts. Crypts were removed from this step for crypt culture experiments and embedded in Matrigel™ with crypt culture media. For ISC isolation, the crypt suspensions were dissociated to individual cells with TrypLE Express (Invitrogen). Cell labeling consisted of an antibody cocktail comprising CD45-PE (eBioscience, 30-F11), CD31-PE (Biolegend, Mec13.3), Ter119-PE (Biolegend, Ter119), CD24-Pacific Blue (Biolegend, M1/69), CD117-APC/Cy7 (Biolegend, 2BS), and EPCAM-APC (eBioscience, G8.8). ISCs were isolated as Lgr5-EGFP$^{hi}$Epcam$^+$CD24$^{low/-}$CD31$^-$Ter119$^-$CD45$^-$7-AAD$^-$. EGFP$^{low}$ progenitors were isolated as EGFP$^{low}$Epcam$^+$CD24$^{low/-}$CD31$^-$Ter119$^-$CD45$^-$7-AAD$^-$, and Paneth cells were isolated as CD24$^{hi}$Sidescatter$^{hi}$Lgr5-EGFP$^-$Epcam$^+$CD31$^-$Ter119$^-$CD45$^-$7-AAD$^-$ with a BD FACS Aria II SORP cell sorter into supplemented crypt culture medium for culture. Dead cells were excluded from the analysis with the viability dye 7-AAD (Life Technologies).

REFERENCES

1. Mihaylova, M. M., Sabatini, D. M. & Yilmaz, O. H. Dietary and metabolic control of stem cell function in physiology and cancer. Cell stem cell 14, 292-305, doi: 10.1016/j.stem. 2014.02.008 (2014).
2. Barker, N. et al. Identification of stem cells in small intestine and colon by marker gene Lgr5. Nature 449, 1003-1007, doi:nature06196 [pii] 10.1038/nature06196 (2007).
3. Munoz, J. et al. The Lgr5 intestinal stem cell signature: robust expression of proposed quiescent '+4' cell markers. The EMBO journal 31, 3079-3091, doi:10.1038/emboj.2012.166 (2012).
4. Sato, T. et al. Paneth cells constitute the niche for Lgr5 stem cells in intestinal crypts. Nature 469, 415-418, doi:10.1038/nature09637 (2011).
5. Yilmaz, O. H. et al. mTORC1 in the Paneth cell niche couples intestinal stem-cell function to calorie intake. Nature 486, 490-495, doi:10.1038/nature11163 (2012).
6. Longo, V. D. & Fontana, L. Calorie restriction and cancer prevention: metabolic and molecular mechanisms. Trends in pharmacological sciences 31, 89-98, doi:10.1016/j.tips.2009.11.004 (2010).
7. Nakada, D., Levi, B. P. & Morrison, S. J. Integrating physiological regulation with stem cell and tissue homeostasis. Neuron 70, 703-718, doi: 10.1016/j.neuron.2011.05.011 (2011).
8. Johnson, S. C., Rabinovitch, P. S. & Kaeberlein, M. mTOR is a key modulator of ageing and age-related disease. Nature 493, 338-345, doi: 10.1038/nature11861 (2013).
9. Barker, N. et al. Crypt stem cells as the cells-of-origin of intestinal cancer. Nature 457, 608-611, doi:nature07602 [pii] 10.1038/nature07602 (2009).
10. Schwitalla, S. et al. Intestinal tumorigenesis initiated by dedifferentiation and acquisition of stem-cell-like properties. Cell 152, 25-38, doi: 10.1016/j.cell.2012.12.012 (2013).
11. Eckel-Mahan, K. L. et al. Reprogramming of the circadian clock by nutritional challenge. Cell 155, 1464-1478, doi:10.1016/j.cell.2013.11.034 (2013).
12. Winzell, M. S. & Ahren, B. The high-fat diet-fed mouse: a model for studying mechanisms and treatment of impaired glucose tolerance and type 2 diabetes. Diabetes 53 Suppl 3, S215-219 (2004).
13. Schuijers, J., van der Flier, L. G., van Es, J. & Clevers, H. Robust cre-mediated recombination in small intestinal stem cells utilizing the olfm4 locus. Stem cell reports 3, 234-241, doi: 10.1016/j.stemcr.2014.05.018 (2014).
14. Sato, T. et al. Single Lgr5 stem cells build crypt-villus structures in vitro without a mesenchymal niche. Nature, doi:nature07935. [pii] 10.1038/nature07935 (2009).
15. Schuijers, J. et al. Ascl2 Acts as an R-spondin/Wnt-Responsive Switch to Control Stemness in Intestinal Crypts. Cell stem cell 16, 158-170, doi:10.1016/j.stem.2014.12.006 (2015).
16. Marsh, V. et al. Epithelial Pten is dispensable for intestinal homeostasis but suppresses adenoma development and progression after Apc mutation. Nature genetics 40, 1436-1444, doi:ng.256 [pii] 10.1038/ng.256 (2008).
17. Buettner, R. et al. Defining high-fat-diet rat models: metabolic and molecular effects of different fat types. Journal of molecular endocrinology 36, 485-501, doi: 10.1677/jme.1.01909 (2006).
18. Peters, J. M., Shah, Y. M. & Gonzalez, F. J. The role of peroxisome proliferator-activated receptors in carcinogenesis and chemoprevention. Nature reviews. Cancer 12, 181-195, doi:10.1038/nrc3214 (2012).
19. Tontonoz, P. & Spiegelman, B. M. Fat and beyond: the diverse biology of PPARgamma. Annual review of biochemistry 77, 289-312, doi: 10.1146/annurev.biochem.77.061307.091829 (2008).
20. Ito, K. et al. A PML-PPAR-delta pathway for fatty acid oxidation regulates hematopoietic stem cell maintenance. *Nature medicine* 18, 1350-1358, doi:10.1038/nm.2882 (2012).
21. Narkar, V. A. et al. AMPK and PPARdelta agonists are exercise mimetics. *Cell* 134, 405-415, doi:10.1016/j.cell.2008.06.051 (2008).
22. van der Flier, L. G. & Clevers, H. Stem Cells, Self-Renewal, and Differentiation in the Intestinal Epithelium. *Annual review of physiology*, doi: 10.1146/annurev-.physiol. 010908.163145 (2008).
23. Myant, K. B. et al. ROS production and NF-kappaB activation triggered by RAC1 facilitate WNT-driven intestinal stem cell proliferation and colorectal cancer initiation. *Cell stem cell* 12, 761-773, doi: 10.1016/j.stem.2013.04.006 (2013).
24. van der Flier, L. G. et al. Transcription factor achaete scute-like 2 controls intestinal stem cell fate. *Cell* 136, 903-912, doi:S0092-8674(09)00079-8 [pii] 10.1016/j.cell.2009.01.031 (2009).
25. Meacham, C. E. & Morrison, S. J. Tumour heterogeneity and cancer cell plasticity. *Nature* 501, 328-337, doi: 10.1038/nature12624 (2013).
26. Pellegrinet, L. et al. Dll1- and dll4-mediated notch signaling are required for homeostasis of intestinal stem cells. *Gastroenterology* 140, 1230-1240 e1231-1237, doi: 10.1053/j.gastro.011.01.005 (2011).
27. Farin, H. F., van Es, J. H. & Clevers, H. Redundant Sources of Wnt Regulate Intestinal Stem Cells and Promote Formation of Paneth Cells. *Gastroenterology*, doi: 10.1053/j.gastro. 2012.08.031 (2012).
28. Finucane, M. M. et al. National, regional, and global trends in body-mass index since 1980: systematic analysis of health examination surveys and epidemiological studies with 960 country-years and 9.1 million participants. *Lancet* 377, 557-567, doi:10.1016/S0140-6736(10) 62037-5 (2011).
29. Calle, F. F. & Kaaks, R. Overweight, obesity and cancer: epidemiological evidence and proposed mechanisms. *Nature reviews. Cancer* 4, 579-591, doi:10.1038/nrc1408 (2004).
30. Baltgalvis, K. A., Berger, F. G., Pena, M. M., Davis, J. M. & Carson, J. A. The interaction of a high-fat diet and regular moderate intensity exercise on intestinal polyp development in Apc Min/+mice. *Cancer prevention research* 2, 641-649, doi:10.1158/1940-6207.CAPR-09-0017 (2009).
31. Tomasetti, C. & Vogelstein, B. Cancer etiology. Variation in cancer risk among tissues can be explained by the number of stem cell divisions. *Science* 347, 78-81, doi: 10.1126/science.1260825 (2015).
32. Mah, A. T., Van Landeghem, L., Gavin, H. E., Magness, S. T. & Lund, P. K. Impact of diet-induced obesity on intestinal stem cells: hyperproliferation but impaired intrinsic function that requires insulin/IGF1. *Endocrinology* 155, 3302-3314, doi:10.1210/en.2014-1112(2014).
33. Scholtysek, C. et al. PPARbeta/delta governs Wnt signaling and bone turnover. *Nature medicine* 19, 608-613, doi:10.1038/nm.3146 (2013).
34. Rodilla, V. et al. Jagged1 is the pathological link between Wnt and Notch pathways in colorectal cancer. *Proceedings of the National Academy of Sciences of the United States of America* 106, 6315-6320, doi: 10.1073/pnas.0813221106 (2009).
35. Kumar, S. R. et al. Preferential induction of EphB4 over EphB2 and its implication in colorectal cancer progression. *Cancer research* 69, 3736-3745, doi:10.1158/0008-5472.CAN-08-3232 (2009).
36. Wang, K. et al. SGKI-dependent intestinal tumor growth in APC-deficient mice. *Cellular physiology and biochemistry: international journal of experimental cellular physiology, biochemistry, and pharmacology* 25, 271-278, doi:10.1159/000276561 (2010).
37. Wang, D. et al. Peroxisome proliferator-activated receptor delta promotes colonic inflammation and tumor growth. *Proceedings of the National Academy of Sciences of the United States of America* 111, 7084-7089, doi: 10.1073/pnas.1324233111 (2014).
38. Wang, D. et al. Crosstalk between peroxisome proliferator-activated receptor delta and VEGF stimulates cancer progression. *Proceedings of the National Academy of Sciences of the United States of America* 103, 19069-19074, doi:10.1073/pnas.0607948103 (2006).
39. Park, B. H., Vogelstein, B. & Kinzler, K. W. Genetic disruption of PPARdelta decreases the tumorigenicity of human colon cancer cells. *Proceedings of the National Academy of Sciences of the United States of America* 98, 2598-2603, doi:10.1073/pnas.051630998 (2001).
40. Zuo, X. et al. Targeted genetic disruption of peroxisome proliferator-activated receptor-delta and colonic tumorigenesis. *Journal of the National Cancer Institute* 101, 762-767, doi: 10.1093/jnci/djp078 (2009).
41. Gupta, R. A. et al. Activation of nuclear hormone receptor peroxisome proliferator-activated receptor-delta accelerates intestinal adenoma growth. *Nature medicine* 10, 245-247, doi:10.1038/nm993 (2004).
42. Barak, Y. et al. Effects of peroxisome proliferator-activated receptor delta on placentation, adiposity, and colorectal cancer. *Proceedings of the National Academy of Sciences of the United States of America* 99, 303-308, doi:10.1073/pnas.012610299 (2002).
43. Colnot, S. et al. Colorectal cancers in a new mouse model of familial adenomatous polyposis: influence of genetic and environmental modifiers. *Laboratory investigation; a journal of technical methods and pathology* 84, 1619-1630, doi: 10.1038/labinvest.3700180 (2004).
44. Gregorieff, A. & Clevers, H. In situ hybridization to identify gut stem cells. *Current protocols in stem cell biology* Chapter 2, Unit 2F 1, doi:10.1002/9780470151808.sc02f01s12 (2010).
45. Trapnell, C., Pachter, L. & Salzberg, S. L. TopHat: discovering splice junctions with RNA-Seq. *Bioinformatics* 25, 1105-1111, doi:10.1093/bioinformatics/btp120 (2009).
46. Anders, S. & Huber, W. Differential expression analysis for sequence count data. *Genome biology* 11, R106, doi:10.1186/gb-2010-11-10-r106 (2010).
47. van der Maaten, L. & Hinton, G. Visualizing Data using t-SNE. *J Mach Learn Res* 9, 2579-2605 (2008).
48. Benjamini, Y. & Hochberg, Y. Controlling the False Discovery Rate—a Practical and Powerful Approach to Multiple Testing. *J Roy Stat Soc B Met* 57, 289-300 (1995).

What is claimed is:

1. A method of stimulating the proliferation and/or self-renewal of one or more intestinal stem cells in mammalian intestinal tissue in a subject, the method comprising contacting a population of cells in the mammalian intestinal tissue with an effective amount of a compound that increases the level and/or activity of peroxisome proliferator activated receptor delta (PPAR-δ) or a PPAR-δ target protein, thereby stimulating the proliferation and/or self-renewal of one or more intestinal stem cells, wherein the contacting of the population of cells with the effective amount of the compound occurs in a subject suffering a disease characterized by intestinal stem cells that require increased proliferation and/or self-renewal, wherein the compound comprises a PPAR-δ agonist or a PPAR-δ target protein agonist selected from the group consisting of a CPT1A agonist, a HMGCS2 agonist, and a FABP1 agonist.

2. A method according to claim 1 wherein the intestinal stem cells comprise leucine-rich repeat-containing G-protein coupled receptor 5-positive (LGR5+) stem cells.

3. A method according to claim 1 wherein the compound comprises a PPAR-δ agonist.

4. A method according to claim 1 wherein the compound comprises 2-[2-methyl-4-[[4-methyl-2-[4-(trifluoromethyl)phenyl]-1,3-thiazol-5-yl]methylsulfanyl]phenoxy]acetic acid (GW501516).

5. A method according to claim 1 wherein the contacting occurs in vivo in a subject.

6. A method according to claim 5 wherein the subject is selected for treatment of a gastrointestinal disorder selected from the group consisting of inflammatory bowel disease, infectious colitis, ischemic colitis, and inflammatory colitis.

7. A method according to claim 5 wherein the subject is selected for treatment of an affliction characterized by intestinal atrophy selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation.

8. A method according to claim 7 wherein exposure to ionizing radiation is from an ionizing radiation source selected from the group consisting of a nuclear power plant, a nuclear weapon, radiotherapy, and space or cosmic radiation.

9. A method according to claim 5 further comprising determining that the subject is in need of enhanced intestinal function.

10. A method of promoting regeneration of mammalian intestinal tissue in a subject, the method comprising contacting a population of cells in the mammalian intestinal tissue with an effective amount of a compound that increases the level and/or activity of peroxisome proliferator activated receptor delta (PPAR-δ) or a PPAR-δ target protein, thereby promoting regeneration of the mammalian intestinal tissue, wherein the contacting of the population of cells with the effective amount of the compound occurs in a subject suffering a disease characterized by mammalian intestinal tissue that requires promoted regeneration, wherein the compound comprises a PPAR-δ agonist or a PPAR-δ target protein agonist selected from the group consisting of a CPT1A agonist, a HMGCS2 agonist, and a FABP1 agonist.

11. A method according to claim 10 wherein the population of cells comprises intestinal stem cells that comprise leucine-rich repeat-containing G-protein coupled receptor 5-positive (LGR5+) stem cells.

12. A method according to claim 10 wherein the compound comprises a PPAR-δ agonist.

13. A method according to claim 10 wherein the compound comprises 2-[2-methyl-4-[[4-methyl-2-[4-(trifluoromethyl)phenyl]-1,3-thiazol-5-yl]methylsulfanyl]phenoxy]acetic acid (GW501516).

14. A method according to claim 10 wherein the contacting occurs in vivo in a subject.

15. A method according to claim 14 wherein the subject is selected for treatment of an affliction characterized by intestinal atrophy selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation.

16. A method of treating an affliction characterized by intestinal atrophy in a subject in need thereof, the method comprising administering to the subject an effective amount of a composition that increases the level and/or activity of PPAR-δ or a PPAR-δ target protein, thereby treating the affliction characterized by intestinal atrophy, wherein the composition comprises a PPAR-δ agonist or a PPAR-δ target protein agonist selected from the group consisting of a CPT1A agonist, a HMGCS2 agonist, and a FABP1 agonist.

17. A method according to claim 16 further comprising determining that the subject is in need of treatment for an affliction characterized by intestinal atrophy.

18. A method according to claim 16 wherein the affliction is selected from the group consisting of an inflammatory disease, an autoimmune disease, vascular disease, cancer, infection, short bowel syndrome, drug-induced or toxin-induced intestinal injury, total parenteral nutrition, and exposure to ionizing radiation.

19. A method according to claim 16 wherein the composition comprises a PPAR-δ agonist and a pharmaceutically acceptable carrier, diluent, or excipient.

20. A method according to claim 19 wherein the PPAR-δ agonist comprises GW501516.

21. A method according to claim 1 wherein the compound comprises a PPAR-δ target protein agonist selected from the group consisting of a CPT1A agonist, a HMGCS2 agonist, and a FABP1 agonist.

22. A method according to claim 3 wherein the PPAR-δ agonist is a compound of formula (I):

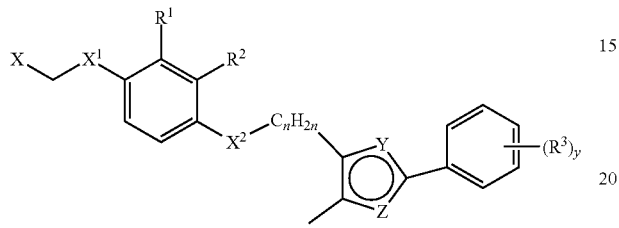

wherein X represents a COOH or a hydrolysable ester thereof; $X^1$ is O or S; $X^2$ is O or S; $R^1$ and $R^2$ independently represent H, $CH_3$, $OCH_3$, or halogen; n is 1 or 2; one of Y and Z is N and the other is S or O; y is 1 or 2; and each $R^3$ independently represents $CF_3$ or halogen.

* * * * *

SEQUENCE LISTING

<160> NUMBER OF SEQ ID NOS: 212

<210> SEQ ID NO 1
<211> LENGTH: 21
<212> TYPE: DNA
<213> ORGANISM: Artificial
<220> FEATURE:
<223> OTHER INFORMATION: forward primer

<400> SEQUENCE: 1
cagcagtcag tgtgcttaca a                                              21

<210> SEQ ID NO 2
<211> LENGTH: 21
<212> TYPE: DNA
<213> ORGANISM: Artificial
<220> FEATURE:
<223> OTHER INFORMATION: reverse primer

<400> SEQUENCE: 2
atggctcttt tatcggcctc a                                              21

<210> SEQ ID NO 3
<211> LENGTH: 21
<212> TYPE: DNA
<213> ORGANISM: Artificial
<220> FEATURE:
<223> OTHER INFORMATION: forward primer

<400> SEQUENCE: 3
atggtgttgc cgacagtgtt a                                              21

<210> SEQ ID NO 4
<211> LENGTH: 21
<212> TYPE: DNA
<213> ORGANISM: Artificial
<220> FEATURE:
<223> OTHER INFORMATION: reverse primer

<400> SEQUENCE: 4
gtttggcacg ctggtgtttt t                                              21

<210> SEQ ID NO 5
<211> LENGTH: 21
<212> TYPE: DNA
<213> ORGANISM: Artificial
<220> FEATURE:
<223> OTHER INFORMATION: forward primer

<400> SEQUENCE: 5
ctggtgcctg ctactgtgta t                                              21

<210> SEQ ID NO 6
<211> LENGTH: 21
<212> TYPE: DNA
<213> ORGANISM: Artificial
<220> FEATURE:
<223> OTHER INFORMATION: reverse primer

<400> SEQUENCE: 6
cccctacccc aacattagtc t                                              21

<210> SEQ ID NO 7
<211> LENGTH: 21
<212> TYPE: DNA
<213> ORGANISM: Artificial

```
<220> FEATURE:
<223> OTHER INFORMATION: forward primer

<400> SEQUENCE: 7
aagcacacct tgactggtac g                                          21

<210> SEQ ID NO 8
<211> LENGTH: 21
<212> TYPE: DNA
<213> ORGANISM: Artificial
<220> FEATURE:
<223> OTHER INFORMATION: reverse primer

<400> SEQUENCE: 8
aagtggacgt ttgcaccttc a                                          21

<210> SEQ ID NO 9
<211> LENGTH: 21
<212> TYPE: DNA
<213> ORGANISM: Artificial
<220> FEATURE:
<223> OTHER INFORMATION: forward primer

<400> SEQUENCE: 9
tgactctcct tccagatccc a                                          21

<210> SEQ ID NO 10
<211> LENGTH: 19
<212> TYPE: DNA
<213> ORGANISM: Artificial
<220> FEATURE:
<223> OTHER INFORMATION: reverse primer

<400> SEQUENCE: 10
tgcccacact aggctgaca                                             19

<210> SEQ ID NO 11
<211> LENGTH: 21
<212> TYPE: DNA
<213> ORGANISM: Artificial
<220> FEATURE:
<223> OTHER INFORMATION: forward primer

<400> SEQUENCE: 11
gatcgccact ccagctactt c                                          21

<210> SEQ ID NO 12
<211> LENGTH: 21
<212> TYPE: DNA
<213> ORGANISM: Artificial
<220> FEATURE:
<223> OTHER INFORMATION: reverse primer

<400> SEQUENCE: 12
gcaggcacta agctcagact t                                          21

<210> SEQ ID NO 13
<211> LENGTH: 21
<212> TYPE: DNA
<213> ORGANISM: Artificial
<220> FEATURE:
<223> OTHER INFORMATION: forward primer

<400> SEQUENCE: 13
gcggagttca cagctctata c                                          21
```

<210> SEQ ID NO 14
<211> LENGTH: 21
<212> TYPE: DNA
<213> ORGANISM: Artificial
<220> FEATURE:
<223> OTHER INFORMATION: reverse primer

<400> SEQUENCE: 14
aaaaggcccc tacagttacc a                                              21

<210> SEQ ID NO 15
<211> LENGTH: 22
<212> TYPE: DNA
<213> ORGANISM: Artificial
<220> FEATURE:
<223> OTHER INFORMATION: forward primer

<400> SEQUENCE: 15
gacaaggaga tgcaggtatt gg                                             22

<210> SEQ ID NO 16
<211> LENGTH: 22
<212> TYPE: DNA
<213> ORGANISM: Artificial
<220> FEATURE:
<223> OTHER INFORMATION: reverse primer

<400> SEQUENCE: 16
tcccgtagag atccacaaaa gt                                             22

<210> SEQ ID NO 17
<211> LENGTH: 20
<212> TYPE: DNA
<213> ORGANISM: Artificial
<220> FEATURE:
<223> OTHER INFORMATION: forward primer

<400> SEQUENCE: 17
gaggctggct tcatccactg                                                20

<210> SEQ ID NO 18
<211> LENGTH: 23
<212> TYPE: DNA
<213> ORGANISM: Artificial
<220> FEATURE:
<223> OTHER INFORMATION: reverse primer

<400> SEQUENCE: 18 cttttttgctt gttgttggtc tcc                                           23

<210> SEQ ID NO 19
<211> LENGTH: 22
<212> TYPE: DNA
<213> ORGANISM: Artificial
<220> FEATURE:
<223> OTHER INFORMATION: forward primer

<400> SEQUENCE: 19 atcccccactt aatgtgtgtc ct                                            22

<210> SEQ ID NO 20
<211> LENGTH: 21
<212> TYPE: DNA
<213> ORGANISM: Artificial
<220> FEATURE:
<223> OTHER INFORMATION: reverse primer

```
<400> SEQUENCE: 20
cttgctggtc tccaagtaac g                                              21

<210> SEQ ID NO 21
<211> LENGTH: 21
<212> TYPE: DNA
<213> ORGANISM: Artificial
<220> FEATURE:
<223> OTHER INFORMATION: forward primer

<400> SEQUENCE: 21
ttcctggtaa ccgaatgctg a                                              21

<210> SEQ ID NO 22
<211> LENGTH: 21
<212> TYPE: DNA
<213> ORGANISM: Artificial
<220> FEATURE:
<223> OTHER INFORMATION: reverse primer

<400> SEQUENCE: 22
cctgaatctc ggcgactttt t                                              21

<210> SEQ ID NO 23
<211> LENGTH: 21
<212> TYPE: DNA
<213> ORGANISM: Artificial
<220> FEATURE:
<223> OTHER INFORMATION: forward primer

<400> SEQUENCE: 23
gcgtaccctg acaccaatct c                                              21

<210> SEQ ID NO 24
<211> LENGTH: 21
<212> TYPE: DNA
<213> ORGANISM: Artificial
<220> FEATURE:
<223> OTHER INFORMATION: reverse primer

<400> SEQUENCE: 24
ctcctcttcg cacttctgct c                                              21

<210> SEQ ID NO 25
<211> LENGTH: 20
<212> TYPE: DNA
<213> ORGANISM: Artificial
<220> FEATURE:
<223> OTHER INFORMATION: forward primer

<400> SEQUENCE: 25
caccattgcc tcaactgtgc                                                20

<210> SEQ ID NO 26
<211> LENGTH: 20
<212> TYPE: DNA
<213> ORGANISM: Artificial
<220> FEATURE:
<223> OTHER INFORMATION: reverse primer

<400> SEQUENCE: 26
ttgtgggctc ctgagtctga                                                20

<210> SEQ ID NO 27
```

```
<211> LENGTH: 20
<212> TYPE: DNA
<213> ORGANISM: Artificial
<220> FEATURE:
<223> OTHER INFORMATION: forward primer

<400> SEQUENCE: 27
cgcaggttct tggtcactgt                                                    20

<210> SEQ ID NO 28
<211> LENGTH: 20
<212> TYPE: DNA
<213> ORGANISM: Artificial
<220> FEATURE:
<223> OTHER INFORMATION: reverse primer

<400> SEQUENCE: 28
tgttcacgaa agccagagcg                                                    20

<210> SEQ ID NO 29
<211> LENGTH: 20
<212> TYPE: DNA
<213> ORGANISM: Artificial
<220> FEATURE:
<223> OTHER INFORMATION: forward primer

<400> SEQUENCE: 29
ggacgcccta cgaatggatg                                                    20

<210> SEQ ID NO 30
<211> LENGTH: 21
<212> TYPE: DNA
<213> ORGANISM: Artificial
<220> FEATURE:
<223> OTHER INFORMATION: reverse primer

<400> SEQUENCE: 30
gtaccggctg tagtgaaact c                                                  21

<210> SEQ ID NO 31
<211> LENGTH: 19
<212> TYPE: DNA
<213> ORGANISM: Artificial
<220> FEATURE:
<223> OTHER INFORMATION: forward primer

<400> SEQUENCE: 31
ggggacaaca tcgtgaccg                                                     19

<210> SEQ ID NO 32
<211> LENGTH: 21
<212> TYPE: DNA
<213> ORGANISM: Artificial
<220> FEATURE:
<223> OTHER INFORMATION: reverse primer

<400> SEQUENCE: 32
aggagtcgaa gactttgcac t                                                  21

<210> SEQ ID NO 33
<211> LENGTH: 22
<212> TYPE: DNA
<213> ORGANISM: Artificial
<220> FEATURE:
<223> OTHER INFORMATION: forward primer

<400> SEQUENCE: 33
```
tgagcaacta ttccaaacca gc                                                22

<210> SEQ ID NO 34
<211> LENGTH: 23
<212> TYPE: DNA
<213> ORGANISM: Artificial
<220> FEATURE:
<223> OTHER INFORMATION: reverse primer

<400> SEQUENCE: 34
gcacgtagtc ttcgatcact atc                                               23

<210> SEQ ID NO 35
<211> LENGTH: 22
<212> TYPE: DNA
<213> ORGANISM: Artificial
<220> FEATURE:
<223> OTHER INFORMATION: forward primer

<400> SEQUENCE: 35
ctcatcaatt ccaacgcgat ca                                                22

<210> SEQ ID NO 36
<211> LENGTH: 20
<212> TYPE: DNA
<213> ORGANISM: Artificial
<220> FEATURE:
<223> OTHER INFORMATION: reverse primer

<400> SEQUENCE: 36
gccctcatag agaactcccg                                                   20

<210> SEQ ID NO 37
<211> LENGTH: 21
<212> TYPE: DNA
<213> ORGANISM: Artificial
<220> FEATURE:
<223> OTHER INFORMATION: forward primer

<400> SEQUENCE: 37
gtactggtga ccttgcttgg a                                                 21

<210> SEQ ID NO 38
<211> LENGTH: 22
<212> TYPE: DNA
<213> ORGANISM: Artificial
<220> FEATURE:
<223> OTHER INFORMATION: reverse primer

<400> SEQUENCE: 38
ccgttcatcg tgaaacgcta ag                                                22

<210> SEQ ID NO 39
<211> LENGTH: 22
<212> TYPE: DNA
<213> ORGANISM: Artificial
<220> FEATURE:
<223> OTHER INFORMATION: forward primer

<400> SEQUENCE: 39
aagaatggtg ttgtctaccg ac                                                22

<210> SEQ ID NO 40
<211> LENGTH: 20
<212> TYPE: DNA

```
<213> ORGANISM: Artificial
<220> FEATURE:
<223> OTHER INFORMATION: reverse primer

<400> SEQUENCE: 40
catccaggtt gctcccttg                                              20

<210> SEQ ID NO 41
<211> LENGTH: 19
<212> TYPE: DNA
<213> ORGANISM: Artificial
<220> FEATURE:
<223> OTHER INFORMATION: forward primer

<400> SEQUENCE: 41
gcaccggagc tgagaatgg                                              19

<210> SEQ ID NO 42
<211> LENGTH: 21
<212> TYPE: DNA
<213> ORGANISM: Artificial
<220> FEATURE:
<223> OTHER INFORMATION: reverse primer

<400> SEQUENCE: 42
gtggcagaag tagacacact c                                           21

<210> SEQ ID NO 43
<211> LENGTH: 19
<212> TYPE: DNA
<213> ORGANISM: Artificial
<220> FEATURE:
<223> OTHER INFORMATION: forward primer

<400> SEQUENCE: 43
tgtggctatg gtcgtgctg                                              19

<210> SEQ ID NO 44
<211> LENGTH: 20
<212> TYPE: DNA
<213> ORGANISM: Artificial
<220> FEATURE:
<223> OTHER INFORMATION: reverse primer

<400> SEQUENCE: 44 ccaagcccctt cccacttagg                                            20

<210> SEQ ID NO 45
<211> LENGTH: 23
<212> TYPE: DNA
<213> ORGANISM: Artificial
<220> FEATURE:
<223> OTHER INFORMATION: forward primer

<400> SEQUENCE: 45
ctgtttcata agtcctccta cgc                                         23

<210> SEQ ID NO 46
<211> LENGTH: 20
<212> TYPE: DNA
<213> ORGANISM: Artificial
<220> FEATURE:
<223> OTHER INFORMATION: reverse primer

<400> SEQUENCE: 46
caccactgaa catggcttcg                                             20
```

<210> SEQ ID NO 47
<211> LENGTH: 19
<212> TYPE: DNA
<213> ORGANISM: Artificial
<220> FEATURE:
<223> OTHER INFORMATION: forward primer

<400> SEQUENCE: 47
gcggctacga cgagaacat                                              19

<210> SEQ ID NO 48
<211> LENGTH: 22
<212> TYPE: DNA
<213> ORGANISM: Artificial
<220> FEATURE:
<223> OTHER INFORMATION: reverse primer

<400> SEQUENCE: 48
ggctaagtca aaatcagcct ca                                          22

<210> SEQ ID NO 49
<211> LENGTH: 21
<212> TYPE: DNA
<213> ORGANISM: Artificial
<220> FEATURE:
<223> OTHER INFORMATION: forward primer

<400> SEQUENCE: 49
catggacacg aaatgggtga c                                           21

<210> SEQ ID NO 50
<211> LENGTH: 22
<212> TYPE: DNA
<213> ORGANISM: Artificial
<220> FEATURE:
<223> OTHER INFORMATION: reverse primer

<400> SEQUENCE: 50
gcggatagga ttcatggctt ca                                          22

<210> SEQ ID NO 51
<211> LENGTH: 21
<212> TYPE: DNA
<213> ORGANISM: Artificial
<220> FEATURE:
<223> OTHER INFORMATION: forward primer

<400> SEQUENCE: 51
cctgcacttg cctgtgttta c                                           21

<210> SEQ ID NO 52
<211> LENGTH: 21
<212> TYPE: DNA
<213> ORGANISM: Artificial
<220> FEATURE:
<223> OTHER INFORMATION: reverse primer

<400> SEQUENCE: 52
tgcttccgac tcacatcatc t                                           21

<210> SEQ ID NO 53
<211> LENGTH: 21
<212> TYPE: DNA
<213> ORGANISM: Artificial
<220> FEATURE:

<223> OTHER INFORMATION: forward primer

<400> SEQUENCE: 53
ctaaatctct gacgcatggc a                                              21

<210> SEQ ID NO 54
<211> LENGTH: 21
<212> TYPE: DNA
<213> ORGANISM: Artificial
<220> FEATURE:
<223> OTHER INFORMATION: reverse primer

<400> SEQUENCE: 54
aactcctgat cggcttgtgt g                                              21

<210> SEQ ID NO 55
<211> LENGTH: 19
<212> TYPE: DNA
<213> ORGANISM: Artificial
<220> FEATURE:
<223> OTHER INFORMATION: forward primer

<400> SEQUENCE: 55
ggtcgcttcg tgagtccag                                                 19

<210> SEQ ID NO 56
<211> LENGTH: 19
<212> TYPE: DNA
<213> ORGANISM: Artificial
<220> FEATURE:
<223> OTHER INFORMATION: reverse primer

<400> SEQUENCE: 56
agcagccgtc tccagtagt                                                 19

<210> SEQ ID NO 57
<211> LENGTH: 21
<212> TYPE: DNA
<213> ORGANISM: Artificial
<220> FEATURE:
<223> OTHER INFORMATION: forward primer

<400> SEQUENCE: 57
atgtaccgag actacgggga a                                              21

<210> SEQ ID NO 58
<211> LENGTH: 19
<212> TYPE: DNA
<213> ORGANISM: Artificial
<220> FEATURE:
<223> OTHER INFORMATION: reverse primer

<400> SEQUENCE: 58
ctgctgctgt cgatgcttg                                                 19

<210> SEQ ID NO 59
<211> LENGTH: 19
<212> TYPE: DNA
<213> ORGANISM: Artificial
<220> FEATURE:
<223> OTHER INFORMATION: forward primer

<400> SEQUENCE: 59
gactgcgaag gtcgctacc                                                 19

```
<210> SEQ ID NO 60
<211> LENGTH: 22
<212> TYPE: DNA
<213> ORGANISM: Artificial
<220> FEATURE:
<223> OTHER INFORMATION: reverse primer

<400> SEQUENCE: 60
ctgatcggtc tcttcatcct ga                                              22

<210> SEQ ID NO 61
<211> LENGTH: 19
<212> TYPE: DNA
<213> ORGANISM: Artificial
<220> FEATURE:
<223> OTHER INFORMATION: forward primer

<400> SEQUENCE: 61
cgctcccagc tacaggatg                                                  19

<210> SEQ ID NO 62
<211> LENGTH: 22
<212> TYPE: DNA
<213> ORGANISM: Artificial
<220> FEATURE:
<223> OTHER INFORMATION: reverse primer

<400> SEQUENCE: 62
ggtctgctat gaagtgttga gg                                              22

<210> SEQ ID NO 63
<211> LENGTH: 22
<212> TYPE: DNA
<213> ORGANISM: Artificial
<220> FEATURE:
<223> OTHER INFORMATION: forward primer

<400> SEQUENCE: 63
gagtgggctg aggtaaaaga gt                                              22

<210> SEQ ID NO 64
<211> LENGTH: 19
<212> TYPE: DNA
<213> ORGANISM: Artificial
<220> FEATURE:
<223> OTHER INFORMATION: reverse primer

<400> SEQUENCE: 64
ggtcggtgct atccaggag                                                  19

<210> SEQ ID NO 65
<211> LENGTH: 22
<212> TYPE: DNA
<213> ORGANISM: Artificial
<220> FEATURE:
<223> OTHER INFORMATION: forward primer

<400> SEQUENCE: 65
atgtgggcga ggaatcttat gg                                              22

<210> SEQ ID NO 66
<211> LENGTH: 20
<212> TYPE: DNA
<213> ORGANISM: Artificial
<220> FEATURE:
<223> OTHER INFORMATION: reverse primer
```

<400> SEQUENCE: 66
ttccctggga caatgccttg					20

<210> SEQ ID NO 67
<211> LENGTH: 19
<212> TYPE: DNA
<213> ORGANISM: Artificial
<220> FEATURE:
<223> OTHER INFORMATION: forward primer

<400> SEQUENCE: 67
ccagccagtg tcaacacga					19

<210> SEQ ID NO 68
<211> LENGTH: 21
<212> TYPE: DNA
<213> ORGANISM: Artificial
<220> FEATURE:
<223> OTHER INFORMATION: reverse primer

<400> SEQUENCE: 68
aatgccggga gctatctttc t					21

<210> SEQ ID NO 69
<211> LENGTH: 21
<212> TYPE: DNA
<213> ORGANISM: Artificial
<220> FEATURE:
<223> OTHER INFORMATION: forward primer

<400> SEQUENCE: 69
atgaaagcct tcagtccggt g					21

<210> SEQ ID NO 70
<211> LENGTH: 19
<212> TYPE: DNA
<213> ORGANISM: Artificial
<220> FEATURE:
<223> OTHER INFORMATION: reverse primer

<400> SEQUENCE: 70
agcagactca tcgggtcgt					19

<210> SEQ ID NO 71
<211> LENGTH: 21
<212> TYPE: DNA
<213> ORGANISM: Artificial
<220> FEATURE:
<223> OTHER INFORMATION: forward primer

<400> SEQUENCE: 71
cgaaaagttc ctccgggttt g					21

<210> SEQ ID NO 72
<211> LENGTH: 19
<212> TYPE: DNA
<213> ORGANISM: Artificial
<220> FEATURE:
<223> OTHER INFORMATION: reverse primer

<400> SEQUENCE: 72
cgtagccggg ctgattcat					19

<210> SEQ ID NO 73
<211> LENGTH: 20

```
<212> TYPE: DNA
<213> ORGANISM: Artificial
<220> FEATURE:
<223> OTHER INFORMATION: forward primer

<400> SEQUENCE: 73
cctcgggtca gtttgagctg                                              20

<210> SEQ ID NO 74
<211> LENGTH: 22
<212> TYPE: DNA
<213> ORGANISM: Artificial
<220> FEATURE:
<223> OTHER INFORMATION: reverse primer

<400> SEQUENCE: 74
ccttgaggca cactttgaag ta                                           22

<210> SEQ ID NO 75
<211> LENGTH: 20
<212> TYPE: DNA
<213> ORGANISM: Artificial
<220> FEATURE:
<223> OTHER INFORMATION: forward primer

<400> SEQUENCE: 75
ccttctacga cgatgccctc                                              20

<210> SEQ ID NO 76
<211> LENGTH: 22
<212> TYPE: DNA
<213> ORGANISM: Artificial
<220> FEATURE:
<223> OTHER INFORMATION: reverse primer

<400> SEQUENCE: 76
ggttcaaggt catgctctgt tt                                           22

<210> SEQ ID NO 77
<211> LENGTH: 21
<212> TYPE: DNA
<213> ORGANISM: Artificial
<220> FEATURE:
<223> OTHER INFORMATION: forward primer

<400> SEQUENCE: 77
aaaggtgcaa gggtgacatt c                                            21

<210> SEQ ID NO 78
<211> LENGTH: 19
<212> TYPE: DNA
<213> ORGANISM: Artificial
<220> FEATURE:
<223> OTHER INFORMATION: reverse primer

<400> SEQUENCE: 78
tccccacgtt cctgtaggt                                               19

<210> SEQ ID NO 79
<211> LENGTH: 21
<212> TYPE: DNA
<213> ORGANISM: Artificial
<220> FEATURE:
<223> OTHER INFORMATION: forward primer

<400> SEQUENCE: 79
```
cagacacggg agattgctac t                                           21

<210> SEQ ID NO 80
<211> LENGTH: 19
<212> TYPE: DNA
<213> ORGANISM: Artificial
<220> FEATURE:
<223> OTHER INFORMATION: reverse primer

<400> SEQUENCE: 80
ccacgttccc caaagggat                                              19

<210> SEQ ID NO 81
<211> LENGTH: 21
<212> TYPE: DNA
<213> ORGANISM: Artificial
<220> FEATURE:
<223> OTHER INFORMATION: forward primer

<400> SEQUENCE: 81
tgtttatccc atcacgggtg g                                           21

<210> SEQ ID NO 82
<211> LENGTH: 21
<212> TYPE: DNA
<213> ORGANISM: Artificial
<220> FEATURE:
<223> OTHER INFORMATION: reverse primer

<400> SEQUENCE: 82
catggaagtg tcgcctgaca g                                           21

<210> SEQ ID NO 83
<211> LENGTH: 22
<212> TYPE: DNA
<213> ORGANISM: Artificial
<220> FEATURE:
<223> OTHER INFORMATION: forward primer

<400> SEQUENCE: 83
cctactcgaa gacttaccca gt                                          22

<210> SEQ ID NO 84
<211> LENGTH: 21
<212> TYPE: DNA
<213> ORGANISM: Artificial
<220> FEATURE:
<223> OTHER INFORMATION: reverse primer

<400> SEQUENCE: 84
gcattggggt gaatgatagc a                                           21

<210> SEQ ID NO 85
<211> LENGTH: 19
<212> TYPE: DNA
<213> ORGANISM: Artificial
<220> FEATURE:
<223> OTHER INFORMATION: forward primer

<400> SEQUENCE: 85
gcccagagca aggttactg                                              19

<210> SEQ ID NO 86
<211> LENGTH: 22
<212> TYPE: DNA
<213> ORGANISM: Artificial

<220> FEATURE:
<223> OTHER INFORMATION: reverse primer

<400> SEQUENCE: 86
gcccacagaa aatacatcgc aa        22

<210> SEQ ID NO 87
<211> LENGTH: 23
<212> TYPE: DNA
<213> ORGANISM: Artificial
<220> FEATURE:
<223> OTHER INFORMATION: forward primer

<400> SEQUENCE: 87
gtgaacatga agtatcagct ccc       23

<210> SEQ ID NO 88
<211> LENGTH: 21
<212> TYPE: DNA
<213> ORGANISM: Artificial
<220> FEATURE:
<223> OTHER INFORMATION: reverse primer

<400> SEQUENCE: 88
tgtagtttgt ggctccgaga t         21

<210> SEQ ID NO 89
<211> LENGTH: 22
<212> TYPE: DNA
<213> ORGANISM: Artificial
<220> FEATURE:
<223> OTHER INFORMATION: forward primer

<400> SEQUENCE: 89
cagtatggct acctacctcc ag        22

<210> SEQ ID NO 90
<211> LENGTH: 21
<212> TYPE: DNA
<213> ORGANISM: Artificial
<220> FEATURE:
<223> OTHER INFORMATION: reverse primer

<400> SEQUENCE: 90
gccttgcctg tcacttgtaa a         21

<210> SEQ ID NO 91
<211> LENGTH: 19
<212> TYPE: DNA
<213> ORGANISM: Artificial
<220> FEATURE:
<223> OTHER INFORMATION: forward primer

<400> SEQUENCE: 91
ctgccactgt cccaggaag            19

<210> SEQ ID NO 92
<211> LENGTH: 21
<212> TYPE: DNA
<213> ORGANISM: Artificial
<220> FEATURE:
<223> OTHER INFORMATION: reverse primer

<400> SEQUENCE: 92
gggagagttt tccagtcatg g         21

<210> SEQ ID NO 93
<211> LENGTH: 20
<212> TYPE: DNA
<213> ORGANISM: Artificial
<220> FEATURE:
<223> OTHER INFORMATION: forward primer

<400> SEQUENCE: 93
agaccccgac acagcatcta                                                  20

<210> SEQ ID NO 94
<211> LENGTH: 20
<212> TYPE: DNA
<213> ORGANISM: Artificial
<220> FEATURE:
<223> OTHER INFORMATION: reverse primer

<400> SEQUENCE: 94
cagcagccca tcgtagtcat                                                  20

<210> SEQ ID NO 95
<211> LENGTH: 21
<212> TYPE: DNA
<213> ORGANISM: Artificial
<220> FEATURE:
<223> OTHER INFORMATION: forward primer

<400> SEQUENCE: 95
atgcccctca acgtgaactt c                                                21

<210> SEQ ID NO 96
<211> LENGTH: 21
<212> TYPE: DNA
<213> ORGANISM: Artificial
<220> FEATURE:
<223> OTHER INFORMATION: reverse primer

<400> SEQUENCE: 96
cgcaacatag gatggagagc a                                                21

<210> SEQ ID NO 97
<211> LENGTH: 19
<212> TYPE: DNA
<213> ORGANISM: Artificial
<220> FEATURE:
<223> OTHER INFORMATION: forward primer

<400> SEQUENCE: 97
gctggacacg ctgacgaaa                                                   19

<210> SEQ ID NO 98
<211> LENGTH: 22
<212> TYPE: DNA
<213> ORGANISM: Artificial
<220> FEATURE:
<223> OTHER INFORMATION: reverse primer

<400> SEQUENCE: 98
tctaggcgaa gcagctctat tt                                               22

<210> SEQ ID NO 99
<211> LENGTH: 23
<212> TYPE: DNA
<213> ORGANISM: Artificial
<220> FEATURE:
<223> OTHER INFORMATION: forward primer

<400> SEQUENCE: 99
gttctcagcc caacaataca aga                                          23

<210> SEQ ID NO 100
<211> LENGTH: 19
<212> TYPE: DNA
<213> ORGANISM: Artificial
<220> FEATURE:
<223> OTHER INFORMATION: reverse primer

<400> SEQUENCE: 100
gtggacgggt cgatgtcac                                               19

<210> SEQ ID NO 101
<211> LENGTH: 21
<212> TYPE: DNA
<213> ORGANISM: Artificial
<220> FEATURE:
<223> OTHER INFORMATION: forward primer

<400> SEQUENCE: 101
atgtggacga gtgtctgttg c                                            21

<210> SEQ ID NO 102
<211> LENGTH: 21
<212> TYPE: DNA
<213> ORGANISM: Artificial
<220> FEATURE:
<223> OTHER INFORMATION: reverse primer

<400> SEQUENCE: 102
ggaagcatag gcacagtcat c                                            21

<210> SEQ ID NO 103
<211> LENGTH: 20
<212> TYPE: DNA
<213> ORGANISM: Artificial
<220> FEATURE:
<223> OTHER INFORMATION: forward primer

<400> SEQUENCE: 103
aaagggaaac ctcccccaag                                              20

<210> SEQ ID NO 104
<211> LENGTH: 22
<212> TYPE: DNA
<213> ORGANISM: Artificial
<220> FEATURE:
<223> OTHER INFORMATION: reverse primer

<400> SEQUENCE: 104
tgttgatgac aagggttcct ga                                           22

<210> SEQ ID NO 105
<211> LENGTH: 20
<212> TYPE: DNA
<213> ORGANISM: Artificial
<220> FEATURE:
<223> OTHER INFORMATION: forward primer

<400> SEQUENCE: 105
gcgccttggt ggtgaaaaac                                              20

<210> SEQ ID NO 106

```
<211> LENGTH: 21
<212> TYPE: DNA
<213> ORGANISM: Artificial
<220> FEATURE:
<223> OTHER INFORMATION: reverse primer

<400> SEQUENCE: 106
ttgtaggaca cgcatacacc t                                              21

<210> SEQ ID NO 107
<211> LENGTH: 20
<212> TYPE: DNA
<213> ORGANISM: Artificial
<220> FEATURE:
<223> OTHER INFORMATION: forward primer

<400> SEQUENCE: 107
cagagctttc caccgaatgg                                                20

<210> SEQ ID NO 108
<211> LENGTH: 19
<212> TYPE: DNA
<213> ORGANISM: Artificial
<220> FEATURE:
<223> OTHER INFORMATION: reverse primer

<400> SEQUENCE: 108
gtccccggca gttgatgag                                                 19

<210> SEQ ID NO 109
<211> LENGTH: 21
<212> TYPE: DNA
<213> ORGANISM: Artificial
<220> FEATURE:
<223> OTHER INFORMATION: forward primer

<400> SEQUENCE: 109
tccatcgtca acaaagacgg g                                              21

<210> SEQ ID NO 110
<211> LENGTH: 21
<212> TYPE: DNA
<213> ORGANISM: Artificial
<220> FEATURE:
<223> OTHER INFORMATION: reverse primer

<400> SEQUENCE: 110
acttgggctc aatgatgtca c                                              21

<210> SEQ ID NO 111
<211> LENGTH: 23
<212> TYPE: DNA
<213> ORGANISM: Artificial
<220> FEATURE:
<223> OTHER INFORMATION: forward primer

<400> SEQUENCE: 111
tccacaaata ctcaggcaaa gag                                            23

<210> SEQ ID NO 112
<211> LENGTH: 19
<212> TYPE: DNA
<213> ORGANISM: Artificial
<220> FEATURE:
<223> OTHER INFORMATION: reverse primer

<400> SEQUENCE: 112
```
gcagctccct ggtcagtag                                                19

<210> SEQ ID NO 113
<211> LENGTH: 20
<212> TYPE: DNA
<213> ORGANISM: Artificial
<220> FEATURE:
<223> OTHER INFORMATION: forward primer

<400> SEQUENCE: 113
ctgctcgaag cacccttacc                                               20

<210> SEQ ID NO 114
<211> LENGTH: 22
<212> TYPE: DNA
<213> ORGANISM: Artificial
<220> FEATURE:
<223> OTHER INFORMATION: reverse primer

<400> SEQUENCE: 114
tcctgaggat gggacatttt ca                                            22

<210> SEQ ID NO 115
<211> LENGTH: 21
<212> TYPE: DNA
<213> ORGANISM: Artificial
<220> FEATURE:
<223> OTHER INFORMATION: forward primer

<400> SEQUENCE: 115
cgaagttacc gagaccaaac a                                             21

<210> SEQ ID NO 116
<211> LENGTH: 23
<212> TYPE: DNA
<213> ORGANISM: Artificial
<220> FEATURE:
<223> OTHER INFORMATION: reverse primer

<400> SEQUENCE: 116
tcactgagaa caaactggat tgc                                           23

<210> SEQ ID NO 117
<211> LENGTH: 20
<212> TYPE: DNA
<213> ORGANISM: Artificial
<220> FEATURE:
<223> OTHER INFORMATION: forward primer

<400> SEQUENCE: 117
agtacccgca tctgcacaac                                               20

<210> SEQ ID NO 118
<211> LENGTH: 20
<212> TYPE: DNA
<213> ORGANISM: Artificial
<220> FEATURE:
<223> OTHER INFORMATION: reverse primer

<400> SEQUENCE: 118
acgaagggtc tcttctcgct                                               20

<210> SEQ ID NO 119
<211> LENGTH: 21
<212> TYPE: DNA

```
<213> ORGANISM: Artificial
<220> FEATURE:
<223> OTHER INFORMATION: forward primer

<400> SEQUENCE: 119
tgggttcacc ctccagactt t                                              21

<210> SEQ ID NO 120
<211> LENGTH: 19
<212> TYPE: DNA
<213> ORGANISM: Artificial
<220> FEATURE:
<223> OTHER INFORMATION: reverse primer

<400> SEQUENCE: 120
ccggcgagaa ctcgtaagg                                                 19

<210> SEQ ID NO 121
<211> LENGTH: 19
<212> TYPE: DNA
<213> ORGANISM: Artificial
<220> FEATURE:
<223> OTHER INFORMATION: forward primer

<400> SEQUENCE: 121
gcgcagatcc ccaagaagg                                                 19

<210> SEQ ID NO 122
<211> LENGTH: 21
<212> TYPE: DNA
<213> ORGANISM: Artificial
<220> FEATURE:
<223> OTHER INFORMATION: reverse primer

<400> SEQUENCE: 122
atcggctacg agacctagag a                                              21

<210> SEQ ID NO 123
<211> LENGTH: 23
<212> TYPE: DNA
<213> ORGANISM: Artificial
<220> FEATURE:
<223> OTHER INFORMATION: forward primer

<400> SEQUENCE: 123
aactcgaaat cttatcgcac caa                                            23

<210> SEQ ID NO 124
<211> LENGTH: 22
<212> TYPE: DNA
<213> ORGANISM: Artificial
<220> FEATURE:
<223> OTHER INFORMATION: reverse primer

<400> SEQUENCE: 124
tgcaaatgtg cagacaagct at                                             22

<210> SEQ ID NO 125
<211> LENGTH: 21
<212> TYPE: DNA
<213> ORGANISM: Artificial
<220> FEATURE:
<223> OTHER INFORMATION: forward primer

<400> SEQUENCE: 125
aggagtgtaa tagggcggag t                                              21
```

<210> SEQ ID NO 126
<211> LENGTH: 21
<212> TYPE: DNA
<213> ORGANISM: Artificial
<220> FEATURE:
<223> OTHER INFORMATION: reverse primer

<400> SEQUENCE: 126
gaggtccgtt ataggtgtcc a                                              21

<210> SEQ ID NO 127
<211> LENGTH: 19
<212> TYPE: DNA
<213> ORGANISM: Artificial
<220> FEATURE:
<223> OTHER INFORMATION: forward primer

<400> SEQUENCE: 127
gaagcacact tcacgctcc                                                 19

<210> SEQ ID NO 128
<211> LENGTH: 20
<212> TYPE: DNA
<213> ORGANISM: Artificial
<220> FEATURE:
<223> OTHER INFORMATION: reverse primer

<400> SEQUENCE: 128
ctccaggcca ttttcagcca                                                20

<210> SEQ ID NO 129
<211> LENGTH: 19
<212> TYPE: DNA
<213> ORGANISM: Artificial
<220> FEATURE:
<223> OTHER INFORMATION: forward primer

<400> SEQUENCE: 129
acggctacca cagaagctg                                                 19

<210> SEQ ID NO 130
<211> LENGTH: 21
<212> TYPE: DNA
<213> ORGANISM: Artificial
<220> FEATURE:
<223> OTHER INFORMATION: reverse primer

<400> SEQUENCE: 130
atggctgttg ttgctatggc a                                              21

<210> SEQ ID NO 131
<211> LENGTH: 20
<212> TYPE: DNA
<213> ORGANISM: Artificial
<220> FEATURE:
<223> OTHER INFORMATION: forward primer

<400> SEQUENCE: 131
gccagacagg gttgccatac                                                20

<210> SEQ ID NO 132
<211> LENGTH: 22
<212> TYPE: DNA
<213> ORGANISM: Artificial
<220> FEATURE:

```
<223> OTHER INFORMATION: reverse primer

<400> SEQUENCE: 132
ggagtgggat ggatgatgtc ag                                              22

<210> SEQ ID NO 133
<211> LENGTH: 20
<212> TYPE: DNA
<213> ORGANISM: Artificial
<220> FEATURE:
<223> OTHER INFORMATION: forward primer

<400> SEQUENCE: 133
tactgatgca ggtactgcgg                                                 20

<210> SEQ ID NO 134
<211> LENGTH: 21
<212> TYPE: DNA
<213> ORGANISM: Artificial
<220> FEATURE:
<223> OTHER INFORMATION: reverse primer

<400> SEQUENCE: 134
tcagggatct caaaggagga c                                               21

<210> SEQ ID NO 135
<211> LENGTH: 20
<212> TYPE: DNA
<213> ORGANISM: Artificial
<220> FEATURE:
<223> OTHER INFORMATION: forward primer

<400> SEQUENCE: 135
cgagcctcct acttccagtg                                                 20

<210> SEQ ID NO 136
<211> LENGTH: 20
<212> TYPE: DNA
<213> ORGANISM: Artificial
<220> FEATURE:
<223> OTHER INFORMATION: reverse primer

<400> SEQUENCE: 136
ggacaggtag cgatccaggt                                                 20

<210> SEQ ID NO 137
<211> LENGTH: 19
<212> TYPE: DNA
<213> ORGANISM: Artificial
<220> FEATURE:
<223> OTHER INFORMATION: forward primer

<400> SEQUENCE: 137
cagcagtaca acggcgaac                                                  19

<210> SEQ ID NO 138
<211> LENGTH: 20
<212> TYPE: DNA
<213> ORGANISM: Artificial
<220> FEATURE:
<223> OTHER INFORMATION: reverse primer

<400> SEQUENCE: 138
gtcctcctga ttcgtgtggc                                                 20
```

-continued

```
<210> SEQ ID NO 139
<211> LENGTH: 20
<212> TYPE: DNA
<213> ORGANISM: Artificial
<220> FEATURE:
<223> OTHER INFORMATION: forward primer

<400> SEQUENCE: 139
gccacacgaa ccaagaggac                                              20

<210> SEQ ID NO 140
<211> LENGTH: 22
<212> TYPE: DNA
<213> ORGANISM: Artificial
<220> FEATURE:
<223> OTHER INFORMATION: reverse primer

<400> SEQUENCE: 140
cgggtgcgta catagagcat aa                                           22

<210> SEQ ID NO 141
<211> LENGTH: 23
<212> TYPE: DNA
<213> ORGANISM: Artificial
<220> FEATURE:
<223> OTHER INFORMATION: forward primer

<400> SEQUENCE: 141
aagactgtaa taatggcgaa ccc                                          23

<210> SEQ ID NO 142
<211> LENGTH: 23
<212> TYPE: DNA
<213> ORGANISM: Artificial
<220> FEATURE:
<223> OTHER INFORMATION: reverse primer

<400> SEQUENCE: 142
tctcttggtt tatgcaaagc ctg                                          23

<210> SEQ ID NO 143
<211> LENGTH: 20
<212> TYPE: DNA
<213> ORGANISM: Artificial
<220> FEATURE:
<223> OTHER INFORMATION: forward primer

<400> SEQUENCE: 143
atggagccgg acagaaaagc                                              20

<210> SEQ ID NO 144
<211> LENGTH: 19
<212> TYPE: DNA
<213> ORGANISM: Artificial
<220> FEATURE:
<223> OTHER INFORMATION: reverse primer

<400> SEQUENCE: 144
cttgccactc agggaagga                                               19

<210> SEQ ID NO 145
<211> LENGTH: 19
<212> TYPE: DNA
<213> ORGANISM: Artificial
<220> FEATURE:
<223> OTHER INFORMATION: forward primer
```

```
<400> SEQUENCE: 145
aagcacccct ggaagaacc                                                   19

<210> SEQ ID NO 146
<211> LENGTH: 21
<212> TYPE: DNA
<213> ORGANISM: Artificial
<220> FEATURE:
<223> OTHER INFORMATION: reverse primer

<400> SEQUENCE: 146
cctgctctga aggcagatgt a                                                21

<210> SEQ ID NO 147
<211> LENGTH: 20
<212> TYPE: DNA
<213> ORGANISM: Artificial
<220> FEATURE:
<223> OTHER INFORMATION: forward primer

<400> SEQUENCE: 147
aggaaaggca tcgaggagtg                                                  20

<210> SEQ ID NO 148
<211> LENGTH: 21
<212> TYPE: DNA
<213> ORGANISM: Artificial
<220> FEATURE:
<223> OTHER INFORMATION: reverse primer

<400> SEQUENCE: 148
tcgctcagtc tctccattct c                                                21

<210> SEQ ID NO 149
<211> LENGTH: 22
<212> TYPE: DNA
<213> ORGANISM: Artificial
<220> FEATURE:
<223> OTHER INFORMATION: forward primer

<400> SEQUENCE: 149
tccgaaagat cagcagaaca ga                                               22

<210> SEQ ID NO 150
<211> LENGTH: 21
<212> TYPE: DNA
<213> ORGANISM: Artificial
<220> FEATURE:
<223> OTHER INFORMATION: reverse primer

<400> SEQUENCE: 150
ggactgcatt agcttccctt c                                                21

<210> SEQ ID NO 151
<211> LENGTH: 23
<212> TYPE: DNA
<213> ORGANISM: Artificial
<220> FEATURE:
<223> OTHER INFORMATION: forward primer

<400> SEQUENCE: 151
ttgttgcttt atgcaaacag acg                                              23

<210> SEQ ID NO 152
<211> LENGTH: 22
```

```
<212> TYPE: DNA
<213> ORGANISM: Artificial
<220> FEATURE:
<223> OTHER INFORMATION: reverse primer

<400> SEQUENCE: 152
gttcgtttaa tggcttcttc gc                                           22

<210> SEQ ID NO 153
<211> LENGTH: 20
<212> TYPE: DNA
<213> ORGANISM: Artificial
<220> FEATURE:
<223> OTHER INFORMATION: forward primer

<400> SEQUENCE: 153
aagggtgctg tgtactggac                                              20

<210> SEQ ID NO 154
<211> LENGTH: 21
<212> TYPE: DNA
<213> ORGANISM: Artificial
<220> FEATURE:
<223> OTHER INFORMATION: reverse primer

<400> SEQUENCE: 154
agaagagaac cttacgggac g                                            21

<210> SEQ ID NO 155
<211> LENGTH: 22
<212> TYPE: DNA
<213> ORGANISM: Artificial
<220> FEATURE:
<223> OTHER INFORMATION: forward primer

<400> SEQUENCE: 155
cagccacttt ccaatttcac tg                                           22

<210> SEQ ID NO 156
<211> LENGTH: 23
<212> TYPE: DNA
<213> ORGANISM: Artificial
<220> FEATURE:
<223> OTHER INFORMATION: reverse primer

<400> SEQUENCE: 156
gctggacata ctccttcacc tta                                          23

<210> SEQ ID NO 157
<211> LENGTH: 23
<212> TYPE: DNA
<213> ORGANISM: Artificial
<220> FEATURE:
<223> OTHER INFORMATION: forward primer

<400> SEQUENCE: 157
tttaaccagg tcgattccat cca                                          23

<210> SEQ ID NO 158
<211> LENGTH: 20
<212> TYPE: DNA
<213> ORGANISM: Artificial
<220> FEATURE:
<223> OTHER INFORMATION: reverse primer

<400> SEQUENCE: 158
```
cggaccgtgc attcctcttt                                          20

<210> SEQ ID NO 159
<211> LENGTH: 21
<212> TYPE: DNA
<213> ORGANISM: Artificial
<220> FEATURE:
<223> OTHER INFORMATION: forward primer

<400> SEQUENCE: 159
gagacggagc tgttggtaaa a                                        21

<210> SEQ ID NO 160
<211> LENGTH: 21
<212> TYPE: DNA
<213> ORGANISM: Artificial
<220> FEATURE:
<223> OTHER INFORMATION: reverse primer

<400> SEQUENCE: 160
ataggcccag attcactggt t                                        21

<210> SEQ ID NO 161
<211> LENGTH: 20
<212> TYPE: DNA
<213> ORGANISM: Artificial
<220> FEATURE:
<223> OTHER INFORMATION: forward primer

<400> SEQUENCE: 161
atgtcggtag ctgtggagac                                          20

<210> SEQ ID NO 162
<211> LENGTH: 19
<212> TYPE: DNA
<213> ORGANISM: Artificial
<220> FEATURE:
<223> OTHER INFORMATION: reverse primer

<400> SEQUENCE: 162
ggacggaaag tcccagcag                                           19

<210> SEQ ID NO 163
<211> LENGTH: 21
<212> TYPE: DNA
<213> ORGANISM: Artificial
<220> FEATURE:
<223> OTHER INFORMATION: forward primer

<400> SEQUENCE: 163
ccctggtgag aggattgtgt c                                        21

<210> SEQ ID NO 164
<211> LENGTH: 23
<212> TYPE: DNA
<213> ORGANISM: Artificial
<220> FEATURE:
<223> OTHER INFORMATION: reverse primer

<400> SEQUENCE: 164
ccttgtcctt gtaagtgaag cac                                      23

<210> SEQ ID NO 165
<211> LENGTH: 23
<212> TYPE: DNA
<213> ORGANISM: Artificial

-continued

<220> FEATURE:
<223> OTHER INFORMATION: forward primer

<400> SEQUENCE: 165
attatttgcc ccaaagtgga ctc                                            23

<210> SEQ ID NO 166
<211> LENGTH: 20
<212> TYPE: DNA
<213> ORGANISM: Artificial
<220> FEATURE:
<223> OTHER INFORMATION: reverse primer

<400> SEQUENCE: 166
gcagcggggt attctccttc                                                20

<210> SEQ ID NO 167
<211> LENGTH: 21
<212> TYPE: DNA
<213> ORGANISM: Artificial
<220> FEATURE:
<223> OTHER INFORMATION: forward primer

<400> SEQUENCE: 167
tatgccacga tacgcttcac c                                              21

<210> SEQ ID NO 168
<211> LENGTH: 23
<212> TYPE: DNA
<213> ORGANISM: Artificial
<220> FEATURE:
<223> OTHER INFORMATION: reverse primer

<400> SEQUENCE: 168
agcttcgctc tcgtaataga aga                                            23

<210> SEQ ID NO 169
<211> LENGTH: 21
<212> TYPE: DNA
<213> ORGANISM: Artificial
<220> FEATURE:
<223> OTHER INFORMATION: forward primer

<400> SEQUENCE: 169
gctcggaggt agaggtcttg t                                              21

<210> SEQ ID NO 170
<211> LENGTH: 19
<212> TYPE: DNA
<213> ORGANISM: Artificial
<220> FEATURE:
<223> OTHER INFORMATION: reverse primer

<400> SEQUENCE: 170
ccacgctgac tggtaggaa                                                 19

<210> SEQ ID NO 171
<211> LENGTH: 19
<212> TYPE: DNA
<213> ORGANISM: Artificial
<220> FEATURE:
<223> OTHER INFORMATION: forward primer

<400> SEQUENCE: 171
ggagcgaatc aaggagcgt                                                 19

<210> SEQ ID NO 172
<211> LENGTH: 22
<212> TYPE: DNA
<213> ORGANISM: Artificial
<220> FEATURE:
<223> OTHER INFORMATION: reverse primer

<400> SEQUENCE: 172
acggaaccac ctagaatctt gt                                              22

<210> SEQ ID NO 173
<211> LENGTH: 22
<212> TYPE: DNA
<213> ORGANISM: Artificial
<220> FEATURE:
<223> OTHER INFORMATION: forward primer

<400> SEQUENCE: 173
agctttctcc actctacgaa ca                                              22

<210> SEQ ID NO 174
<211> LENGTH: 21
<212> TYPE: DNA
<213> ORGANISM: Artificial
<220> FEATURE:
<223> OTHER INFORMATION: reverse primer

<400> SEQUENCE: 174
aatccagaga gatcgggggt c                                               21

<210> SEQ ID NO 175
<211> LENGTH: 22
<212> TYPE: DNA
<213> ORGANISM: Artificial
<220> FEATURE:
<223> OTHER INFORMATION: forward primer

<400> SEQUENCE: 175
caatgacacc actccagatg ag                                              22

<210> SEQ ID NO 176
<211> LENGTH: 19
<212> TYPE: DNA
<213> ORGANISM: Artificial
<220> FEATURE:
<223> OTHER INFORMATION: reverse primer

<400> SEQUENCE: 176
ggccaaagaa gtcgttgcg                                                  19

<210> SEQ ID NO 177
<211> LENGTH: 21
<212> TYPE: DNA
<213> ORGANISM: Artificial
<220> FEATURE:
<223> OTHER INFORMATION: forward primer

<400> SEQUENCE: 177
ggctgggatt accaaagcct c                                               21

<210> SEQ ID NO 178
<211> LENGTH: 22
<212> TYPE: DNA
<213> ORGANISM: Artificial
<220> FEATURE:
<223> OTHER INFORMATION: reverse primer

```
<400> SEQUENCE: 178
caccaataac cacctgtctt gt                                              22

<210> SEQ ID NO 179
<211> LENGTH: 20
<212> TYPE: DNA
<213> ORGANISM: Artificial
<220> FEATURE:
<223> OTHER INFORMATION: forward primer

<400> SEQUENCE: 179
gagccggatc tgaagaggga                                                 20

<210> SEQ ID NO 180
<211> LENGTH: 20
<212> TYPE: DNA
<213> ORGANISM: Artificial
<220> FEATURE:
<223> OTHER INFORMATION: reverse primer

<400> SEQUENCE: 180
gcttgacgtg tggcttgttc                                                 20

<210> SEQ ID NO 181
<211> LENGTH: 20
<212> TYPE: DNA
<213> ORGANISM: Artificial
<220> FEATURE:
<223> OTHER INFORMATION: forward primer

<400> SEQUENCE: 181
atgtgccgga tagcgggagc                                                 20

<210> SEQ ID NO 182
<211> LENGTH: 20
<212> TYPE: DNA
<213> ORGANISM: Artificial
<220> FEATURE:
<223> OTHER INFORMATION: reverse primer

<400> SEQUENCE: 182
tacaccgtgc cgtcctcgtc                                                 20

<210> SEQ ID NO 183
<211> LENGTH: 20
<212> TYPE: DNA
<213> ORGANISM: Artificial
<220> FEATURE:
<223> OTHER INFORMATION: forward primer

<400> SEQUENCE: 183
cacctggaga gaggccatgt                                                 20

<210> SEQ ID NO 184
<211> LENGTH: 20
<212> TYPE: DNA
<213> ORGANISM: Artificial
<220> FEATURE:
<223> OTHER INFORMATION: reverse primer

<400> SEQUENCE: 184
tgggaaacat gagcagctct                                                 20

<210> SEQ ID NO 185
```

```
<210> SEQ ID NO 185
<211> LENGTH: 20
<212> TYPE: DNA
<213> ORGANISM: Artificial
<220> FEATURE:
<223> OTHER INFORMATION: forward primer

<400> SEQUENCE: 185
ggctgtattc ccctccatcg                                              20

<210> SEQ ID NO 186
<211> LENGTH: 22
<212> TYPE: DNA
<213> ORGANISM: Artificial
<220> FEATURE:
<223> OTHER INFORMATION: reverse primer

<400> SEQUENCE: 186
ccagttggta acaatgccat gt                                           22

<210> SEQ ID NO 187
<211> LENGTH: 21
<212> TYPE: DNA
<213> ORGANISM: Artificial
<220> FEATURE:
<223> OTHER INFORMATION: forward primer

<400> SEQUENCE: 187
aggtcggtgt gaacggattt g                                            21

<210> SEQ ID NO 188
<211> LENGTH: 23
<212> TYPE: DNA
<213> ORGANISM: Artificial
<220> FEATURE:
<223> OTHER INFORMATION: reverse primer

<400> SEQUENCE: 188
tgtagaccat gtagttgagg tca                                          23

<210> SEQ ID NO 189
<211> LENGTH: 21
<212> TYPE: DNA
<213> ORGANISM: Artificial
<220> FEATURE:
<223> OTHER INFORMATION: forward primer

<400> SEQUENCE: 189
ccaccaactt cggaatcagc t                                            21

<210> SEQ ID NO 190
<211> LENGTH: 22
<212> TYPE: DNA
<213> ORGANISM: Artificial
<220> FEATURE:
<223> OTHER INFORMATION: reverse primer

<400> SEQUENCE: 190
tttgtggatc cggcagttaa ga                                           22

<210> SEQ ID NO 191
<211> LENGTH: 20
<212> TYPE: DNA
<213> ORGANISM: Artificial
<220> FEATURE:
<223> OTHER INFORMATION: forward primer

<400> SEQUENCE: 191
```
agagccccat ctgtcctctc                                              20

<210> SEQ ID NO 192
<211> LENGTH: 22
<212> TYPE: DNA
<213> ORGANISM: Artificial
<220> FEATURE:
<223> OTHER INFORMATION: reverse primer

<400> SEQUENCE: 192
actggtagtc tgcaaaacca aa                                           22

<210> SEQ ID NO 193
<211> LENGTH: 21
<212> TYPE: DNA
<213> ORGANISM: Artificial
<220> FEATURE:
<223> OTHER INFORMATION: forward primer

<400> SEQUENCE: 193
tccatcgtca acaaagacgg g                                            21

<210> SEQ ID NO 194
<211> LENGTH: 21
<212> TYPE: DNA
<213> ORGANISM: Artificial
<220> FEATURE:
<223> OTHER INFORMATION: reverse primer

<400> SEQUENCE: 194
acttgggctc aatgatgtca c                                            21

<210> SEQ ID NO 195
<211> LENGTH: 23
<212> TYPE: DNA
<213> ORGANISM: Artificial
<220> FEATURE:
<223> OTHER INFORMATION: forward primer

<400> SEQUENCE: 195
cggacttcca agttttt gtc aga                                         23

<210> SEQ ID NO 196
<211> LENGTH: 21
<212> TYPE: DNA
<213> ORGANISM: Artificial
<220> FEATURE:
<223> OTHER INFORMATION: reverse primer

<400> SEQUENCE: 196
gcagccacta ggatggagat g                                            21

<210> SEQ ID NO 197
<211> LENGTH: 20
<212> TYPE: DNA
<213> ORGANISM: Artificial
<220> FEATURE:
<223> OTHER INFORMATION: forward primer

<400> SEQUENCE: 197
cgtttctgct ctttcggctg                                              20

<210> SEQ ID NO 198
<211> LENGTH: 20
<212> TYPE: DNA

<213> ORGANISM: Artificial
<220> FEATURE:
<223> OTHER INFORMATION: reverse primer

<400> SEQUENCE: 198
tgcaactgtg aactgccaag                                                    20

<210> SEQ ID NO 199
<211> LENGTH: 24
<212> TYPE: DNA
<213> ORGANISM: Artificial
<220> FEATURE:
<223> OTHER INFORMATION: forward primer

<400> SEQUENCE: 199
gggaagaaaa tcaaactcac catc                                               24

<210> SEQ ID NO 200
<211> LENGTH: 24
<212> TYPE: DNA
<213> ORGANISM: Artificial
<220> FEATURE:
<223> OTHER INFORMATION: reverse primer

<400> SEQUENCE: 200
agttgtcacc attttattgt cacc                                               24

<210> SEQ ID NO 201
<211> LENGTH: 20
<212> TYPE: DNA
<213> ORGANISM: Artificial
<220> FEATURE:
<223> OTHER INFORMATION: forward primer

<400> SEQUENCE: 201
agggaggtcg agctgttctc                                                    20

<210> SEQ ID NO 202
<211> LENGTH: 21
<212> TYPE: DNA
<213> ORGANISM: Artificial
<220> FEATURE:
<223> OTHER INFORMATION: reverse primer

<400> SEQUENCE: 202
ggagtgttca ctaagcggtc a                                                  21

<210> SEQ ID NO 203
<211> LENGTH: 22
<212> TYPE: DNA
<213> ORGANISM: Artificial
<220> FEATURE:
<223> OTHER INFORMATION: forward primer

<400> SEQUENCE: 203
ataccaccaa cgcctgttat gg                                                 22

<210> SEQ ID NO 204
<211> LENGTH: 22
<212> TYPE: DNA
<213> ORGANISM: Artificial
<220> FEATURE:
<223> OTHER INFORMATION: reverse primer

<400> SEQUENCE: 204
caatgtcacc acagaccacc ag                                                 22

<210> SEQ ID NO 205
<211> LENGTH: 22
<212> TYPE: DNA
<213> ORGANISM: Artificial
<220> FEATURE:
<223> OTHER INFORMATION: forward primer

<400> SEQUENCE: 205
ccatgaagcc ctcaaacaga tc                                    22

<210> SEQ ID NO 206
<211> LENGTH: 21
<212> TYPE: DNA
<213> ORGANISM: Artificial
<220> FEATURE:
<223> OTHER INFORMATION: reverse primer

<400> SEQUENCE: 206
atcacaccca ccaccacgat a                                     21

<210> SEQ ID NO 207
<211> LENGTH: 20
<212> TYPE: DNA
<213> ORGANISM: Artificial
<220> FEATURE:
<223> OTHER INFORMATION: forward primer

<400> SEQUENCE: 207
ggctgtattc ccctccatcg                                       20

<210> SEQ ID NO 208
<211> LENGTH: 19
<212> TYPE: DNA
<213> ORGANISM: Artificial
<220> FEATURE:
<223> OTHER INFORMATION: reverse primer

<400> SEQUENCE: 208
ccagttggta acgccatgt                                        19

<210> SEQ ID NO 209
<211> LENGTH: 20
<212> TYPE: DNA
<213> ORGANISM: Artificial
<220> FEATURE:
<223> OTHER INFORMATION: forward primer

<400> SEQUENCE: 209
catttattat cgcggcccta                                       20

<210> SEQ ID NO 210
<211> LENGTH: 20
<212> TYPE: DNA
<213> ORGANISM: Artificial
<220> FEATURE:
<223> OTHER INFORMATION: reverse primer

<400> SEQUENCE: 210
tgttgggttg tttgatcctg                                       20

<210> SEQ ID NO 211
<211> LENGTH: 20
<212> TYPE: DNA
<213> ORGANISM: Artificial
<220> FEATURE:

```
<223> OTHER INFORMATION: forward primer

<400> SEQUENCE: 211
gaagcgattc tagggagcag                                              20

<210> SEQ ID NO 212
<211> LENGTH: 21
<212> TYPE: DNA
<213> ORGANISM: Artificial
<220> FEATURE:
<223> OTHER INFORMATION: reverse primer

<400> SEQUENCE: 212
ggagcagcga ttctgagtag a                                            21
```